(12) United States Patent
Malandain et al.

(10) Patent No.: US 8,043,335 B2
(45) Date of Patent: Oct. 25, 2011

(54) PERCUTANEOUS SPINAL IMPLANTS AND METHODS

(75) Inventors: Hugues F. Malandain, Mountain View, CA (US); Avram Allan Edidin, Portola Valley, CA (US); Robert Alexander Vandervelde, Tervuren (BE)

(73) Assignee: Kyphon SARL, Neuchatel (CH)

( * ) Notice: Subject to any disclaimer, the term of this patent is extended or adjusted under 35 U.S.C. 154(b) by 858 days.

(21) Appl. No.: 11/927,835

(22) Filed: Oct. 30, 2007

(65) Prior Publication Data

US 2008/0051893 A1    Feb. 28, 2008

Related U.S. Application Data

(63) Continuation of application No. 11/625,604, filed on Jan. 22, 2007, which is a continuation-in-part of application No. 11/454,153, filed on Jun. 16, 2006, and a continuation-in-part of application No. 11/454,156, filed on Jun. 16, 2006, and a continuation-in-part of application No. 11/454,194, filed on Jun. 16, 2006, said application No. 11/454,153 is a continuation-in-part of application No. PCT/US2006/005580, filed on Feb. 17, 2006, said application No. 11/454,156 is a continuation-in-part of application No. PCT/US2006/005580, filed on Feb. 17, 2006, said application No. 11/454,194 is a continuation-in-part of application No. PCT/US2006/005580, filed on Feb. 17, 2006, said application No. 11/454,153 is a continuation-in-part of application No. 11/059,526, filed on Feb. 17, 2005, now abandoned, said application No. 11/454,156 is a continuation-in-part of application No. 11/059,526, (Continued)

(51) Int. Cl.
*A61F 2/44* (2006.01)
(52) U.S. Cl. .................. 606/249; 606/279; 623/17.11
(58) Field of Classification Search .... 623/17.11–17.16; 606/246–249, 279, 86 A, 99, 105
See application file for complete search history.

(56) References Cited

U.S. PATENT DOCUMENTS 2,677,369 A    5/1954    Knowles
(Continued)

FOREIGN PATENT DOCUMENTS

DE    2821678 A1    11/1979
(Continued)

OTHER PUBLICATIONS

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

(Continued)

*Primary Examiner* — Eduardo C Robert
*Assistant Examiner* — Tara R Carter

(57) ABSTRACT

A method includes positioning a medical device within a body between adjacent spinous processes, moving the medical device from a collapsed configuration to an expanded configuration within the body using an actuator removably coupled to the medical device, and removing the actuator from the body while the medical device remains between the adjacent spinous processes.

24 Claims, 82 Drawing Sheets

Related U.S. Application Data filed on Feb. 17, 2005, now abandoned, said application No. 11/454,194 is a continuation-in-part of application No. 11/059,526, filed on Feb. 17, 2005, now abandoned, said application No. 11/454,153 is a continuation-in-part of application No. 11/252,879, filed on Oct. 19, 2005, which is a continuation-in-part of application No. 11/059,526, filed on Feb. 17, 2005, now abandoned, said application No. 11/454,156 is a continuation-in-part of application No. 11/252,879, filed on Oct. 19, 2005, which is a continuation-in-part of application No. 11/059,526, filed on Feb. 17, 2005, now abandoned, said application No. 11/454,194 is a continuation-in-part of application No. 11/252,879, filed on Oct. 19, 2005, which is a continuation-in-part of application No. 11/059,526, filed on Feb. 17, 2005, now abandoned, said application No. 11/454,153 is a continuation-in-part of application No. 11/252,880, filed on Oct. 19, 2005, now abandoned, which is a continuation-in-part of application No. 11/059,526, filed on Feb. 17, 2005, now abandoned, said application No. 11/454,194 is a continuation-in-part of application No. 11/252,880, filed on Oct. 19, 2005, now abandoned, which is a continuation-in-part of application No. 11/059,526, filed on Feb. 17, 2005, now abandoned, said application No. 11/454,156 is a continuation-in-part of application No. 11/252,880, filed on Oct. 19, 2005, now abandoned, which is a continuation-in-part of application No. 11/059,526, filed on Feb. 17, 2005, now abandoned, said application No. 11/625,604 is a continuation-in-part of application No. 11/356,301, filed on Feb. 17, 2006, which is a continuation-in-part of application No. 11/252,879, filed on Oct. 19, 2005, and a continuation-in-part of application No. 11/252,880, filed on Oct. 19, 2005, now abandoned, which is a continuation-in-part of application No. 11/059,526, filed on Feb. 17, 2005, now abandoned, said application No. 11/625,604 is a continuation-in-part of application No. 11/356,301, filed on Feb. 17, 2006, which is a continuation-in-part of application No. 11/252,879, filed on Oct. 19, 2005, and a continuation-in-part of application No. 11/252,880, filed on Oct. 19, 2005, now abandoned, and a continuation-in-part of application No. 11/059,526, filed on Feb. 17, 2005, now abandoned, said application No. 11/625,604 is a continuation-in-part of application No. 11/356,301, filed on Feb. 17, 2006, which is a continuation-in-part of application No. 11/252,879, filed on Oct. 19, 2005, and a continuation-in-part of application No. 11/252,880, filed on Oct. 19, 2005, now abandoned, which is a continuation-in-part of application No. 11/059,526, filed on Feb. 17, 2005, now abandoned, said application No. 11/625,604 is a continuation-in-part of application No. 11/356,296, filed on Feb. 17, 2006, now Pat. No. 7,927,354, which is a continuation-in-part of application No. 11/252,879, filed on Oct. 19, 2005, and a continuation-in-part of application No. 11/252,880, filed on Oct. 19, 2005, now abandoned, which is a continuation-in-part of application No. 11/059,526, filed on Feb. 17, 2005, now abandoned, said application No. 11/625,604 is a continuation-in-part of application No. 11/252,879, filed on Oct. 19, 2005, which is a continuation-in-part of application No. 11/059,526, filed on Feb. 17, 2005, now abandoned, said application No. 11/625,604 is a continuation-in-part of application No. 11/059,526, filed on Feb. 17, 2005, now abandoned, and a continuation-in-part of application No. PCT/US2006/005580, filed on Feb. 17, 2006, and a continuation-in-part of application No. 11/356,294, filed on Feb. 17, 2006, now abandoned, which is a continuation-in-part of application No. 11/252,879, filed on Oct. 19, 2005, which is a continuation-in-part of application No. 11/059,526, filed on Feb. 17, 2005, now abandoned, said application No. 11/252,880 is a continuation-in-part of application No. 11/059,526, filed on Feb. 17, 2005, now abandoned.

(60) Provisional application No. 60/869,038, filed on Dec. 7, 2006, provisional application No. 60/695,836, filed on Jul. 1, 2005.

(56) References Cited

U.S. PATENT DOCUMENTS

| | | |
|---|---|---|
| 3,397,699 A | 8/1968 | Kohl |
| 3,648,691 A | 3/1972 | Lumb et al. |
| 4,011,602 A | 3/1977 | Rybicki et al. |
| 4,257,409 A | 3/1981 | Bacal et al. |
| 4,327,736 A | 5/1982 | Inoue |
| 4,554,914 A | 11/1985 | Kapp et al. |
| 4,573,454 A | 3/1986 | Hoffman |
| 4,604,995 A | 8/1986 | Stephens et al. |
| 4,686,970 A | 8/1987 | Dove et al. |
| 4,721,103 A | 1/1988 | Freedland |
| 4,827,918 A | 5/1989 | Olerud |
| 5,011,484 A | 4/1991 | Breard |
| 5,047,055 A | 9/1991 | Bao et al. |
| 5,092,866 A | 3/1992 | Breard et al. |
| 5,201,734 A | 4/1993 | Cozad et al. |
| 5,306,275 A | 4/1994 | Bryan |
| 5,316,422 A | 5/1994 | Coffman |
| 5,360,430 A | 11/1994 | Lin |
| 5,366,455 A | 11/1994 | Dove |
| 5,415,661 A | 5/1995 | Holmes |
| 5,437,672 A | 8/1995 | Alleyne |
| 5,454,812 A | 10/1995 | Lin |
| 5,496,318 A | 3/1996 | Howland et al. |
| 5,609,634 A | 3/1997 | Voydeville |
| 5,628,756 A | 5/1997 | Barker, Jr. et al. |
| 5,645,599 A | 7/1997 | Samani |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,132,464 A | 10/2000 | Martin |
| 6,214,037 B1 | 4/2001 | Mitchell et al. |
| 6,293,949 B1 | 9/2001 | Justis et al. |
| 6,352,537 B1 | 3/2002 | Strnad |
| 6,364,883 B1 | 4/2002 | Santilli |
| 6,402,750 B1 | 6/2002 | Atkinson et al. |
| 6,419,703 B1 | 7/2002 | Fallin et al. |
| 6,440,169 B1 | 8/2002 | Elberg et al. |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,626,944 B1 | 9/2003 | Taylor |
| 6,645,207 B2 | 11/2003 | Dixon et al. |
| 6,669,729 B2 | 12/2003 | Chin |
| 6,695,842 B2 | 2/2004 | Zucherman et al. |
| 6,699,246 B2 | 3/2004 | Zucherman et al. |
| 6,709,435 B2 | 3/2004 | Lin |

| | | |
|---|---|---|
| 6,723,126 B1 | 4/2004 | Berry |
| 6,733,534 B2 | 5/2004 | Sherman |
| 6,761,720 B1 | 7/2004 | Senegas |
| 6,835,205 B2 | 12/2004 | Atkinson et al. |
| 6,902,580 B2 | 6/2005 | Fallin et al. |
| 6,946,000 B2 | 9/2005 | Senegas et al. |
| 7,041,136 B2 | 5/2006 | Goble et al. |
| 7,048,736 B2 | 5/2006 | Robinson et al. |
| 7,087,083 B2 | 8/2006 | Pasquet et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,604,652 B2 | 10/2009 | Arnin et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,901,430 B2 | 3/2011 | Matsuura et al. |
| 2001/0016743 A1 | 8/2001 | Zucherman et al. |
| 2002/0143331 A1 | 10/2002 | Zucherman et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0133280 A1 | 7/2004 | Trieu |
| 2004/0199255 A1 | 10/2004 | Mathieu et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0267579 A1 | 12/2005 | Reiley et al. |
| 2005/0288672 A1 | 12/2005 | Ferree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1* | 4/2006 | Kim ............... 623/17.11 |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1 | 6/2006 | Taylor |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0043362 A1 | 2/2007 | Malandain et al. |
| 2007/0043363 A1 | 2/2007 | Malandain et al. |
| 2007/0100340 A1 | 5/2007 | Lange et al. |
| 2007/0123861 A1 | 5/2007 | Dewey et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0195152 A1 | 8/2008 | Altarac et al. |
| 2008/0215094 A1 | 9/2008 | Taylor |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0240283 A1 | 9/2009 | Carls et al. |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003-079649 | 3/2003 |
| SU | 988281 | 1/1983 |
| SU | 1484348 A1 | 6/1989 |

| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | 2004084743 A1 | 10/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertebrale, Alternative à L'arthrodèse dans le Traitement des Instabilités Degeneratives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation á un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," Spine, 1991, pp. S298-S301, vol. 16, No. 6, Supplement.

Zucherman et al., "Clinical Efficacy of Spinal Instrumentation in Lumbar Degenerative Disc Disease," Spine, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "DIAM Device For Low Back Pain in Degenerative Disc Disease 24 Months Follow-up," Advances in Minimally Invasive Surgery and Therapy For Spine And Nerves, Alexandre et al., eds., 2011, pp. 177-182, Spinger-Verlat/Wien.

Phillips et al., "Biomechanics of Posterior Dynamic Stabilizing Device (DIAM) After Facetectomy and Discectomy," The Spine Journal, 2006, vol. 6, pp. 714-722.

Taylor et al., "Device For Intervertebral Assisted ion: Technique and Initial Results," Neurosurg. Focus, Jan. 2007, vol. 22, No. 1, pp. 1-6.

Wilke et al., "Biomechanical Effect of Different Lumbar Interspinous Implants on Flexibility and Intradiscal Pressure," Eur. Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

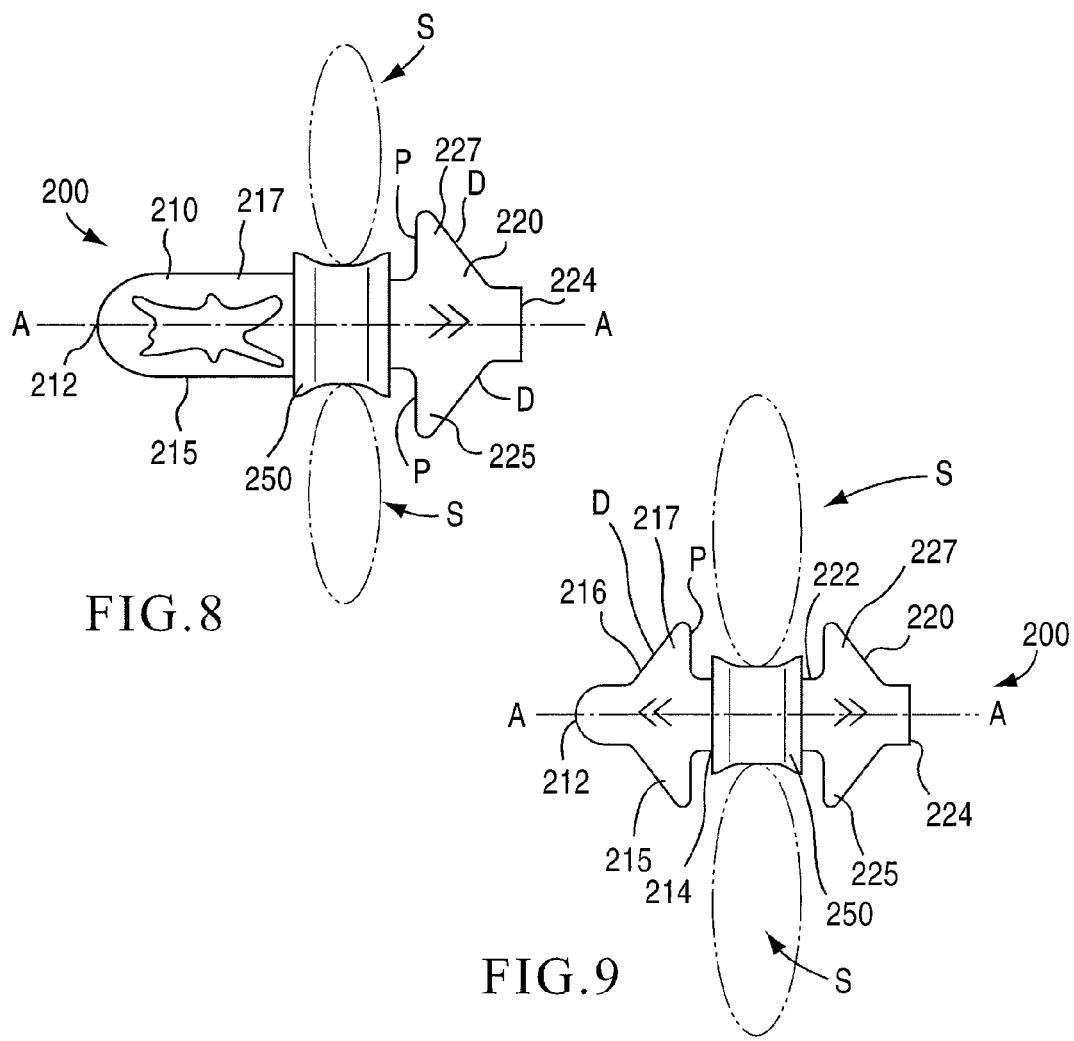
FIG.8
FIG.9
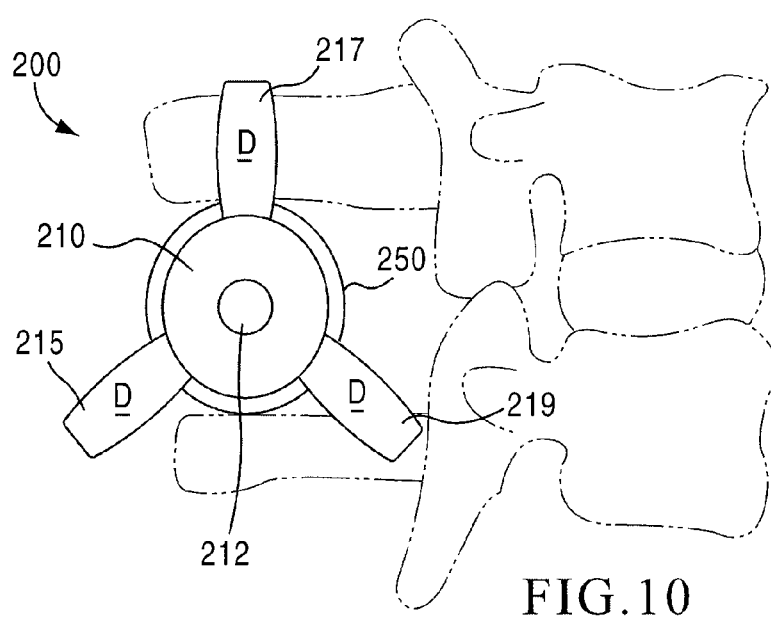
FIG.10

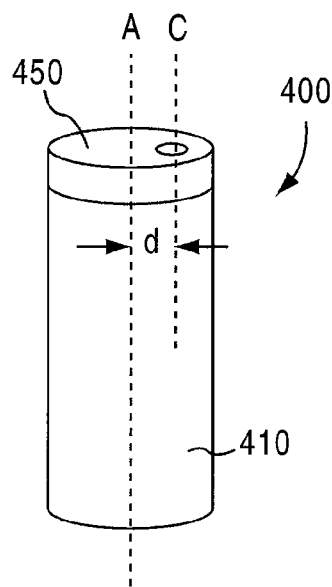
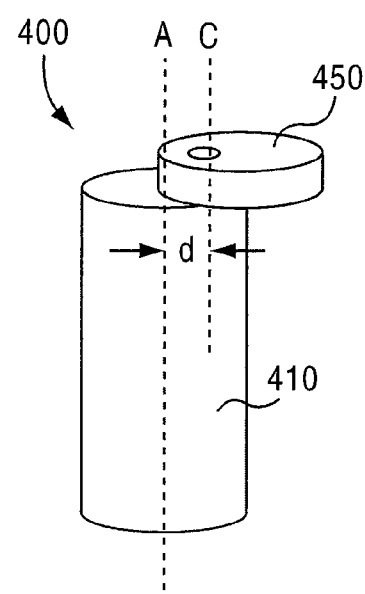
FIG.18    FIG.19
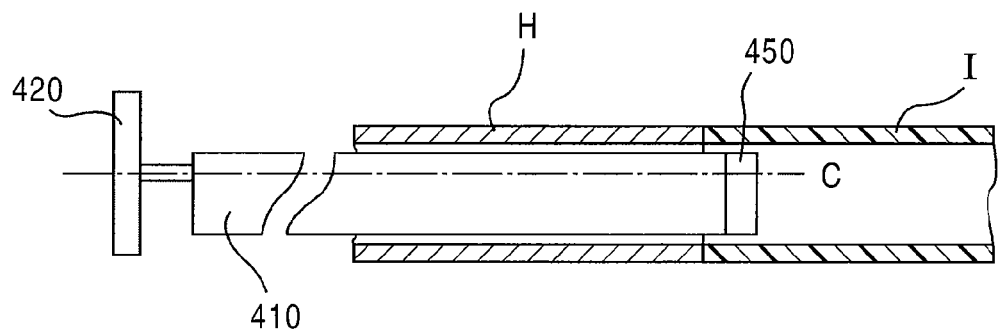
FIG.20
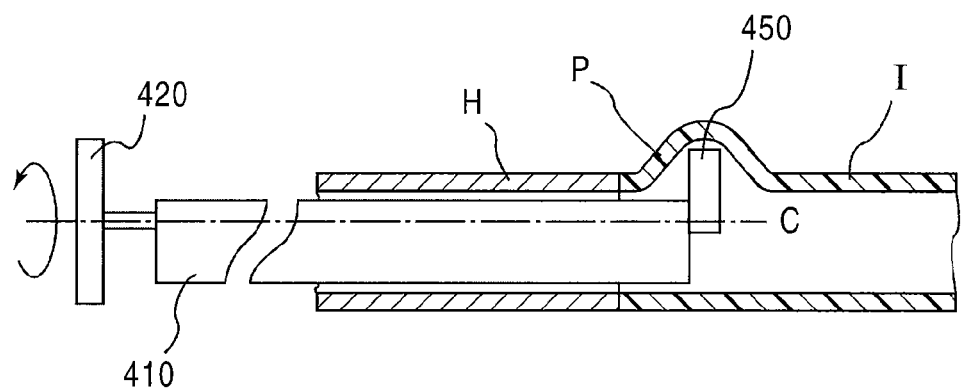
FIG.21

FIG.49A
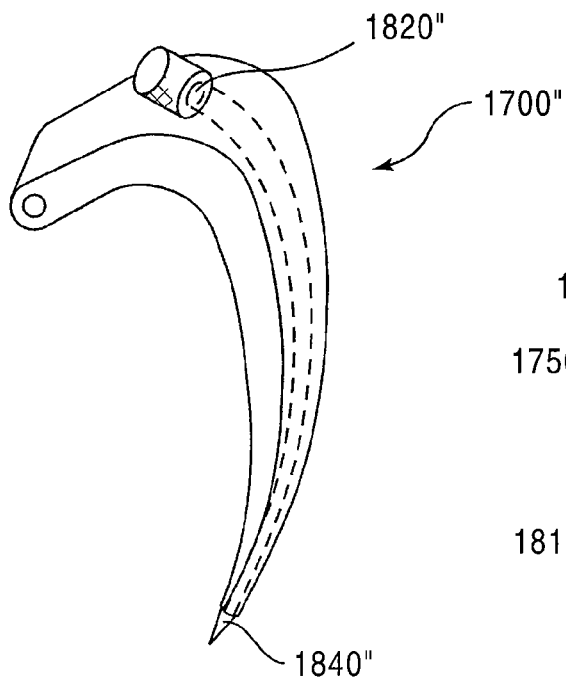
FIG.49B
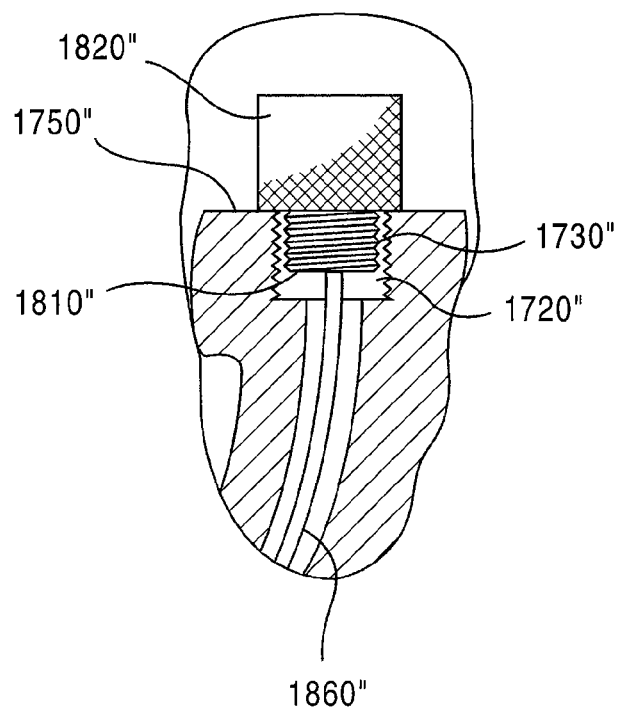
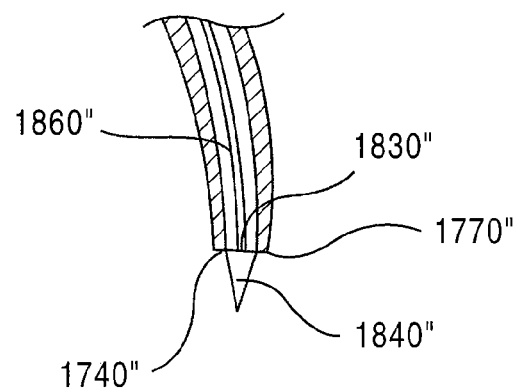
FIG.49C

PERCUTANEOUS SPINAL IMPLANTS AND METHODS

CROSS-REFERENCE TO RELATED APPLICATIONS

This application is a continuation of U.S. patent application Ser. No. 11/625,604, entitled "Percutaneous Spinal Implants and Methods," filed Jan. 22, 2007, which is a continuation-in-part of each of U.S. patent application Ser. Nos. 11/454,153, 11/454,156 and 11/454,194, each entitled "Percutaneous Spinal Implants and Methods," and filed Jun. 16, 2006, each of which is a continuation-in-part of International Patent Application No. PCT/US2006/005580, entitled "Percutaneous Spinal Implants and Methods," filed Feb. 17, 2006. Each of U.S. patent application Ser. Nos. 11/454,153, 11/454, 156 and 11/454,194 is also a continuation-in-part of U.S. patent application Ser. No. 11/059,526, entitled "Apparatus and Method for Treatment of Spinal Conditions," filed Feb. 17, 2005 now abandoned. Each of U.S. patent application Ser. Nos. 11/454,153, 11/454,156 and 11/454,194 is also a continuation-in-part of U.S. patent application Ser. No. 11/252, 879, entitled "Percutaneous Spinal Implants and Methods, "filed Oct. 19, 2005, which is a continuation-in-part of U.S. patent application Ser. No. 11/059,526, entitled "Apparatus and Method for Treatment of Spinal Conditions,"filed Feb. 17, 2005, now abandoned and which claims the benefit of U.S. Provisional Application Ser. No. 60/695,836 entitled "Percutaneous Spinal Implants and Methods," filed Jul. 1, 2005. Each of U.S. patent application Ser. Nos. 11/454,153, 11/454,156 and 11/454,194 is also a continuation-in-part of U.S. patent application Ser. No. 11/252,880, entitled "Percutaneous Spinal Implants and Methods," filed Oct. 19, 2005, now abandoned which is a continuation-in-part of U.S. patent application Ser. No. 11/059,526, entitled "Apparatus and Method for Treatment of Spinal Conditions," filed Feb. 17, 2005, now abandoned and which claims the benefit of U.S. Provisional Application Ser. No. 60/695,836 entitled "Percutaneous Spinal Implants and Methods," filed Jul. 1, 2005. Each of the above-identified applications is incorporated herein by reference in its entirety.

U.S. patent application Ser. No. 11/625,604 is also a continuation-in-part of each of U.S. patent application Ser. Nos. 11/356,301, 11/356,302, 11/356,296, 11/356,295 and 11/356,294, each entitled "Percutaneous Spinal Implants and Methods," filed Feb. 17, 2006. Each of U.S. patent application Ser. Nos. 11/356,301, 11/356,302, 11/356,296 now U.S. Pat. No. 7,927,354, 11/356,295 and 11/356,294 is a continuation-in-part of U.S. patent application Ser. Nos. 11/252,879 and 11/252,880, each entitled "Percutaneous Spinal Implants and Methods," and filed Oct. 19, 2005, each of which is a continuation-in-part of U.S. patent application Ser. No. 11/059, 526, entitled "Apparatus and Method for Treatment of Spinal Conditions," filed Feb. 17, 2005, now abandoned and each of which claims the benefit of U.S. Provisional Application Ser. No. 60/695,836 entitled "Percutaneous Spinal Implants and Methods," filed Jul. 1, 2005. Each of the above-identified applications is incorporated herein by reference in its entirety.

U.S. patent application Ser. No. 11/625,604 is also a continuation-in-part of International Patent Application No. PCT/US2006/005580, entitled "Percutaneous Spinal Implants and Methods," filed Feb. 17, 2006; and is a continuation-in-part of U.S. patent application Ser. No. 11/059,526, entitled "Apparatus and Method for Treatment of Spinal Conditions," filed Feb. 17, 2005. Each of the above-identified applications is incorporated herein by reference in its entirety.

U.S. patent application Ser. No. 11/625,604 is also and is a continuation-in-part of each of U.S. patent application Ser. Nos. 11/252,879 and 11/252,880, each entitled "Percutaneous Spinal Implants and Methods," filed Oct. 19, 2005, each of which is a continuation-in-part of U.S. patent application Ser. No. 11/059,526, entitled "Apparatus and Method for Treatment of Spinal Conditions," filed Feb. 17, 2005, and each of which claims the benefit of U.S. Provisional Application Ser. No. 60/695,836 entitled "Percutaneous Spinal Implants and Methods," filed Jul. 1, 2005. Each of the above-identified applications is incorporated herein by reference in its entirety.

U.S. patent application Ser. No. 11/625,604 also claims the benefit of U.S. Provisional Application Ser. No. 60/869,038, entitled "Percutaneous Spinal Implants and Methods," filed on Dec. 7, 2006, which is incorporated herein by reference in its entirety.

This application is related to U.S. patent application Ser. Nos. 11/927,824, 11/927,830, and 11/927,831 each entitled "Percutaneous Spinal Implants and Methods," filed on Oct. 30, 2007, and incorporated herein by reference in their entirety.

BACKGROUND

The invention relates generally to the treatment of spinal conditions, and more particularly, to the treatment of spinal compression using percutaneous spinal implants for implantation between adjacent spinous processes.

A back condition that impacts many individuals is spinal stenosis. Spinal stenosis is a progressive narrowing of the spinal canal that causes compression of the spinal cord. Each vertebra in the spinal column has an opening that extends through it. The openings are aligned vertically to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. This may be due to bending forward creates more vertebral space, which may temporarily relieve nerve compression. Because spinal stenosis is a progressive disease, the source of pressure may have to be surgically corrected (decompressive laminectomy) as the patient has increasing pain. The surgical procedure can remove bone and other tissues that have impinged upon the spinal canal or put pressure on the spinal cord. Two adjacent vertebrae may also be fused during the surgical procedure to prevent an area of instability, improper alignment or slippage, such as that caused by spondylolisthesis. Surgical decompression can relieve pressure on the spinal cord or spinal nerve by widening the spinal canal to create more space. This procedure requires that the patient be given a general anesthesia as an incision is made in the patient to access the spine to remove the areas that are contributing to the pressure. This procedure, however, may result in blood loss and an increased chance of significant complications, and usually results in an extended hospital stay.

Minimally-invasive procedures have been developed to provide access to the space between adjacent spinous processes such that major surgery is not required. Such known procedures, however, may not be suitable in conditions where the spinous processes are severely compressed. Moreover, such procedures typically involve large or multiple incisions.

Thus, a need exists for improvements in the treatment of spinal conditions such as spinal stenosis.

SUMMARY OF THE INVENTION

Medical devices and related methods for the treatment of spinal conditions are described herein. In some embodiments, a method includes placement of two or more support members (e.g., spacers, inter-spinous implants, expandable devices, extension limiting devices or the like) at two or more inter-spinous spaces through a single incision. Tools configured to facilitate placement of two or more support members at different locations along the length of the patient's spine through a single incision are also described herein. In one embodiment, the tools are configured with one or more curvatures such that support members that are introduced through the same incision can be directed towards different inter-spinous locations along the length of a patient's spine.

In some embodiments, a method includes positioning a medical device within a body between adjacent spinous processes, moving the medical device from a collapsed configuration to an expanded configuration within the body using an actuator removably coupled to the medical device, and removing the actuator from the body while the medical device remains between the adjacent spinous processes.

BRIEF DESCRIPTION OF THE DRAWINGS

FIG. 8 is a posterior view of a medical device according to an embodiment of the invention, a portion of which is in a second configuration.

FIG. 9 is a posterior view of the medical device illustrated in FIG. 7 fully deployed in the second configuration.

FIG. 10 is a front plan view of the medical device illustrated in FIG. 7 in the second configuration.

FIG. 18 is a perspective view of an implant expansion device according to an embodiment of the invention in a first position.

FIG. 19 is a perspective view of the implant expansion device illustrated in FIG. 18 in a second position.

FIG. 20 is a partial cross-sectional illustration of the implant expansion device as illustrated in FIG. 18 inserted in a spinal implant.

FIG. 21 is a partial cross-sectional illustration of the implant expansion device as illustrated in FIG. 19 inserted in a spinal implant.

FIG. 49a is a perspective view of an apparatus according to an embodiment of the invention.

FIG. 49b is an exploded view of a portion of the apparatus illustrated in FIG. 49a.

FIG. 49c is an exploded view of a portion of the apparatus illustrated in FIG. 49a.

FIG. 119 is a cross-sectional view of the implant of FIG. 118 taken along line 119-119.

FIG. 120 is a side perspective view of the implant of FIG. 118 shown in an expanded configuration.

FIG. 121 is a rear perspective view of the implant of FIG. 118 shown in a collapsed configuration.

FIG. 122 is cross-sectional view of the implant of FIG. 118 shown in a collapsed configuration taken along line 122-122.

FIG. 123 is a rear perspective view of an implant according to an embodiment of the invention shown in a collapsed configuration.

FIG. 124 is a cross-sectional view of the implant of FIG. 123 shown in a collapsed configuration.

FIG. 125 is a perspective view of the implant of FIG. 123 in a collapsed configuration disposed on an expansion tool according to an embodiment of the invention.

FIG. 126 is a perspective view of the implant and the expansion tool of FIG. 125 taken along region 126.

FIG. 127 is a side cross-sectional view of the implant and the expansion tool of FIG. 125.

FIG. 128 is a side cross-sectional view of the implant and the expansion tool as shown in FIG. 127 taken along region 128.

FIG. 129 is a perspective view of the implant of FIG. 123 in an expanded configuration disposed on an expansion tool according to an embodiment of the invention.

FIG. 130 is a perspective view of the implant and the expansion tool of FIG. 129 taken along region 130.

Figure 129:
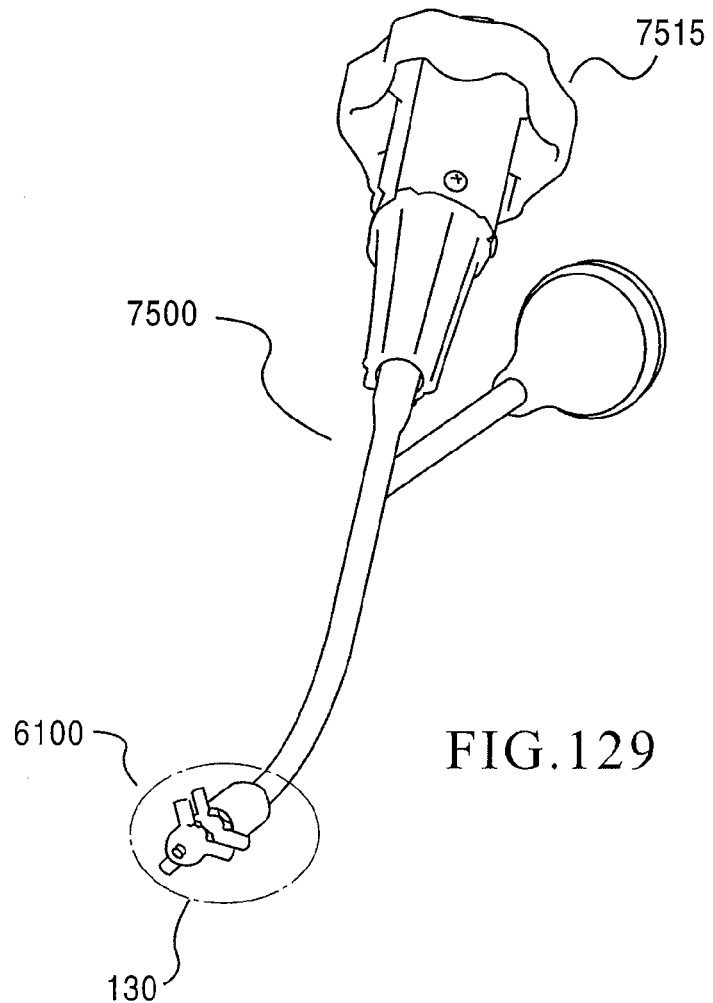
Figure 131:
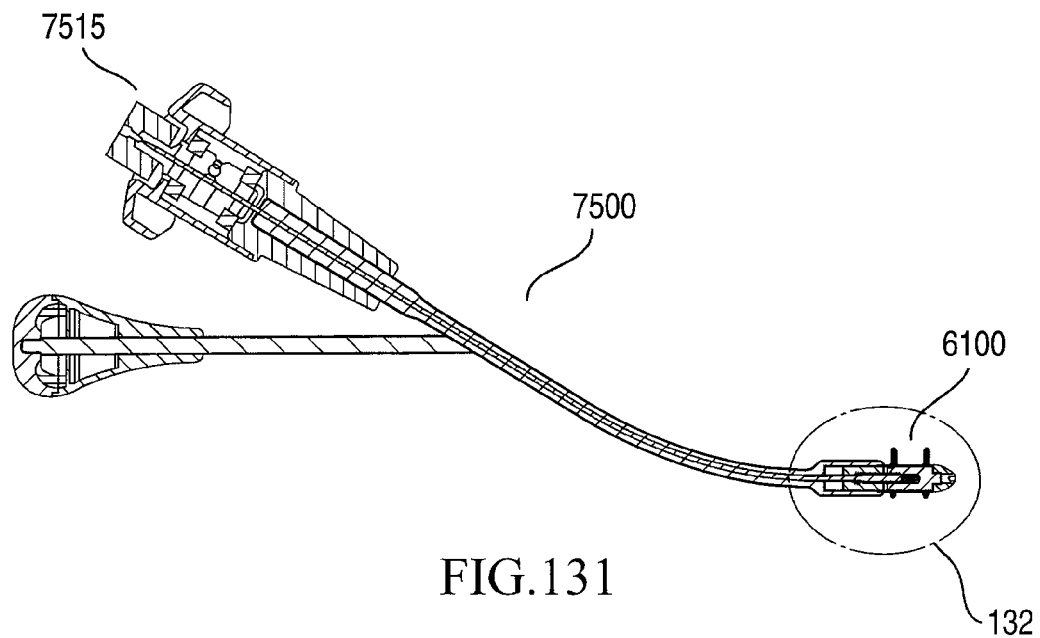

FIG. 131 is a side cross-sectional view of the implant and the expansion tool of FIG. 129.

Figure 132:
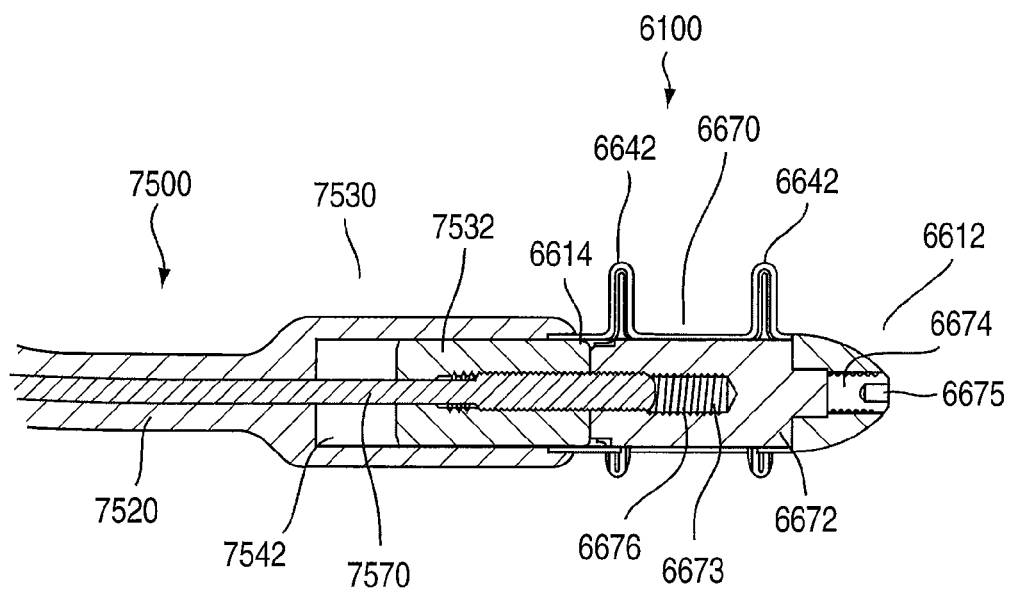

FIG. 132 is a side cross-sectional view of the implant and the expansion tool as shown in FIG. 131 taken along region 132.

Figure 133:
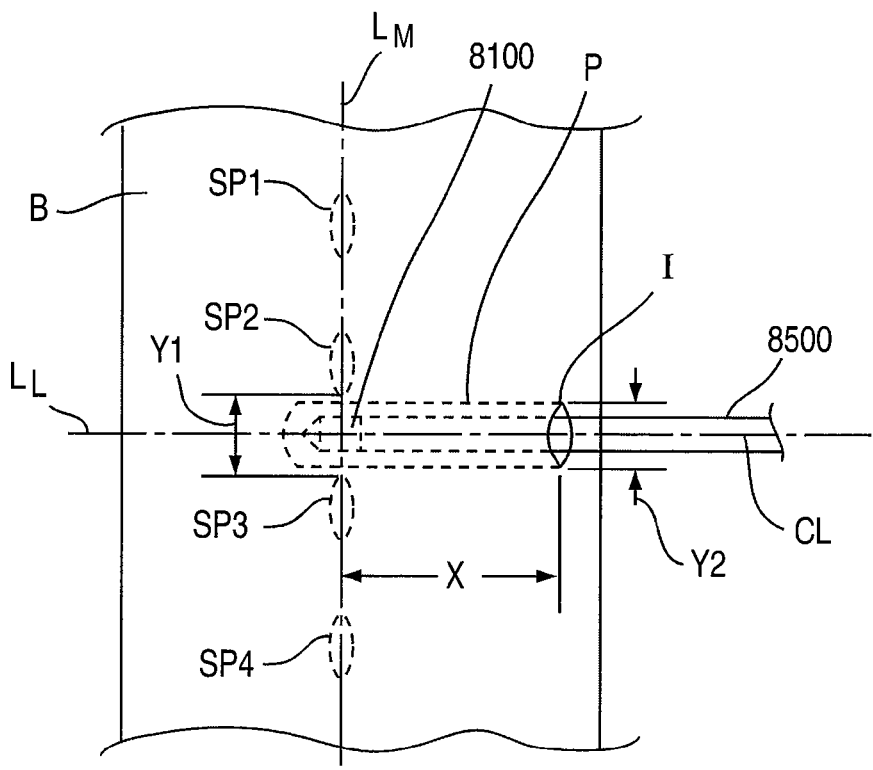

FIG. 133 is a posterior view of a portion of a medical device according to an embodiment of the invention disposed within a body between a pair of spinous processes.

Figure 134:
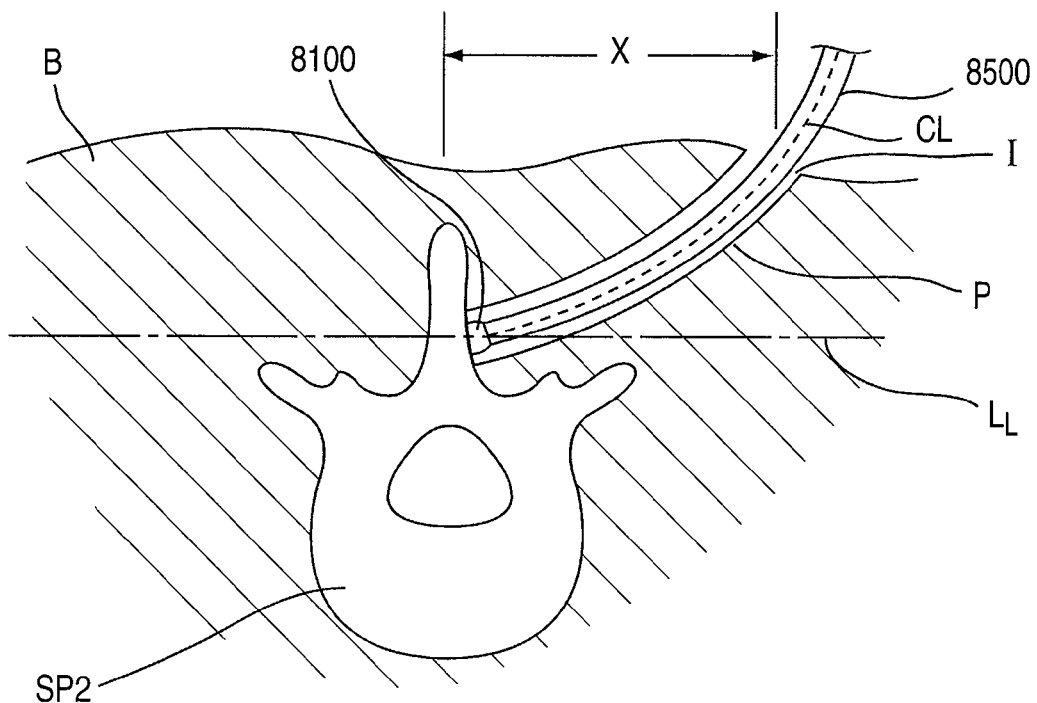

FIG. 134 is a side view of the portion of medical device shown in FIG. 133 taken along the lateral axis $L_L$.

Figure 135:
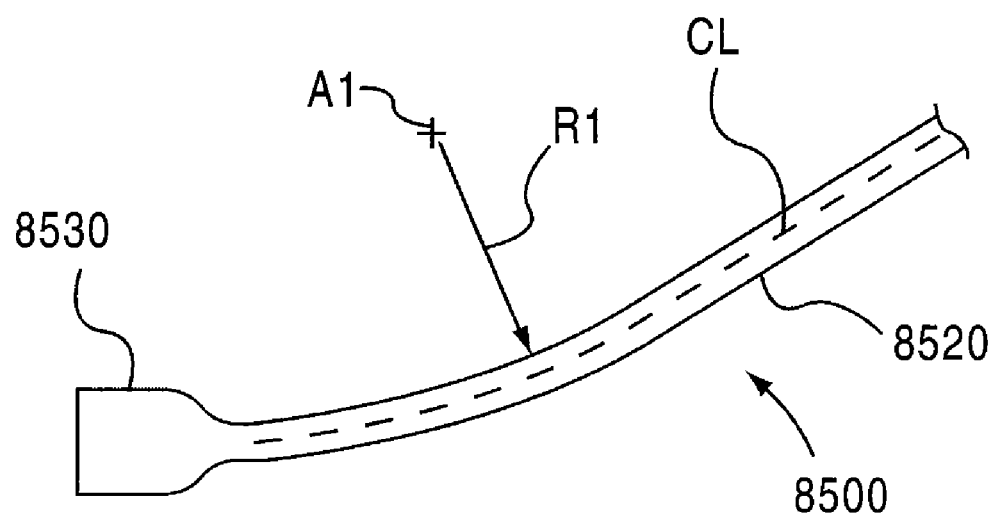
Figure 136:
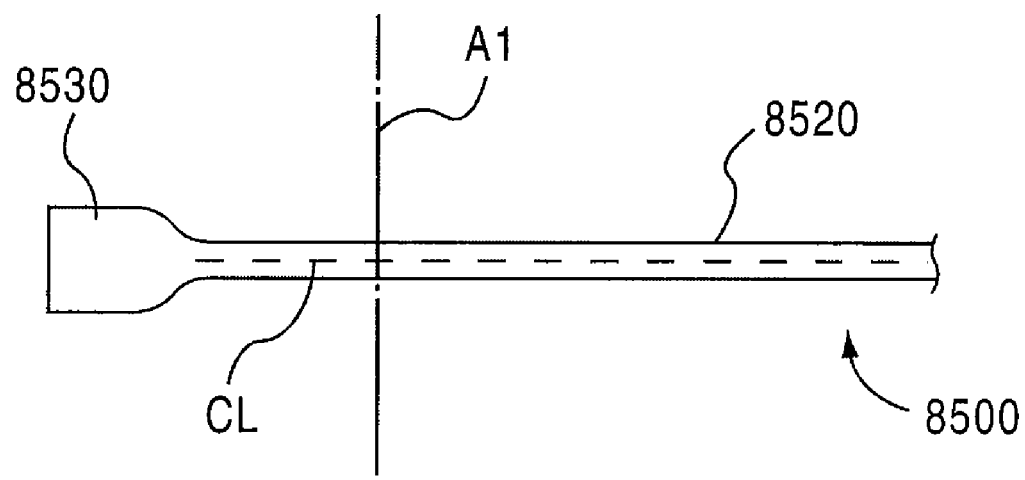

FIGS. 135 and 136 are a side view and a top plan view, respectively, of the portion of medical device shown in FIG. 133.

Figure 137:
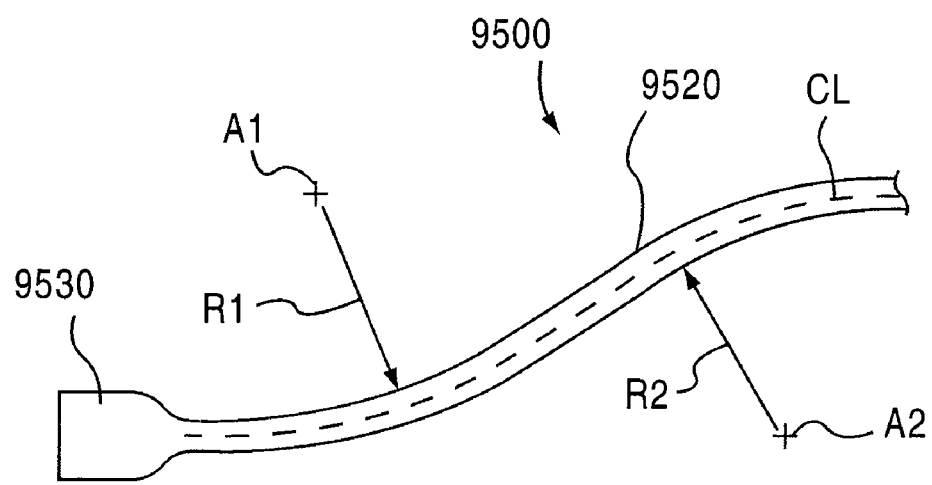
Figure 138:
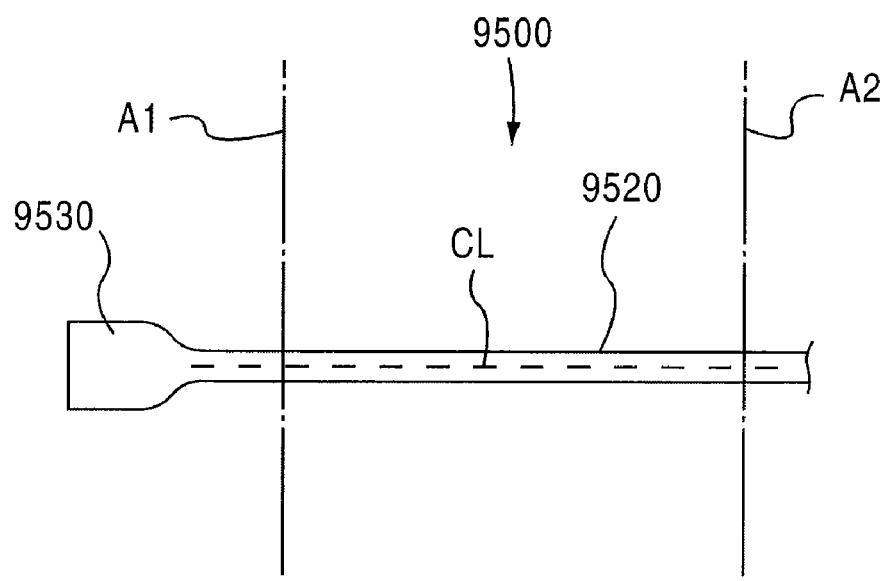

FIGS. 137 and 138 are a side view and a top plan view, respectively, of a portion of a medical device according to an embodiment of the invention.

Figure 139:
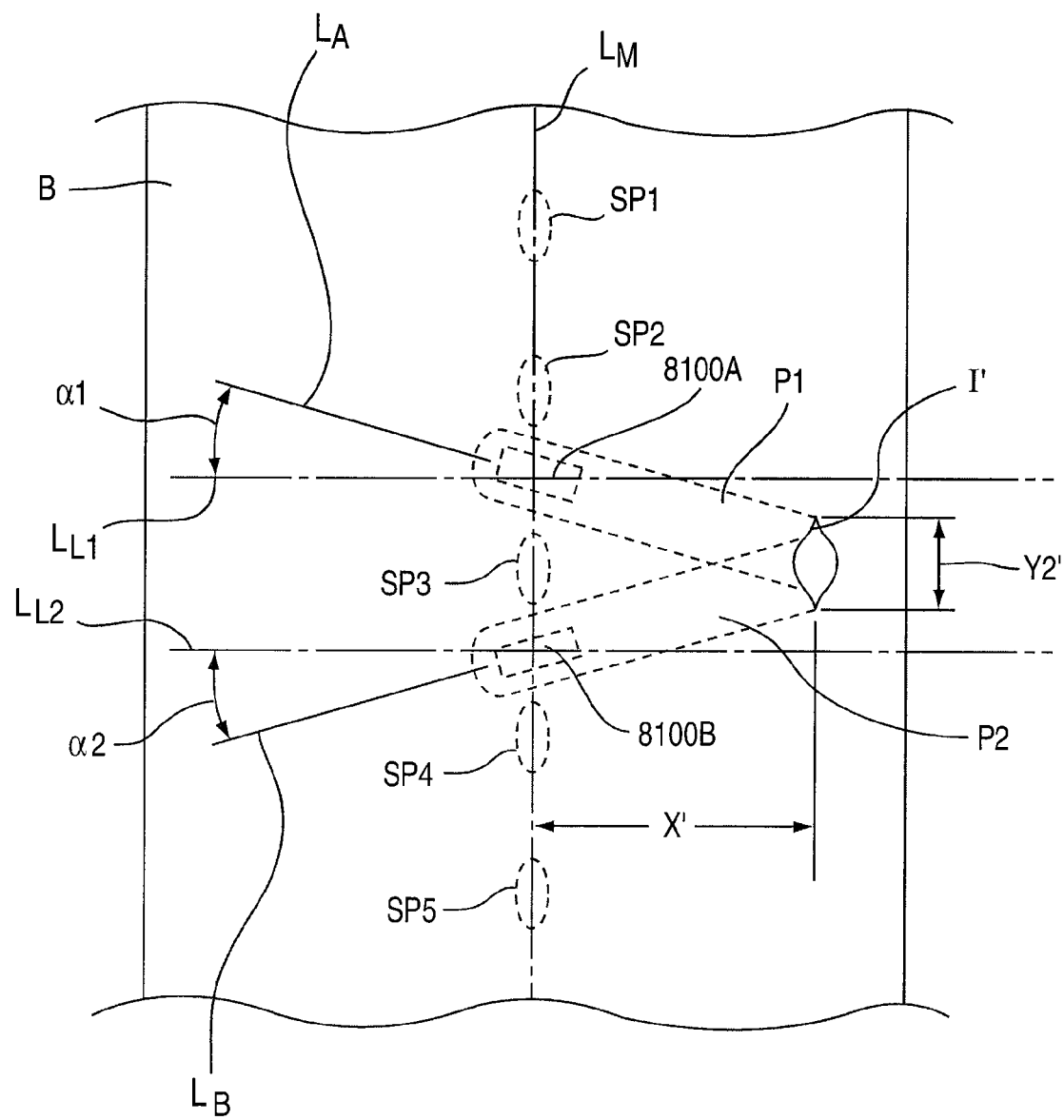

FIG. 139 is a posterior view of a two spinal implants according to an embodiment of the invention disposed within a body, each disposed between a pair of spinous processes.

Figure 140:
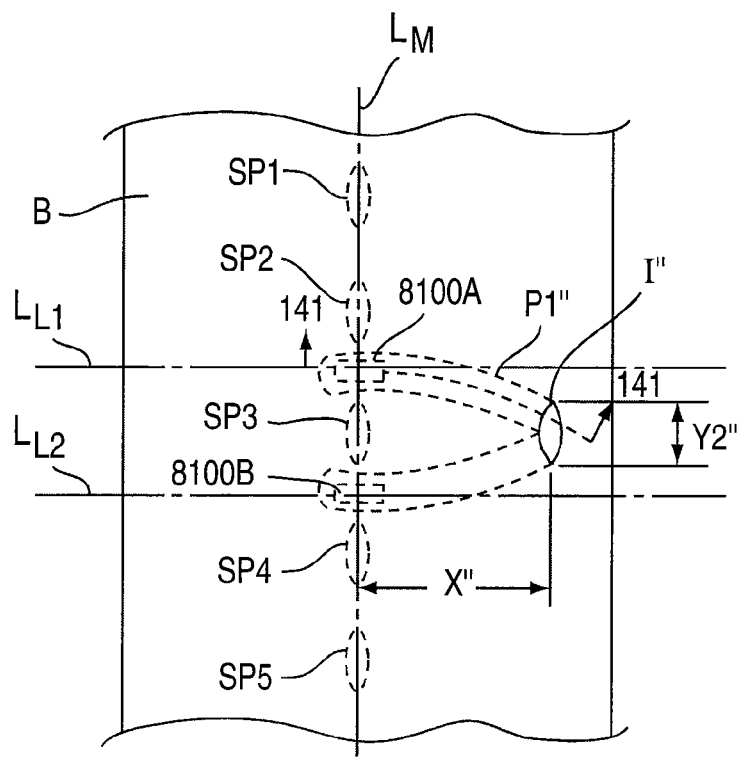

FIG. 140 is a posterior view of a portion of a medical device according to an embodiment of the invention disposed within a body between a pair of spinous processes.

Figure 141:
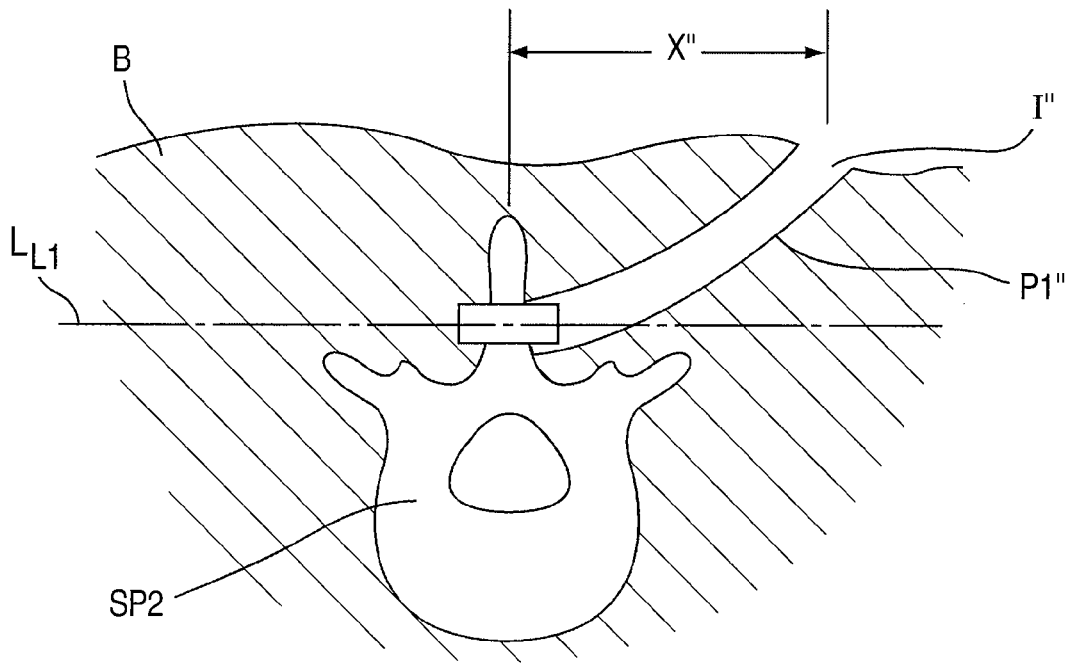

FIG. 141 is a cross-sectional side view of the portion of medical device shown in FIG. 140 taken along the line 141-141.

Figure 142:
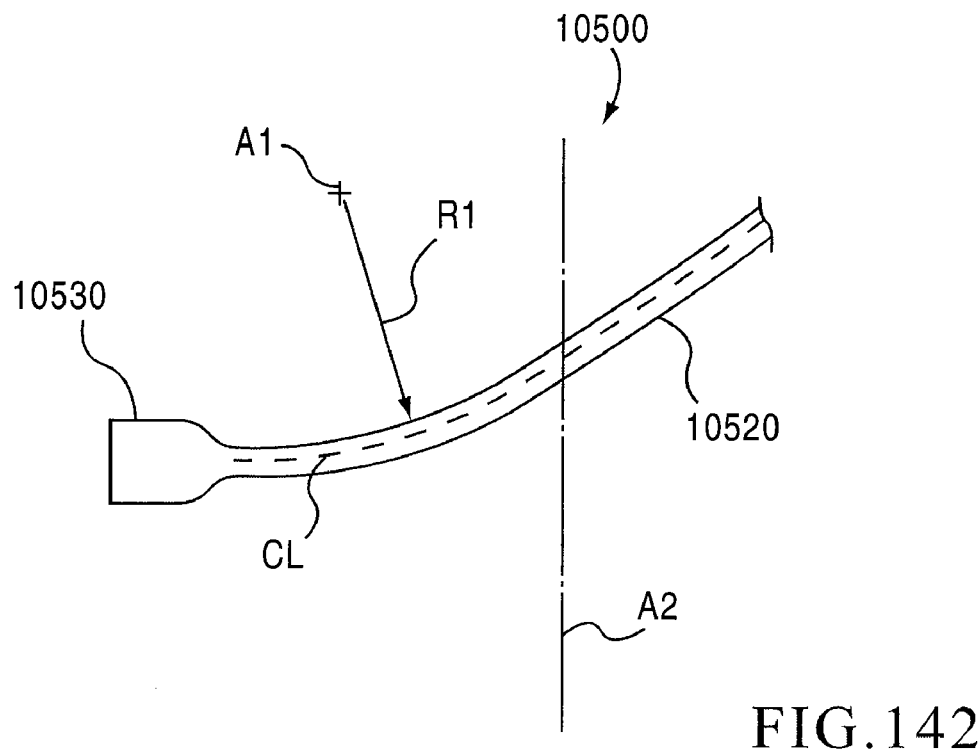
Figure 143:
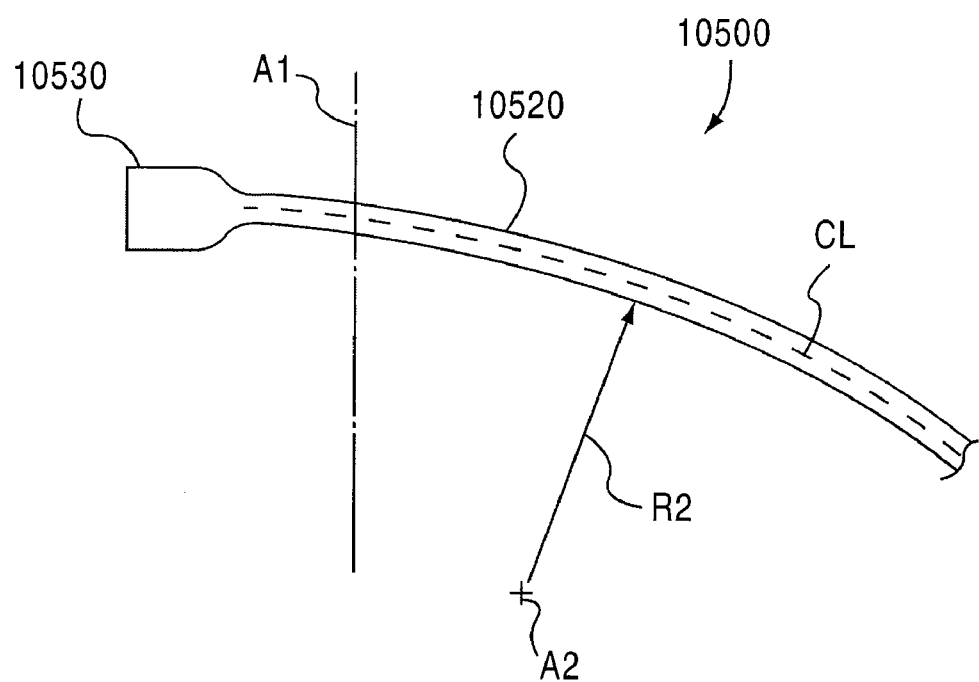

FIGS. 142 and 143 are a side view and a top plan view, respectively, of a portion of a medical device according to an embodiment of the invention.

Figure 144:
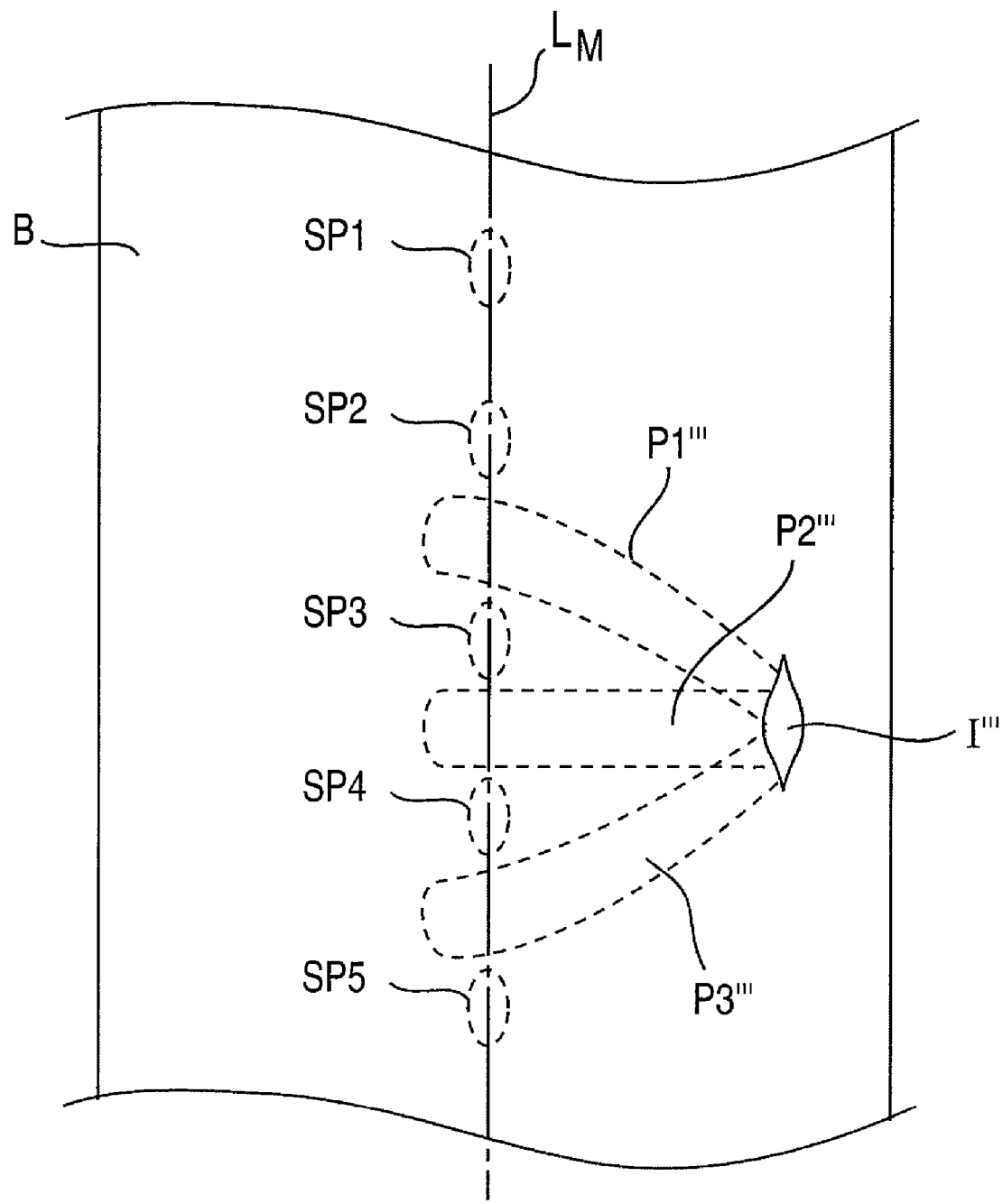

FIG. 144 shows a posterior view of a multi-level insertion operation in which a medical device is disposed within a body according to an embodiment of the invention.

Figure 145:
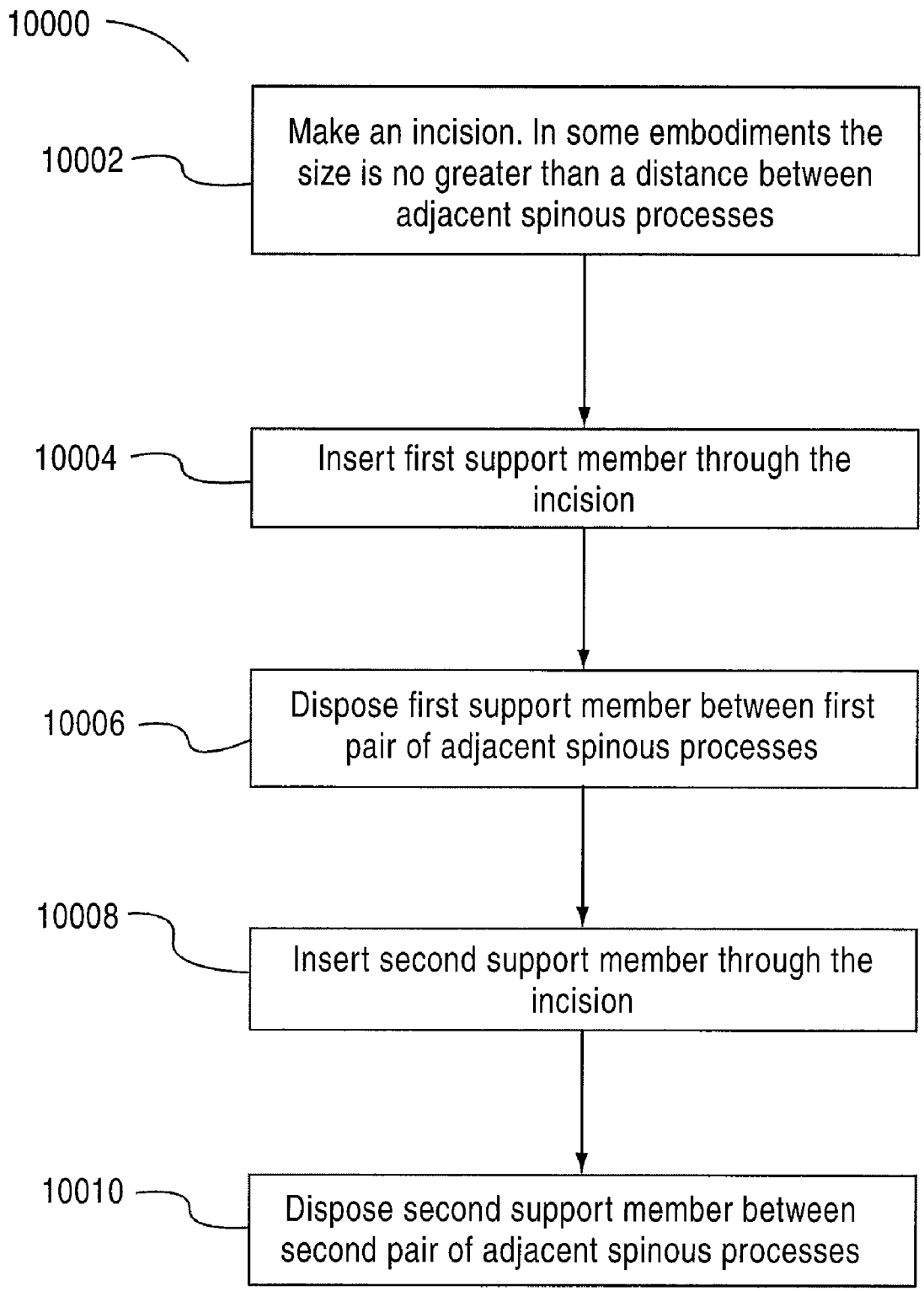

FIG. 145 is a flow chart of a method of inserting a spinal implant according to an embodiment of the invention.

Figure 146:
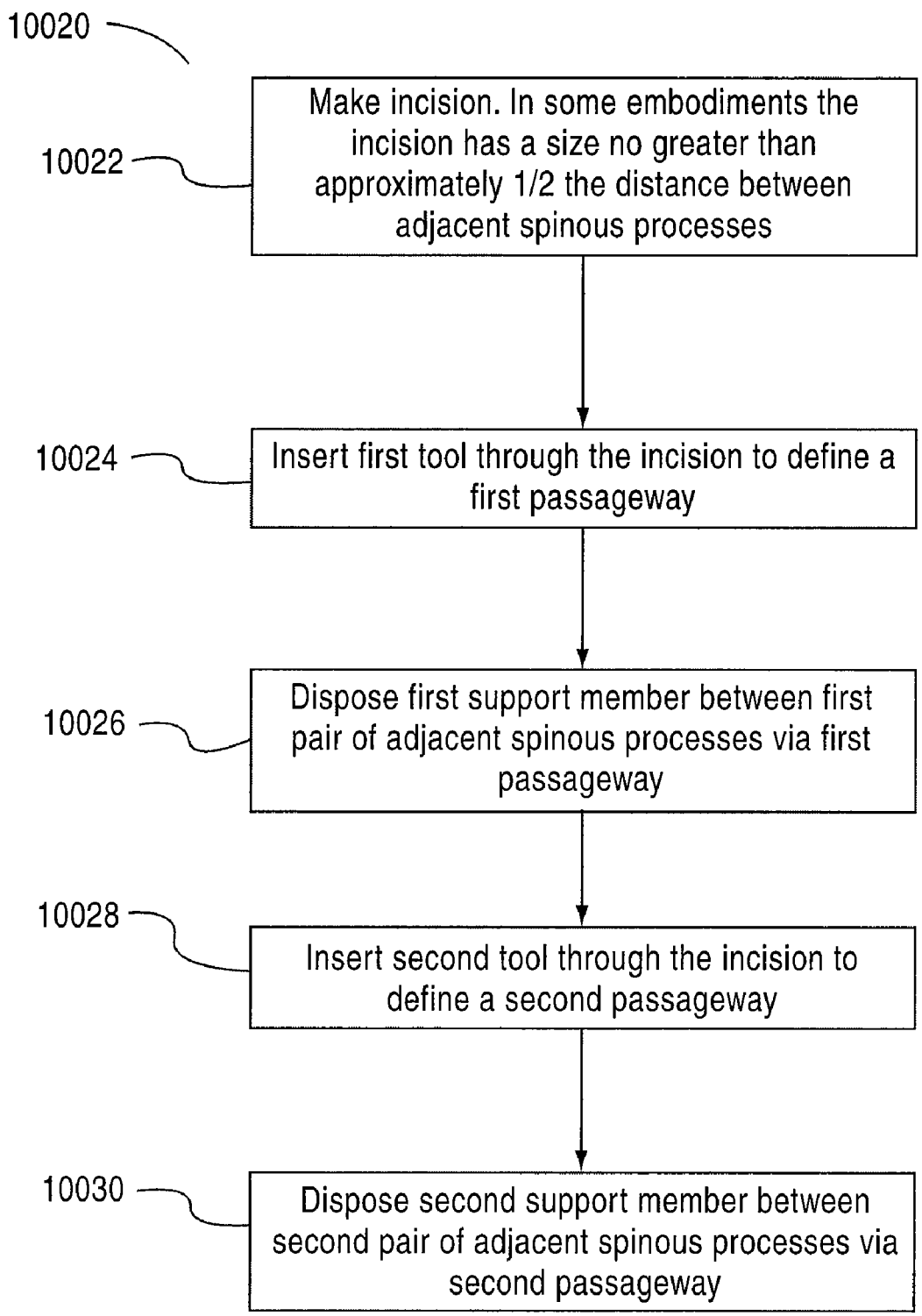

FIG. 146 is a flow chart of a method of inserting a spinal implant according to an embodiment of the invention.

DETAILED DESCRIPTION

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

In some embodiments, a method includes placement of two or more support members (e.g., spacers, inter-spinous implants, expandable devices, extension limiting devices or the like) at two or more inter-spinous spaces through a single incision. Tools configured to facilitate placement of two or more support members at different locations along the length of the patient's spine through a single incision are also described herein. In one embodiment, the tools are configured with one or more curvatures such that support members that are introduced through the same incision can be directed towards different inter-spinous locations along the length of a patient's spine.

In some embodiments, a single incision is made on a patient's back, lateral to the mid-line of the patient's body. In some embodiments, the incision can be at least 3 cm lateral to the mid-line. In other embodiments, the incision can be at least 5 cm lateral to the mid-line. In yet other embodiments, the incision can be positioned 6-8 cm lateral to the mid-line. A curved trocar or tunneling device is inserted into the incision to establish a first path to a first location between two adjacent spinous processes. The distal portion of the trocar may be utilized to create an opening between the two adjacent spinous processes for receiving a support member. A first support member is inserted through the first path and placed at the first location. The first support member may be inserted in a compressed state and then expanded to secure it between the two spinous processes. Preferably, a curved instrument is used to carry the support member through the first path and deploy the support member between the two spinous processes. A trocar, which may be the same trocar or a different trocar used to establish the first path, can then be used to establish a second path from the same incision to a second location, one or two levels below or above the first location. Again, the distal portion of the trocar may be utilized to create an opening at the second location between two adjacent spinous processes for receiving a support member. A second support member is inserted through the second path and placed at the second location. The second support member may be inserted in a compressed state and then expanded to secure it between the two spinous processes. Similar to the placement of the first support member, preferably, a curved instrument is used to carry the second support member through the second path and deploy the support member at the second location between two adjacent spinous processes. Optionally, a third path may be established through the same incision to place a third support member at a third location along the length of the patient's spine. Once the support members are implanted, the surgeon can remove the surgical instrument and close the incision.

In some embodiments, a method includes making an incision in a body, the incision having a size no greater than a distance between a pair of adjacent spinous processes. In some embodiments, for example, the incision can have a size no greater than 50 mm. In other embodiments, the incision can have a size no greater than about 30 mm. In yet other embodiments, the incision can have a size no greater than about 15 mm. A first support member is inserted percutaneously through the incision. The first support member is disposed between a first pair of adjacent spinous processes. A second support member is inserted percutaneously through the incision. The second support member is disposed between a second pair of adjacent spinous processes.

In some embodiments, a method includes making an incision in a body, the incision having a size no greater than approximately one half a distance between a first pair of adjacent spinous processes. A first tool is inserted percutaneously through the incision to define a first passageway extending from the incision to a space between the first pair of adjacent spinous processes. A first support member is disposed, via the first passageway, into the space between the first pair of adjacent spinous processes. A second tool is inserted percutaneously through the incision to define a second passageway extending from the incision to a space between a second pair of adjacent spinous processes. A second support member is disposed, via the second passageway, into the space between the second pair of adjacent spinous processes.

In some embodiments, an apparatus includes an elongate member, such as, for example a rigid shaft. The elongate member has a distal end portion configured to releasably engage a spinal implant. A portion of the elongate member is curved such that the elongate member can insert percutaneously through an incision a first spinal implant between a first pair of adjacent spinous processes and insert percutaneously through the incision a second spinal implant between a second pair of adjacent spinous processes. In some embodiments, the incision can be, for example, a lateral incision having a length of 15 mm or less.

In some embodiments, an apparatus includes an elongate member having a distal end portion and a curved portion. The elongate member, which can be, for example a rigid shaft, is configured to insert percutaneously a spinal implant between a pair of adjacent spinous processes. The distal end portion of the elongate member is configured to releasably engage the spinal implant. The curved portion of the elongate member defines a first radius of curvature about a first axis substantially normal to a center line of the elongate member and a second radius of curvature about a second axis substantially normal to the center line of the elongate member. In some embodiments, a portion of the elongate member is disposed between the first axis and the second axis. In some embodiments, the second axis is substantially normal to the first axis.

In some embodiments, a kit includes a spinal implant and an insertion tool. The spinal implant is reconfigurable between an expanded configuration and a collapsed configuration while disposed between a pair of adjacent spinous processes. The insertion tool is configured to be releasably coupled to the spinal implant. The insertion tool is curved to allow the insertion tool to insert percutaneously through a lateral incision the spinal implant within a space between the pair of adjacent spinous processes, the lateral incision being offset from the space between the pair of adjacent spinous processes.

In some embodiments, a kit includes a first spinal implant, a second spinal implant, a first insertion tool and a second insertion tool. The first and second spinal implants are each reconfigurable between an expanded configuration and a collapsed configuration while disposed between adjacent spinous processes. The first and second insertion tools are each configured to be releasably coupled to a spinal implant. The first insertion tool is configured to insert percutaneously through a lateral incision the first spinal implant within a space between a first pair of adjacent spinous processes. The second insertion tool is configured to insert percutaneously through the same lateral incision the second spinal implant within a space between a second pair of adjacent spinous processes. In some embodiments, the incision can have a length of not greater than 15 mm.

Figure 1:
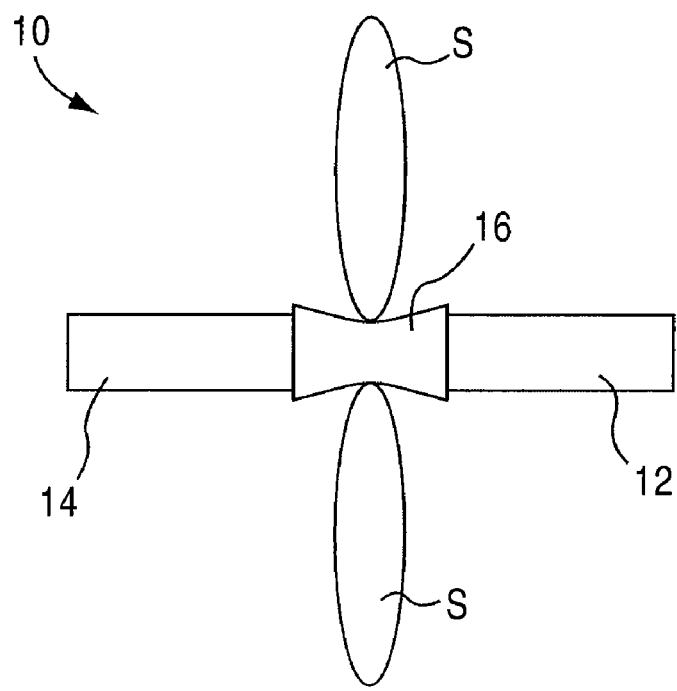
FIG. 1 is a schematic illustration of a posterior view of a medical device according to an embodiment of the invention in a first configuration adjacent two adjacent spinous processes.

FIG. 1 is a schematic illustration of a medical device according to an embodiment of the invention adjacent two adjacent spinous processes. The medical device 10 includes a proximal portion 12, a distal portion 14 and a central portion 16. The medical device 10 has a first configuration in which it can be inserted between adjacent spinous processes S. The central portion 16 is configured to contact the spinous processes S to prevent over-extension/compression of the spinous processes S. In some embodiments, the central portion 16 does not substantially distract the adjacent spinous processes S. In other embodiments, the central portion 16 does not distract the adjacent spinous processes S.

In the first configuration, the proximal portion 12, the distal portion 14 and the central portion 16 are coaxial (i.e., share a common longitudinal axis). In some embodiments, the proximal portion 12, the distal portion 14 and the central portion 16 define a tube having a constant inner diameter. In other embodiments, the proximal portion 12, the distal portion 14 and the central portion 16 define a tube having a constant outer diameter and/or inner diameter.

Figure 2:
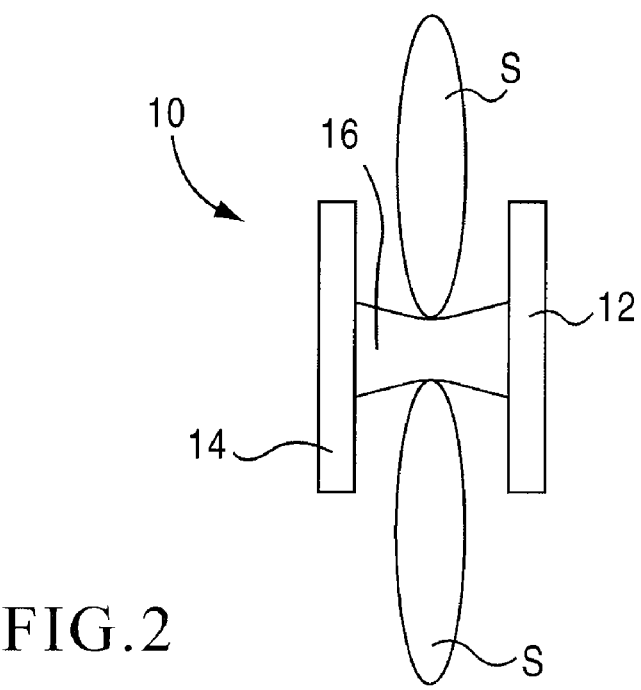
FIG. 2 is a schematic illustration of a posterior view of a medical device according to an embodiment of the invention in a second configuration adjacent two adjacent spinous processes.

The medical device 10 can be moved from the first configuration to a second configuration as illustrated in FIG. 2. In the second configuration, the proximal portion 12 and the distal portion 14 are positioned to limit lateral movement of the device 10 with respect to the spinous processes S. The proximal portion 12 and the distal portion 14 are configured to engage the spinous process (i.e., either directly or through surrounding tissue) in the second configuration. For purposes of clarity, the tissue surrounding the spinous processes S is not illustrated.

In some embodiments, the proximal portion 12, the distal portion 14 and the central portion 16 are monolithically formed. In other embodiments, one or more of the proximal portion 12, the distal portion 14 and the central portion 16 are separate components that can be coupled together to form the medical device 10. For example, the proximal portion 12 and distal portion 14 can be monolithically formed and the central portion can be a separate component that is coupled thereto.

In use, the spinous processes S can be distracted prior to inserting the medical device 10. Distraction of spinous processes is discussed below. When the spinous processes are distracted, a trocar can be used to define an access passage for the medical device 10. In some embodiments, the trocar can be used to define the passage as well as distract the spinous processes S. Once an access passage is defined, the medical device 10 is inserted percutaneously and advanced between the spinous processes, distal end 14 first, until the central portion 16 is located between the spinous processes S. Once the medical device 10 is in place between the spinous processes, the proximal portion 12 and the distal portion 14 are moved to the second configuration, either serially or simultaneously.

In some embodiments, the medical device 10 is inserted percutaneously (i.e., through an opening in the skin) and in a minimally-invasive manner. For example, as discussed in detail herein, the size of portions of the implant is expanded after the implant is inserted between the spinous processes. Once expanded, the size of the expanded portions of the implant is greater than the size of the opening. For example, the size of the opening/incision in the skin may be between 3 millimeters in length and 25 millimeters in length. In some embodiments, the size of the implant in the expanded configuration is between 3 and 25 millimeters.

Figure 3:
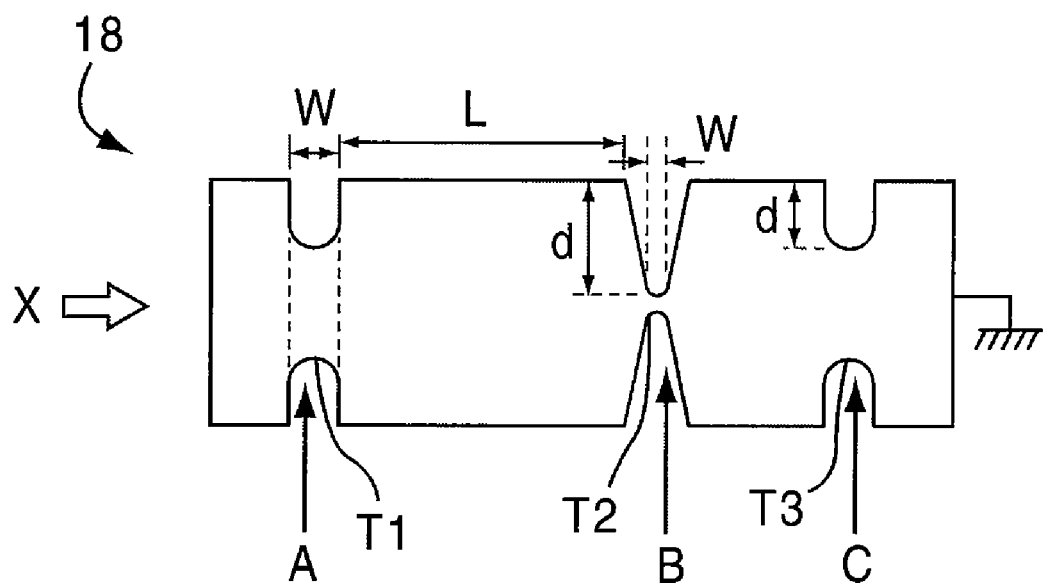
FIG. 3 is a schematic illustration of a deforming element according to an embodiment of the invention in a first configuration.

FIG. 3 is a schematic illustration of a deformable element 18 that is representative of the characteristics of, for example, the distal portion 14 of the medical device 10 in a first configuration. The deformable member 18 includes cutouts A, B, C along its length to define weak points that allow the deformable member 18 to deform in a predetermined manner. Depending upon the depth d of the cutouts A, B, C and the width w of the throats T1, T2, T3, the manner in which the deformable member 18 deforms under an applied load can be controlled and varied. Additionally, depending upon the length L between the cutouts A, B, C (i.e., the length of the material between the cutouts) the manner in which the deformable member 18 deforms can be controlled and varied.

Figure 4:
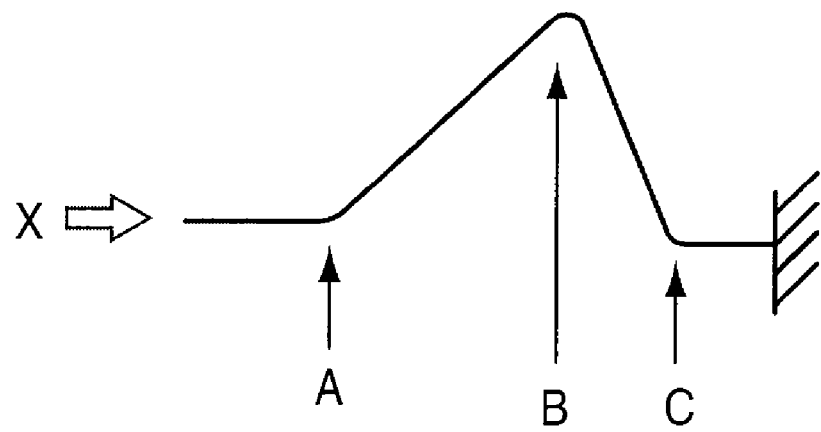
FIG. 4 is a schematic illustration of a side view of the expanding element illustrated in FIG. 3.

FIG. 4 is a schematic illustration of the expansion properties of the deformable member 18 illustrated in FIG. 3. When a load is applied, for example, in the direction indicated by arrow X, the deformable member 18 deforms in a predetermined manner based on the characteristics of the deformable member 18 as described above. As illustrated in FIG. 4, the deformable member 18 deforms most at cutouts B and C due to the configuration of the cutout C and the short distance between cutouts B and C. In some embodiments, the length of the deformable member 18 between cutouts B and C is sized to fit adjacent a spinous process.

The deformable member 18 is stiffer at cutout A due to the shallow depth of cutout A. As indicated in FIG. 4, a smooth transition is defined by the deformable member 18 between cutouts A and B. Such a smooth transition causes less stress on the tissue surrounding a spinous process than a more drastic transition such as between cutouts B and C. The dimensions and configuration of the deformable member 18 can also determine the timing of the deformation at the various cutouts. The weaker (i.e., deeper and wider) cutouts deform before the stronger (i.e., shallower and narrower) cutouts.

Figures 5, 6:
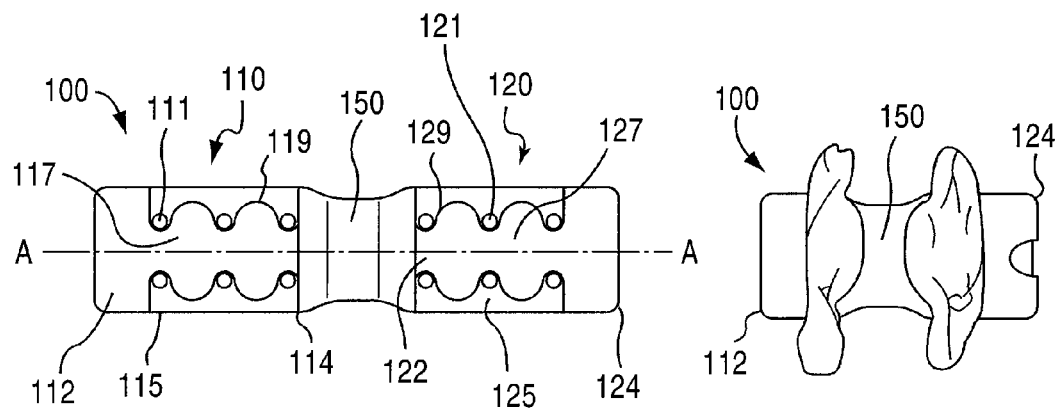
FIG. 5 is a side view of a medical device according to an embodiment of the invention in a first configuration.
FIG. 6 is a side view of the medical device illustrated in FIG. 5 in a second configuration.

FIGS. 5 and 6 illustrate a spinal implant 100 in a first configuration and second configuration, respectively. As shown in FIG. 5, the spinal implant 100 is collapsed in a first configuration and can be inserted between adjacent spinous processes. The spinal implant 100 has a first expandable portion 110, a second expandable portion 120 and a central portion 150. The first expandable portion 110 has a first end 112 and a second end 1140. The second expandable portion 120 has a first end 122 and a second end 124. The central portion 150 is coupled between second end 1140 and first end 122. In some embodiment, the spinal implant 100 is monolithically formed.

The first expandable portion 110, the second expandable portion 120 and the central portion 150 have a common longitudinal axis A along the length of spinal implant 100. The central portion 150 can have the same inner diameter as first expandable portion 110 and the second expandable portion 120. In some embodiments, the outer diameter of the central portion 150 is smaller than the outer diameter of the first expandable portion 110 and the second expandable portion 120.

In use, spinal implant 100 is inserted percutaneously between adjacent spinous processes. The first expandable portion 110 is inserted first and is moved past the spinous processes until the central portion 150 is positioned between the spinous processes. The outer diameter of the central portion 150 can be slightly smaller than the space between the spinous processes to account for surrounding ligaments and tissue. In some embodiments, the central portion directly contacts the spinous processes between which it is positioned. In some embodiments, the central portion of spinal implant 100 is a fixed size and is not compressible or expandable.

The first expandable portion 110 includes expanding members 115, 117 and 119. Between the expanding members 115, 117, 119, openings 111 are defined. As discussed above, the size and shape of the openings 111 influence the manner in which the expanding members 115, 117, 119 deform when an axial load is applied. The second expandable portion 120 includes expanding members 125, 127 and 129. Between the expanding members 125, 127, 129, openings 121 are defined. As discussed above, the size and shape of the openings 121 influence the manner in which the expanding members 125, 127, 129 deform when an axial load is applied.

When an axial load is applied to the spinal implant 100, the spinal implant 100 expands to a second configuration as illustrated in FIG. 6. In the second configuration, first end 112 and second end 1140 of the first expandable portion 110 move towards each other and expanding members 115, 117, 119 project substantially laterally away from the longitudinal axis A. Likewise, first end 122 and second end 124 of the second expandable portion 120 move towards one another and expanding members 125, 127, 129 project laterally away from the longitudinal axis A. The expanding members 115, 117, 119, 125, 127, 129 in the second configuration form projections that extend to positions adjacent to the spinous processes between which the spinal implant 100 is inserted. In the second configuration, the expanding members 115, 117, 119, 125, 127, 129 inhibit lateral movement of the spinal implant 100, while the central portion 150 prevents the adjacent spinous processes from moving together any closer than the distance defined by the diameter of the central portion 150.

Figure 7:
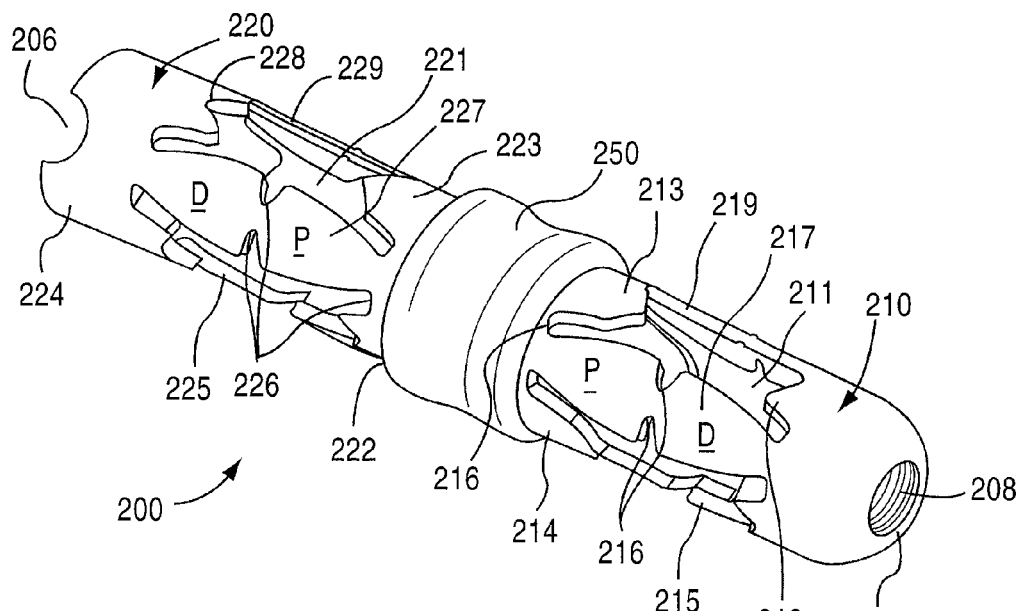
FIG. 7 is a perspective view of a medical device according to an embodiment of the invention in a first configuration.
Figure 11:
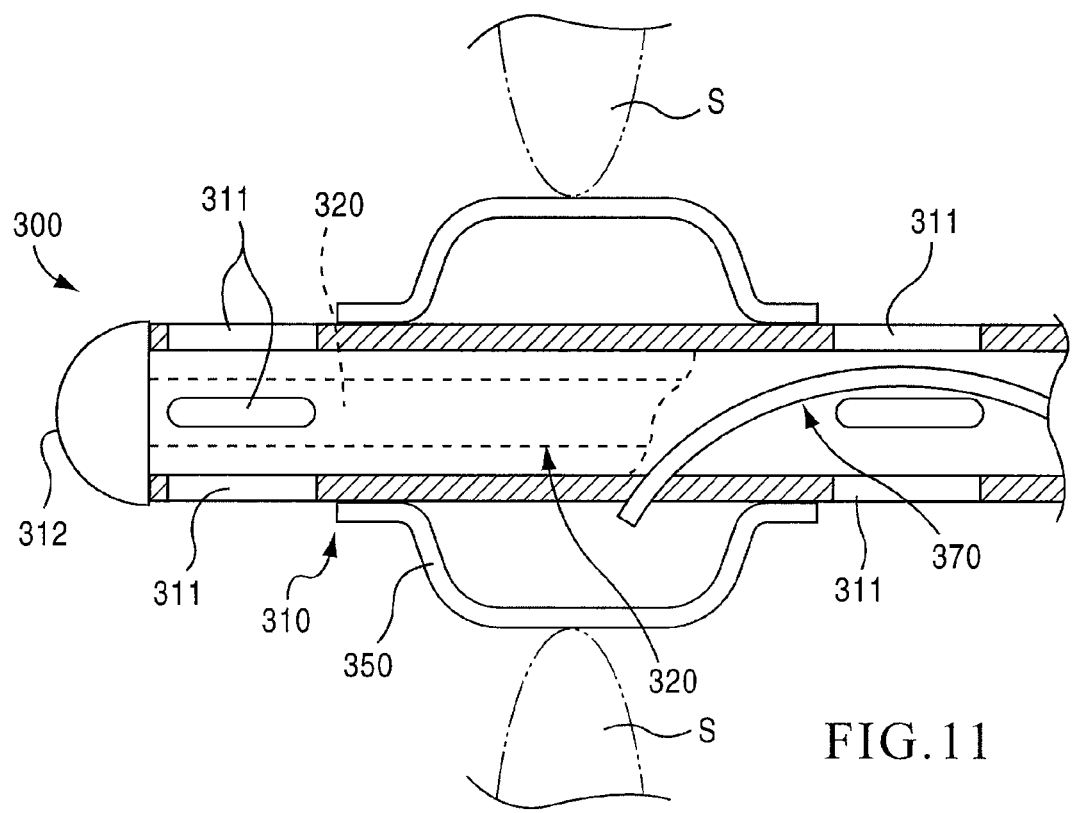
FIG. 11 is a cross-sectional, side view of a medical device according to another embodiment of the invention in a first configuration.

A spinal implant 200 according to an embodiment of the invention is illustrated in FIGS. 7-9 in various configurations. Spinal implant 200 is illustrated in a completely collapsed configuration in FIG. 7 and can be inserted between adjacent spinous processes. The spinal implant 200 has a first expandable portion 210, a second expandable portion 220 and a central portion 250. The first expandable portion 210 has a first end 212 and a second end 214. The second expandable portion 220 has a first end 222 and a second end 224. The central portion 250 is coupled between second end 214 and first end 222.

The first expandable portion 210, the second expandable portion 220 and the central portion 250 have a common longitudinal axis A along the length of spinal implant 200. The central portion 250 can have the same inner diameter as first expandable portion 210 and the second expandable portion 220. The outer diameter of the central portion 250 is greater than the outer diameter of the first expandable portion 210 and the second expandable portion 220. The central portion 250 can be monolithically formed with the first expandable portion 210 and the second expandable portion 220 or can be a separately formed sleeve coupled thereto or thereupon.

In use, spinal implant 200 is inserted percutaneously between adjacent spinous processes S. The first expandable portion 210 is inserted first and is moved past the spinous processes S until the central portion 250 is positioned between the spinous processes S. The outer diameter of the central portion 250 can be slightly smaller than the space between the spinous processes S to account for surrounding ligaments and tissue. In some embodiments, the central portion 250 directly contacts the spinous processes S between which it is positioned. In some embodiments, the central portion 250 of spinal implant 200 is a fixed size and is not compressible or expandable. In other embodiments, the central portion 250 can compress to conform to the shape of the spinous processes.

The first expandable portion 210 includes expanding members 215, 217 and 219. Between the expanding members 215, 217, 219, openings 211 are defined. As discussed above, the size and shape of the openings 211 influence the manner in which the expanding members 215, 217, 219 deform when an axial load is applied. Each expanding member 215, 217, 219 of the first expandable portion 210 includes a tab 213 extending into the opening 211 and an opposing mating slot 218. In some embodiments, the first end 212 of the first expandable portion 210 is rounded to facilitate insertion of the spinal implant 200.

The second expandable portion 220 includes expanding members 225, 227 and 229. Between the expanding members 225, 227, 229, openings 221 are defined. As discussed above, the size and shape of the openings 221 influence the manner in which the expanding members 225, 227, 229 deform when an axial load is applied. Each expanding member 225, 227, 229 of the second expandable portion 220 includes a tab 223 extending into the opening 221 and an opposing mating slot 228.

When an axial load is applied to the spinal implant 200, the spinal implant moves to a partially expanded configuration as illustrated in FIG. 8. In the partially expanded configuration, first end 222 and second end 224 of the second expandable portion 220 move towards one another and expanding members 225, 227, 229 project laterally away from the longitudinal axis A. To prevent the second expandable portion 220 from over-expanding, the tab 223 engages slot 228 and acts as a positive stop. As the axial load continues to be imparted to the spinal implant 200 after the tab 223 engages slot 228, the load is transferred to the first expandable portion 210. Accordingly, the first end 212 and the second end 214 then move towards one another until tab 213 engages slot 218 in the fully expanded configuration illustrated in FIG. 9. In the second configuration, expanding members 215, 217, 219 project laterally away from the longitudinal axis A. In some alternative embodiments, the first expandable portion and the second expandable portion expand simultaneously under an axial load.

The order of expansion of the spinal implant 200 can be controlled by varying the size of openings 211 and 221. For example, in the embodiments shown in FIGS. 7-9, the opening 221 is slightly larger than the opening 211. Accordingly, the notches 226 are slightly larger than the notches 216. As discussed above with respect to FIGS. 3 and 4, for this reason, the second expandable portion 220 will expand before the first expandable portion 210 under an axial load.

In the second configuration, the expanding members 215, 217, 219, 225, 227, 229 form projections that extend adjacent the spinous processes S. Once in the second configuration, the expanding members 215, 217, 219, 225, 227, 229 inhibit lateral movement of the spinal implant 200, while the central portion 250 prevents the adjacent spinous processes from moving together any closer than the distance defined by the diameter of the central portion 250.

The portion P of each of the expanding members 215, 217, 219, 225, 227, 229 proximal to the spinous process S expands such that portion P is substantially parallel to the spinous process S. The portion D of each of the expanding members 215, 217, 219, 225, 227, 229 distal from the spinous process S is angled such that less tension is imparted to the surrounding tissue.

In the second configuration, the expanding members 225, 227, 229 are separate by approximately 120 degrees from an axial view as illustrated in FIG. 10. While three expanding members are illustrated, two or more expanding members may be used and arranged in an overlapping or interleaved fashion when multiple implants 200 are inserted between multiple adjacent spinous processes. Additionally, regardless of the number of expanding members provided, the adjacent expanding members need not be separated by equal angles or distances.

The spinal implant 200 is deformed by a compressive force imparted substantially along the longitudinal axis A of the spinal implant 200. The compressive force is imparted, for example, by attaching a rod (not illustrated) to the first end 212 of the first expandable portion 210 and drawing the rod along the longitudinal axis while imparting an opposing force against the second end 224 of the second expandable portion 220. The opposing forces result in a compressive force causing the spinal implant 200 to expand as discussed above.

The rod used to impart compressive force to the spinal implant 200 can be removably coupled to the spinal implant 200. For example, the spinal implant 200 can include threads 208 at the first end 212 of the first expandable portion 210. The force opposing that imparted by the rod can be applied by using a push bar (not illustrated) that is removably coupled to the second end 224 of the second expandable portion 220. The push rod can be aligned with the spinal implant 200 by an alignment notch 206 at the second end 224. The spinal implant 200 can also be deformed in a variety of other ways, examples of which are discussed in detail below.

FIGS. 11-14 illustrate a spinal implant 300 according to an embodiment of the invention. Spinal implant 300 includes an elongated tube 310 configured to be positioned between adjacent spinous processes S and having a first end 312 and a second end 314. The elongated tube 310 has longitudinal slots 311 defined along its length at predetermined locations. The slots 311 are configured to allow portions of the elongated tube 310 to expand outwardly to form projections 317. An inflatable member 350 is disposed about the elongated tube between adjacent sets of slots 311.

The inflatable member 350 is configured to be positioned between adjacent spinous processes S as illustrated in FIGS. 11-14. Once inserted between the adjacent spinous processes, the inflatable member 350 is inflated with a liquid and/or a gas, which can be, for example, a biocompatible material. The inflatable member 350 is inflated to maintain the spinal implant 300 in position between the spinous processes S. In some embodiments, the inflatable member 350 is configured to at least partially distract the spinous processes S when inflated. The inflatable member 350 can be inflated to varied dimensions to account for different spacing between spinous processes S.

The inflatable member 350 can be inflated via an inflation tube 370 inserted through the spinal implant 300 once spinal implant 300 is in position between the spinous processes S. Either before or after the inflatable member 350 is inflated, the projections 317 are expanded. To expand the projections 317, an axial force is applied to the spinal implant 300 using draw bar 320, which is coupled to the first end 312 of the spinal implant 300.

Figure 12:
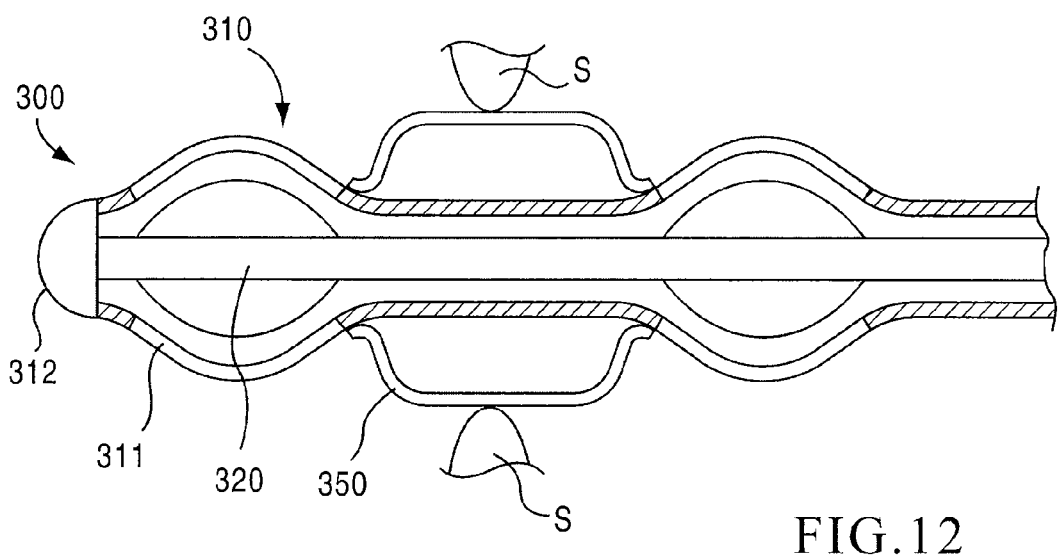
FIG. 12 is a cross sectional, side view of the medical device illustrated in FIG. 11 in a partially expanded configuration.
Figure 13:
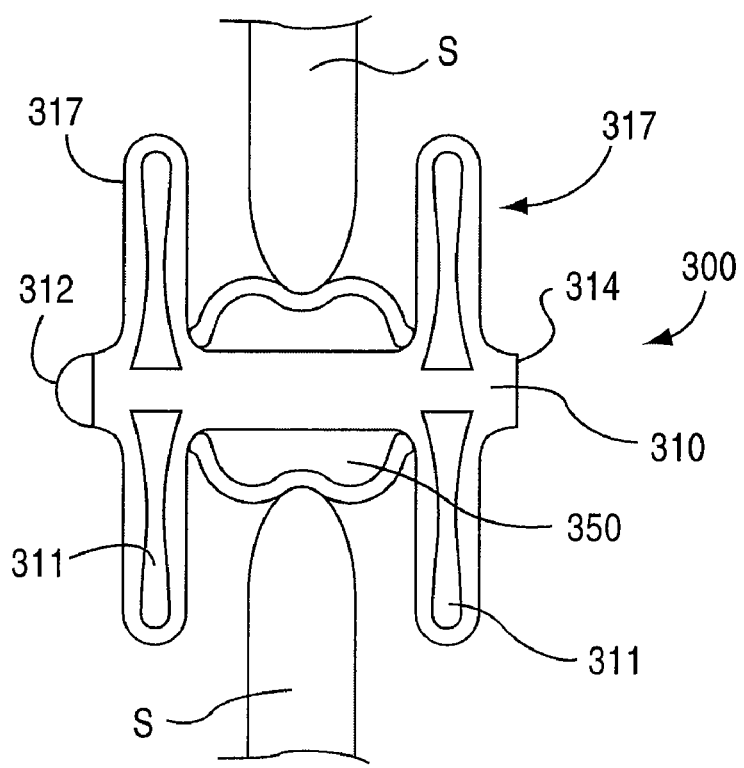
FIG. 13 is a posterior view of the medical device illustrated in FIG. 11 inserted between adjacent spinous processes in a second configuration.

As the draw bar 320 is pulled, the axial load causes the projections 317 to buckle outwardly, thereby preventing the spinal implant from lateral movement with respect to the spinous processes S. FIG. 12 is an illustration of the spinal implant 300 during deformation, the projections 317 being only partially formed. Although illustrated as deforming simultaneously, the slots 311 alternatively can be dimensioned such that the deformation occurs at different times as described above. Once the spinal implant is in the expanded configuration (see FIG. 13), the draw bar 320 is removed from the elongated tube 310.

Figure 14:
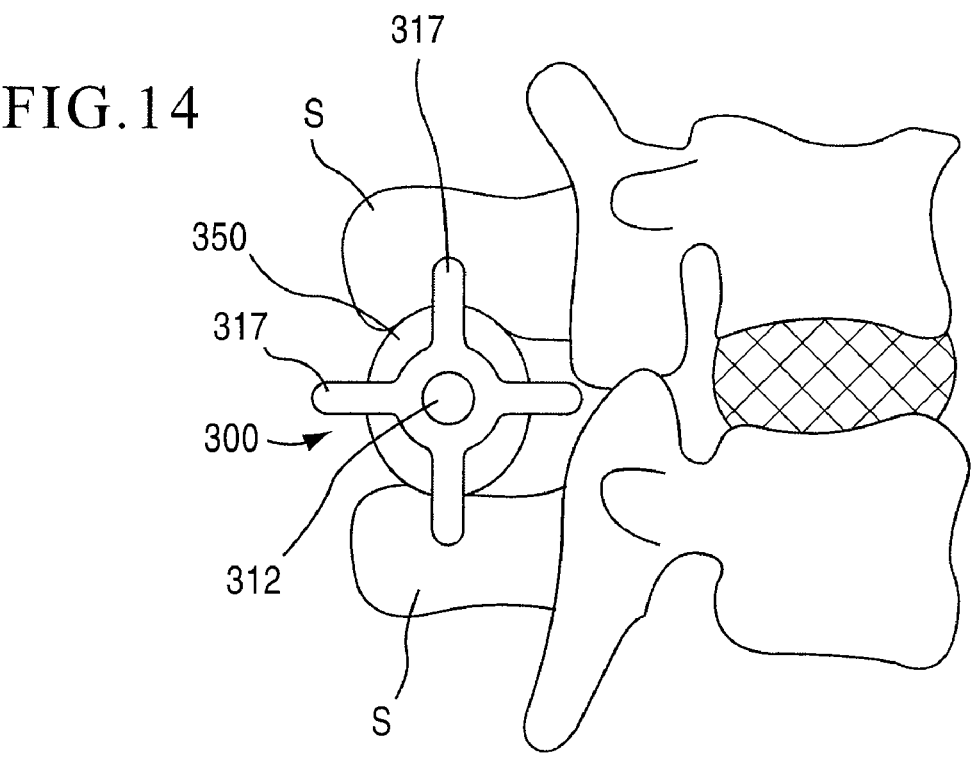
FIG. 14 is a lateral view of the medical device illustrated in FIG. 11 inserted between adjacent spinous processes in a second configuration.

The orientation of the spinal implant 300 need not be such that two projections are substantially parallel to the axis of the portion of the spine to which they are adjacent as illustrated in FIG. 14. For example, the spinal implant 300 can be oriented such that each of the projections 317 is at a 45 degree angle with respect to the spinal axis.

The spinal implants 100, 200, 300 can be deformed from their first configuration to their second configuration using a variety of expansion devices. For example, portions of the spinal implants 100, 200, 300, as well as other types of implants I, can be deformed using expansion devices described below. While various types of implants I are illustrated, the various expansion devices described can be used with any of the implants described herein.

Figure 15:
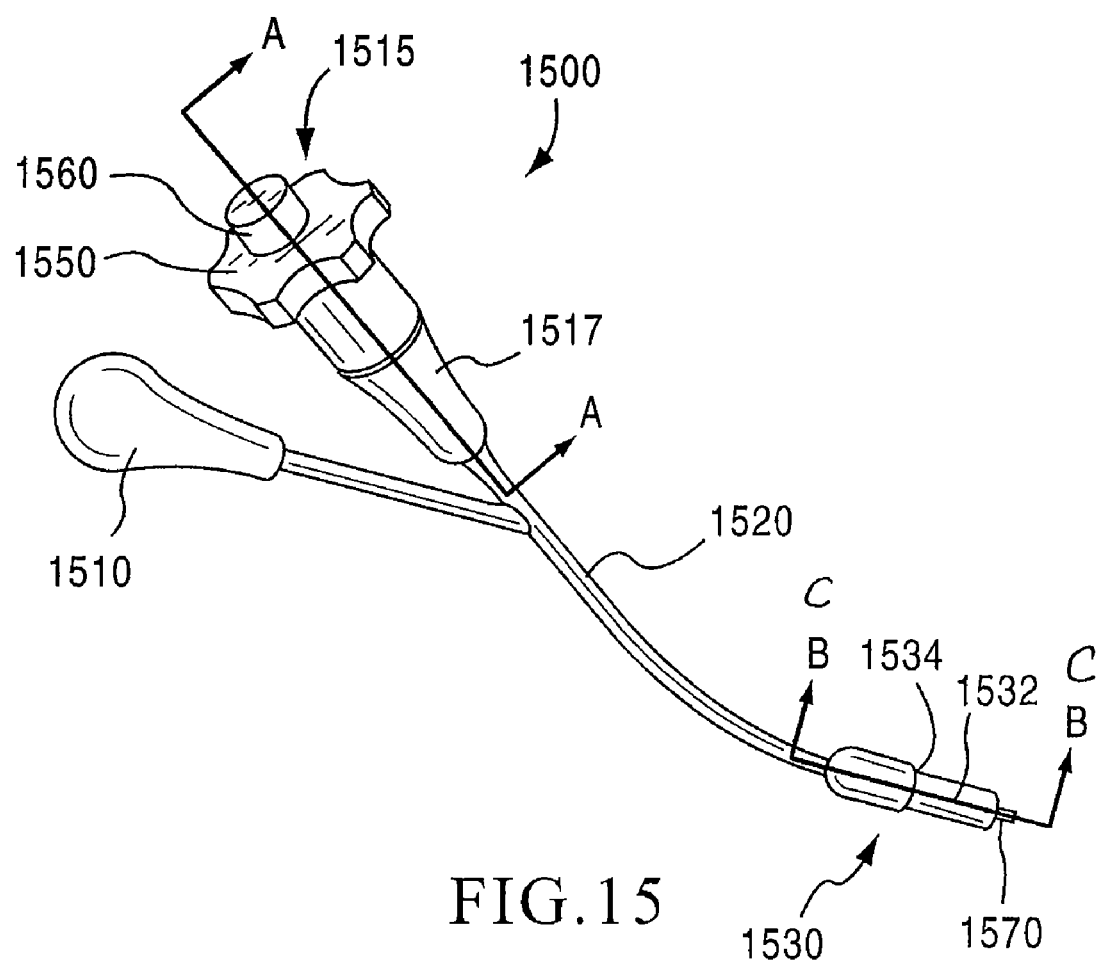
FIG. 15 is a perspective view of an implant expansion device according to an embodiment of the invention.
Figure 16:
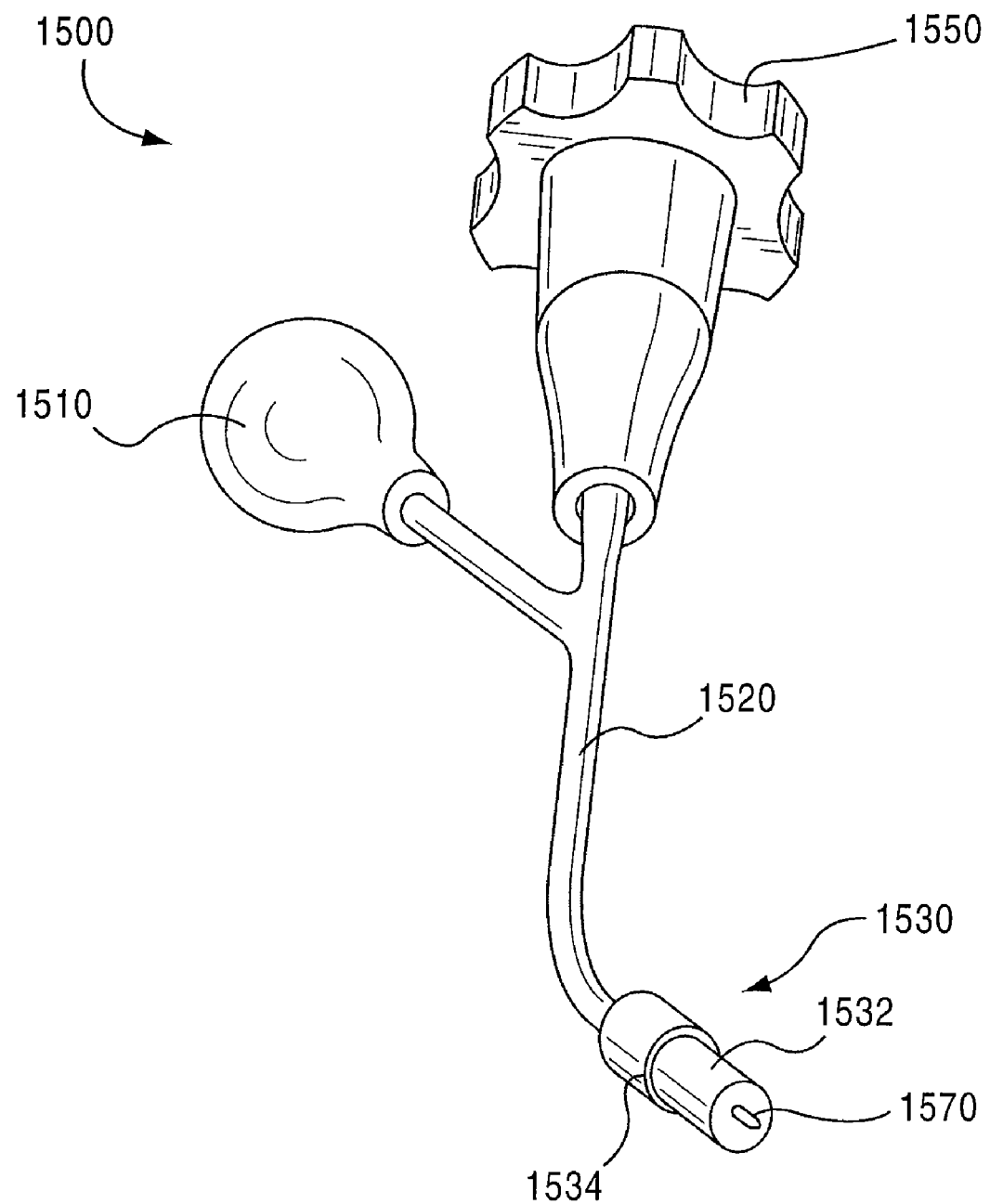
FIG. 16 is an alternative perspective view of the implant expansion device illustrated in FIG. 15.
Figure 17:
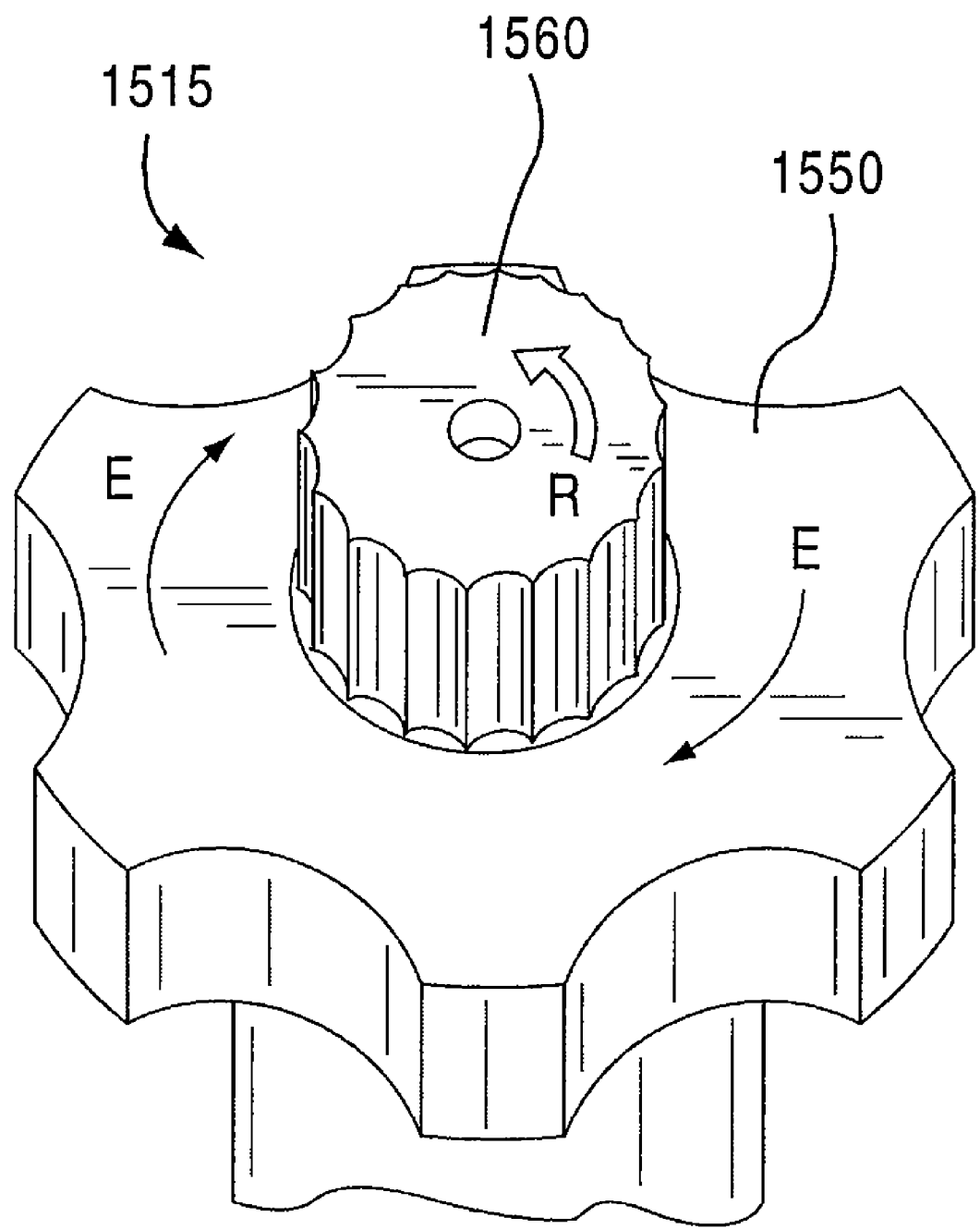
FIG. 17 is a perspective view of a portion of the implant expansion device illustrated in FIG. 15.

FIGS. 15-17 illustrate an embodiment of an expansion device 1500 (also referred to herein as an insertion tool or a deployment tool). The expansion device 1500 includes a guide handle 1510, a knob assembly 1515, a shaft 1520, a rod 1570 and an implant support portion 1530. The expansion device 1500 is used to insert an implant (not illustrated) in between adjacent spinous processes and expand the implant such that it is maintained in position between the spinous processes as described above. Both the guide handle 1510 and the knob assembly 1515 can be grasped to manipulate the expansion device 1500 to insert the implant. As described in more detail herein, the knob assembly 1515 is configured such that as the knob assembly 1515 is actuated, the rod 1570 translates and/or rotates within the shaft 1520; when the rod 1570 translates, the implant (not illustrated) is moved between its collapsed configuration and its expanded configuration; when the rod 1570 rotates, the implant is disengaged from the rod 1570. While no particular implant is illustrated in FIGS. 15-17, for purposes of clarity, an implant such as, for example, implant 200 (see FIG. 7) can be used with the expansion device 1500.

Figure 15A:
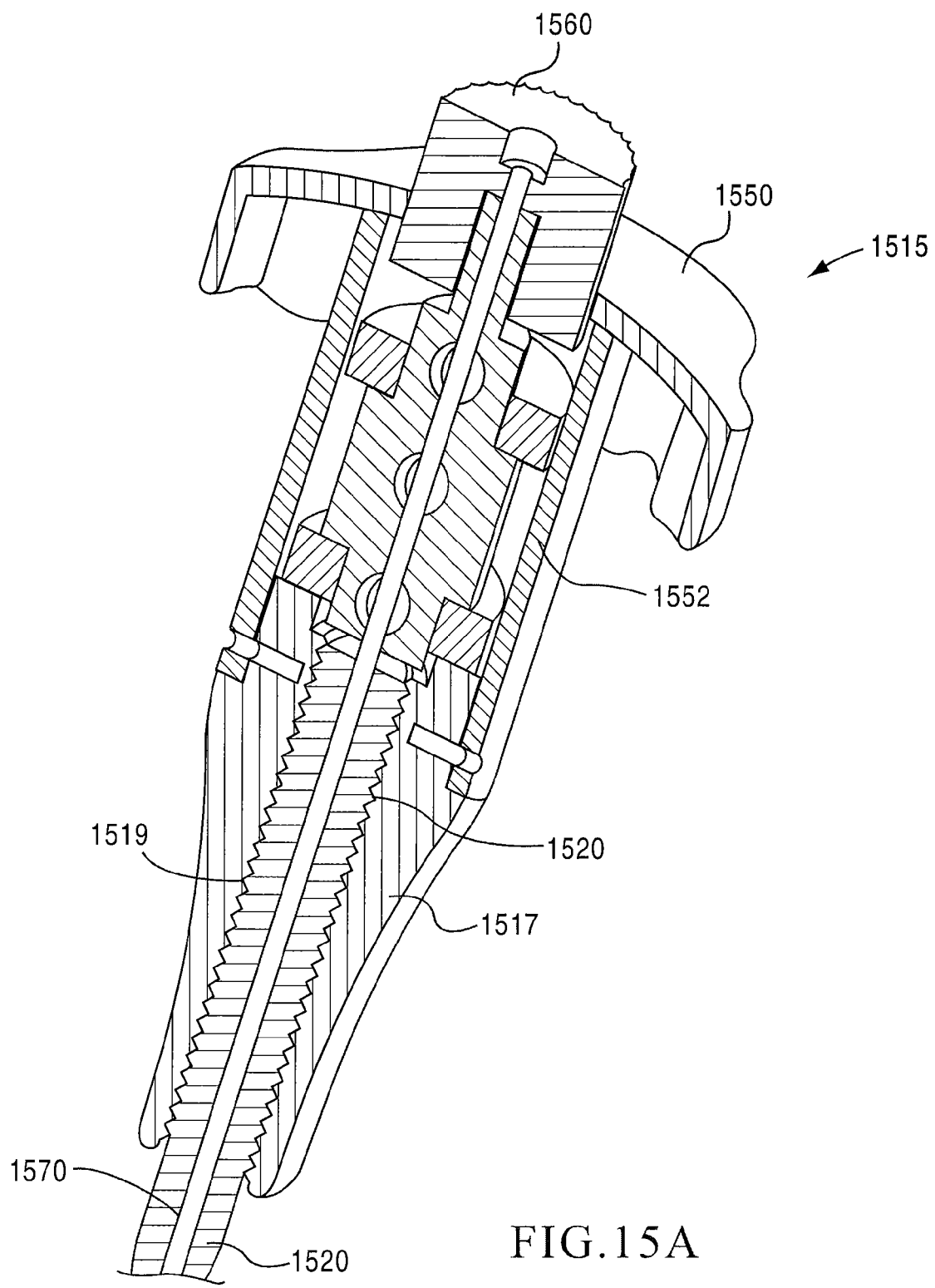
FIG. 15A is a cross-sectional view of a portion of the device illustrated in FIG. 15, taken along line A-A in FIG. 15.
Figure 15B:
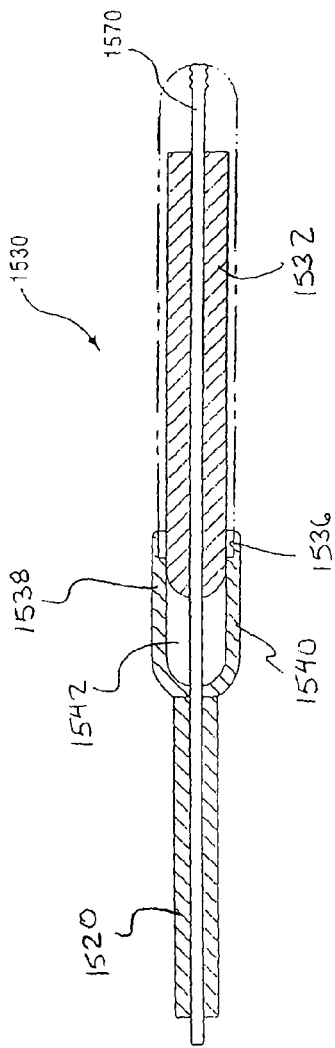
FIG. 15B is a cross-sectional view of a portion of the device illustrated in FIG. 15 in a first configuration, taken along line B-B in FIG. 15.
Figure 15C:
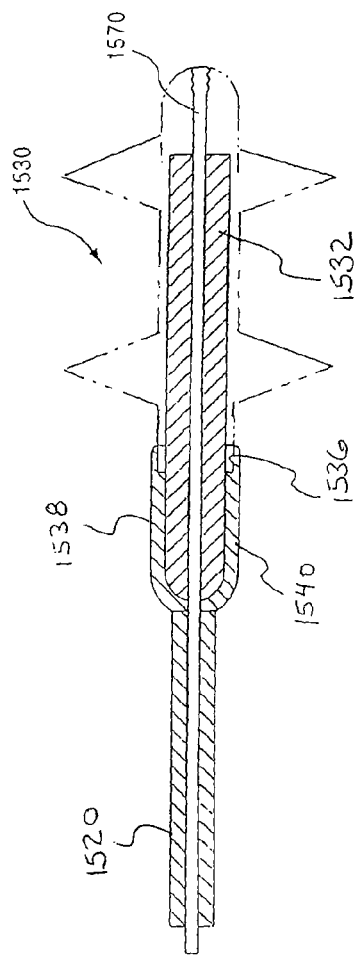
FIG. 15C is a cross-sectional view of a portion of the device illustrated in FIG. 15 in a second configuration, taken along line C-C in FIG. 15.

As best illustrated in FIG. 15B, the implant support portion 1530 includes a receiving member 1538 and a spacer 1532. The receiving member 1538 includes a side wall 1540 that is coupled to and supported by the distal end of the shaft 1520. The side wall 1540 defines an alignment protrusion 1536 and a receiving area 1542 configured to receive a portion of the spacer 1532. The implant slides over spacer 1532 until its proximal end is received within a recess 1534 defined by the side wall 1540 and the outer surface of the spacer 1532. The alignment protrusion 1536 is configured to mate with a corresponding notch on the implant (see, e.g., alignment notch 206 in FIG. 7) to align the implant with respect to the expansion device. Once the implant is aligned within the implant support portion 1530, the distal end of the implant is threadedly coupled to the distal end of rod 1570.

As illustrated, the spacer 1532 ensures that the implant is aligned longitudinally during the insertion and expansion process. The spacer 1532 can also be configured to maintain the shape of the implant during insertion and to prevent the expandable portions of the implant from extending inwardly during deployment of the implant. For example, in some embodiments, the spacer 1532 can be constructed from a solid, substantially rigid material, such as stainless steel, having an outer diameter and length corresponding to the inner diameter and length of the implant. In other embodiments, the expansion device can be configured to be used with implants that include an inner core configured to provide structural support to the implant (see, for example, FIGS. 118-124). In such embodiments, as described in more detail herein, the spacer of the insertion tool can be configured to cooperate with the inner core of the implant to provide the alignment and structural support of the implant during insertion and expansion.

The knob assembly 1515 includes an upper housing 1517 that threadedly receives the shaft 1520, an actuator knob 1550 and a release knob 1560 as best illustrated in FIG. 15A. Upper housing 1517 includes internal threads 1519 that mate with external threads 1521 on shaft 1520. The proximal end of rod 1570 is coupled to the knob assembly 1515 by an adapter 1554, which is supported by two thrust bearings 1552. Actuator knob 1550 is coupled to the upper housing 1517 and is engaged with the adapter 1554 such that when actuator knob 1550 is turned in the direction indicated by arrows E (see FIG. 17), the rod 1570 translates axially relative to the shaft 1520 towards the proximal end of the device 1500, thereby acting as a draw bar and opposing the movement of the implant in the distal direction. In other words, when the implant is inserted between adjacent spinous processes and the actuator knob 1515 is turned, the distal end of the implant support portion 1530 imparts an axial force against the proximal end of the implant, while the rod 1570 causes an opposing force in the proximal direction. In this manner, the forces imparted by the implant support portion and the rod 1570 cause portions of the implant to expand in a transverse configuration such that the implant is maintained in position between the spinous processes as described above. The expansion device 1500 can also be used to move the implant from its expanded configuration to its collapsed configuration by turning the actuator knob 1550 in the opposite direction.

Once the implant is in position and fully expanded, the release knob 1560 is turned in the direction indicated by arrow R (see FIG. 17) thereby causing the rod 1570 to rotate within the shaft 1520. In this manner, the implant can be disengaged from the rod 1570. During this operation, the implant is prevented from rotating by the alignment protrusion 1536, which is configured to mate with a corresponding notch on the implant. Once the implant is decoupled from the rod 1570, the expansion tool 1500 can then be removed from the patient.

Although the knob assembly 1515 is shown and described as including an actuator knob 1550 and a release knob 1560 that are coaxially arranged with a portion of the release knob 1560 being disposed within the actuator knob 1550, in some embodiments, the release knob is disposed apart from the actuator knob. In other embodiments, the release knob and the actuator knob are not coaxially located. In yet other embodiments, the knob assembly 1515 does not include knobs having a circular shape, but rather includes levers, handles or any other device suitable for actuating the rod relative to the shaft as described above.

FIG. 18 illustrates a portion of expansion device 400 in a collapsed configuration. Expansion device 400 can be used to selectively form protrusions on the implant I (not illustrated in FIG. 18) at desired locations. The expansion device 400 includes a guide shaft 410, which can guide the expansion device 400 into the implant I and a cam actuator 450 mounted thereto and positionable into an eccentric position. The expansion device 400 has a longitudinal axis A and the cam actuator 450 has a cam axis C that is laterally offset from the longitudinal axis A by a distance d. FIG. 19 illustrates the expansion device 400 in the expanded configuration with the cam actuator 450 having been rotated about the cam axis C.

The expansion device 400 can be inserted into an implant I through an implant holder H as illustrated in FIG. 20. The implant holder H is coupled to the implant and is configured to hold the implant in position while the expansion device 400 is being manipulated to deform the implant I. Once the implant I is satisfactorily deformed, the implant holder H can be detached from the implant I and removed from the patient, leaving the implant I behind.

Figure 22:
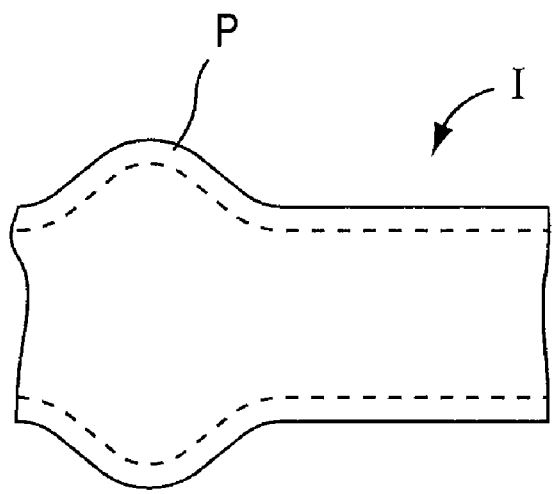
FIG. 22 is a side view of a partially expanded spinal implant.

Referring to FIGS. 20 and 21, the expansion device 400 includes a handle 420 that is used to deploy the cam actuator 450. When the handle 420 is rotated, the cam actuator 450 is deployed and deforms the implant I. Once the cam actuator 450 is fully deployed (e.g., 180 degrees from its original position) and locked in place, the entire expansion device 400 is rotated to deform the implant I around the circumference of implant I. The cam actuator 450 circumscribes a locus of points that is outside the original diameter of the implant I, forming the projection P (see FIG. 22). The expansion device 400 can be rotated either by grasping the guide shaft 410 or by using the handle 420 after it has been locked in place.

Figure 23:
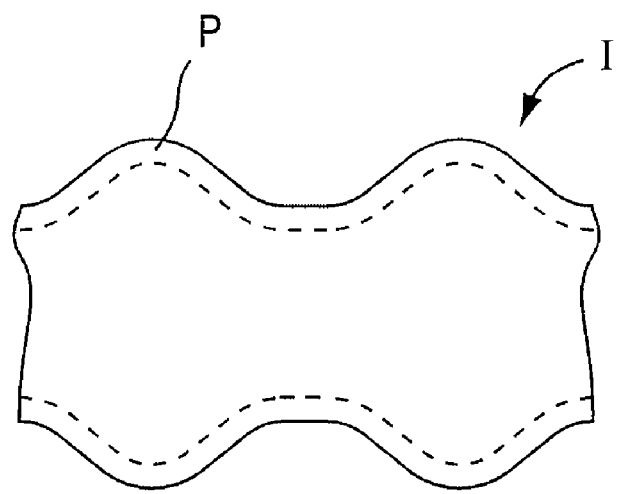
FIG. 23 is a side view of an expanded spinal implant.

The expansion device 400 can be used to form multiple projections P. Once a first projection P is formed, the cam actuator 450 can be rotated back to its first configuration and the expansion device 400 advanced through the implant I to a second position. When the expansion device 400 is appropriately positioned, the cam actuator 450 can again be deployed and the expansion device 400 rotated to form a second projection P (see FIG. 23). In some embodiments, the implant I is positioned between adjacent spinous processes and the projections P are formed on the sides of the spinous processes to prevent lateral (i.e., axial) displacement of the implant I.

Figure 24:
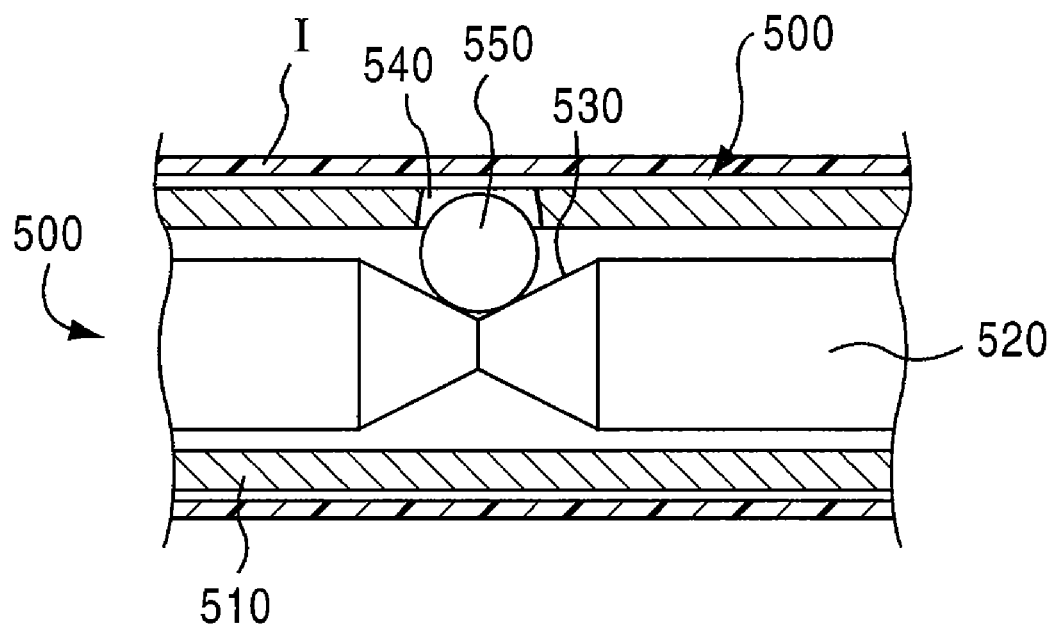
FIG. 24 is a cross-sectional, side view of an implant expansion device according to an alternative embodiment of the invention in a first configuration.
Figure 25:
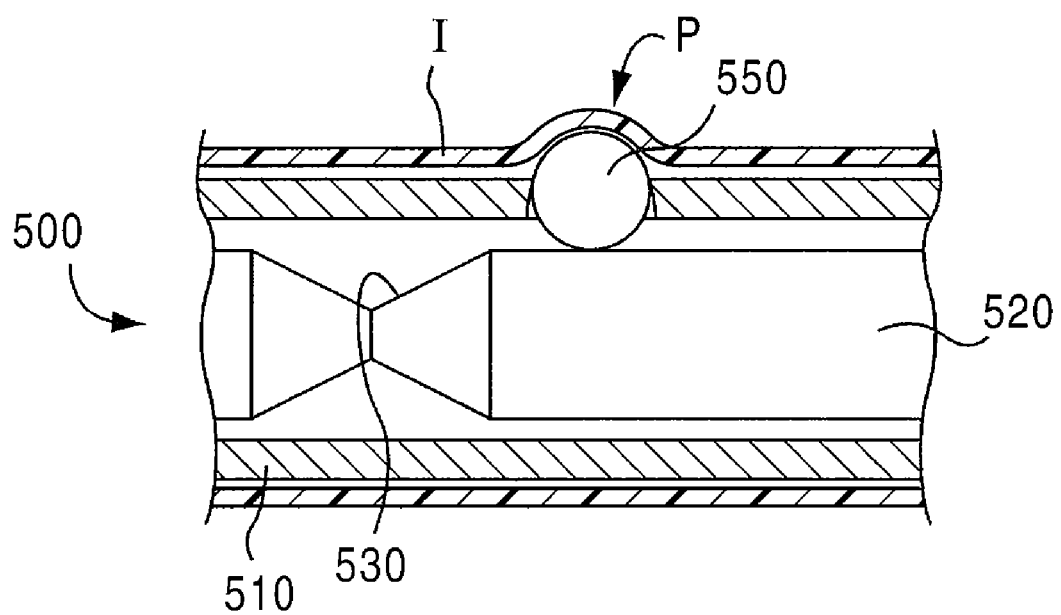
FIG. 25 is a cross-sectional, side view of the implant expansion device illustrated in FIG. 24 in a second configuration.

An alternative expansion device 500 is illustrated in FIGS. 24 and 25. FIG. 24 illustrates the expansion device 500 in a first configuration and FIG. 25 illustrates the expansion device 500 in a second configuration. The expansion device 500 includes a guide shaft 510 that is inserted into an implant I. An axial cam shaft actuator 520 is slidably disposed within the guide shaft 520. The axial cam shaft actuator 520 has a sloped recess 530 to receive a movable object 550. When the cam shaft actuator 520 is moved, the movable object 550 is displaced along the sloped recess 530 until it protrudes through an opening 540 in the guide shaft 510.

The movable object 550 is configured to displace a portion of the implant I, thereby forming a projection P. Multiple movable objects 550 can be used around the circumference of the guide shaft 510 to form a radially extending protrusions P around the circumference of the implant I. Additionally, the protrusions can be formed at multiple locations along the length of the implant I by advancing the expansion device 500 along the length of the implant to a second position as discussed above. Alternatively, the expansion device can have multiple recesses that displace other sets of movable objects.

In alternative embodiments, the expansion device can also serve as an implant. For example, the expansion device 500 can be inserted between adjacent spinous processes S, the movable objects moved out through openings 540, and the expansion device 500 left behind in the body. In such an embodiment, the movable objects prevent the expansion device 500 from lateral movement with respect to the spinous processes S.

In another alternative embodiment, rather than having openings 540 in the expansion device 500, the movable objects 550 can be positioned against a weaker (e.g., thinner) portion of the wall of the expansion device and move that portion of the expansion device 500 to a protruded configuration.

Figure 26:
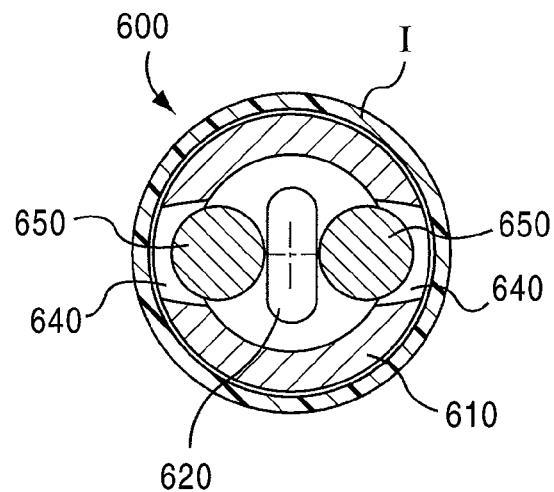
FIG. 26 is a cross-sectional, plan view of an implant expansion device according to a further embodiment of the invention in a first configuration.
Figure 27:
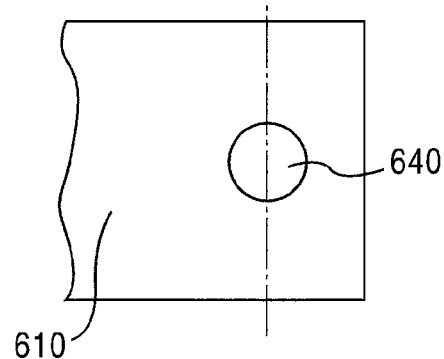
FIG. 27 is a partial side view of an implant for use with the implant expansion device illustrated in FIG. 26.
Figure 28:
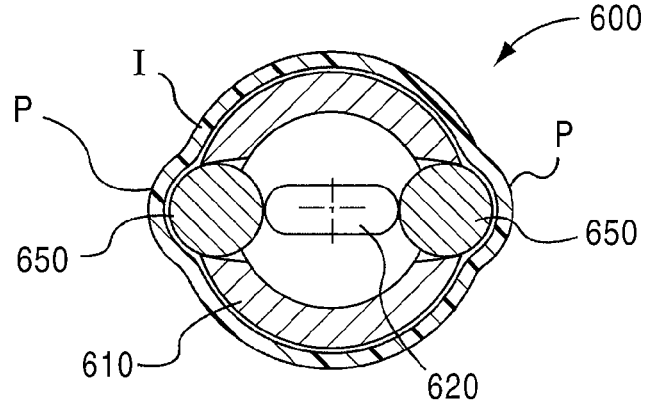
FIG. 28 is a cross-sectional, plan view of the implant expansion device illustrated in FIG. 26 in a second configuration.

Another alternative expansion device 600 is illustrated in FIGS. 26-28. FIG. 26 illustrates the expansion device 600 in a first configuration and FIG. 28 illustrates the expansion device in a second configuration. The expansion device 600 includes a guide shaft 610 that is inserted into an implant I. The guide shaft 610 has openings 640 defined therein. An axial cam shaft actuator 620 is rotatably coupled within the guide shaft 610. Displaceable objects 650 are positioned within the guide shaft 610 and are configured to protrude through the openings 640 in the guide shaft 610. When the cam shaft actuator 620 is rotated approximately 90 degrees, the movable objects 650 move through the openings 640 and deform the implant I, forming the projection P. Alternatively, the expansion device can have multiple cams that displace other sets of movable objects.

Multiple movable objects 650 can be used around the circumference of the guide shaft 610 to form radially extending protrusions P around the implant I. Additionally, the protrusions can be formed at multiple locations along the length of the implant I by advancing the expansion device 600 along the length of the implant I to a second position as discussed above.

Figure 29:
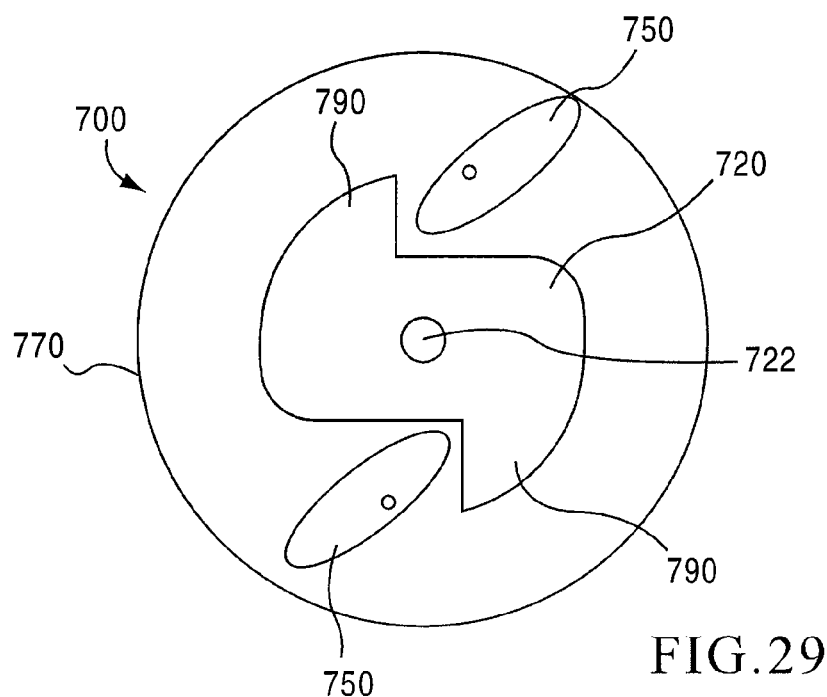
FIG. 29 is a cross-sectional, plan view of an implant expansion device according to another embodiment of the invention in a first configuration.
Figure 30:
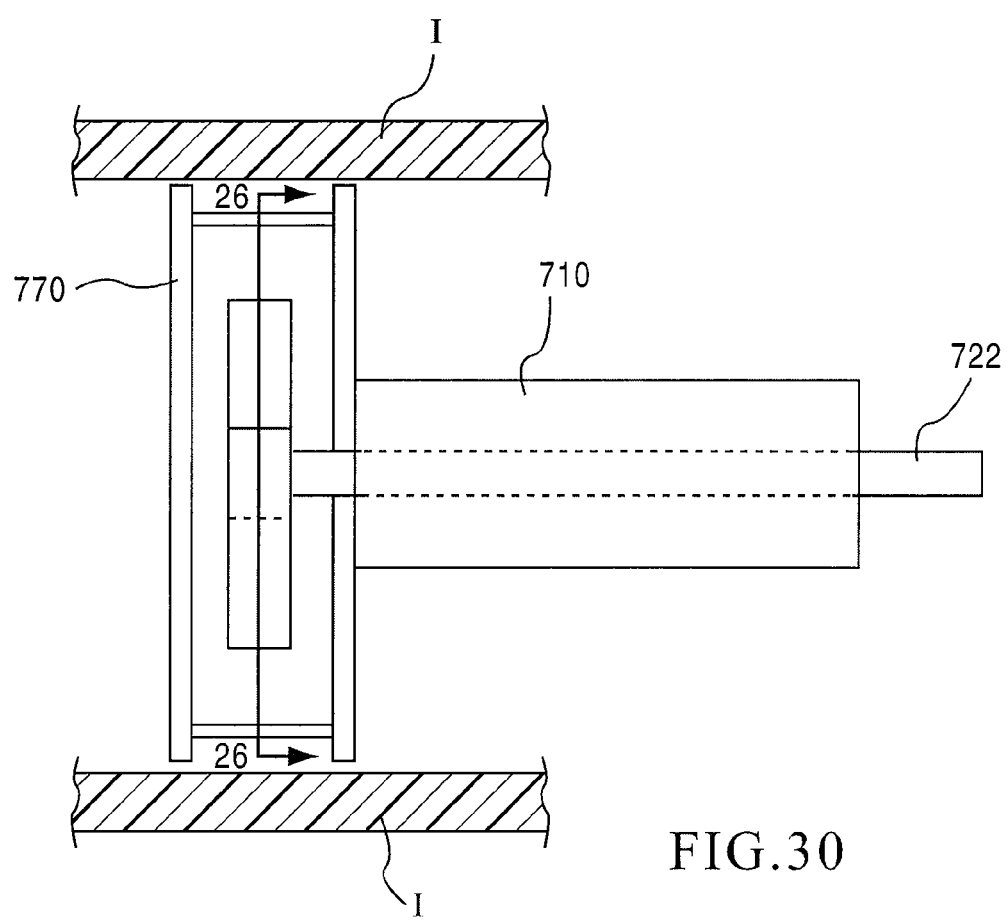
FIG. 30 is a cross-sectional, side view of the implant expansion device illustrated in FIG. 29.

An implant expansion device 700 is illustrated in FIGS. 29 and 30. The implant expansion device 700 is configured to be inserted into an implant I. The implant 700 includes a guide shaft 710 coupled to a housing 770. A cam actuator 720 is rotatably mounted within the housing 770 and includes arms 790 that extend in opposite directions from one another. The cam actuator 720 is rotated using rod 722.

As the cam actuator 720 rotates, the arms 790 engage movable objects 750. The movable objects 750 are configured to project out of the housing 770 when the cam actuator is rotated in a clockwise manner. Once the movable objects 750 are fully extended, they engage the implant I and the expansion device 700 can be rotated a complete revolution to form a protrusion in the implant I.

After one protrusion is formed, the rod 722 can be rotated counterclockwise to disengage the movable objects 750 from the implant I. Once disengaged, the expansion device 700 can be advanced to another location within the implant I as discussed above.

Figure 31:
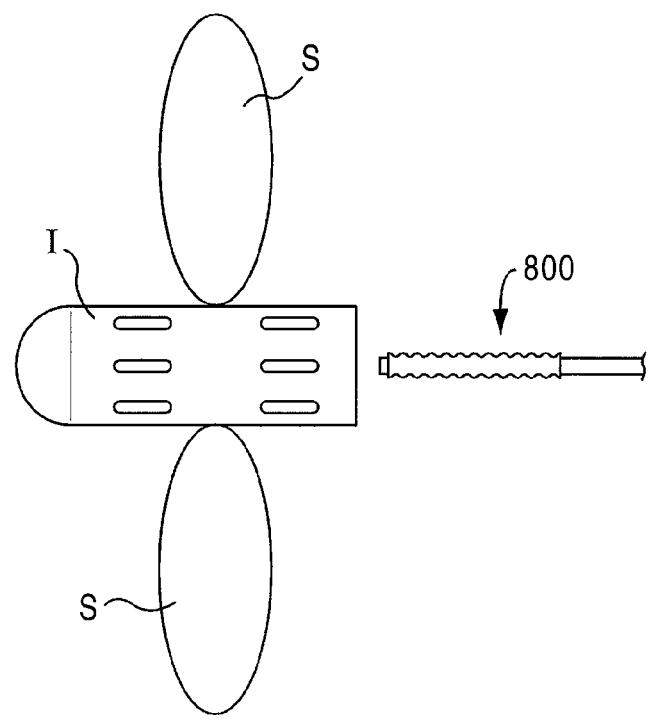
FIGS. 31 and 32 illustrate a posterior view of a spinal implant expandable by an expansion device implant expander according to another embodiment of the invention in a first configuration and a second configuration, respectively.
Figure 32:
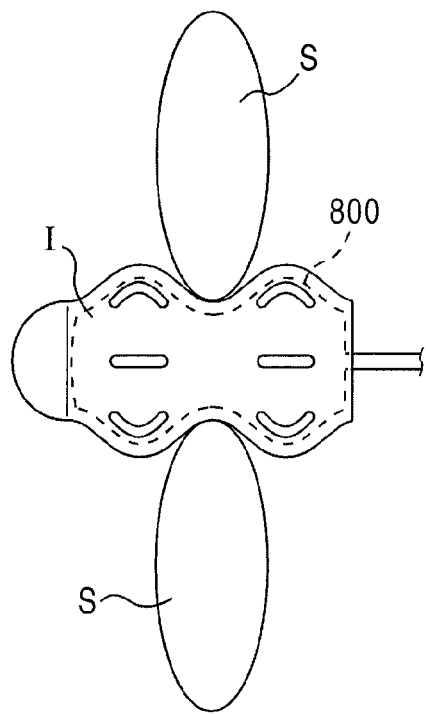

In some other embodiments, the implant I can be balloon actuated. FIG. 31 illustrates an implant I positioned between adjacent spinous processes S. A balloon actuator 800 in inserted into the implant I and expanded as illustrated in FIG. 32 to move the implant I to its expanded configuration. Once expanded, the balloon actuator 800 can be deflated and removed, leaving the implant I in an expanded configuration.

In some embodiments, the balloon actuator 800 can have multiple lobes, one that expands on each side of the spinous process S. In other embodiments, multiple balloon actuators 800 can be used to expand the implant I.

Figure 33:
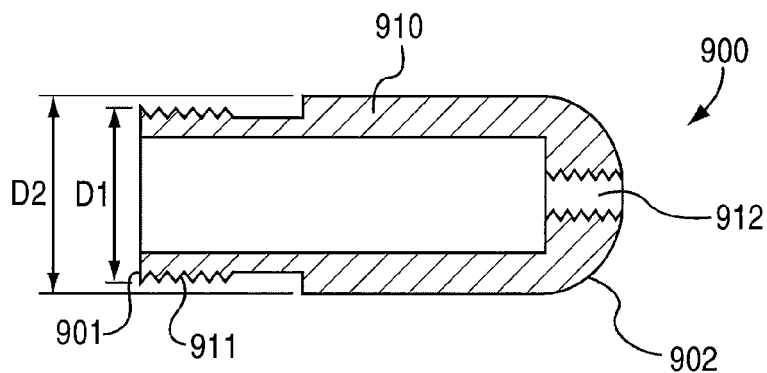
FIG. 33 illustrates a cross-sectional, side view of a spinal implant according to an embodiment of the invention.
Figure 34:
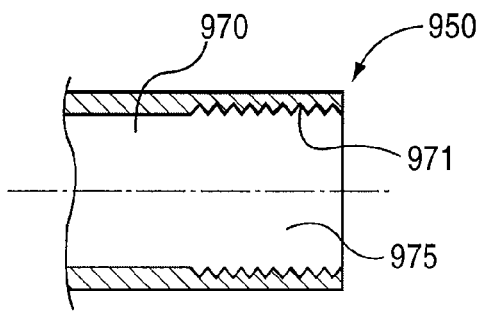
FIG. 34 is a cross-sectional, side view
Figure 35:
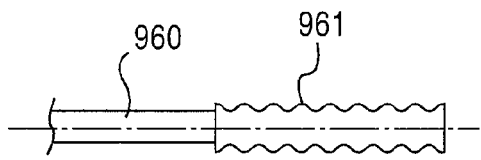
FIG. 35 is a side view of an implant expansion device according to an embodiment of the invention for use with the spinal implant illustrated in FIG. 33.
Figure 36:
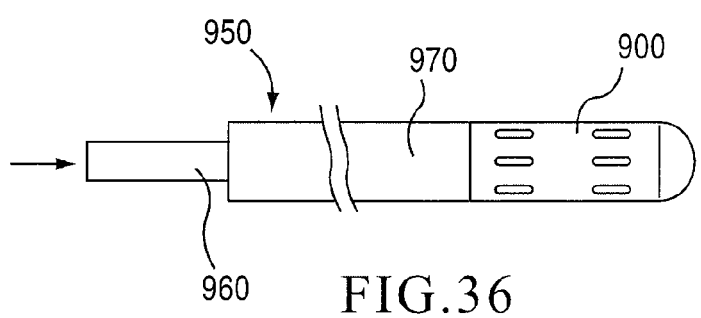
FIGS. 36 and 37 illustrate the use of the implant expansion device illustrated in FIGS. 34 and 35 with the spinal implant illustrated in FIG. 33.
Figure 37:
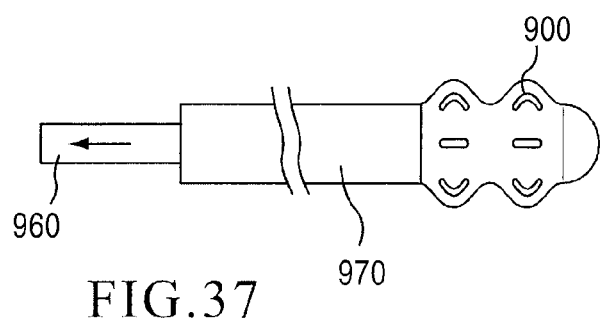

FIG. 33 is a cross-sectional view of an expandable implant 900 that can be expanded using an expansion device 950, illustrated in FIGS. 34-37. The implant 900 has an elongated body portion 910 having a first end 901 and a second end 902. The first end 901 has an externally threaded portion 911 and the second end 902 has an internally threaded portion 912. The implant 900 has a first outer diameter D1 at the externally threaded portion 911 and a second outer diameter D2, which wider than the first outer diameter D1.

The expansion device 950 includes a draw bar 960 and a compression bar 970. In some embodiments, the compression bar 970 defines a channel 975 having internal threads 971 to mate with the externally threaded portion 911 of the implant 900 (see FIG. 34). The draw bar 960 has external threads 961 to mate with the internally threaded portion 912 of implant 900.

In use, the compression bar 970 is coupled to the first end 901 of the implant 900 and abuts the implant 900 at the transition between the first outer diameter D1 and the second outer diameter D2, which serves as a stop for the compression bar 970. In some embodiments, the outer diameter of the entire implant 900 is substantially constant and the inner diameter of the compression bar 970 narrows to serve as the stop for the compression bar 970. With the compression bar 970 in place, the draw bar 960 is inserted through the channel 975 and is coupled to the second end 902 of the implant 900 via the internally threaded portion 912 of implant 900 (see FIG. 35). Once the compression bar 970 and the draw bar 960 are coupled to the implant 900, the draw bar 960 can be pulled while imparting an opposing force on the compression bar 970 to expand the implant 900 (see FIG. 36). When the implant 900 is fully expanded, the compression bar 970 and the draw bar 960 are removed and the implant is left behind in the body.

With the expansion devices described herein, the location of protrusions can be selected in vivo, rather than having predetermined expansion locations. Such a configuration reduces the need to have multiple sizes of spacers available. Additionally, the timing of the deployment of the protrusions can be varied.

The various implants 100, 200, 300 described herein can be made from, for example, stainless steel, plastic, polyetheretherketone (PEEK), carbon fiber, ultra-high molecular weight (UHMW) polyethylene, etc. The material can have a tensile strength similar to or higher than that of bone.

In other embodiments of the invention, an apparatus includes a first clamp having a first end and a second end. The second end of the first clamp is configured to engage a first spinous process. A second clamp has a first end and a second end. The second end of the second clamp is configured to engage a second spinous process spaced apart from the first spinous process. A connector is coupled to the first end of the first clamp and the first end of the second clamp.

Figure 38:
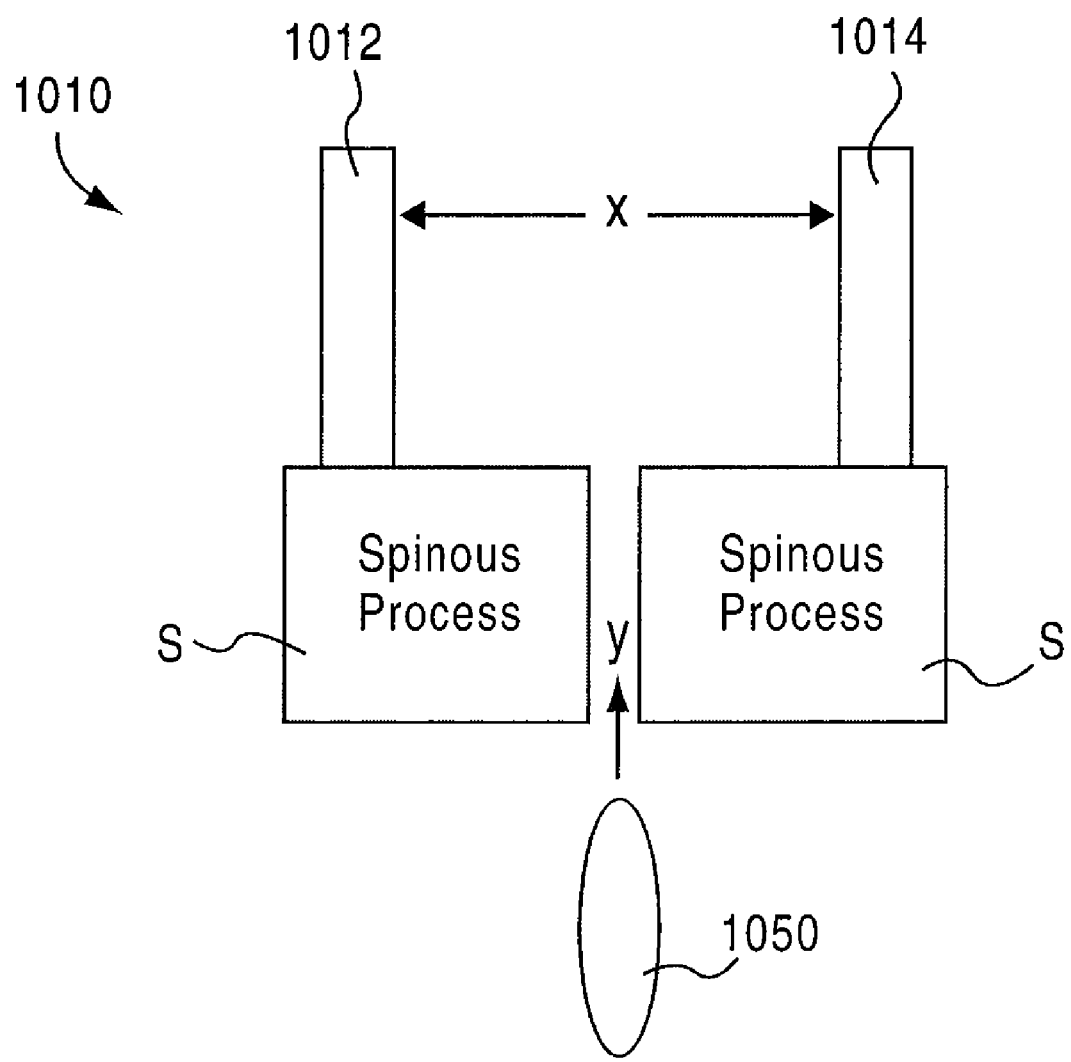
FIG. 38 is a schematic illustration of an apparatus according to an embodiment of the invention.

FIG. 38 is a schematic illustration of a medical device according to an embodiment of the invention attached to two adjacent spinous processes. The apparatus 1010 includes a first clamp 1012 configured to be coupled to a first spinous process S and a second clamp 1014 configured to be coupled to a second spinous process S. The first clamp 1012 and the second clamp 1014 are configured to be moved apart from one another in the direction indicated by arrows X. As the first clamp 1012 and the second clamp 1014 are moved apart, an opening between adjacent spinous processes S expands. An insert 1050 can be inserted between the spinous processes S in the direction indicated by arrow Y to maintain the opening between the spinous processes S. The clamps 1012, 1014 engage the spinous processes S with sufficient force such that when the clamps 1012, 1014 are spread apart, they cause lateral displacement of the spinous processes S.

Figure 39:
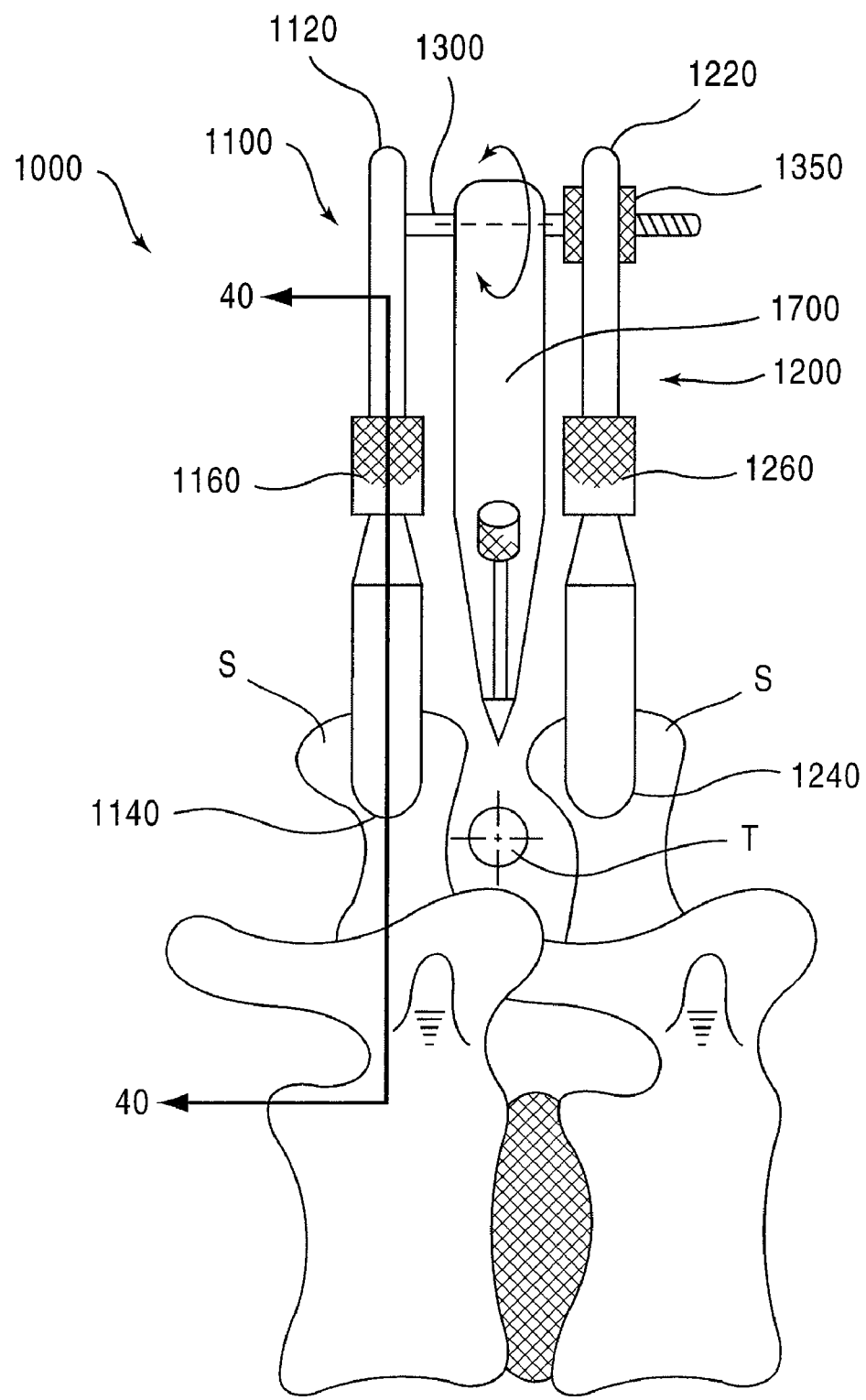
FIG. 39 is a front plan view of an apparatus according to an embodiment of the invention and a portion of a spine.

FIG. 39 is a side view of a medical device according to an embodiment of the invention coupled to a portion of a spine. The tissue surrounding the spine is not illustrated for the sake of clarity. The medical device 1000 includes a first clamp 1100 and a second clamp 1200. The first clamp 1100 has a proximal end 1120 and a distal end 1140. The distal end 1140 of the first clamp 1100 is configured to engage a first spinous process S. The second clamp 1200 has a first end 1220 and a second end 1240. The second end 1240 of the second clamp 1200 is configured to engage a second spinous process S that is spaced apart from the first spinous process S.

A connector 1300 is coupled to the proximal end 1120 of the first clamp 1100 and the first end 1220 of the second clamp 1200. The position of the connector 1300 relative to the first clamp 1100 and the second clamp 1200 can be adjusted such that the distance between the first clamp 1100 and the second clamp 1200 can be adjusted. In other words, the connector 1300 is reconfigurable between a first configuration and a second configuration. The first clamp 1100 is a first distance from the second clamp 1200 when the connector 1300 is in its first configuration and is a second distance from the second clamp 1200 when the connector 1300 is in its second configuration.

Figure 40:
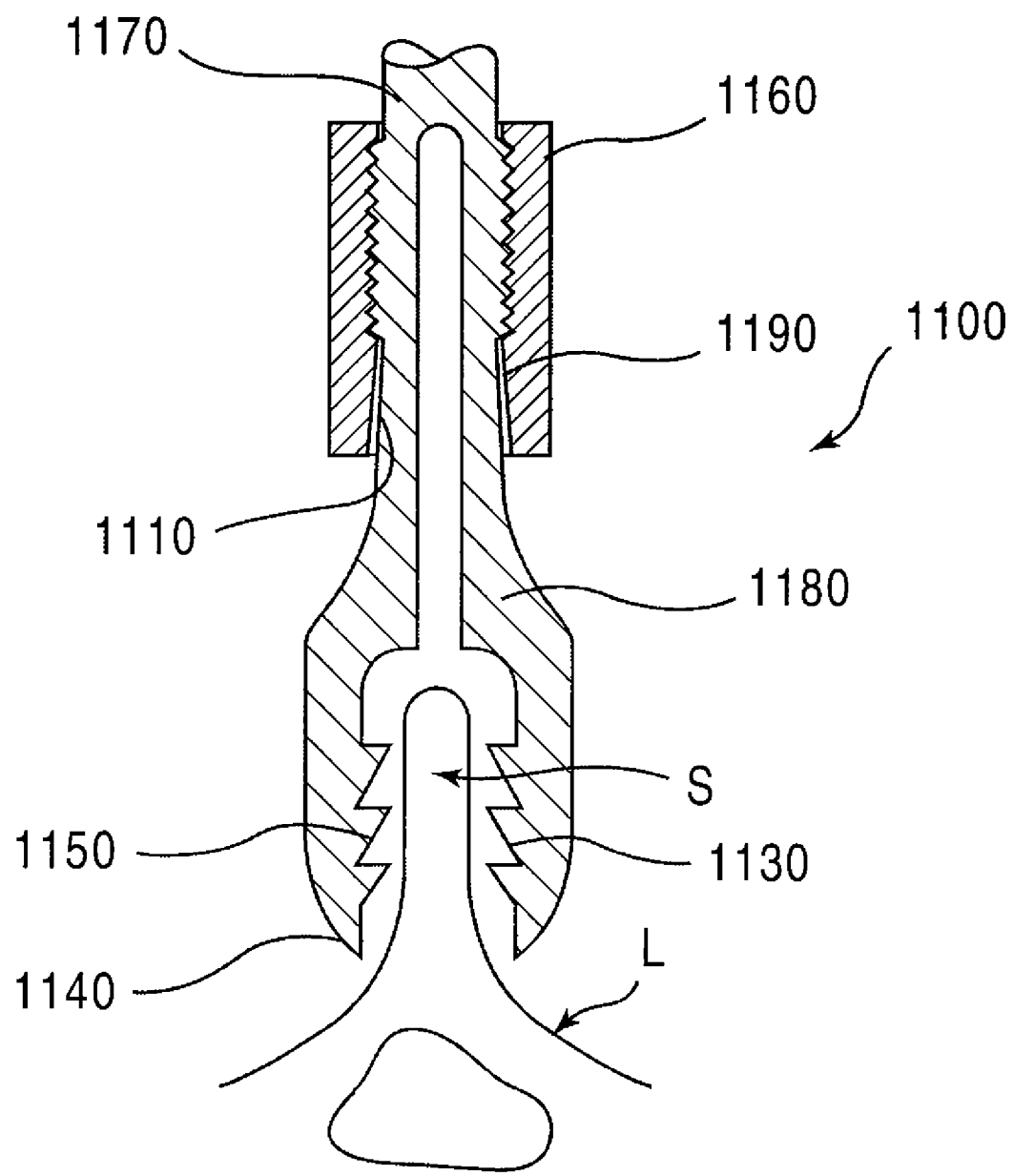
FIG. 40 is a cross-sectional view of a component of the apparatus and the portion of the spine illustrated in FIG. 39, taken along line 40-40 in FIG. 39.

Referring to FIG. 40, in which the first clamp 1100 is illustrated, the first clamp 1100 includes a first jaw 1150 and a second jaw 1130 opposite the first jaw 1150. The first jaw 1150 and the second jaw 1130 are configured to be movable between a first configuration and a second configuration. The first jaw 1150 and the second jaw 1130 are closer together in the second configuration than in the first configuration. In the second configuration, the first jaw 1150 and the second jaw 1130 engage the spinous process S with sufficient force to substantially maintain the orientation of the first clamp 1100 and the second clamp 1200 with respect to the spinous process S when the connector 1300 is moved to its second configuration, thereby spreading the spinous processes S. The second clamp 1200 has a similar configuration, but is not illustrated for ease of reference. The material of the jaws 1150, 1130 are such that they can sufficiently engage the spinous processes S as described, but to not damage the spinous processes. Adequate materials include, for example, stainless steel, polyetheretherketone (PEEK), carbon fiber, ultra-high molecular weight (UHMW) polyethylene, etc. The material can have a tensile strength similar to or higher than that of bone. In some embodiments, the clamp 1200 can be manufactured from stainless steel and a coating and/or an over-mold or over-layer of PEEK or carbon fiber can be applied to the jaws 1150, 1130.

In some embodiments, the medical device 100 is used to spread adjacent spinous processes of severely compressed vertebrae. Additionally, the medical device 100 stabilizes the spinous processes during procedures without penetrating the vertebrae.

In some embodiments, the first clamp 1100 includes a first arm 1170 and a second arm 1180 and a tension member 1160. The first arm 1170 and second arm 1180 can be resiliently coupled such that as tension member 1160 is advanced towards the distal end 1140 of the clamp 1100, the first arm 1170 and the second arm 1180 are moved towards one another, but as the tension member 1160 is moved away from the distal end 1140 of the clamp 1100, the first arm 1170 and the second arm 1180 return to their default position (i.e., spaced apart).

The tension member 1160 is configured to move the first jaw 1150 and the second jaw 1130 between their first configuration and their second configuration as the first arm 1170 and the second arm 1180 move towards one another. As the tension member 1160 is moved towards the first jaw 1150 and the second jaw 1130, the first jaw 1150 and the second jaw 1130 engage the spinous process S. In some applications, a distal end 1140 of the clamp 1100 is positioned adjacent the lamina L of the vertebra to which it is coupled. In some embodiments, the clamp 1100 is attached close to the lamina L to minimize the lever arm on the spinous process. The distal end 1140 of clamp 1100 need not penetrate the lamina L.

In an alternative embodiment, the tension member includes threads that engage threads on the first clamp. In such an embodiment, the tension member is moved along the length of the first clamp by turning the tension member. Returning to FIG. 40, the tension member 1160 may optionally include a tapered portion 1190 that matingly engages a tapered portion 1110 of first clamp 1100. Such a configuration can ensure appropriate distribution of the forces to the spinous process S. The second clamp 1200 is similarly configured and includes a tension member 126 and opposing jaws.

A swing arm 1700 is pivotably coupled to the connector 1300 between the first clamp 1100 and the second clamp 1200. The swing arm 1700 has an arcuate portion 173 and travels along a range of motion. The arcuate portion 173 of the swing arm 1700 has a first end 1750 and a second end 1770.

Figure 41:
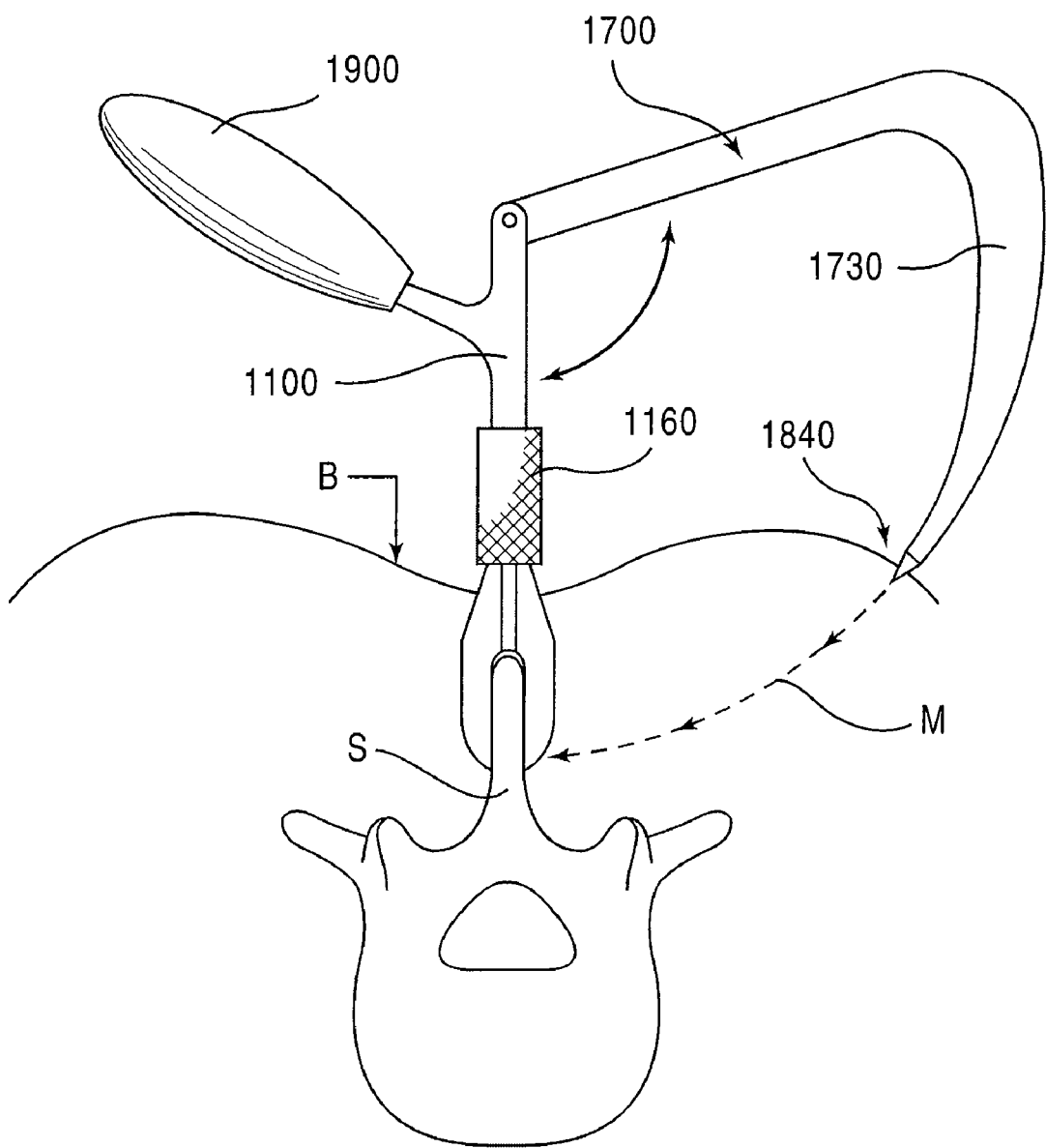
FIG. 41 is a side plan view of the apparatus illustrated in FIG. 39.
Figure 42:
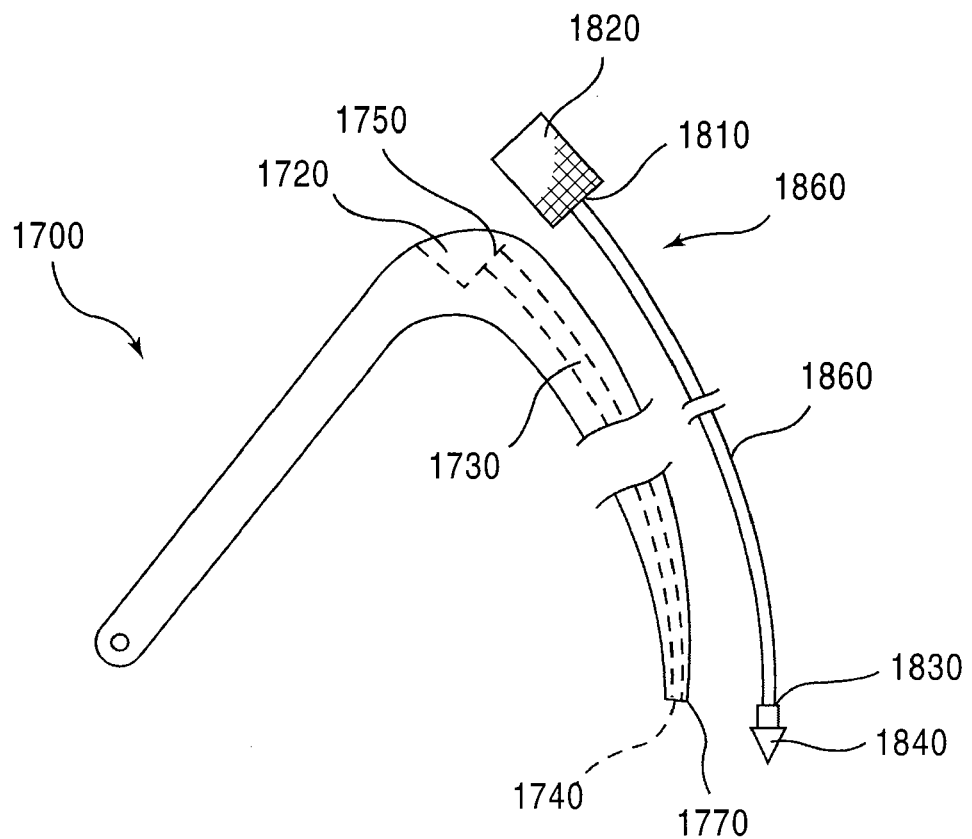
FIG. 42 is a side plan view of a component of the apparatus illustrated in FIG. 39.

As best seen in FIGS. 41 and 42, the second end 1770 of the arcuate portion 173 of swing arm 1700 is configured to receive a working tool 1840, such as, for example, a pointed trocar tip. The swing arm 1700 defines an opening 1740 in which at least a portion of the working tool 1840 is received. In some embodiments, the opening 1740 extends along the entire length of the arcuate portion 173 between the first end 1750 and the second end 1770. In some embodiments, an optional handle 190 can be coupled to the first clamp 1100 and/or the second clamp 1200 to facilitate insertion of the clamps 1100, 1200 and increase stability of the apparatus 1000 during use.

Figure 43:
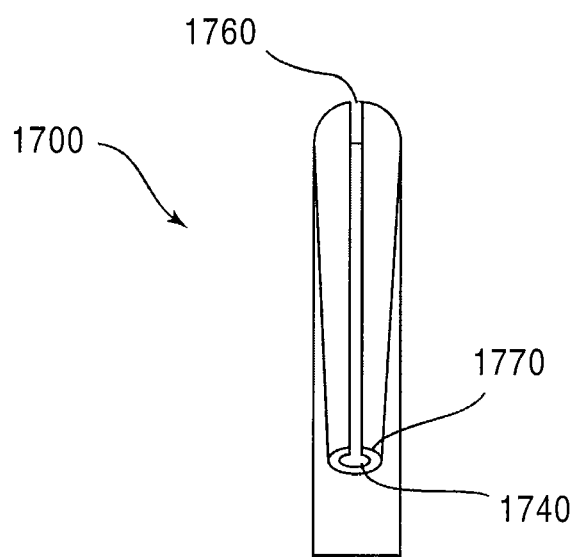
FIG. 43 is a front plan view of the component of the apparatus illustrated in FIG. 42.

The working tool 1840 is coupled to a guide wire 1860. The guide wire 1860 has a first end 1810 and a second end 1830. The second end 1830 of the guide wire 1860 is coupled to the working tool 1840. A retainer 1820 (discussed in detail below) is coupled to the first end 1810 of the guide wire 1860 and is configured to maintain the position of the working tool 1840 with respect to the swing arm 1700. The retainer 1820 is matingly received in a recess 1720 in the swing arm 1700. The guide wire 1860 is received in the opening 1740 defined in the swing arm 1700. The guide wire is received in the opening 1740 through a channel 1760 defined in the swing arm 1700 as best seen in FIG. 43. In some alternative embodiments, the guide wire does not extend through the opening 1740 of the swing arm 1700. In yet other alternative embodiments, the guide wire is not present.

Figures 44, 45:
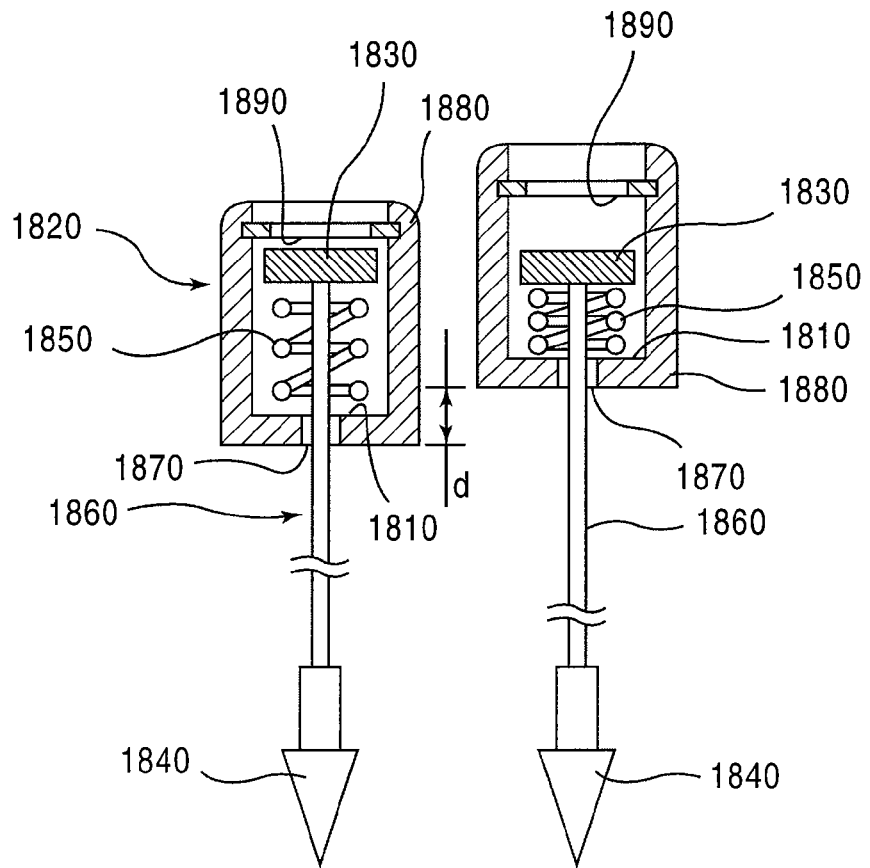
FIG. 44 is a partial cross-sectional view of a detachable trocar tip for use with an apparatus according to an embodiment of the invention in a first configuration.
FIG. 45 is a partial cross-sectional view of the detachable trocar tip for use with the apparatus according to an embodiment of the invention in a second configuration.

FIGS. 44 and 45 illustrate the retainer 1820 in a first configuration and a second configuration, respectively. The retainer 1820 includes a housing 1880 that defines an opening 1870 through which guide wire 1860 is movably disposed. The guide wire 1860 is coupled to a retention member 1830. The retention member 1830 is biased towards a first end 1890 of housing 1880 by a spring 1850. The spring 1850 is between a second end 1810 of the housing 1880 and the retention member 1830.

In use, when the retainer 1850 is in the first configuration (FIG. 44), the working tool is maintained in the swing arm 1700. When the retainer 1820 is moved to its second configuration (FIG. 45), the working tool 1840 can be removed from the swing arm 1700. When moved to the second configuration, the retainer 1820 is displaced a distance d, thereby increasing the effective length of the guide wire 1860, allowing movement of the working tool 1840 with respect to the end of the swing arm 1700. In some embodiments, the distance d is approximately the same as the length of the portion of the working tool 1840 received in the swing arm 1700.

Figure 46:
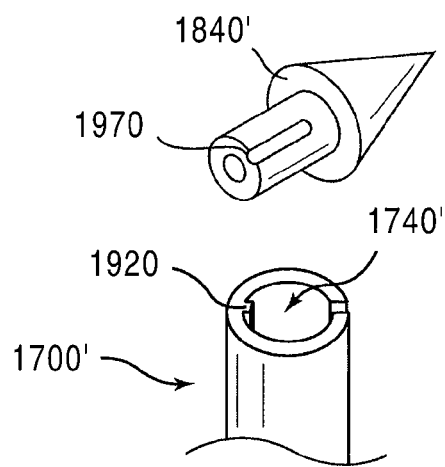
FIG. 46 is a partial exploded view of a detachable trocar tip for use with the apparatus according to an embodiment of the invention.

As shown in FIG. 46, a working tool 1840' is inserted into an opening 1740' defined by a swing arm 1700'. The swing arm 1700' includes a projection 1920 within opening 1740' that mates with a recess 1970 on working tool 1840'.

Returning to FIGS. 39-42, in use, a first clamp 1100 is inserted through a body B and coupled to a spinous process S. The tension member 1160 is moved towards the distal end 1140 of the first clamp to engage the first jaw 1150 and the second jaw 1130 with the spinous process S. The second clamp 1200 is then inserted and similarly coupled to the adjacent spinous process S. The connector 1300 is actuated to increase the distance between the first clamp 1100 and the second clamp 1200, thereby separating the adjacent spinous processes S. Once the spinous processes S are separated, the swing arm 1700 is moved through its range of motion M.

The swing arm 1700 is moved from a location outside a body B through a range of motion M (see, e.g., FIG. 41). The swing arm 1700 enters the body B and moves through range of motion M until it is at target T (see, e.g., FIG. 39) between adjacent spinous processes S.

The movement of the swing arm 1700 into the body defines a path within the tissue (not illustrated). The tissue is penetrated by a pointed projection (i.e., working tool 1840). The path M defined by the swing arm 1700 includes the target T between the adjacent spinous processes S. Once the path is defined, the swing arm 1700 can be removed and a spacer 500 (see FIG. 49), discussed in detail below, can be inserted between the adjacent spinous processes S. In some embodiments of the invention, the spacer 5000 can be removably attached to the swing arm 1700, inserted into the body and then removed from the swing arm 1700.

Figure 47:
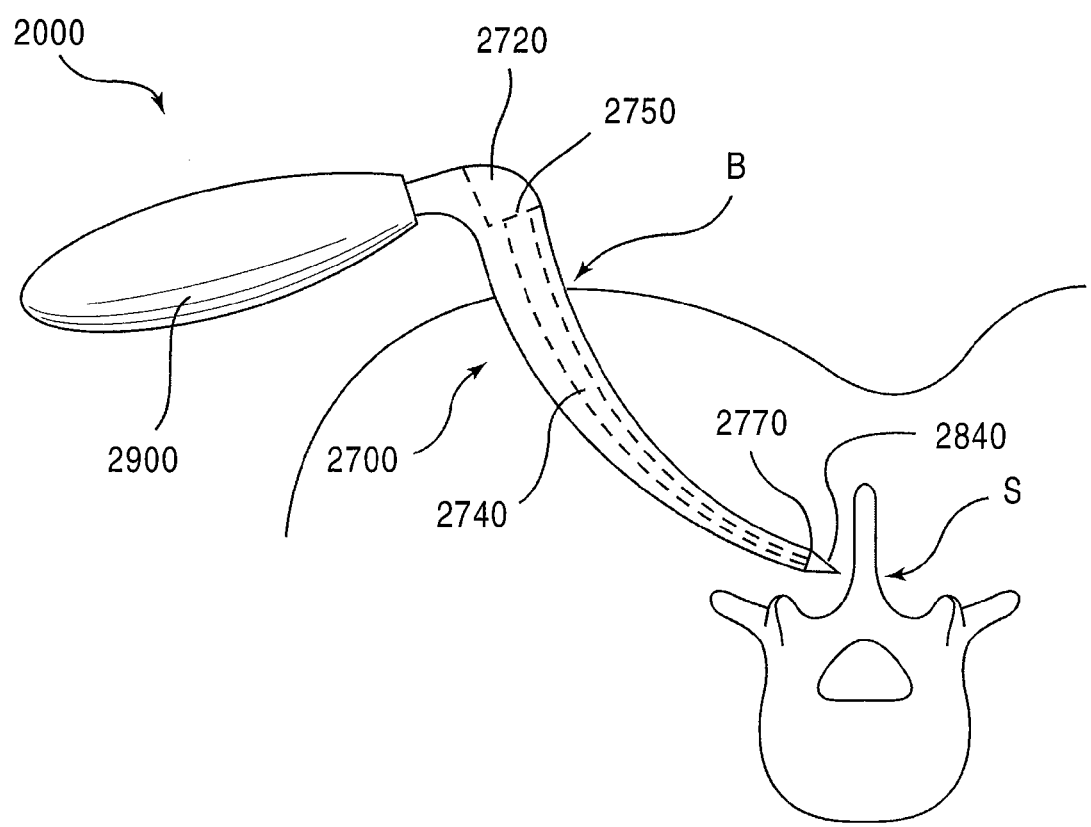
FIG. 47 is a side plan view of a medical device according to another embodiment of the invention.

A medical device 2000 according to an embodiment of the invention is illustrated in FIG. 47. Medical device 2000 includes a handle 2900 coupled to an arm 2700. The arm 2700 has a first end 2750 and a second end 2770 and defines an opening 2740 along its length. A working tool 2840 can be received within opening 2740 adjacent the second end 2770. The arm 2700 also includes a recess 2720 to receive a retainer (not illustrated) similar to retainer 1850 discussed above. Medical device 2000 is inserted between adjacent spinous process in a manner similar to swing arm 1700 discussed above. The depth and placement of the arm 2700, however is determined by the user of the medical device 2000. Such a medical device can be used with or without the benefit of the clamps 1100, 1200 discussed above. In other words, the medical device 2000 can be inserted between adjacent spinous processes S without first separating the spinous processes S.

Figure 48:
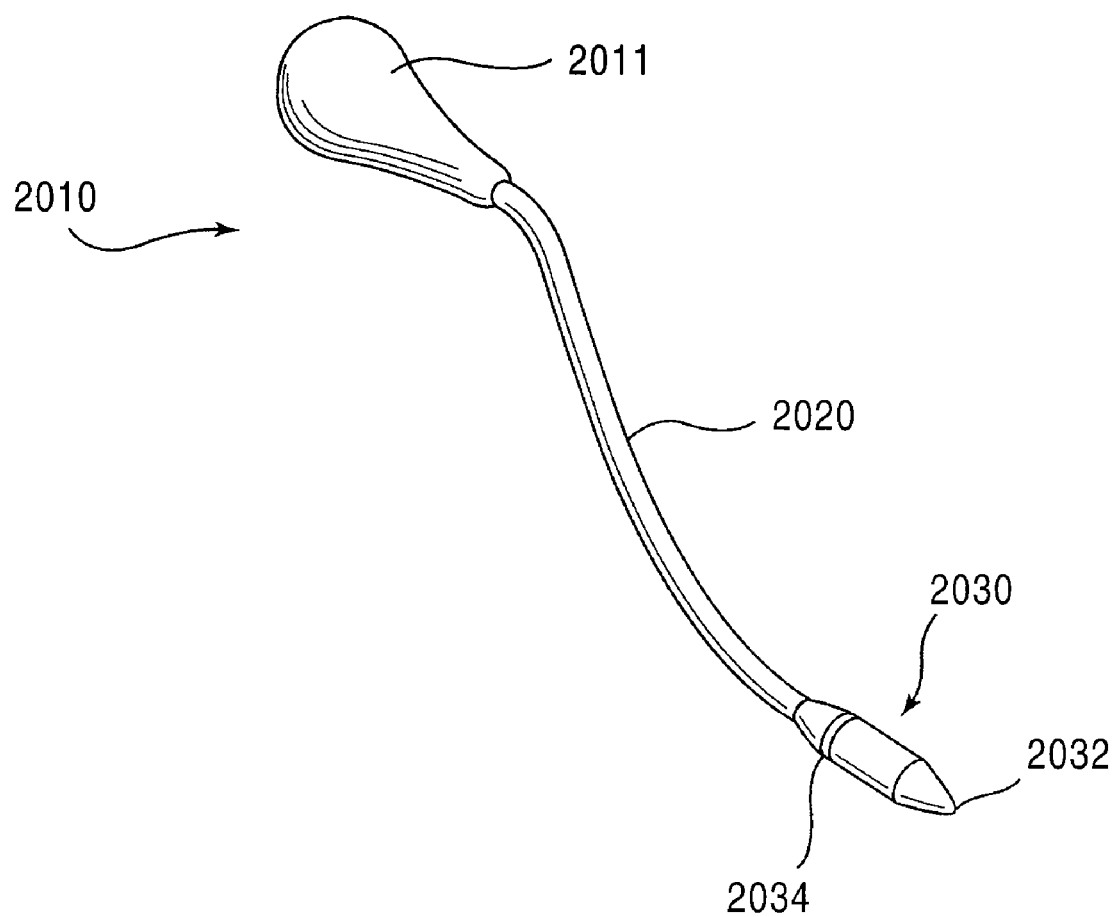
FIG. 48 is a perspective view of a medical device according to another embodiment of the invention.
Figures 50, 51, 52:
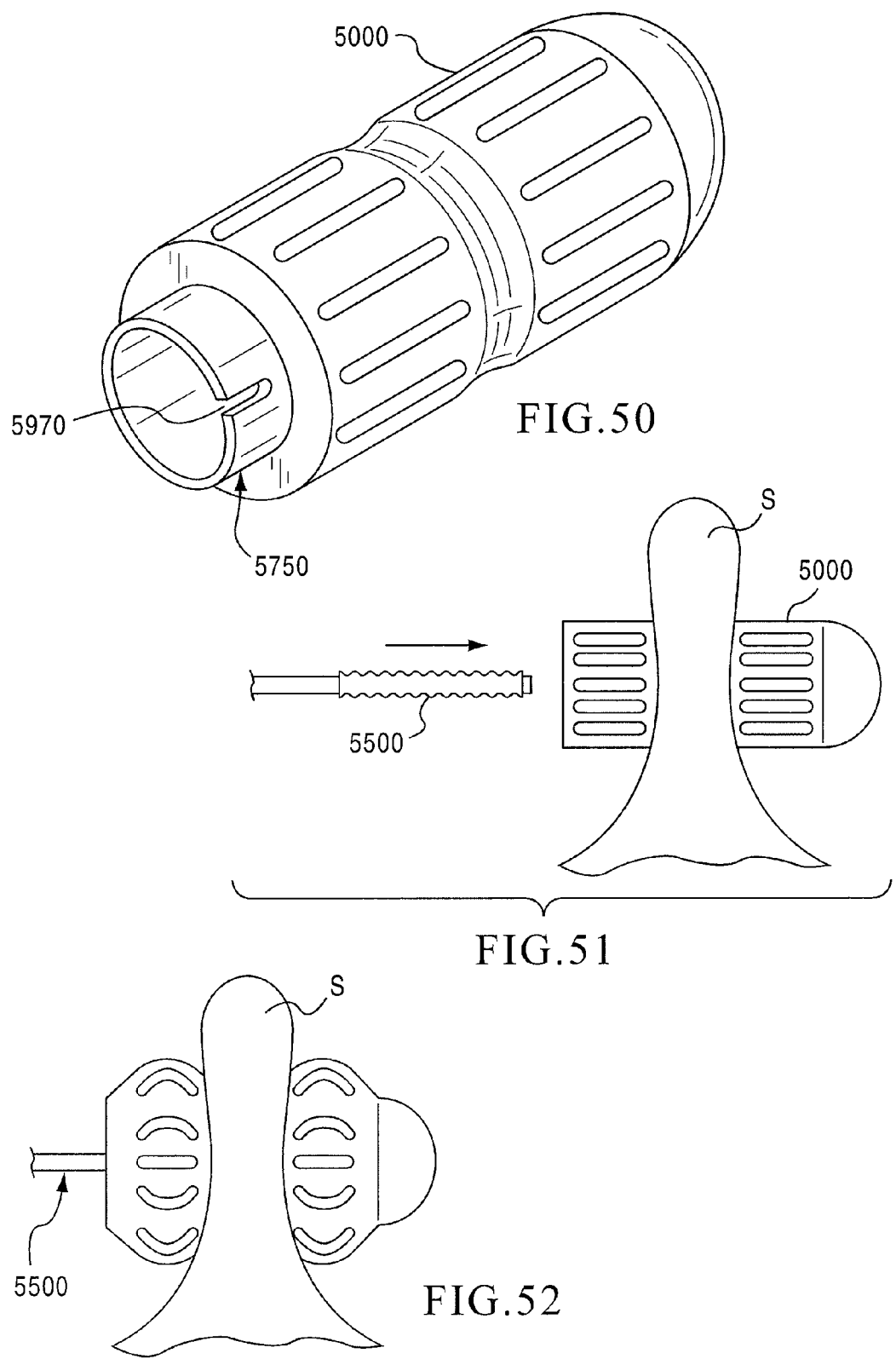
FIG. 50 is a perspective view of a spacer configured to be inserted between adjacent spinous processes according to an embodiment of the invention.
FIG. 51 is a side view of a spacer according to an embodiment of the invention in a first configuration inserted between adjacent spinous processes.
FIG. 52 is a side view of the spacer illustrated in FIG. 49 in a second configuration inserted between adjacent spinous processes.
Figures 53, 54:
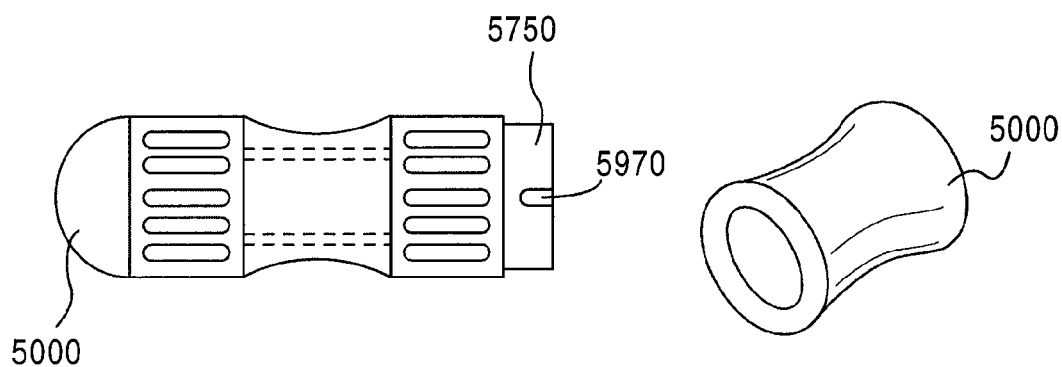
FIGS. 53-55 are illustrations of spacers according to alternative embodiments of the invention.
Figure 55:
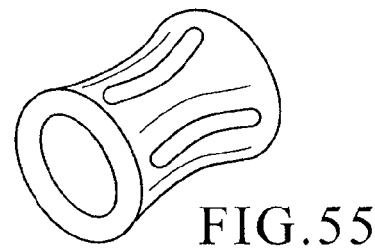
Figure 56:
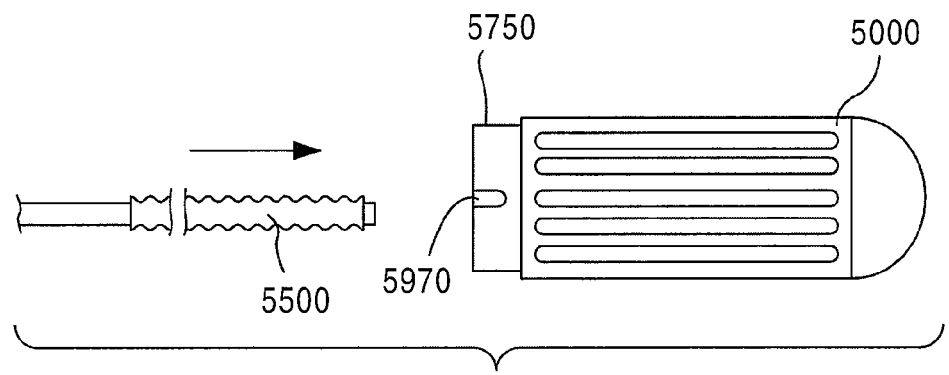
FIG. 56 is a side view of a spacer according to an alternative embodiment of the invention in a first configuration.
Figure 57:
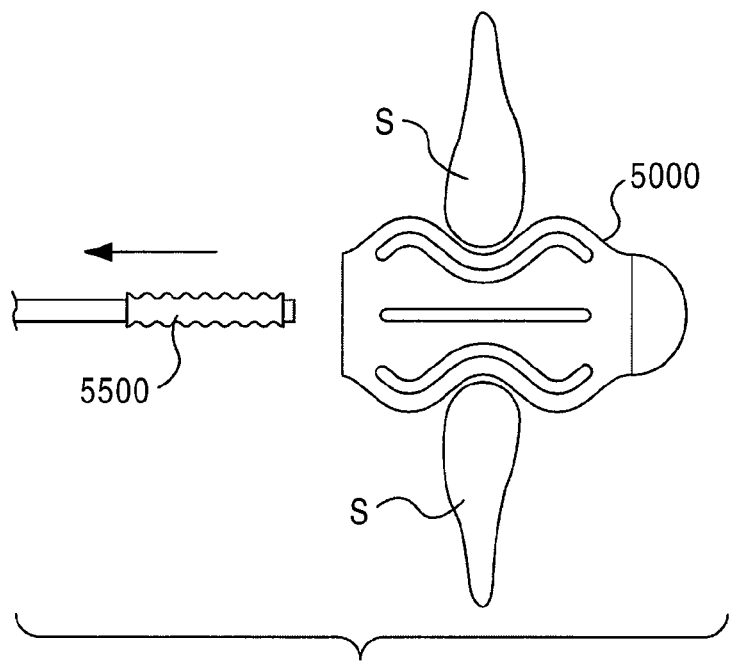
FIG. 57 is a side view of the spacer illustrated in FIG. 56 in a second configuration inserted between adjacent spinous processes.
Figure 58:
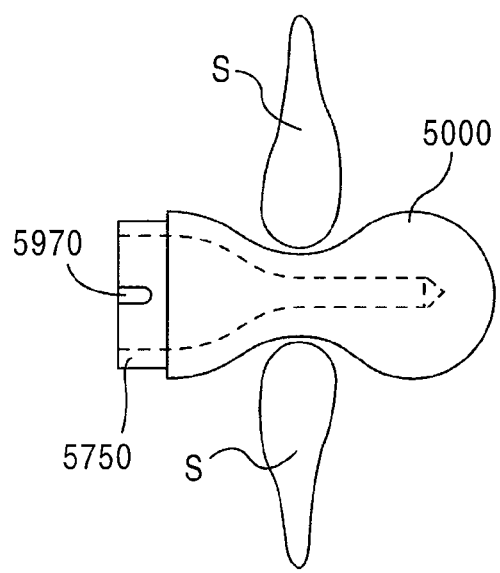
FIG. 58 is a side view of a spacer according to a further alternative embodiment of the invention inserted between adjacent spinous processes.
Figure 59:
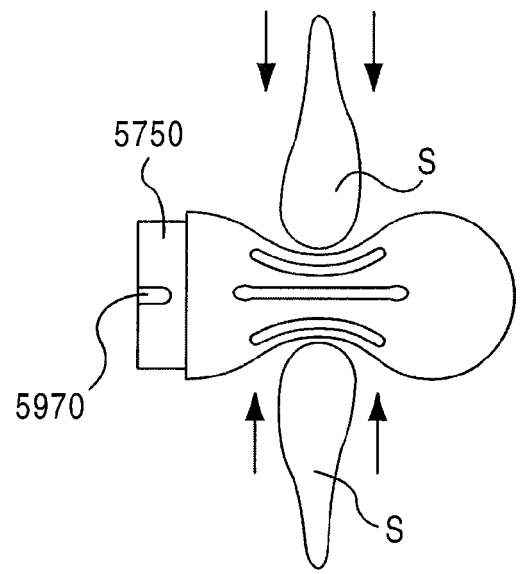
FIG. 59 is a side view of a spacer according to another alternative embodiment of the invention inserted between adjacent spinous processes.

A medical device according to another embodiment of the invention is illustrated in FIG. 48. Medical device 2010 is a distraction tool having a handle 2011, a curved shaft 2020 and a distraction portion 2030. The distraction portion 2030 includes a pointed tip 2032 and an insertion position indicator 2034. The medical device 2010 is inserted into a patient's back and moved in between adjacent spinous processes from the side of the spinous processes (i.e., a posterior-lateral approach). The configuration of the curved shaft 2020 assists in the use of a lateral approach to the spinous processes. The distraction portion 2030 defines a path through the patient's tissue and between the adjacent spinous processes.

The position indicator 2034 can be a physical ridge or detent such that the physician can identify through tactile sensation when the medical device 2010 has been inserted an appropriate distance (e.g., when the position indicator 2034 engages the spinous processes). The position indicator 2034 can alternatively be a radioopaque strip that can be imaged using a fluoroscope. As a further alternative, multiple fluoroscopic markings (not illustrated) can be placed on the shaft 2020 within the distraction portion 2030. The markings can be imaged to determine the spacing between the spinous processes and/or the position of the distraction portion 2030 relative to the spinous processes. Once the spinous processes are adequately distracted, the medical device 2010 is removed. After the medical device 2010 is removed, an implant (not illustrated in FIG. 48) is positioned between spinous processes using an insertion tool to limit the minimum distance between the spinous processes during their range of motion.

An alternative swing arm 1700" for use with medical device 100 according to an embodiment of the invention is illustrated in FIGS. 49a-49c. As best seen in FIGS. 49a and 45c, the second end 1770" of swing arm 1700" is configured to receive a working tool 1840", such as, for example, a pointed trocar tip. The swing arm 1700" defines an opening 1740" in which at least a portion of the working tool 1840" is received. In some embodiments, the opening 1740" extends along the entire length of the swing arm 1700" between the first end 1750" and the second end 1770" to define a passageway or lumen. The opening 1740" is slightly larger than the diameter of the working tool 1840" such that the working tool 1840" is positioned within the opening 1740" during use.

The working tool 1840" is coupled to a wire 1860". The wire 1860" has a first end 1810" and a second end 1830". The second end 1830" of the wire 1860" is coupled to the working tool 1840". A retainer 1820" (discussed in detail below) is coupled to the first end 1810" of the wire 1860" and is configured to maintain the position of the working tool 1840" with respect to the swing arm 1700". In some embodiments, the wire 1860" is substantially rigid such that the working tool 1840" is not retracted into the opening 1740" when force is imparted against the working tool 1840".

The retainer 1820" is received in a recess 1720" in the swing arm 1700". The retainer 1820" is maintained in the recess 1720" using threaded fasteners 173". In some alternative embodiments, the wire 1860" does not extend through the opening 1740" of the swing arm 1700". In yet other alternative embodiments, the wire 1860" is not present.

FIGS. 50-59 illustrate various spacers 5000 that can be inserted between adjacent spinous processes S. Once the spacer 5000 is inserted between the spinous processes S, depending upon the type of spacer 5000, the spacer 5000 can be deformed to be held in place. For example, in some embodiments, a balloon actuator 5500 can be inserted into the spacer and expanded, thereby expanding the ends of the spacer 5000 to retain the spacer 5000 between the spinous processes S (see, e.g., FIGS. 50, 52 and 56). Once the spacer 5000 is expanded, the balloon actuator 5500 can be deflated and removed (see, e.g., FIG. 57).

In some embodiments of the invention, the spacer 5000 includes an end portion 5750 that includes a recess 5970 that is configured to mate with the projection 1920 on swing arm 1700' (see FIG. 46).

In another embodiment, a method includes percutaneously inserting into a body an expandable member having a first configuration, a second configuration and a third configuration. The expandable member includes a support portion and a retention portion. The support portion has a longitudinal axis and is configured to be disposed between adjacent spinous processes. The retention portion is configured to limit movement of the support portion along the longitudinal axis. When the expandable member is in the first configuration, it is disposed in a first location between the adjacent spinous processes. The expandable member is then expanded from the first configuration to the second configuration. The expandable member is then contracted from the second configuration to the third configuration and disposed in a second location, the second location being different from the first location.

In some embodiments, an apparatus includes an expandable member having a support portion, a retention portion, a first configuration, and a second configuration. The support portion has a longitudinal axis and is configured to be disposed between adjacent spinous processes. The retention portion is disposed adjacent to the support portion and is configured to limit movement of the support portion along the longitudinal axis. When in the first configuration, the expandable member has a first volume. When in the second configuration, the expandable member has a second volume, the second volume being greater than the first volume. The expandable member is configured to move from the first configuration to the second configuration and to move from the second configuration to the first configuration.

In some embodiments, the apparatus includes a sensor coupled to the expandable member. The sensor can be, for example, a strain gauge sensor or a piezoelectric sensor that measures a force applied to the expandable member and/or a pressure of a fluid within the expandable member.

In some embodiments, an apparatus includes a substantially rigid support member, a first expandable member and a second expandable member. The support member is configured to be disposed between adjacent spinous processes. The first expandable member is coupled to a proximal portion of the support member and has a first configuration in which it has a first volume and a second configuration in which it has a second volume, which is greater than the first volume. Similarly, the second expandable member is coupled to a distal portion of the support member and has a first configuration in which it has a first volume and a second configuration in which it has a second volume, which is greater than the first volume.

Figure 60A:
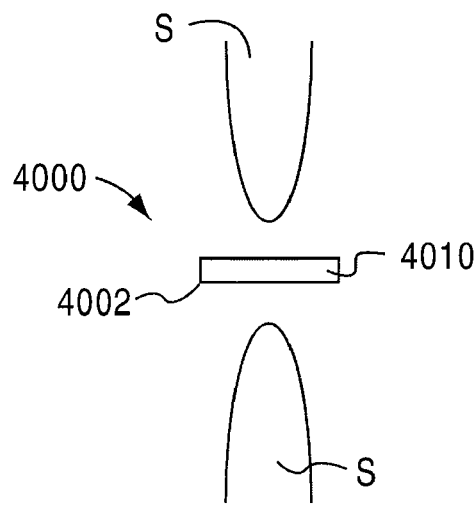
FIGS. 60A-60D are schematic illustrations of a posterior view of a medical device according to an embodiment of the invention in a first configuration (FIG. 60A), a second (FIGS. 60B and 60D) configuration and a third configuration (FIG. 60C).
Figure 60B:
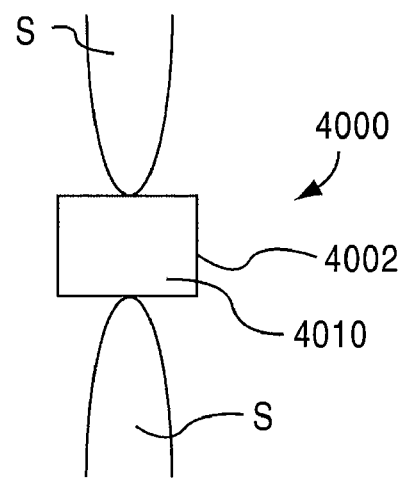
Figure 60C:
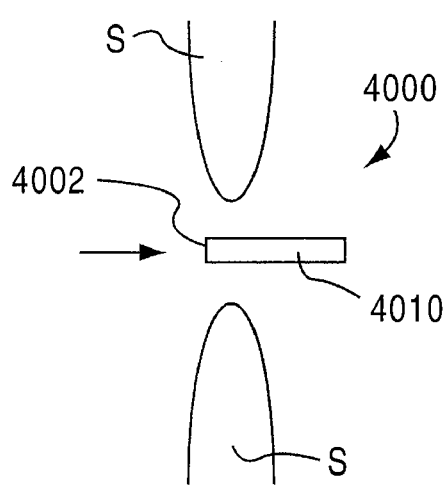

FIGS. 60A-60D are schematic illustrations of a posterior view of a medical device 4000 according to an embodiment of the invention positioned adjacent two adjacent spinous processes S in a first configuration (FIG. 60A), a second configuration (FIGS. 60B and 60D) and a third configuration (FIG. 60C). The medical device 4000 includes an expandable member 4002 having an inner area (not shown) and an outer surface 4010. The outer surface 4010 is configured to be disposed between the spinous processes S to prevent over-extension/compression of the spinous processes S. In some embodiments, the expandable member 4002 distracts the adjacent spinous processes S. In other embodiments, the expandable member 4002 does not distract the adjacent spinous processes S.

Figure 60D:
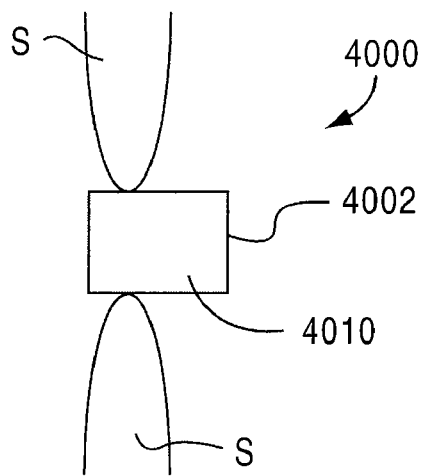

The expandable member 4002 has a first configuration, a second configuration and a third configuration. When in each configuration, the expandable member 4002 has an associated volume. As illustrated in FIG. 60A, the first configuration represents a substantially contracted condition in which the expandable member 4002 has a minimal volume. When the expandable member 4002 is in the first configuration, the medical device 4000 is inserted between the adjacent spinous processes S. As illustrated in FIGS. 60B and 60D, the second configuration represents an expanded condition in which the expandable member 4002 has a large volume. When the expandable member 4002 is in the second configuration, the outer surface 4010 of the medical device 4000 contacts the adjacent spinous processes S during at least a portion of the range of motion of the spinous processes. As illustrated in FIG. 60C, the third configuration represents a partially expanded condition in which the expandable member 4002 has a volume between that associated with the first configuration and that associated with the second configuration. When the expandable member 4002 is in the third configuration, the medical device 4000 can be repositioned between the adjacent spinous processes, as indicated by the arrow in FIG. 60C. The medical device can then be subsequently re-expanded into the second configuration, as illustrated in FIG. 60D.

Figure 61A:
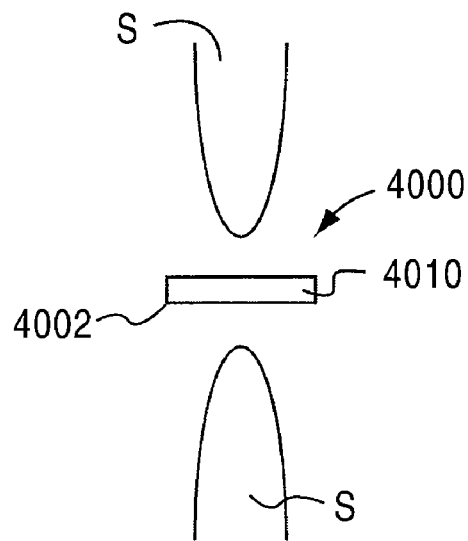
FIGS. 61A-61C are schematic illustrations of a posterior view of a medical device according to an embodiment of the invention in a first configuration, a second configuration and a third configuration, respectively.
Figure 61B:
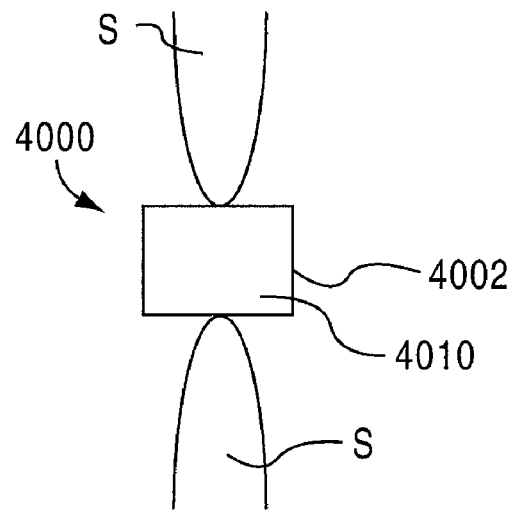
Figure 61C:
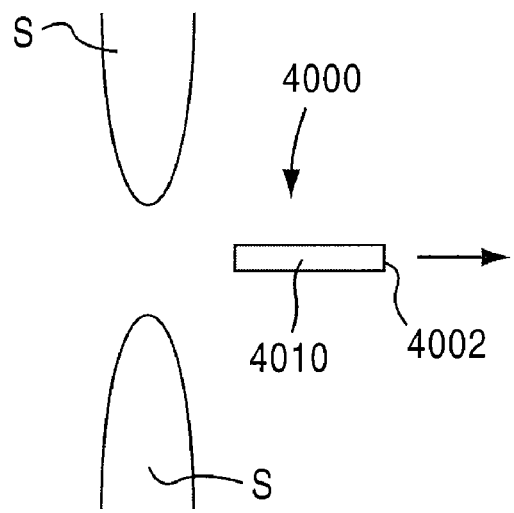

FIGS. 61A-61C are schematic illustrations of a posterior view of the medical device 4000 positioned adjacent two adjacent spinous processes S in a first configuration, a second configuration and a third configuration, respectively. As described above, when the expandable member 4002 is in the first configuration, the medical device 4000 is inserted between the adjacent spinous processes S. The expandable member 4002 is then expanded to the second configuration, in which the outer surface 4010 of the medical device 4000 is disposed between the adjacent spinous processes S. The expandable member 4002 is then contracted to the third configuration to facilitate removal of the medical device 4000, as shown in FIG. 61C. In some embodiments, the third configuration can be the same as the first configuration.

In use, the adjacent spinous processes S can be distracted prior to inserting the medical device 4000 into a body. Distraction of spinous processes described herein. When the spinous processes S are distracted, a trocar (not shown) can be used to define an access passageway (not shown) for the medical device 4000. In some embodiments, the trocar can be used to define the passage as well as to distract the spinous processes S. Once an access passageway is defined, the medical device 4000 is inserted percutaneously and advanced between the spinous processes S and placed in the desired position between the adjacent spinous processes S. Once the medical device 4000 is in the desired position, the expandable member is expanded to the second condition, causing the outer surface 4010 to engage the spinous processes S.

In some embodiments, the adjacent spinous processes can be distracted by a first expandable member (not shown) configured to distract bone. Upon distraction, the first expandable member is contracted and removed from the body. The medical device 4000 is then inserted percutaneously, advanced between the spinous processes S, placed in the desired position and expanded, as described above.

In some embodiments, the medical device 4000 is inserted percutaneously (i.e., through an opening in the skin) and in a minimally-invasive manner. For example, as discussed in detail herein, the overall sizes of portions of the medical device 4000 are increased by transitioning the expandable member 4002 from the first configuration to the second configuration after the medical device 4000 is inserted between the adjacent spinous processes S. When in the expanded second configuration, the sizes of portions of the medical device 4000 are greater than the size of the opening. For example, the size of the opening/incision in the skin can be between 3 millimeters in length and 25 millimeters in length across the opening. In some embodiments, the size of the medical device 4000 in the expanded second configuration is between 3 and 25 millimeters across the opening.

Figure 62A:
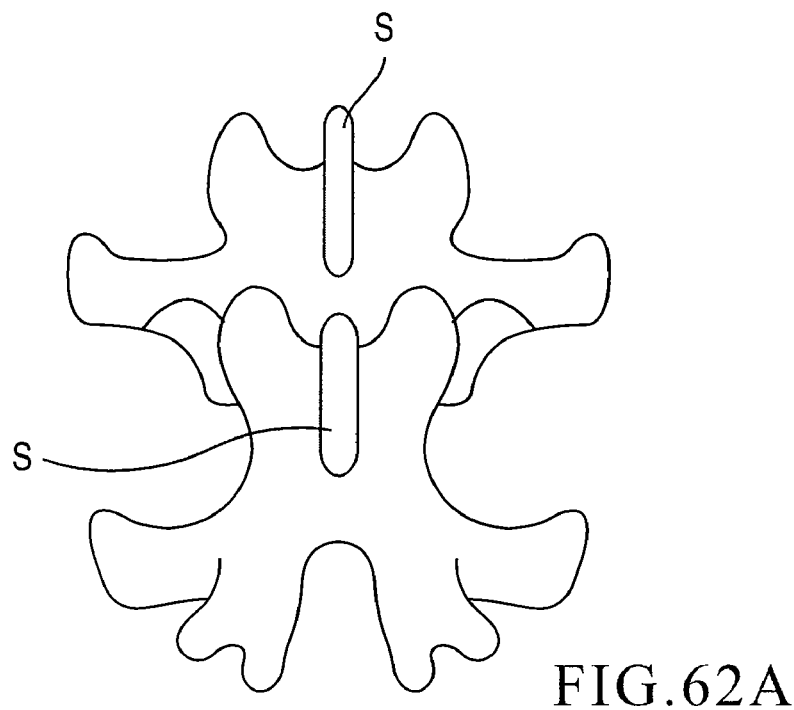
FIGS. 62A-62F are posterior views of a medical device according to an embodiment of the invention inserted between adjacent spinous processes in a first lateral positions and a second lateral position.
Figure 62B:
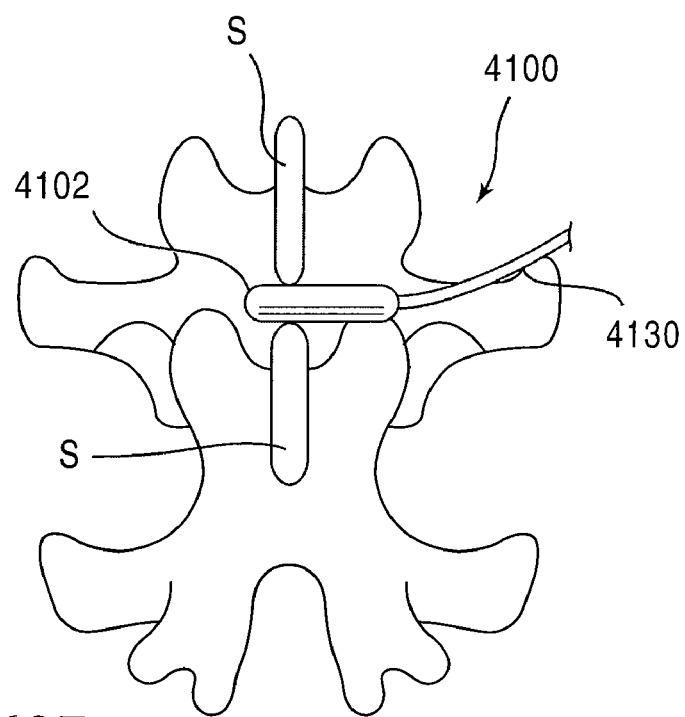
Figure 62C:
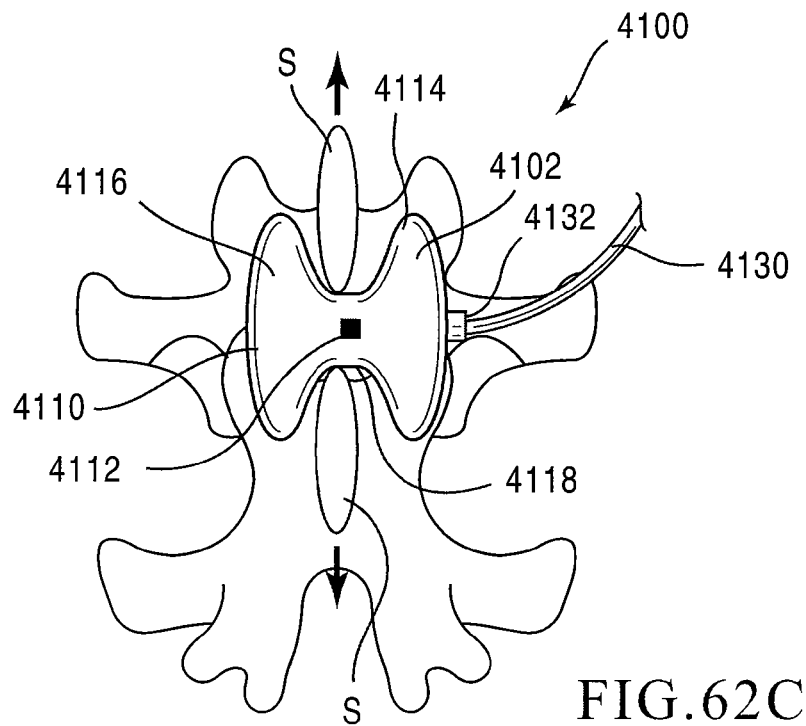
Figure 62D:
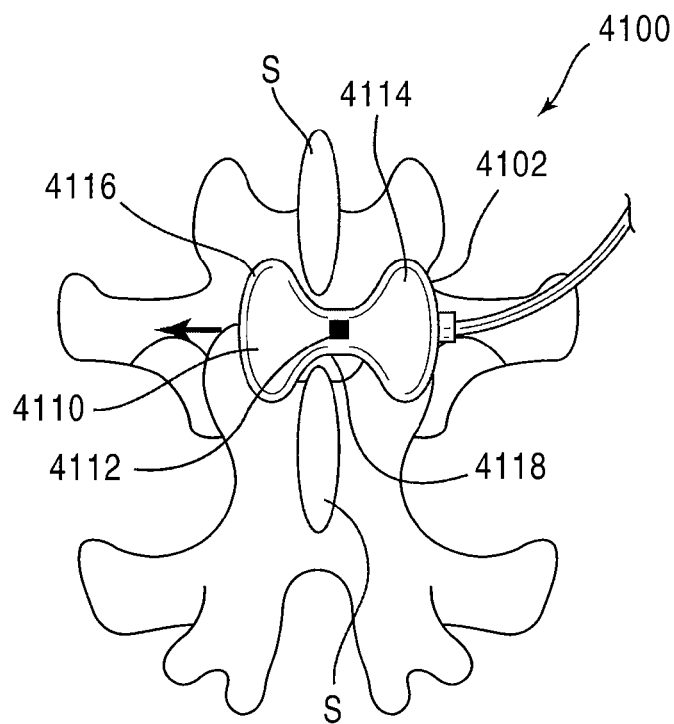
Figure 62E:
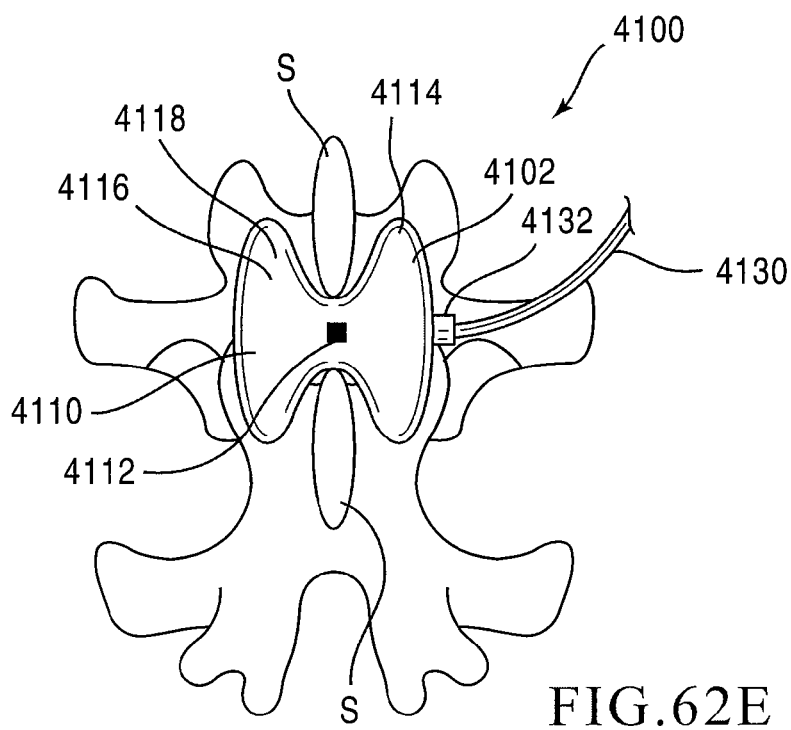

FIGS. 62A-62F are posterior views of a spinal implant 4100 according to an embodiment of the invention inserted between adjacent spinous processes S in a first lateral position (FIG. 62C) and a second lateral position (FIG. 62E). The spinal implant 4100 includes an expandable member 4102, a sensor 4112 and a valve 4132. The expandable member 4102 has an inner area (not shown), an outer surface 4110, a support portion 4118, a proximal retention portion 4114 and a distal retention portion 4116. The expandable member 4102 is repeatably positionable in a first configuration (FIG. 62B), a second configuration (FIGS. 62C, 62E and 62F) and a third configuration (FIG. 62D). When in each configuration, the expandable member 4102 has an associated volume, as will be discussed below.

In use, the spinal implant 4100 is positioned in the substantially contracted first configuration during insertion and/or removal (see FIG. 62B). As discussed above, the spinal implant 4100 is inserted percutaneously between adjacent spinous processes S. The distal retention portion 4116 of the expandable member 4102 is inserted first and is moved past the spinous processes S until the support portion 4118 is positioned between the spinous processes S. When in the first configuration, the support portion 4118 can be can be sized to account for ligaments and tissue surrounding the spinous processes S. For purposes of clarity, such surrounding ligaments and tissue are not illustrated.

As illustrated in FIG. 62C, once in position, the expandable member 4102 is expanded into the second configuration by conveying a fluid (not shown) from an area outside of the expandable member 4102 to the inner area of the expandable member 4102. The fluid is conveyed by an expansion tool 4130, such as a catheter, that is matingly coupled to the valve 4132. The valve 4132 can be any valve suitable for sealably connecting the inner area of the expandable member 4102 to an area outside of the expandable member 4102. For example, in some embodiments, the valve 4132 can be, for example a poppet valve, a pinch valve or a two-way check valve. In other embodiments, the valve includes a coupling portion (not shown) configured to allow the expansion tool 4130 to be repeatably coupled to and removed from the valve 4132. For example, in some embodiments, the valve 4132 can include a threaded portion configured to matingly couple the expansion tool 4130 and the valve 4132.

The fluid is configured to retain fluidic properties while resident in the inner area of the expandable member 4102. In this manner, the spinal implant 4100 can be repeatably transitioned from the expanded second configuration to the first configuration and/or the third configuration by removing the fluid from the inner area of the expandable member 4102. In some embodiments, the fluid can be a biocompatible liquid having constant or nearly constant properties. Such liquids can include, for example, saline solution. In other embodiments, the fluid can be a biocompatible liquid configured to have material properties that change over time while still retaining fluidic properties sufficient to allow removal of the fluid. For example, the viscosity of a fluid can be increased by adding a curing agent or the like. In this manner, the fluid can provide both the requisite structural support while retaining the ability to be removed from the inner area of the expandable member 4102 via the valve 4132. In yet other embodiments, the fluid can be a biocompatible gas.

The outer surface 4110 of the support portion 4118 can distract the adjacent spinous processes S as the expandable member 4102 expands to the second configuration, as indicated by the arrows shown in FIG. 62C. In some embodiments, the support portion 4118 does not distract the adjacent spinous processes S. For example, as discussed above, the adjacent spinous processes S can be distracted by a trocar and/or any other device suitable for distraction.

When in the second configuration, the outer surface 4110 of the support portion 4118 is configured to engage the spinous processes S for at least a portion of the range of motion of the spinous processes S to prevent over-extension/compression of the spinous processes S. In some embodiments, the engagement of the spinous processes S by the outer surface 4110 of the support portion 4118 is not continuous, but occurs upon spinal extension.

When in the second configuration, the proximal retention portion 4114 and the distal retention portion 4116 each have a size S1 (shown in FIG. 63) that is greater than the vertical distance D1 (shown in FIG. 63) between the spinous processes. In this manner, the proximal retention portion 4114 and the distal retention portion 4116 are disposed adjacent the sides of spinous processes S (i.e., either through direct contact or through surrounding tissue), thereby limiting movement of the spinal implant 4100 laterally along a longitudinal axis of the support portion 4118.

The expandable member 4102 can be made from any number of biocompatible materials, such as, for example, PET, Nylons, cross-linked Polyethylene, Polyurethanes, and PVC. In some embodiments, the chosen material can be substantially inelastic, thereby forming a low-compliant expandable member 4102. In other embodiments, the chosen material can have a higher elasticity, thereby forming a high-compliant expandable member 4102. In yet other embodiments, the expandable member 4102 can be made from a combination of materials such that one portion of the expandable member 4102, such as the support portion 4118, can be low-compliant while other portions of the expandable member 4102, such as the proximal retention portion 4114 and/or distal retention portion 4116 are more highly compliant. In yet other embodiments, a portion of the expandable member 4102 can include a rigid, inflexible material to provide structural stiffness. For example, the support portion 4118 can be constructed of a composite material that includes a rigid, inflexible material to facilitate distraction of the adjacent spinous processes.

In some embodiments, the expandable member 4102 includes a radiopaque material, such as bismuth, to facilitate tracking the position of the spinal implant 4100 during insertion and/or repositioning. In other embodiments, the fluid used to expand the expandable member 4102 includes a radiopaque tracer to facilitate tracking the position of the spinal implant 4100.

In the illustrated embodiment, the spinal implant 4100 includes a sensor 4112 coupled to the expandable member 4102. In some embodiments, the sensor 4112 is a strain gauge sensor that measures a force applied to the support portion 4118 of the expandable member 4102. The sensor 4112 can include multiple strain gauges to facilitate measuring multiple force quantities, such as a compressive force and/or a tensile force. In other embodiments, the sensor 4112 is a variable capacitance type pressure sensor configured to measure a force and/or a pressure of the fluid contained within the inner portion of the expandable member 4102. In yet other embodiments, the sensor 4112 is a piezoelectric sensor that measures a pressure of the fluid contained within the inner portion of the expandable member 4102. In still other embodiments, the spinal implant 4100 can include multiple sensors 4112 located at various locations to provide a spatial profile of the force and/or pressure applied to the expandable member 4102. In this manner, a practitioner can detect changes in the patient's condition, such those that may result in a loosening of the spinal implant 4100.

In some embodiments, the sensor 4112 can be remotely controlled by an external induction device. For example, an external radio frequency (RF) transmitter (not shown) can be used to supply power to and communicate with the sensor 4112. In other embodiments, an external acoustic signal transmitter (not shown) can be used to supply power to and communicate with the sensor 4112. In such an arrangement, for example, the sensor can include a pressure sensor, of the types described above, for measuring a pressure; an acoustic transducers, and an energy storage device. The acoustic transducer converts energy between electrical energy and acoustic energy. The energy storage device stores the electrical energy converted by the acoustic transducer and supplies the electrical energy to support the operation of the pressure sensor. In this manner, acoustic energy from an external source can be received and converted into electrical energy used to power the pressure sensor. Similarly, an electrical signal output from the pressure sensor can be converted into acoustic energy and transmitted to an external source.

Figure 62F:
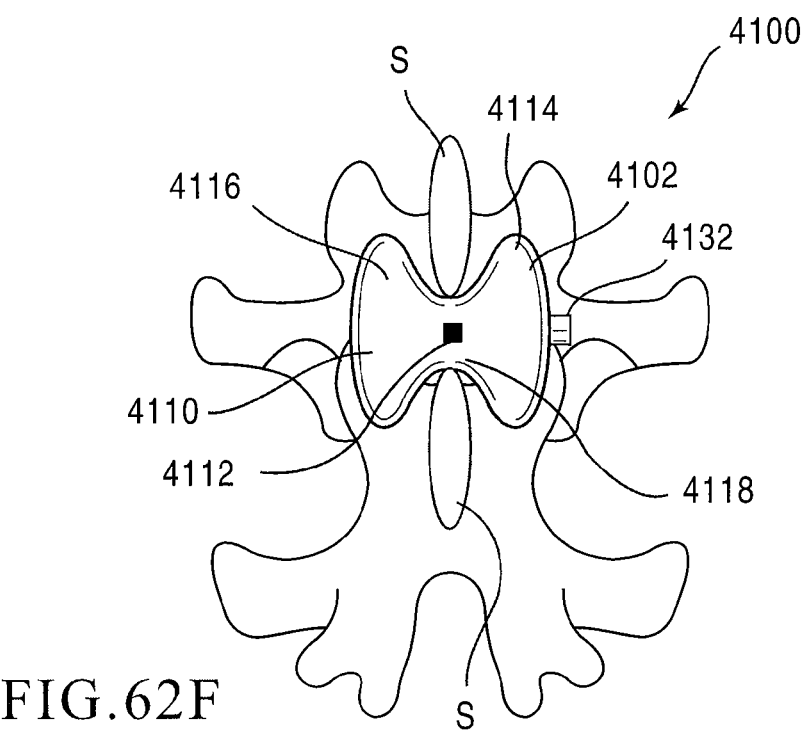

At times, the spinal implant 4100 may need to be repositioned. Such repositioning can be required, for example, to optimize the lateral position of the support portion 4118 during the insertion process. In other instances, the spinal implant 4100 can require repositioning subsequent to the insertion process to accommodate changes in the conditions of the patient. In yet other instances, the spinal implant 4100 can be removed from the patient. To allow for such repositioning and/or removal, the spinal implant is repeatably positionable in the first configuration, the second configuration and/or the third configuration. In FIG. 62D, for example, the expandable member 4102 is contracted to the third configuration by removing all or a portion of the fluid contained in the inner area, as described above. In this manner, the spinal implant 4100 can be repositioned in a lateral direction, as indicated by the arrow. Once in the desired position, the expandable member is reexpanded to the second condition as described above. Finally, as shown in FIG. 62F, the expansion tool 4130 is removed from the valve 4132.

Figure 63:
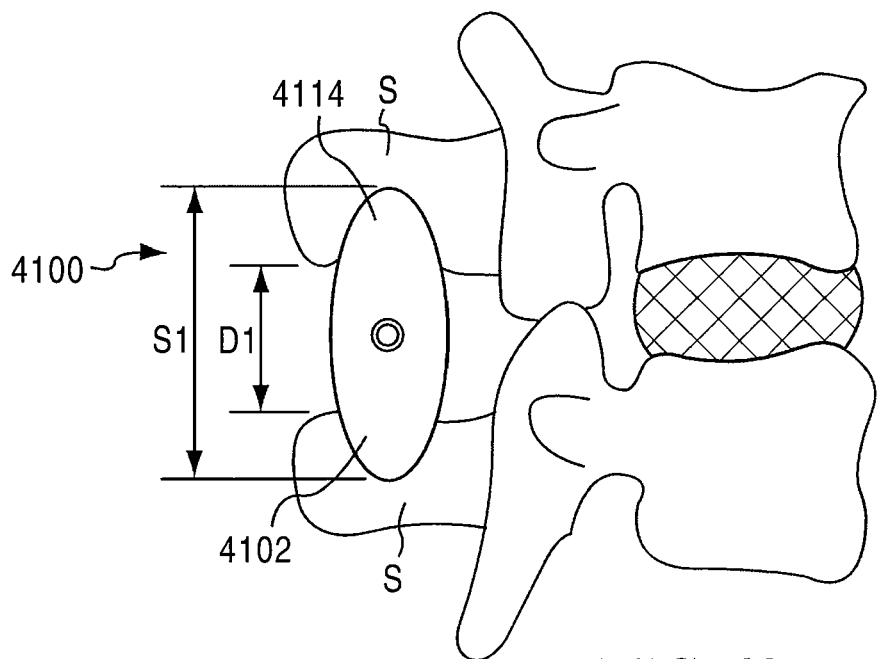
FIG. 63 is a lateral view of the medical device illustrated in FIGS. 62A-62F inserted between adjacent spinous processes in a second configuration.

FIG. 63 is a lateral view of the spinal implant 4100 illustrated in FIGS. 62A-62F inserted between adjacent spinous processes S in a second configuration. Although FIG. 63 only shows the proximal retention portion 4114 of the expandable member 4102, it should be understood that the distal retention portion 4116 has characteristics and functionality similar to those described below for proximal retention portion 4114. As illustrated, the proximal retention portion 4114 has a size S1 that is greater than the vertical distance D1 between the spinous processes S. In this manner, the proximal retention portion 4114 and the distal retention portion 4116 limit the lateral movement of the spinal implant 4100 when in the second configuration, as discussed above.

Figure 64:
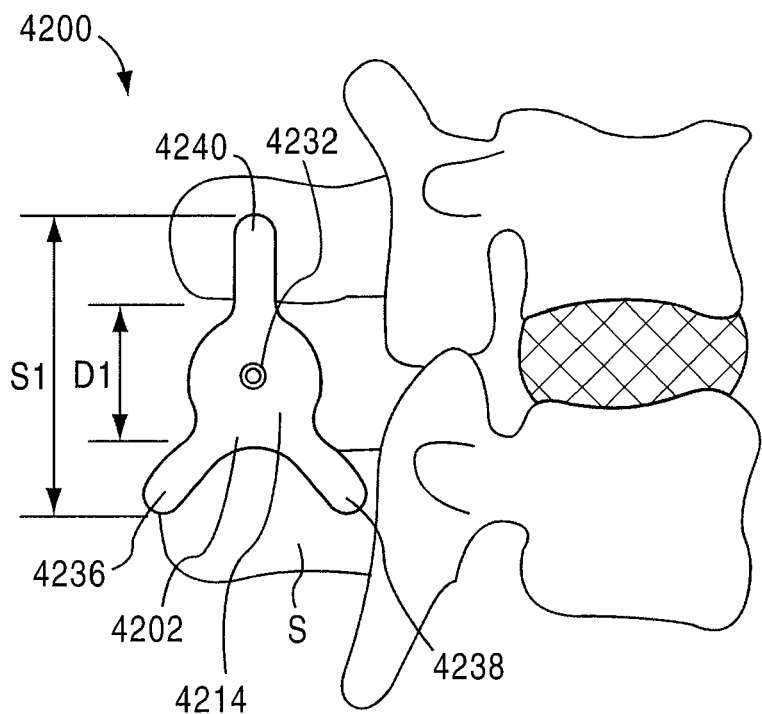
FIG. 64 is a lateral view of a medical device according to an embodiment of the invention inserted between adjacent spinous processes in a second configuration.

FIG. 64 is a lateral view of a spinal implant 4200 according to an embodiment of the invention inserted between adjacent spinous processes and in a second configuration. Similar to the spinal implant 4100 discussed above, the spinal implant 4200 includes an expandable member 4202 and a valve 4232. The expandable member 4202 has a support portion (not shown), a proximal retention portion 4214 and a distal retention portion (not shown). The expandable member 4202 is repeatably positionable in a first configuration, a second configuration and/or a third configuration. When in each configuration, the expandable member 4202 has an associated volume, as discussed above.

In the illustrated embodiment, the proximal retention portion 4214 of the expandable member 4202 has a first radial extension 4236, a second radial extension 4238 and a third radial extension 4240. As illustrated, the distance S1 between the ends of the radial extensions is greater than the vertical distance D1 between the spinous processes S. In this manner, the proximal retention portion 4214 and the distal retention portion limit the lateral movement of the spinal implant 4200 when in the second configuration. In some embodiments, the proximal retention portion and the distal retention portion can assume a variety of different shapes.

Figure 65A:
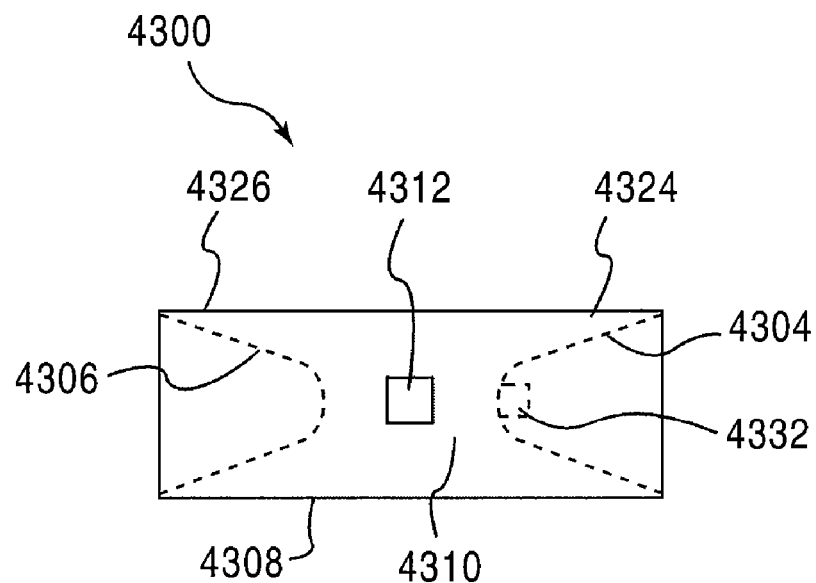
FIGS. 65A and 65B are front views of a medical device according to an embodiment of the invention in a first configuration and a second configuration, respectively.
Figure 65B:
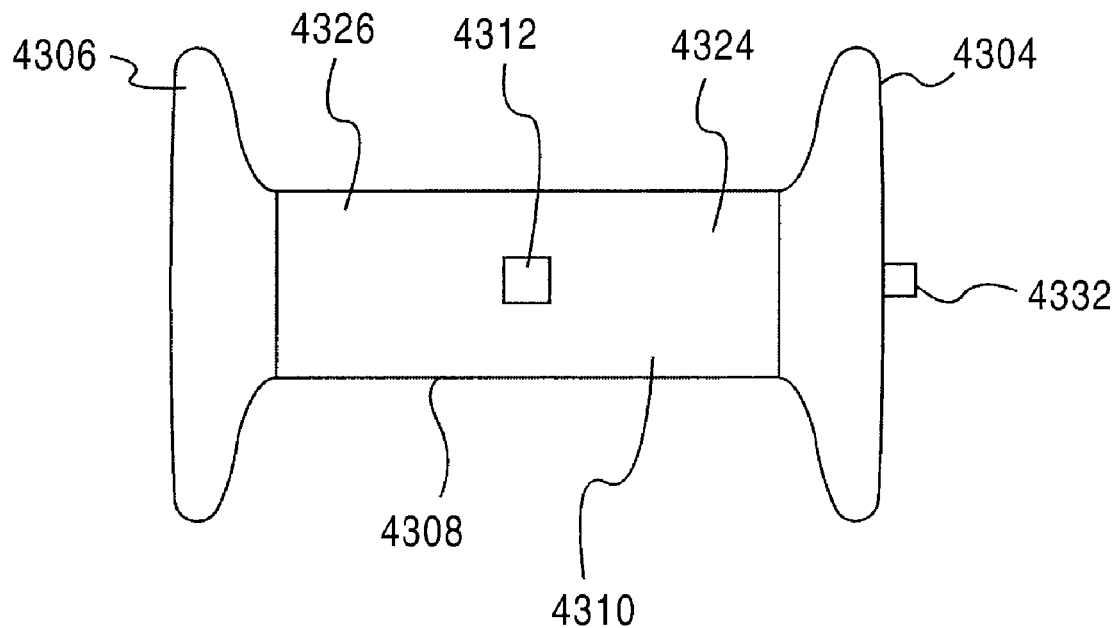

FIGS. 65A and 65B are front views of a spinal implant 4300 according to an embodiment of the invention in a first configuration and a second configuration, respectively. The spinal implant 4300 includes a proximal expandable member 4304, a distal expandable member 4306, a support member 4308, a sensor 4312 and a valve 4332. The support member 4308 has an inner area (not shown) and an outer surface 4310. The outer surface 4310 is configured to contact the spinous processes (not shown). In some embodiments, the support member 4308 distracts the adjacent spinous processes. In other embodiments, the support member 4308 does not distract the adjacent spinous processes. In yet other embodiments, the engagement of the spinous processes by the support member 4308 is not continuous, but occurs upon spinal extension.

The support member 4308 has a proximal portion 4324, to which the proximal expandable member 4304 is coupled, and a distal portion 4326, to which the distal expandable member 4306 is coupled. The proximal expandable member 4304 and the distal expandable member 4306 are each repeatably positionable in a first configuration (FIG. 65A) and a second configuration (FIG. 65B). As described above, the first configuration represents a substantially contracted condition in which the proximal expandable member 4304 and the distal expandable member 4306 each have a minimal volume. When the spinal implant 4300 is in the first configuration, it can be inserted, repositioned and/or removed. In the illustrated embodiment, the proximal expandable member 4304 and the distal expandable member 4306 are each contained within the inner area of the support member 4308 when the spinal implant 4300 is in the first configuration. In some embodiments, the proximal expandable member 4304 and the distal expandable member 4306 are not contained within the support member 4308.

Conversely, the second configuration represents an expanded condition in which the proximal expandable member 4304 and the distal expandable member 4306 each have a large volume. When the spinal implant 4300 is in the second configuration, the proximal expandable member 4304 and the distal expandable member 4306 each have a size that is greater than the vertical distance between the spinous processes, as described above. In this manner, the proximal expandable member 4304 and the distal expandable member 4306 engage the spinous processes, thereby limiting the lateral movement of the spinal implant 4300.

The proximal expandable member 4304 and the distal expandable member 4306 are expanded into the second configuration by conveying a fluid (not shown) from an area outside of each expandable member 4304, 4306 to an inner area defined by each expandable member 4304, 4306. The fluid is conveyed through a valve 4332, as described above. In the illustrated embodiment, the inner area of the proximal expandable member 4304, the inner area of the distal expandable member 4306 and the inner area of the support member 4308 are in fluid communication with each other to form a single inner area. As such, the fluid can be conveyed to both the inner area of the proximal expandable member 4304 and the inner area of the distal expandable member 4306 by a single valve 4332. In some embodiments, the inner areas of the proximal expandable member 4304 and the distal expandable member 4306 are not in fluid communication. In such an arrangement, each expandable member can be independently transformed between configurations.

The support member 4308 can be made from any number of biocompatible materials, such as, for example, stainless steel, plastic, polyetheretherketone (PEEK), carbon fiber, ultra-high molecular weight (UHMW) polyethylene, and the like. The material of the support member 4308 can have a tensile strength similar to or higher than that of bone. In some embodiments, the support member 4308 is substantially rigid. In other embodiments, the support member 4308 or portions thereof is elastically deformable, thereby allowing it to conform to the shape of the spinous processes. In yet other embodiments, the support member 4308 includes a radiopaque material, such as bismuth, to facilitate tracking the position of the spinal implant 4300 during insertion and/or repositioning.

The proximal expandable member 4304 and the distal expandable member 4306 can be made from any number of biocompatible materials, as discussed above. The proximal expandable member 4304 and the distal expandable member 4306 can be coupled to the support member by an suitable means, such as a biocompatible adhesive.

In the illustrated embodiment, the spinal implant 4300 includes a sensor 4312 coupled to the support member 4308. As described above, the sensor 4312 can be configured to measure multiple force quantities and/or a pressure of the fluid contained within the proximal expandable member 4304 and the distal expandable member 4306.

In another embodiment, the apparatus includes a support member, a proximal retention member, and a distal retention member. The support member is configured to be disposed between adjacent spinous processes. The proximal retention member has a first configuration in which the proximal retention member is substantially disposed within a proximal portion of the support member and a second configuration in which a portion of the proximal retention member is disposed outside of the support member. The distal retention member has a first configuration in which the distal retention member is substantially disposed within a distal portion of the support member and a second configuration in which a portion of the distal retention member is disposed outside of the support member.

In some embodiments, each of the proximal retention member and the distal retention member includes a first elongate member and a second elongate member. The second elongate member is configured to be slidably disposed within the first elongate member. The support member includes a side wall defining a multiple openings, each opening being configured to receive a portion of at least one of the first elongate member or the second elongate member therethrough.

In some embodiments, each of the proximal retention member and the distal retention member includes an elongate member having a longitudinal axis and a rotating member having a longitudinal axis normal to the longitudinal axis of the elongate member. A portion of the elongate member is flexible in a direction normal to its longitudinal axis. The rotating member is coupled to the elongate member and configured to rotate about its longitudinal axis, thereby moving the elongate member along its longitudinal axis.

In some embodiments, a method includes percutaneously inserting into a body a support member configured to be disposed between adjacent spinous processes. The support member defines an inner area and an opening substantially normal to the longitudinal axis that connects the inner area and an area outside the support member. The support member includes a retention member having a first configuration in which the retention member is substantially disposed within the inner area, and a second configuration in which a portion of the retention member is disposed through the opening to the area outside the support member. The support member is disposed to a location between the adjacent spinous processes when retention member is in the first configuration. The retention member is moved from the first configuration to the second configuration.

Although specific portions of the apparatus, such as one or more retention members, are configured to move between a first, a second configuration and/or a third configuration, for ease of reference, the entire apparatus may be referred to as being in a first configuration, a second configuration and/or a third configuration. However, one of ordinary skill in the art having the benefit of this disclosure would appreciate that the apparatus may be configured to include four or more configurations. Additionally, in some embodiments, the apparatus can be in many positions during the movement between the first, second and/or third configurations. For ease of reference, the apparatus is referred to as being in either a first configuration, a second configuration or a third configuration. Finally, in some embodiments, although an apparatus includes one or more retention members, the figures and accompanying description may show and describe only a single retention member. In such instances, it should be understood that the description of a single retention member applies to some or all other retention members that may be included in the embodiment.

Figure 66A:
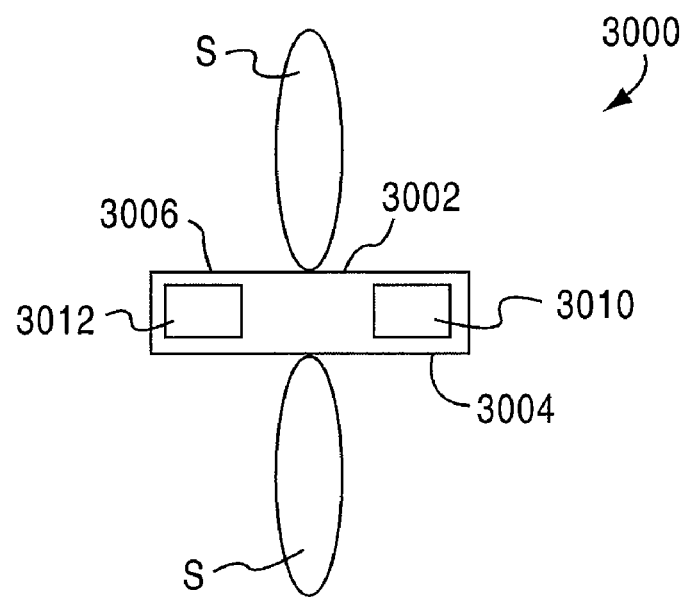
FIG. 66A is a schematic illustration of a posterior view of a medical device according to an embodiment of the invention in a first configuration disposed between two adjacent spinous processes.
Figure 66B:
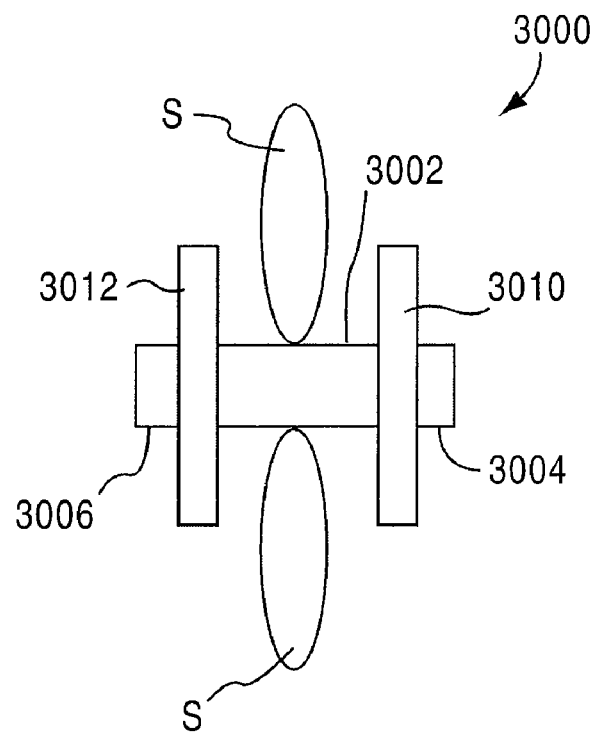
FIG. 66B is a schematic illustration of a posterior view of a medical device according to an embodiment of the invention in a second configuration disposed between two adjacent spinous processes.

FIGS. 66A and 66B are schematic illustrations of a posterior view of a medical device 3000 according to an embodiment of the invention disposed between two adjacent spinous processes S in a first configuration and a second configuration, respectively. The medical device 3000 includes a support member 3002, a proximal retention member 3010 and a distal retention member 3012. The support member 3002 has a proximal portion 3004 and a distal portion 3006, and is configured to be disposed between the spinous processes S to prevent over-extension/compression of the spinous processes S. In some embodiments, the support member 3002 distracts the adjacent spinous processes S. In other embodiments, the support member 3002 does not distract the adjacent spinous processes S.

The proximal retention member 3010 has a first configuration in which it is substantially disposed within the proximal portion 3004 of the support member 3002, as illustrated in FIG. 66A. Similarly, the distal retention member 3012 has a first configuration in which it is substantially disposed within the distal portion 3006 of the support member 3002. When the proximal retention member 3010 and the distal retention member 3012 are each in their respective first configuration, the medical device 3000 can be inserted between the adjacent spinous processes S.

The proximal retention member 3010 can be moved from the first configuration to a second configuration in which a portion of it is disposed outside of the support member 3002, as illustrated in FIG. 66B. Similarly, the distal retention member 3012 can be moved from the first configuration to a second configuration. When each is in their respective second configuration, the proximal retention member 3010 and the distal retention member 3012 limit lateral movement of the support member 3002 with respect to the spinous processes S by contacting the spinous processes S (i.e., either directly or through surrounding tissue). For purposes of clarity, the tissue surrounding the spinous processes S is not illustrated.

In use, the adjacent spinous processes S can be distracted prior to inserting the medical device 3000 into the patient. When the spinous processes S are distracted, a trocar (not shown in FIG. 66A or 66B) can be used to define an access passageway (not shown in FIGS. 66A and 66B) for the medical device 3000. In some embodiments, the trocar can be used to define the passage as well as to distract the spinous processes S.

Once an access passageway is defined, the medical device 3000 is inserted percutaneously and advanced, distal portion 3006 first, between the spinous processes S. The medical device 3000 can be inserted from the side of the spinous processes S (i.e., a posterior-lateral approach). The use of a curved shaft assists in the use of a lateral approach to the spinous processes S. Once the medical device 3000 is in place between the spinous processes S, the proximal retention member 3010 and the distal retention member 3012 are moved to their second configurations, either serially or simultaneously. In this manner, lateral movement of the support member 3002 with respect to the spinous processes S is limited.

When it is desirable to change the position of the medical device 3000, the proximal retention member 3010 and the distal retention member 3012 are moved back to their first configurations, thereby allowing the support member 3002 to be moved laterally. Once the support member 3002 is repositioned, the medical device 3000 can be returned to the second configuration. Similarly, when it is desirable to remove the medical device 3000, proximal retention member 3010 and the distal retention member 3012 are moved to their first configurations, thereby allowing the support member 3002 to be removed.

In some embodiments, the medical device 3000 is inserted percutaneously (i.e., through an opening in the skin) and in a minimally-invasive manner. For example, as discussed in detail herein, the overall sizes of portions of the medical device 3000 can be increased by moving the proximal retention member 3010 and the distal retention member 3012 to their respective second configurations after the medical device 3000 is inserted between the adjacent spinous processes S. When in the expanded second configuration, the sizes of portions of the medical device 3000 can be greater than the size of the opening. For example, the size of the opening/incision in the skin can be between 3 millimeters in length and 25 millimeters in length across the opening. In some embodiments, the size of the medical device 3000 in the expanded second configuration is between 3 and 25 millimeters across the opening.

Figure 67A:
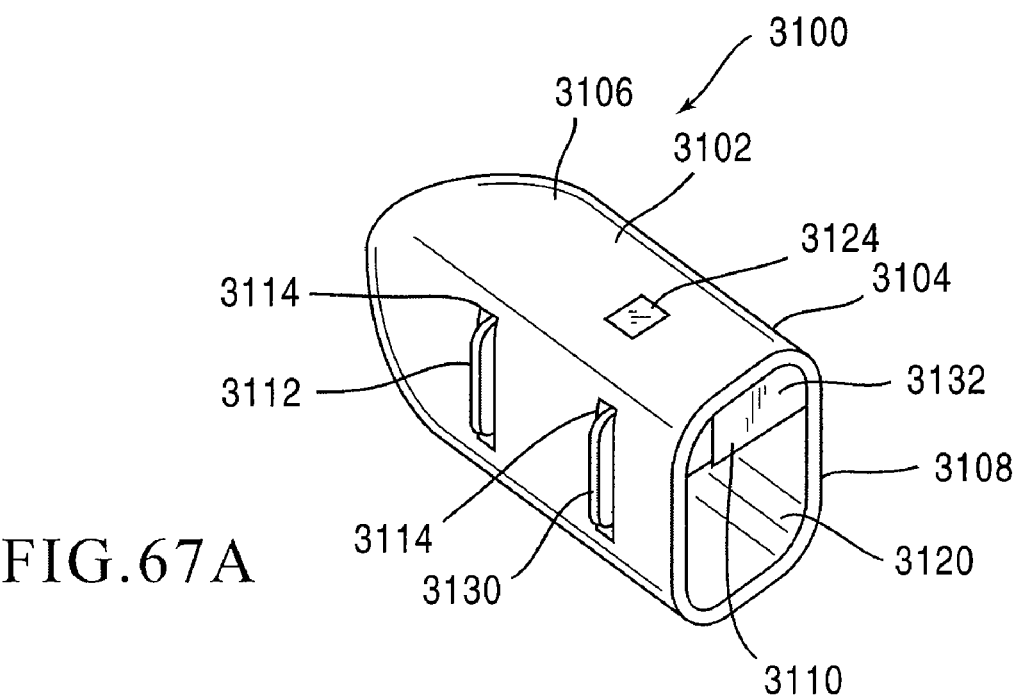
FIGS. 67A and 67B are perspective views of a medical device according to an embodiment of the invention in a first configuration and a second configuration, respectively.
Figure 67B:
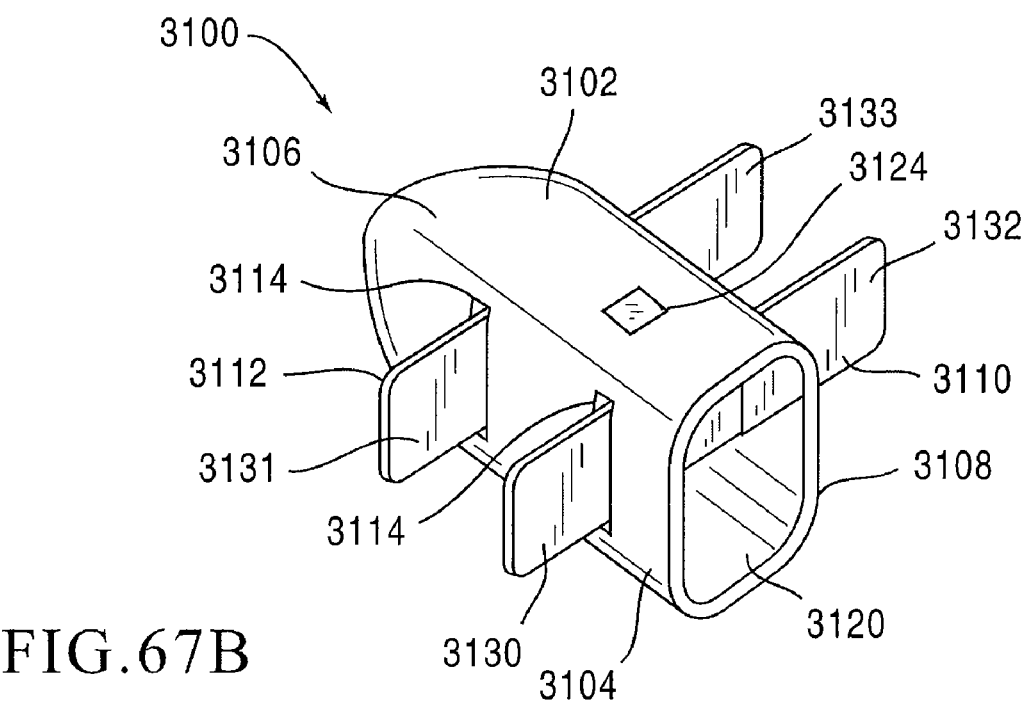
Figure 68:
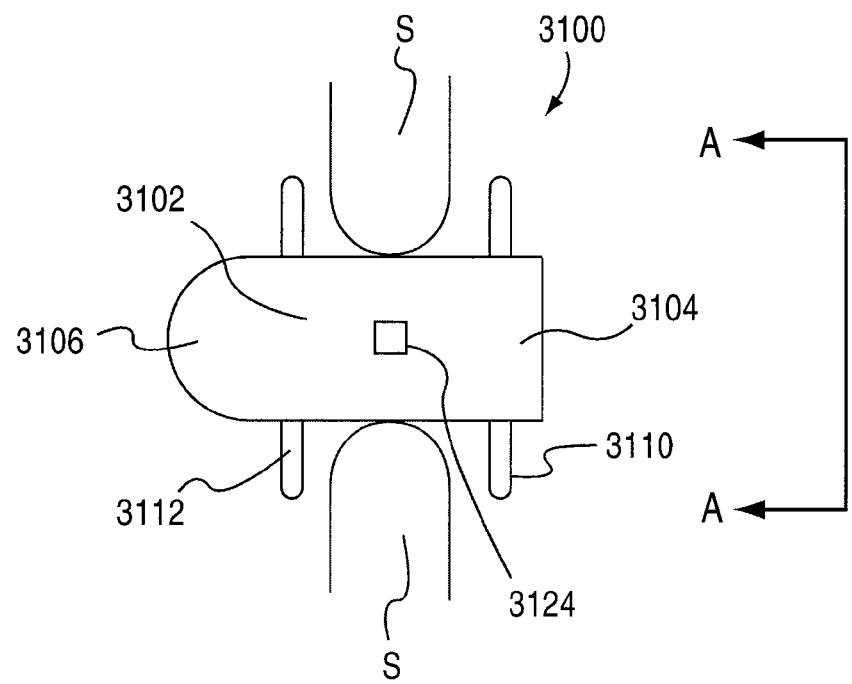
FIG. 68 is a posterior view of the medical device illustrated in FIGS. 67A and 67B disposed between adjacent spinous processes in a second configuration.
Figure 69:
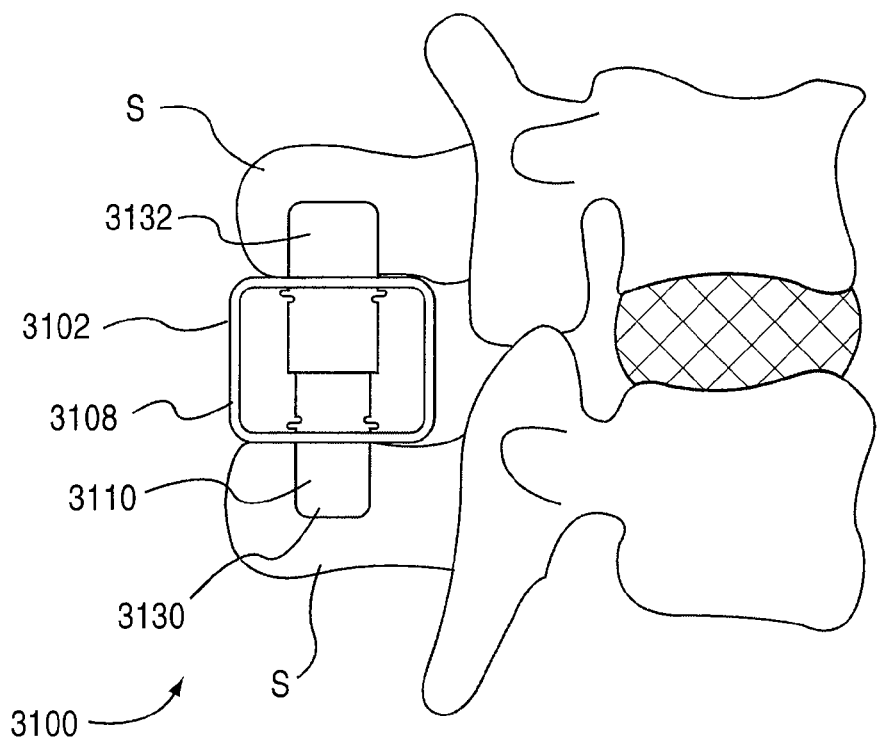
FIG. 69 is a lateral view taken from a proximal perspective A-A of the medical device illustrated in FIG. 68 disposed between adjacent spinous processes in a second configuration.

FIGS. 67A, 67B, 68-71 illustrate a spinal implant 3100 according to an embodiment of the invention. FIGS. 67A and 67B are perspective views of the spinal implant 3100 in a first configuration and a second configuration, respectively. The spinal implant 3100 includes a support member 3102, a proximal retention member 3110 and a distal retention member 3112. The support member 3102 is positioned between adjacent spinous processes S, as illustrated in FIGS. 68 and 69. As shown in FIGS. 67A and 67B, the proximal retention member 3110 and the distal retention member 3112 are each repeatably positionable in a first configuration in which they are substantially disposed within the support member 3102 (FIG. 67A), and a second configuration in which a portion of each retention member 3110, 3112 is disposed outside of the support member 3102 (FIG. 67B). When the spinal implant 3100 is in the first configuration, it can be inserted between the adjacent spinous processes S, repositioned between the adjacent spinous processes and/or removed from the patient. When the spinal implant 3100 is in the second configuration, its lateral movement is limited, thereby allowing the desired position of the support member 3102 to be maintained.

In some embodiments, the support member 3102 distracts the adjacent spinous processes S. In other embodiments, the support member 3102 does not distract the adjacent spinous processes S. In yet other embodiments, the engagement of the spinous processes S by the support member 3102 is not continuous, but occurs upon spinal extension.

The support member 3102 can be made from any number of biocompatible materials, such as, for example, stainless steel, plastic, polyetheretherketone (PEEK), carbon fiber, ultra-high molecular weight (UHMW) polyethylene, and the like. The material of the support member 3102 can have a tensile strength similar to or higher than that of bone. In some embodiments, the support member 3102 is substantially rigid. In other embodiments, the support member 3102 or portions thereof is elastically deformable, thereby allowing it to conform to the shape of the spinous processes. In yet other embodiments, the support member 3102 includes a radio-paque material, such as bismuth, to facilitate tracking the position of the spinal implant 3100 during insertion and/or repositioning.

In the illustrated embodiment, the spinal implant 3100 includes a sensor 3124 coupled to the support member 3102. In some embodiments, the sensor 3124 is a strain gauge sensor that measures a force applied to the support member 3102. In some embodiments, the sensor 3124 can include multiple strain gauges to facilitate measuring multiple force quantities, such as a compressive force and/or a bending moment. In other embodiments, the sensor 3124 is a variable capacitance type pressure sensor configured to measure a force and/or a pressure applied to the support member 3102. In yet other embodiments, the sensor 3124 is a piezoelectric sensor that measures a force and/or a pressure applied to the support member 3102. In still other embodiments, the spinal implant 3100 can include multiple sensors located at various locations to provide a spatial profile of the force and/or pressure applied to the support member 3102. In this manner, a practitioner can detect changes in the patient's condition, such those that may result in a loosening of the spinal implant.

In some embodiments, the sensor 3124 can be remotely controlled by an external induction device. For example, an external radio frequency (RF) transmitter (not shown) can be used to supply power to and communicate with the sensor 3124. In other embodiments, an external acoustic signal transmitter (not shown) can be used to supply power to and communicate with the sensor 3124. In such an arrangement, for example, the sensor can include a pressure sensor, of the types described above, for measuring a pressure; an acoustic transducers, and an energy storage device. The acoustic transducer converts energy between electrical energy and acoustic energy. The energy storage device stores the electrical energy converted by the acoustic transducer and supplies the electrical energy to support the operation of the pressure sensor. In this manner, acoustic energy from an external source can be received and converted into electrical energy used to power the pressure sensor. Similarly, an electrical signal output from the pressure sensor can be converted into acoustic energy and transmitted to an external source.

The support member 3102 includes a sidewall 3108 that defines an inner area 3120 and multiple openings 3114 that connect the inner area 3120 to an area outside of the support member 3102. When the spinal implant 3100 is in the first configuration, the proximal retention member 3110 and the distal retention member 3112 are substantially disposed within the inner area 3120 of the support member 3102, as shown in FIG. 67A. When the spinal implant 3100 is in the second configuration, a portion of each of the proximal retention member 3110 and the distal retention member 3112 extends through the openings 3114 to an area outside of the support member 3102. In the second configuration, the proximal retention member 3110 and the distal retention member 3112 engage the adjacent spinous processes, thereby limiting lateral movement of the spinal implant 3100.

Figure 71:
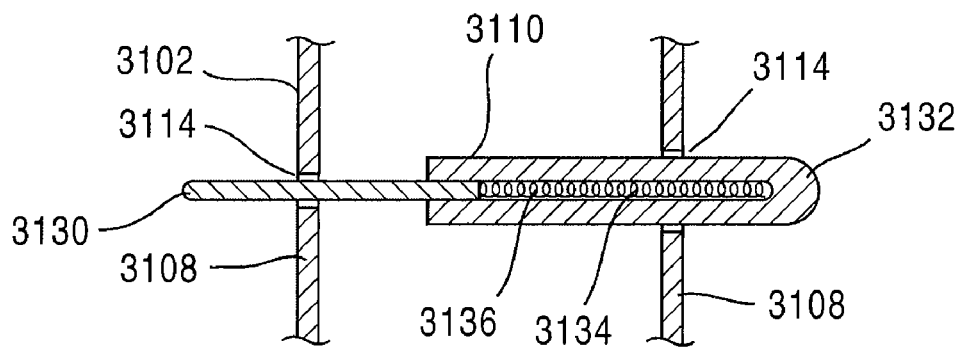
FIG. 71 is a cross-sectional plan view taken along section A-A of the medical device illustrated in FIGS. 67A and 67B in a second configuration.

The proximal retention member 3110 includes a first elongate member 3130 and a second elongate member 3132. Similarly, the distal retention member 3112 includes a first elongate member 3131 and a second elongate member 3133. As illustrated in FIG. 71, which shows is a cross-sectional plan view of the proximal portion 3104 of the support member 3102, the first elongate member 3130 is slidably disposed within a pocket 3134 defined by the second elongate member 3132. A biasing member 3136, such as a spring or an elastic member, is disposed within the pocket 3134 and is coupled to the first elongate member 3130 and the second elongate member 3132. In this manner, the retention members can be biased in the second configuration. In other embodiments, the biasing member 3136 can be configured to bias the retention members in the first configuration. In yet other embodiments, the retention members do not include a biasing member, but instead use other mechanisms to retain a desired configuration. Such mechanisms can include, for example, mating tabs and slots configured to lockably engage when the retention members are in a desired configuration.

In use, the spinal implant 3100 is positioned in the first configuration during insertion, removal or repositioning. As discussed above, the spinal implant 3100 is inserted percutaneously between adjacent spinous processes. The distal portion 3106 of the support member 3102 is inserted first and is moved past the spinous processes until the support member 3102 is positioned between the spinous processes. The support member 3102 can be sized to account for ligaments and tissue surrounding the spinous processes S. In some embodiments, the support member 3102 contacts the spinous processes between which it is positioned during a portion of the range of motion of the spinous processes S. In some embodiments, the support member 3102 of spinal implant 3100 is a fixed size and is not compressible or expandable. In yet other embodiments, the support member 3102 can compress to conform to the shape of the spinous processes S. Similarly, in some embodiments, the proximal retention member 3110 and the distal retention member 3112 are substantially rigid. In other embodiments, the retention members or portions thereof are elastically deformable, thereby allowing them to conform to the shape of the spinous processes.

Figure 70:
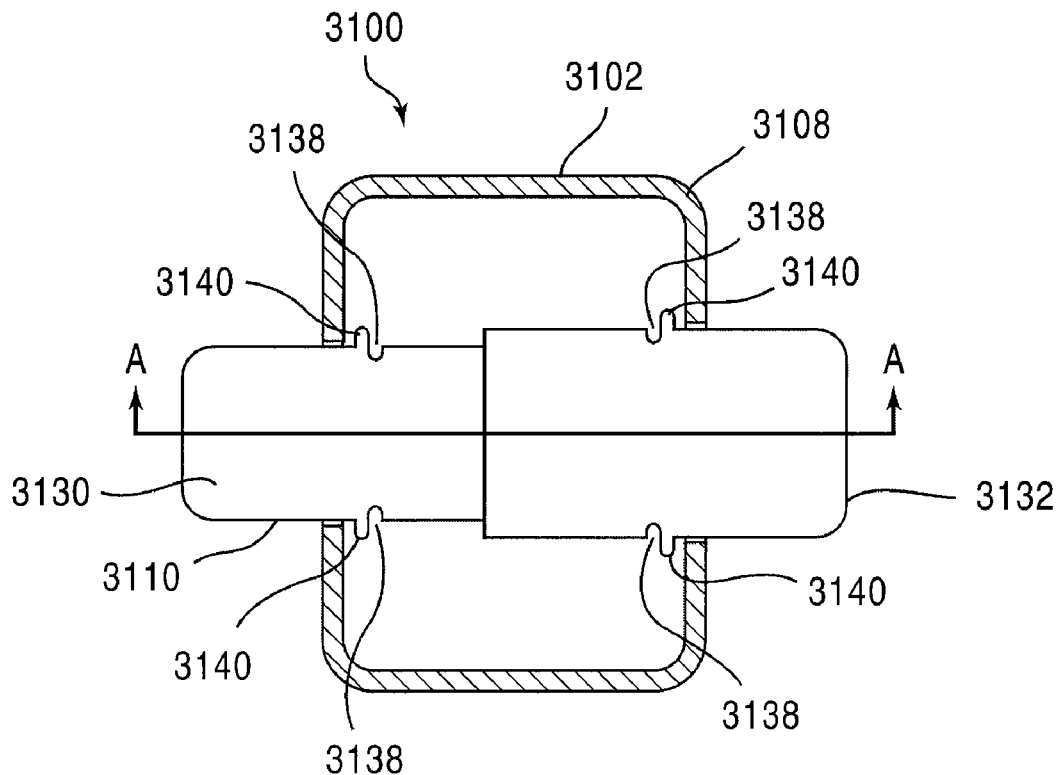
FIG. 70 is a cross-sectional front view of the medical device illustrated in FIGS. 67A and 67B in a second configuration.

In the illustrated embodiment, the spinal implant 3100 is held in the first configuration by an insertion tool (not shown) that overcomes the force exerted by the biasing member 3136, thereby disposing a portion of the first elongate member 3130 within the pocket 3134 of the second elongate member 3132. In this manner, the spinal implant 3100 can be repeatedly moved from the first configuration to the second configuration, thereby allowing it to be repositioned and/or removed percutaneously. As illustrated in FIG. 70, the first elongate member 3130 and the second elongate member 3132 each include notches 3138 configured to receive a portion of the insertion tool. When the insertion tool is released, the biasing member 3136 is free to extend, thereby displacing a portion of the first elongate member 3130 out of the pocket 3134 of the second elongate member 3132. In this manner, portions of both the first elongate member 3130 and the second elongate member 3132 are extended through the adjacent openings 3114 and to an area outside of the support member 3102. In some embodiments, the proximal retention member 3110 and the distal retention member 3112 are transitioned between their respective first and second configurations simultaneously. In other embodiments, the proximal retention member 3110 and the distal retention member 3112 are transitioned between their first and second configurations serially.

As illustrated, the first elongate member 3130 and the second elongate member 3132 each include one or more tabs 3140 that engage the side wall 3108 of the support member 3102 when in the second configuration, thereby ensuring that the first and second elongate members remain coupled to each other and that portions of the first and second elongate members remain suitably disposed within the support member 3102. In other embodiments, the first elongate member 3130 and the second elongate member 3132 are coupled to each other by other suitable mechanisms, such as mating tabs and slots configured to engage when the retention member reaches a predetermined limit of extension.

Figure 72:
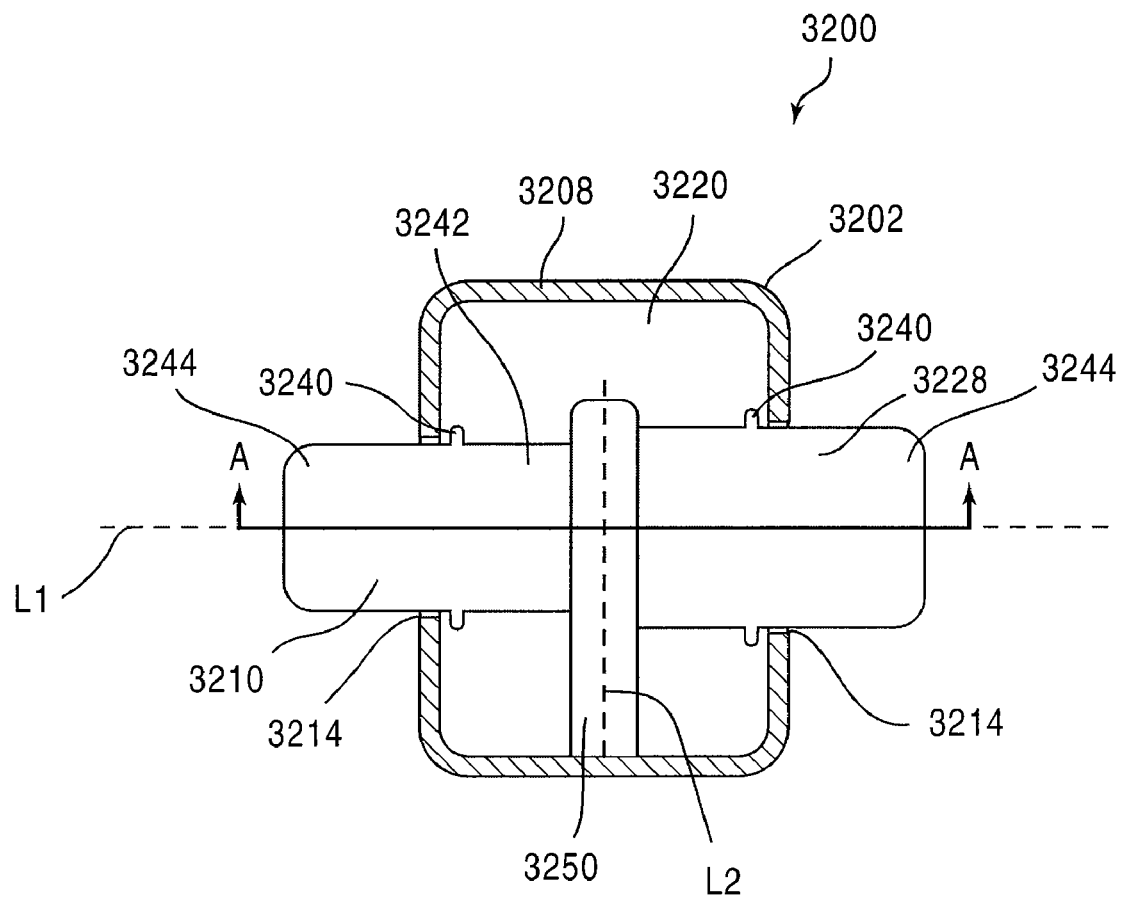
FIG. 72 is a cross-sectional front view of a medical device according to an embodiment of the invention in a second configuration.
Figure 73A:
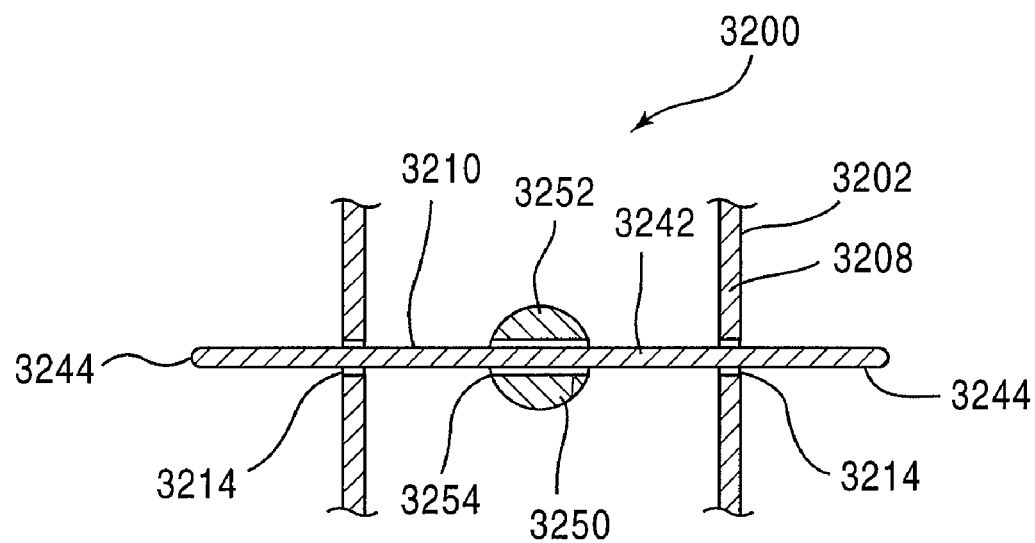
FIGS. 73A and 73B are cross-sectional plan views taken along section A-A of the medical device illustrated in FIG. 72 in a second configuration and a first configuration, respectively.
Figure 73B:
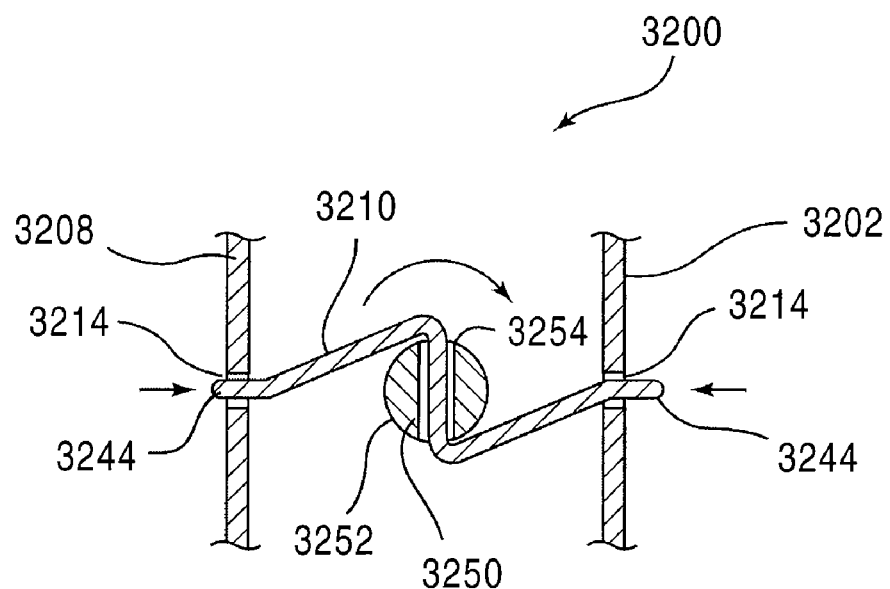

FIGS. 72, 73A and 73B are cross-sectional views of a spinal implant 3200 according to an embodiment of the invention. FIG. 72 illustrates a cross-sectional front view of the spinal implant 3200 in a second configuration, while FIGS. 73A and 73B illustrate a cross-sectional plan view of the spinal implant 3200 in the second configuration and a first configuration, respectively. The illustrated spinal implant 3200 includes a support member 3202, a retention member 3210 and a rotating member 3250. Although shown and described as including only a single retention member 3210, some embodiments can include one or more additional retention members having characteristics and functionality similar to those described for the retention member 3210.

As shown in FIGS. 73A and 73B, the retention member 3210 is repeatably positionable in a first configuration in which it is substantially disposed within the support member 3202, and a second configuration in which a portion the retention member 3210 is disposed outside of the support member 3102. When the spinal implant 3200 is in the first configuration, it can be inserted between adjacent spinous processes, repositioned between adjacent spinous processes and/or removed from the patient. When the spinal implant 3200 is in the second configuration, its lateral movement is limited, thereby allowing the desired position of the support member 3202 to be maintained.

The support member 3202 includes a sidewall 3208 that defines an inner area 3220 and multiple openings 3214 that connect the inner area 3220 to an area outside of the support member 3202. When the spinal implant 3200 is in the first configuration, the retention member 3210 is substantially disposed within the inner area 3220 of the support member 3202, as shown in FIG. 73B. When the spinal implant 3200 is in the second configuration, a portion of the proximal retention member 3210 extends through the openings 3214 to an area outside of the support member 3202. In the second configuration, the retention member 3210 is disposed adjacent the spinous processes, thereby limiting lateral movement of the spinal implant 3200.

The retention member 3210 includes an elongate member 3228 having two end portions 3244, a central portion 3242, and a longitudinal axis L1 (shown in FIG. 72). A portion of the elongate member 3228 is flexible such that it can be wound along the rotating member 3250, as described below. In some embodiments, the elongate member 3228 is monolithically formed such that it is flexible enough to be wound along the rotating member 3250 yet rigid enough to limit lateral movement of the support member 3202 when positioned in the second configuration. In other embodiments, the elongate member 3228 includes separate components that are coupled together to form the elongate member 3228. For example, the central portion 3242 of the elongate member 3228 can be a distinct component having a greater amount of flexibility, while the end portions 3244 can be distinct components having a greater amount of rigidity.

In the illustrated embodiment, elongate member 3228 has one or more tabs 3240 that engage the side wall 3208 of the support member 3202 when in the second configuration, thereby ensuring that the elongate member 3228 does not freely extend entirely outside of the support member 3202. In other embodiments, a portion of the elongate member 3228 is retained within the support member 3202 by other suitable mechanisms. For example, the width of the central portion 3242 of the elongate member 3228 can be greater than the width of the openings 3214, thereby ensuring that a portion of the elongate member 3228 will remain within the support member 3202.

The rotating member 3250 defines an outer surface 3252 and a slot 3254 through which the elongate member 3228 is disposed. The rotating member 3250 has a longitudinal axis L2 (shown in FIG. 72) about which it rotates. As illustrated in FIG. 73B, as the rotating member 3250 rotates, the elongate member 3228 is wound along the outer surface 3252 of the rotating member 3250. This causes the elongate member 3228 to move along its longitudinal axis L1, thereby causing the end portions 3244 of the elongate member 3228 to be retracted inwardly through the openings 3214. In this manner, the retention member 3210 can be repeatedly transitioned between the first configuration and the second configuration.

In some embodiments, the rotating member 3250 is rotated using an insertion tool (not shown) that includes a ratchet mechanism. The insertion tool can rotate the rotating member 3250 in a number of different ways, such as, for example, manually, pneumatically or electronically.

Figure 74:
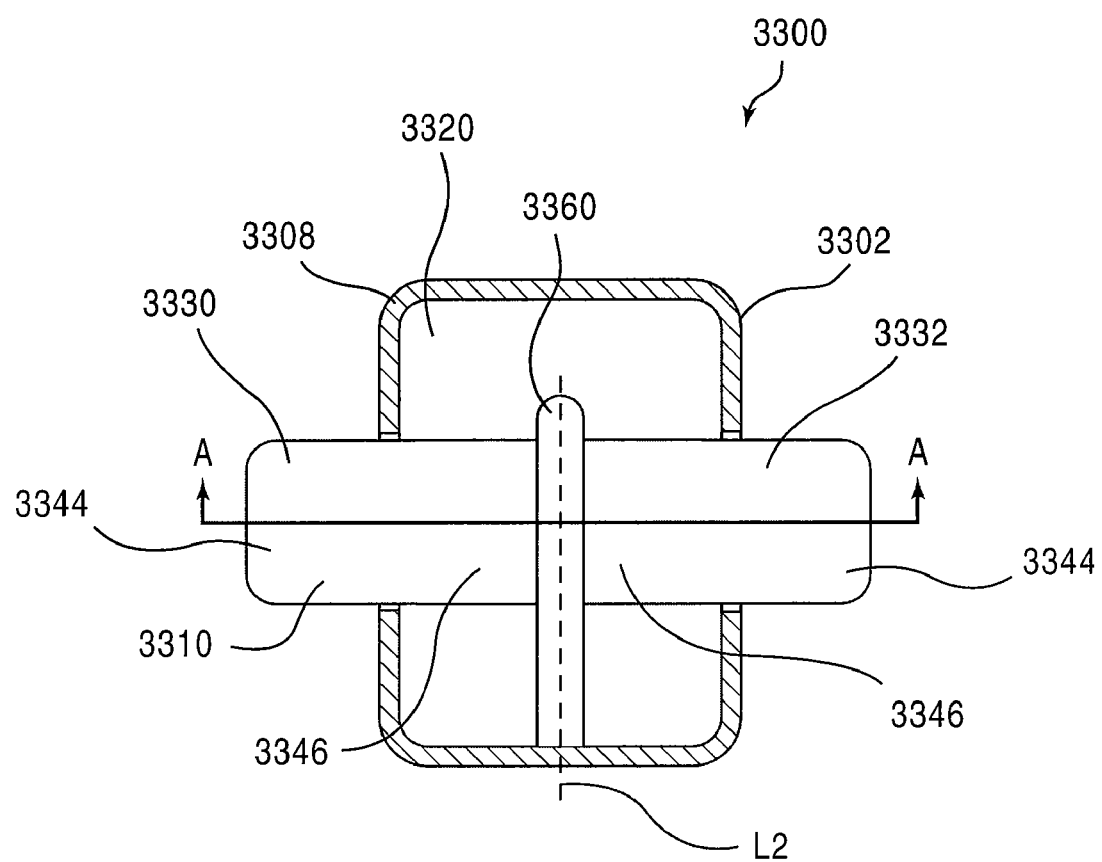
FIG. 74 is a cross-sectional front view of a medical device according to an embodiment of the invention in a second configuration.
Figure 75A:
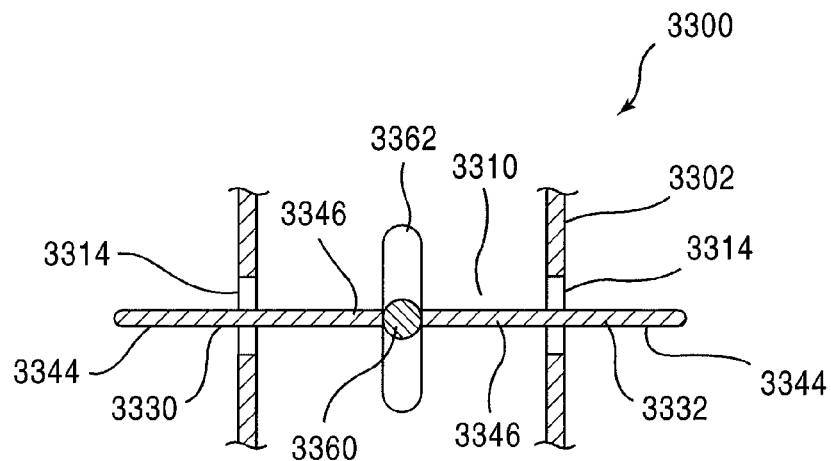
FIGS. 75A through 75C are cross-sectional plan views taken along section A-A of the medical device illustrated in FIG. 74 in a second configuration, a first configuration, and a third configuration respectively.
Figure 75B:
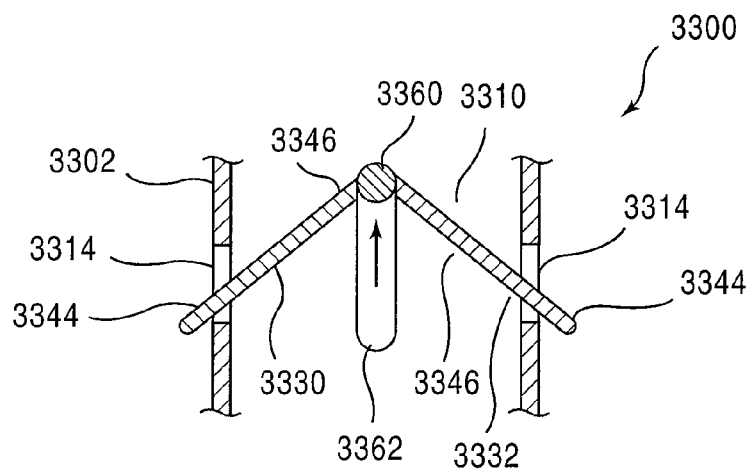
Figure 75C:
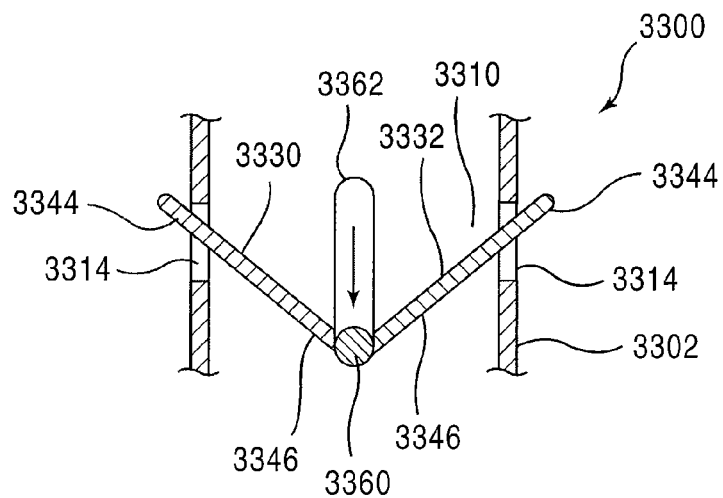

FIGS. 74 and 75A-75C are cross-sectional views of a spinal implant 3300 according to an embodiment of the invention. FIG. 74 illustrates a cross-sectional front view of the spinal implant 3300 in a second configuration, while FIGS. 75A-75C illustrate a cross-sectional plan view of the spinal implant 3300 in the second configuration, a first configuration, and a third configuration, respectively. The illustrated spinal implant 3300 includes a support member 3302 and a retention member 3310. Although shown and described as including only a single retention member 3310, some embodiments can include one or more additional retention members having characteristics and functionality similar to those described for the retention member 3310.

As shown in FIGS. 75A-75C, the retention member 3310 is repeatably positionable in a first configuration, a second configuration and a third configuration. A portion the retention member 3310 is disposed outside of the support member 3302 when positioned in the second configuration. The retention member 3310 is substantially disposed within the support member 3202 when positioned in each of the first and third configurations. As illustrated in FIGS. 75B and 75C, the orientation of the retention member 3310 differs between the first and third configurations. In this manner, the position of the spinal implant 3300 can be positioned appropriately depending on the direction in which it is being moved. For example, the spinal implant 3300 may be positioned in the first configuration to facilitate lateral movement of the support member 3302 in a distal direction, such as during insertion. Conversely, the spinal implant 3300 may be positioned in the third configuration to facilitate lateral movement of the support member 3302 in a proximal direction, such as during removal.

The support member 3302 includes a sidewall 3308 that defines an inner area 3320 and multiple openings 3314 that connect the inner area 3320 to an area outside of the support member 3302. When the spinal implant 3300 is in the second configuration, a portion of the proximal retention member 3310 extends through the openings 3314 to an area outside of the support member 3302.

The retention member 3310 includes a first elongate member 3330, a second elongate member 3332, and a hinge 3360 having a longitudinal axis L2 (shown in FIG. 74). Each of the first elongate member 3330 and the second elongate member 3332 has a distal end portion 3344 that extends through the openings 3314 when the spinal implant 3300 is in the second configuration and a proximal end portion 3346 that is pivotally coupled to the hinge 3360. In use, the hinge 3360 moves in a direction normal to its longitudinal axis L2, as indicated by the arrows in FIGS. 75B and 75C. The motion of the hinge is guided by a slot 3362 defined by the side wall 3308 of the support member 3302. The movement of the hinge 3360 allows the each of the first elongate member 3330 and the second elongate member 3332 to rotate about the longitudinal axis L2 of the hinge 3360, thereby positioning the distal end portion 3344 of each elongate member substantially within the inner area 3320 of the support member 3302.

In some embodiments, the slot 3362 includes detents or any other suitable mechanism (not shown) to maintain the hinge 3360 in the desired position. In other embodiments the hinge 3360 includes a biasing member (not shown) configured to bias the hinge 3360 in one of the first, second, or third configurations. In yet other embodiments, the elongate members include other suitable mechanisms to retain the retention member in a desired configuration. Such mechanisms can include, for example, mating tabs and slots configured to lockably engage when the elongate members are in a desired configuration.

In some embodiments, the first elongate member 3330 and the second elongate member 3332 are monolithically formed of a substantially rigid material. In other embodiments, the first elongate member 3330 and the second elongate member 3332 include separate components having different material properties. For example, the distal end portion 3344 can be formed from a material having a greater amount of flexibility, while the proximal end portion 3346 can be formed from a substantially rigid material. In this manner, movement of the spinal implant 3300 is not restricted when a portion of the of the distal end portion 3344 protrudes from the openings 3314 in either the first configuration or the third configuration.

Figure 76A:
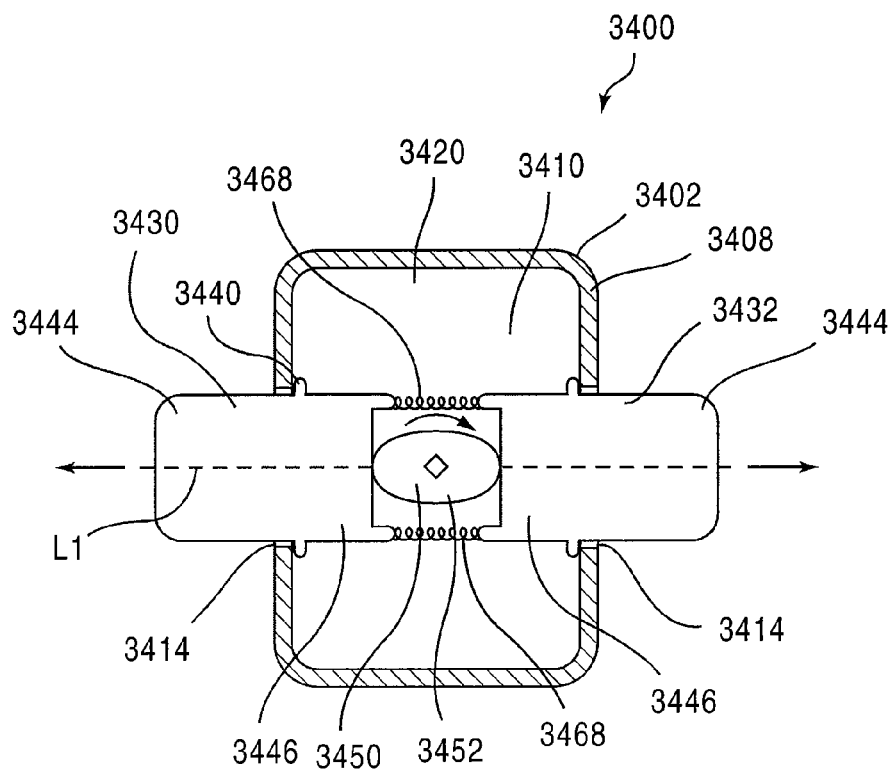
FIGS. 76A and 76B are cross-sectional front views of a medical device according to an embodiment of the invention in a second configuration and a first configuration, respectively.
Figure 76B:
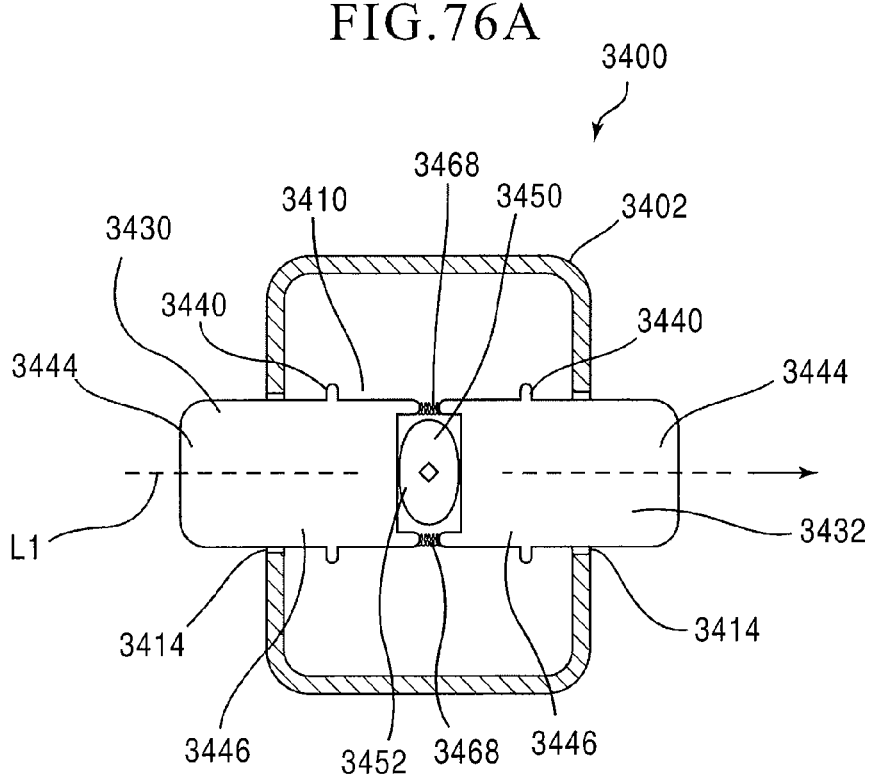

FIGS. 76A and 76B are cross-sectional front views of a spinal implant 3400 according to an embodiment of the invention. The illustrated spinal implant 3400 includes a support member 3402, a retention member 3410 and a rotating member 3450. As shown in FIGS. 76A and 76B, the retention member 3410 is repeatably positionable in a first configuration in which it is substantially disposed within the support member 3402, and a second configuration in which a portion the retention member 3410 is disposed outside of the support member 3402. Although shown and described as including only a single retention member 3410, some embodiments include one or more additional retention members having characteristics and functionality similar to those described for the retention member 3410.

The support member 3402 includes a sidewall 3408 that defines an inner area 3420 and multiple openings 3414 that connect the inner area 3420 to an area outside of the support member 3402. When the spinal implant 3400 is in the second configuration, a portion of the proximal retention member 3410 extends through the openings 3414 to an area outside of the support member 3402.

The retention member 3410 includes a first elongate member 3430 and a second elongate member 3432, each having a distal end portion 3444 that extends through the openings 3414 when the spinal implant 3400 is in the second configuration, a proximal end portion 3446, and a longitudinal axis L1. As illustrated, the proximal end portions 3346 are coupled by two elastic members 3468, such as a spring or an elastic band. In some embodiments, the proximal end portions 3346 are coupled by a single elastic member. In other embodiments, the proximal end portions 3346 are indirectly coupled via the rotating member 3450. In such an arrangement, for example, a biasing member can be placed between the sidewall of the support member and each elongate member, thereby biasing each elongate member against the rotating member.

In the illustrated embodiment, the elongate members each include one or more tabs 3440 that engage the side wall 3408 of the support member 3402 when in the second configuration, thereby ensuring that the elongate members 3430, 3432 does not freely extend entirely outside of the support member 3402. In other embodiments, the elongate members do not include tabs, but are retained within the support member 3402 solely by the elastic members 3468. In yet other embodiments, the width of a portion of the elongate members can be greater than the width of the openings 3414, thereby ensuring that the elongate members will remain within the support member 3402.

The rotating member 3450 defines an outer surface 3452 having an eccentric shape and includes a longitudinal axis (not shown) about which it rotates. As illustrated in FIGS. 76A and 76B, as the rotating member 3450 rotates about its longitudinal axis, a portion of the proximal end portion 3346 of the first elongate member 3430 and the second elongate member 3432 engage the outer surface 3452 of the rotating member 3250. This causes the first elongate member 3430 and the second elongate member 3432 to move along their respective longitudinal axes L1, thereby causing the end portions 3444 of each elongate member to be extended outwardly through the openings 3414, as indicated by the arrows in FIG. 76A. In this manner, the retention member 3410 can be repeatedly transitioned between the first configuration and the second configuration.

In some embodiments, the rotating member 3450 is rotated using an insertion tool (not shown) that includes a ratchet mechanism. The insertion tool can rotate the rotating member 3450 in a number of different ways, such as, for example, manually, pneumatically or electronically.

Figure 77:
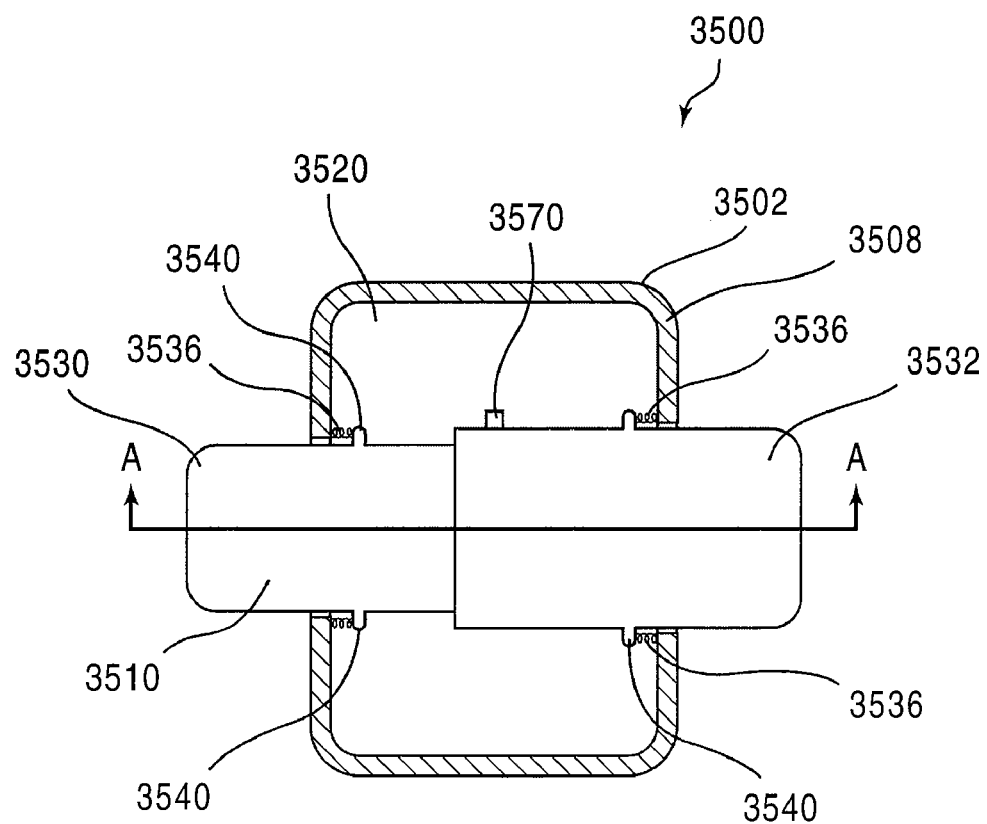
FIG. 77 is a cross-sectional front view of a medical device according to an embodiment of the invention in a second configuration.
Figure 78:
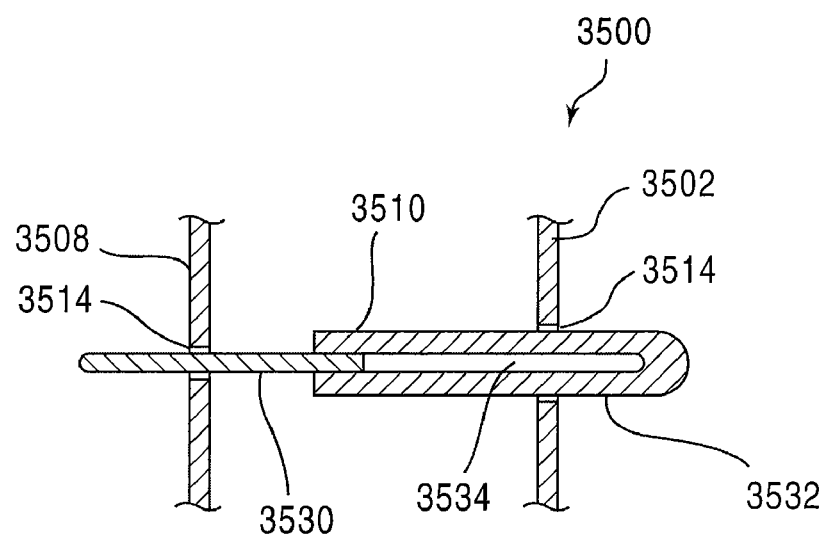
FIG. 78 is a cross-sectional plan view taken along section A-A of the medical device illustrated in FIG. 77 in a second configuration.

FIGS. 77 and 78 illustrate a spinal implant 3500 according to an embodiment of the invention. FIG. 77 is a cross-sectional front view of the spinal implant 3500 in a second configuration. FIG. 78 is a cross-sectional plan view of the spinal implant 3500 taken along section A-A. The spinal implant 3500 includes a support member 3502 and a retention member 3510. Although only shown as being in a second or expanded configuration, it is understood from the previous descriptions that the retention member 3510 is repeatably positionable in a first configuration in which it is substantially disposed within the support member 3502, and the second configuration in which a portion the retention member 3510 is disposed outside of the support member 3502.

As illustrated, the retention member 3510 includes a first elongate member 3530 and a second elongate member 3532. The first elongate member 3530 is slidably disposed within a pocket 3534 defined by the second elongate member 3532. The first elongate member 3530 and the second elongate member 3532 each include one or more tabs 3540 that are coupled to the side wall 3508 of the support member 3502 by one or more biasing members 3536. In this manner, the retention member 3510 is biased in the first or retracted configuration. In other embodiments, the biasing members 3536 can be configured to bias the retention member 3510 in the second configuration. In yet other embodiments, the retention member 3510 is not retained by a biasing member 3536, but rather uses other suitable mechanisms to retain the desired configuration.

In use, the retention member 3510 is transitioned from the first configuration to the second configuration by supplying a pressurized fluid (not shown) to the pocket 3534 via valve 3570. The pressure exerted by the fluid on each of the first elongate member 3530 and the second elongate member 3532 overcomes the force exerted by the biasing members 3536, thereby causing a portion the first elongate member 3530 to extend outwardly from the pocket 3534 of the second elongate member 3132, thereby allowing a portion of each elongate member to extend through the adjacent openings 3514 and to an area outside of the support member 3502. Similarly, the retention member 3510 is transitioned from the second configuration to the first configuration by opening the valve 3570 and relieving the pressure within the pocket 3534. In this manner, the spinal implant 3500 can be repeatedly moved from the first configuration to the second configuration, thereby allowing it to be repositioned and/or removed percutaneously.

Figure 79A:
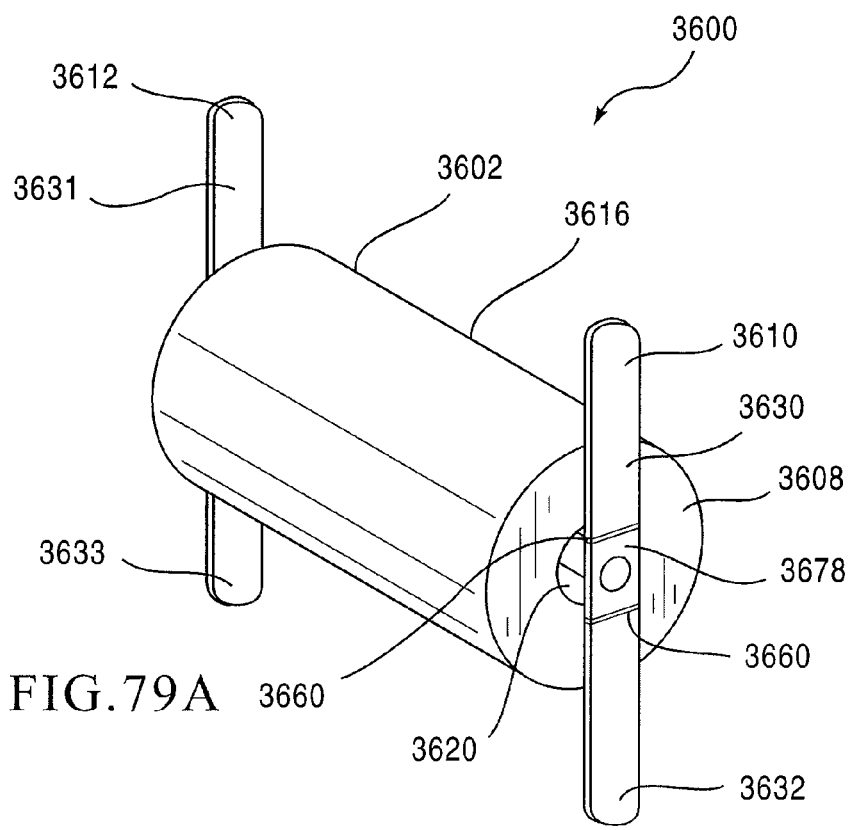
FIGS. 79A and 79B are perspective views of a medical device according to an embodiment of the invention in a second configuration and a first configuration, respectively.
Figure 79B:
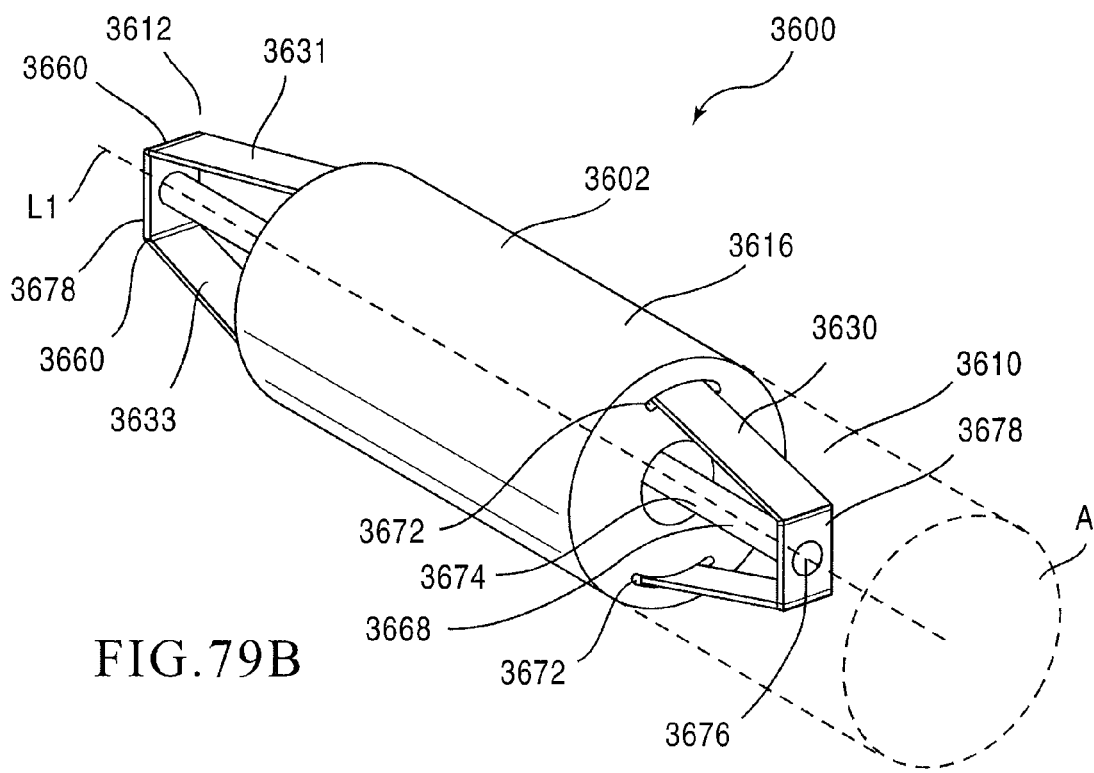

FIGS. 79A and 79B illustrate perspective views of a spinal implant 3600 according to an embodiment of the invention. The spinal implant 3600 includes a support member 3602, a proximal retention member 3610, a distal retention member 3612, and an elastic member 3668. The support member 3602 defines a longitudinal axis L1 and has a sidewall 3608 that defines an inner area 3620 and has an outer surface 3616. As illustrated in FIG. 79B, the outer surface 3616 defines an area A normal to the longitudinal axis L1. As shown, the proximal retention member 3610 and the distal retention member 3612 are each repeatably positionable in a first configuration in which they are substantially disposed within the area A (FIG. 79B), and a second configuration in which a portion of each retention member 3610, 3612 is disposed outside of the area A (FIG. 79A).

As illustrated, the proximal retention member 3610 and the distal retention member 3612 are coupled by the elastic member 3668, a portion of which is disposed within the inner area 3620 of the support member 3602. In the illustrated embodiment, the elastic member 3668 has a sidewall 3674 that defines a lumen 3676. In other embodiments, the elastic member can be, for example, a spring, an elastic band, or any other suitable device for elastically coupling the proximal retention member 3610 and the distal retention member 3612.

The proximal retention member 3610 includes a first elongate member 3630 and a second elongate member 3632, each of which are pivotally coupled to a connection member 3678 by a hinge 3660. Similarly, the distal retention member 3612 includes a first elongate member 3631 and a second elongate member 3633 each of which are pivotally coupled to a connection member 3678 by a hinge 3660.

As illustrated in FIG. 79A, when the spinal implant 3600 is in the second configuration, the elastic member 3668 exerts a biasing force on each connection member 3678, thereby causing the connection members 3678 to remain adjacent to the support member 3602. In this configuration, the first elongate member 3630 and the second elongate member 3632 are fully extended. The spinal implant 3600 is transitioned from the second configuration to the first configuration by stretching the elastic member 3668, which allows the connection members 3678 to be disposed apart from the support member 3602, thereby allowing the elongate members to move within the area A, as illustrated in FIG. 79B. The support member 3602 includes slots 3672 in which the end portion of each elongate member can be disposed to maintain the spinal implant 3600 in the first configuration.

The elastic member 3668 can be stretched by an insertion tool (not shown), a portion of which can be configured to be disposed within the lumen 3676 of the elastic member 3668. For example, a first portion of an insertion tool can engage the connection member 3678 of the proximal retention member 3610 while a second portion of the insertion tool can engage the connection member 3678 of the distal retention member 3612. The tool can then be configured to exert an outward force on each of the connection members 3678, thereby stretching the elastic member 3668 and allowing the spinal implant to transition from the second configuration to the first configuration.

Figure 80A:
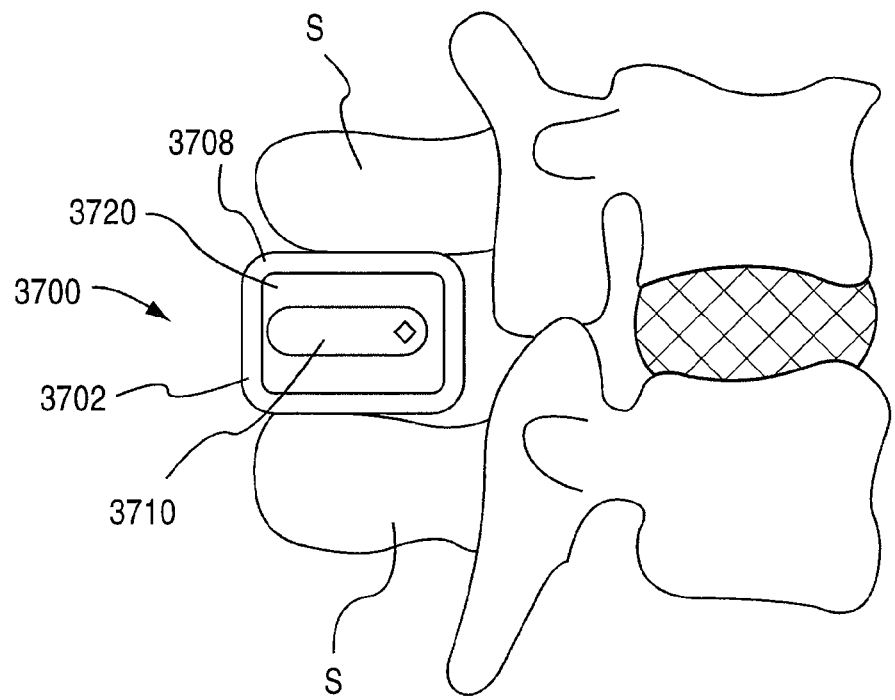
FIGS. 80A and 80B are lateral views of a medical device according to an embodiment of the invention in a first configuration and a second configuration, respectively.
Figure 80B:
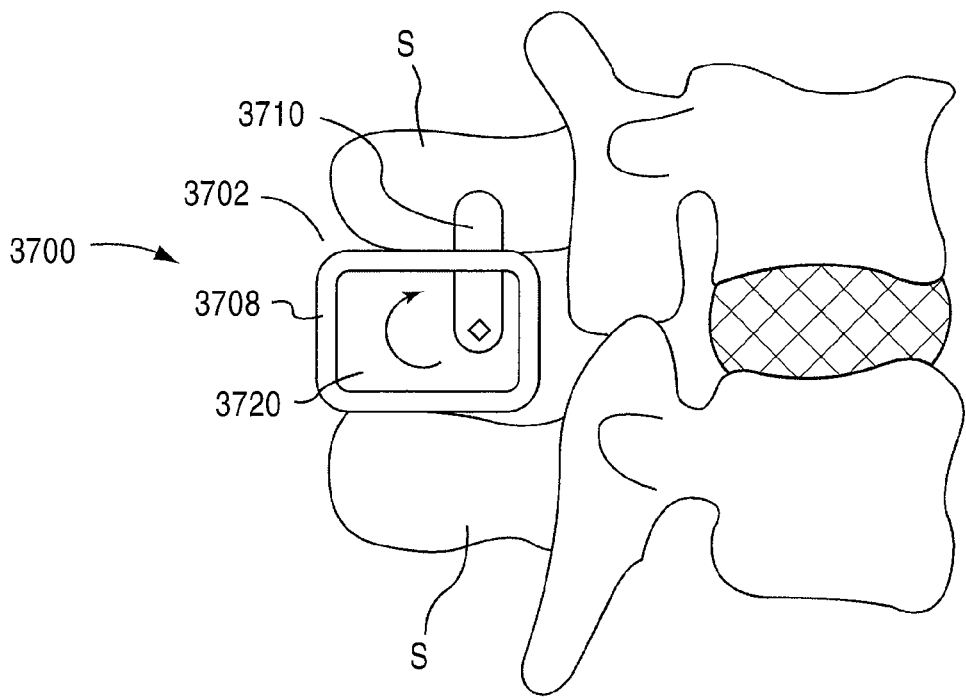
Figure 81A:
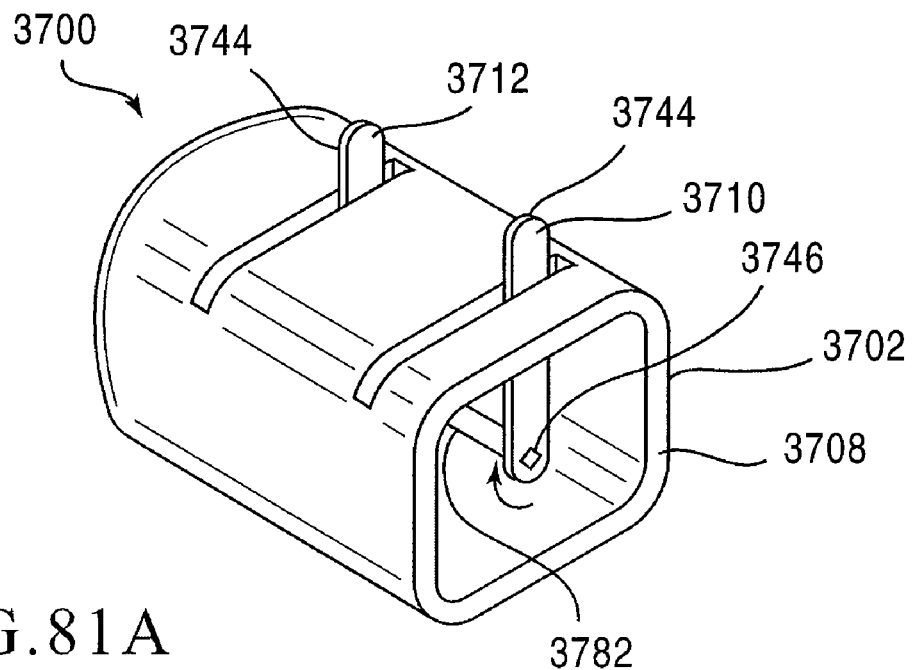
FIGS. 81A and 81B are perspective views of the medical device illustrated in FIGS. 80A and 80B in a first configuration and a second configuration, respectively.
Figure 81B:
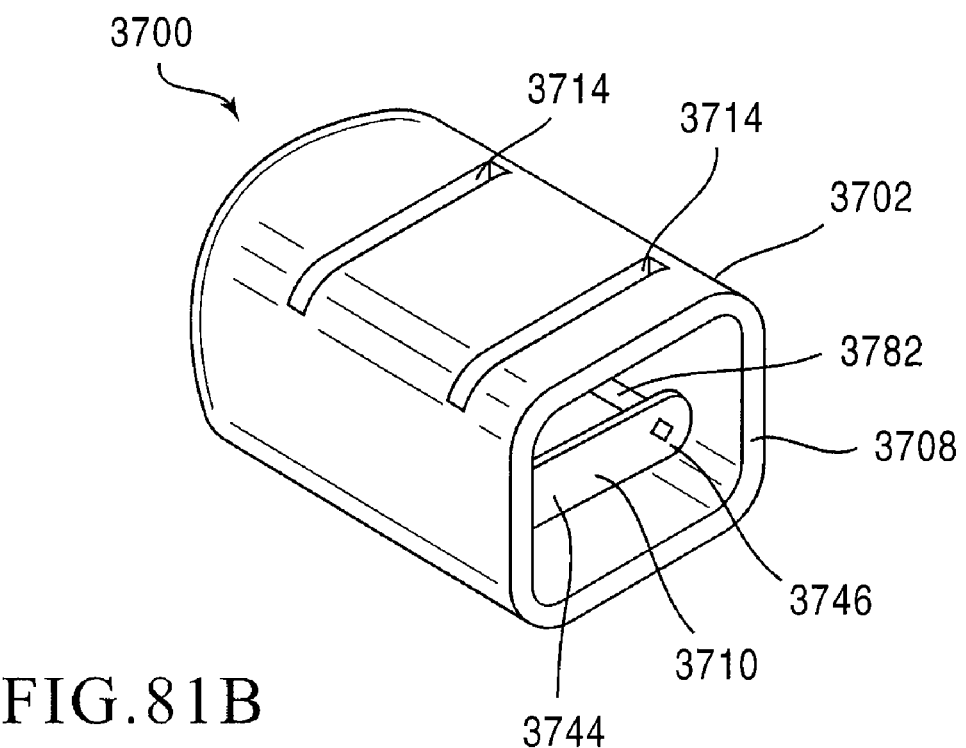
Figure 82:
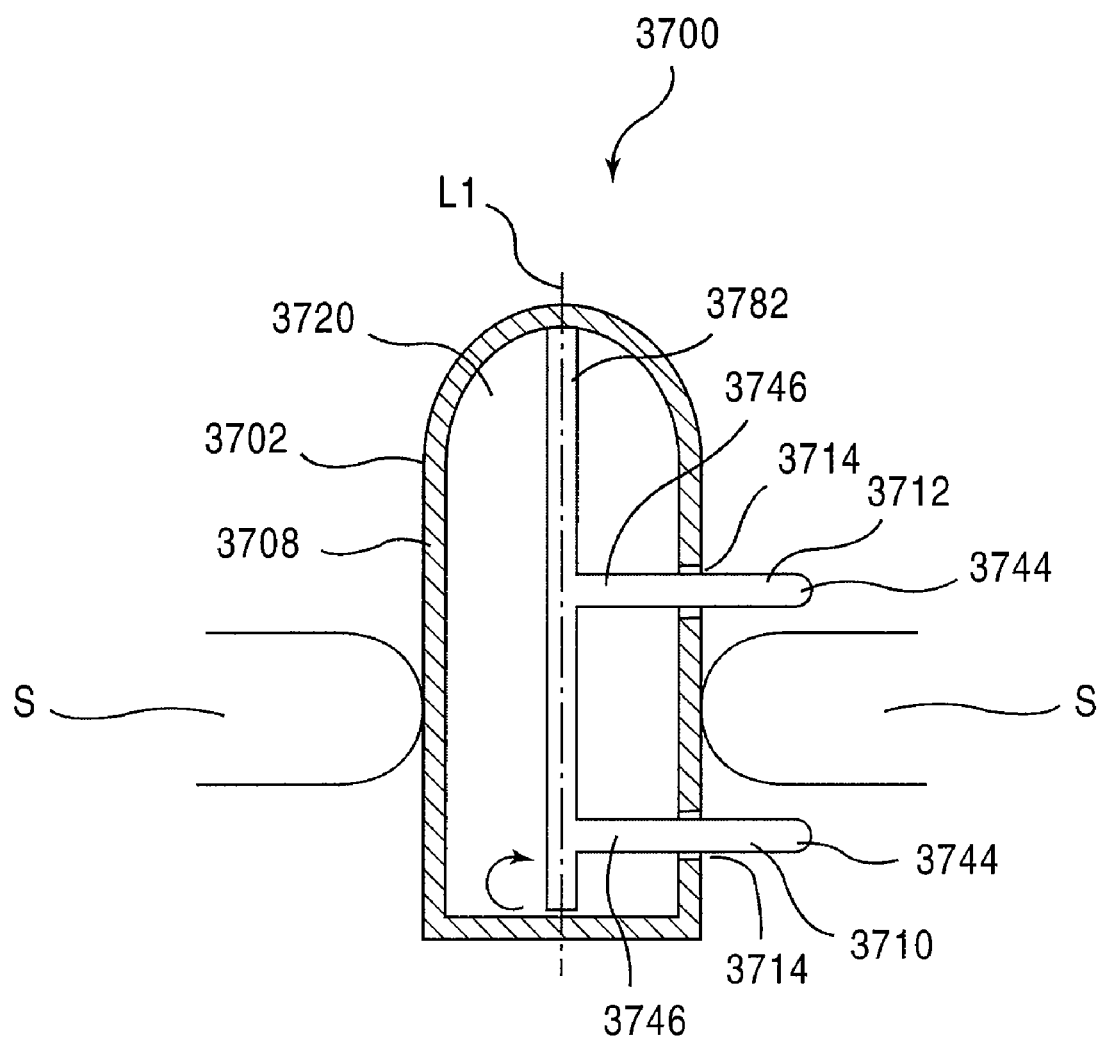
FIG. 82 is a cross-sectional plan view of the medical device illustrated in FIGS. 80A and 80B in a second configuration.

While the spinal implants are shown and described above as having one or more retention members that extend substantially symmetrically from a support member when in a second configuration, in some embodiments, a spinal implant includes a retention member that extends asymmetrically from a support member when in a second configuration. For example, FIGS. 80-82 illustrate a spinal implant 3700 according to an embodiment of the invention that includes a proximal retention member 3710 and a distal retention member 3712 that extend asymmetrically from a support member 3702. As shown in FIGS. 80 and 81, the proximal retention member 3710 and the distal retention member 3712 are each repeatably positionable in a first configuration in which they are substantially disposed within the support member 3702, and a second configuration in which a portion each is disposed outside of the support member 3702.

The support member 3702 includes a sidewall 3708 that defines an inner area 3720 and two openings 3714 that connect the inner area 3720 to an area outside of the support member 3702. When the spinal implant 3700 is in the second configuration, a portion of the proximal retention member 3710 and a portion of the distal retention member 3712 extend through the openings 3714 to an area outside of the support member 3702.

In the illustrated embodiment, the proximal retention member 3710 and the distal retention member 3712 each include a first end portion 3746 and a second end portion 3744. The first end portions 3746 of the proximal retention member 3710 and the distal retention member 3712 are coupled by a connecting member 3782 that has a longitudinal axis L1 (shown in FIG. 77). In some embodiments, the connecting member 3782, the proximal retention member 3710 and the distal retention member 3712 are separate components that are coupled together to form the illustrated structure. In other embodiments, the connecting member 3782, the proximal retention member 3710 and the distal retention member 3712 are monolithically formed.

The connecting member 3782 defines a longitudinal axis L1, about which it rotates. As illustrated, as the connecting member 3782 rotates, the proximal retention member 3710 and the distal retention member 3712 also rotate, thereby causing the end portions 3744 of the proximal retention member 3710 and the distal retention member 3712 to extend outwardly through the openings 3714. In this manner, the retention member 3210 can be repeatedly transitioned between the first configuration and the second configuration.

In some embodiments, the connecting member 3782 is rotated using an insertion tool (not shown) that includes a ratchet mechanism. The insertion tool can rotate the connecting member 3782 in a number of different ways, such as, for example, manually, pneumatically or electronically.

In one embodiment, an apparatus includes a first body coupled to a second body. The first body and the second body collectively are configured to be releasably coupled to an implant device configured to be disposed between adjacent spinous processes. A first engaging portion is coupled to the first body, and a second engaging portion is coupled to the second body. The first engaging portion and/or the second engaging portion is configured to be received within a first opening defined by the implant device. The first body configured to be moved relative to the second body such that a distance between the first engaging portion and the second engaging portion is moved between a first distance and a second distance, and simultaneously a length of the implant device is moved between a first length and a second length.

In another embodiment, a kit includes an implant that is reconfigurable between an expanded configuration and a collapsed configuration while disposed between adjacent spinous processes. The implant has a longitudinal axis and defines an opening. A deployment tool is configured to be releasably coupled to the implant. The deployment tool includes an engaging portion configured to be removably received within the opening of the implant and extend in a transverse direction relative to the longitudinal axis when the deployment tool is coupled to the implant. The deployment tool is configured to move the implant between the collapsed configuration and the expanded configuration while the implant is disposed between the adjacent spinous processes.

Figure 83:
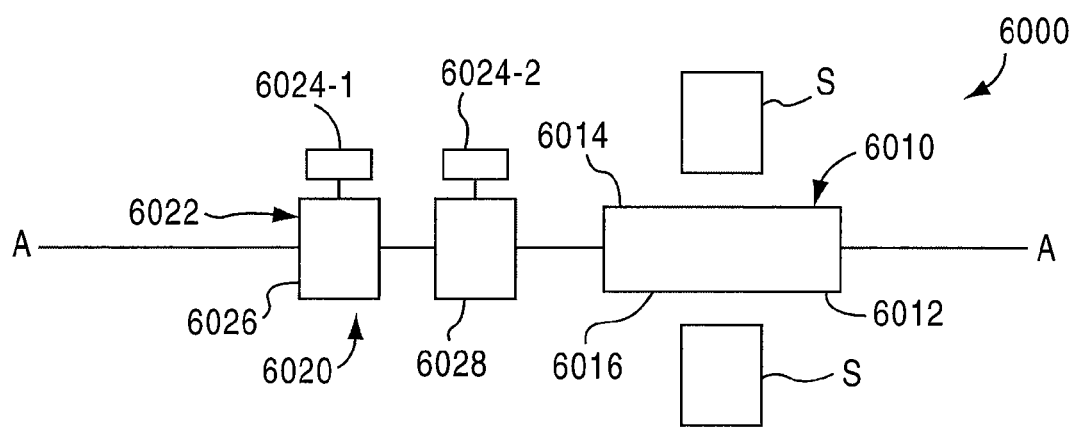
FIG. 83 is a schematic illustration of a medical device according to an embodiment of the invention in a collapsed configuration adjacent two spinous processes.
Figure 84:
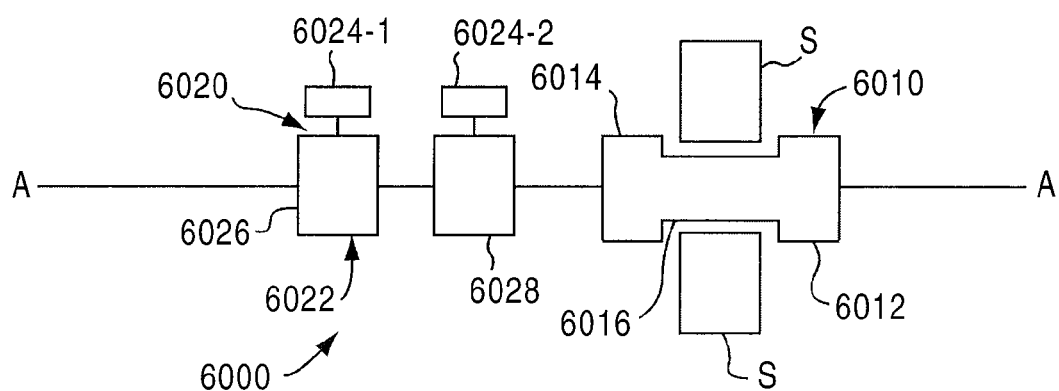
FIG. 84 is a schematic illustration of the medical device of FIG. 83 in an expanded configuration adjacent two spinous processes.

FIGS. 83 and 84 are schematic illustrations of a medical device according to an embodiment of the invention positioned between two adjacent spinous processes. FIG. 83 illustrates the medical device in a first configuration, and FIG. 84 illustrates the medical device in a second configuration. The medical device 6000 includes an implant 6010 and a deployment tool 6020. The implant 6010 includes a distal portion 6012, a proximal portion 6014, and a central portion 6016. The implant 6010 is configured to be inserted between adjacent spinous processes S. The central portion 6016 is configured to contact and provide a minimum spacing between the spinous processes S when adjacent spinous processes S move toward each other during their range of motion to prevent over-extension/compression of the spinous processes S. In some embodiments, the central portion 6016 does not substantially distract the adjacent spinous processes S. In other embodiments, the central portion 6016 does distract the adjacent spinous processes S. The implant 6010 and the deployment tool 6020 can each be inserted into a patient's back and moved in between adjacent spinous processes from the side of the spinous processes (i.e., a posterior-lateral approach). The use of a curved insertion shaft assists in the use of a lateral approach to the spinous processes S.

The implant 6010 has a collapsed configuration in which the proximal portion 6014, the distal portion 6012 and the central portion 6016 share a common longitudinal axis. In some embodiments, the proximal portion 6014, the distal portion 6012 and the central portion 6016 define a tube having a constant inner diameter. In other embodiments, the proximal portion 6014, the distal portion 6012 and the central portion 6016 define a tube having a constant outer diameter and/or inner diameter. In yet other embodiments, the proximal portion 6014, the distal portion 6012 and/or the central portion 6016 have different inner diameters and/or outer diameters.

The implant 6010 can be moved from the collapsed configuration to an expanded configuration, as illustrated in FIG. 84. In the expanded configuration, the proximal portion 6014 and the distal portion 6012 each have a larger outer perimeter (e.g., outer diameter) than when in the collapsed configuration, and the proximal portion 6014 and the distal portion 6012 each have a larger outer perimeter (e.g., outer diameter) than the central portion 6016. In the expanded configuration, the proximal portion 6014 and the distal portion 6012 are positioned to limit lateral movement of the implant 6010 with respect to the spinous processes S. The proximal portion 6014 and the distal portion 6012 are configured to engage the spinous process (i.e., either directly or through surrounding tissue and depending upon the relative position of the adjacent spinous processes S) in the expanded configuration. For purposes of clarity, the tissue surrounding the spinous processes S is not illustrated.

In some embodiments, the proximal portion 6014, the distal portion 6012 and the central portion 6016 are monolithically formed. In other embodiments, one or more of the proximal portion 6014, the distal portion 6012 and/or the central portion 6016 are separate components that can be coupled together to form the implant 6010. For example, the proximal portion 6014 and distal portion 6012 can be monolithically formed and the central portion 6016 can be a separate component that is coupled thereto. These various portions can be coupled, for example, by a friction fit, welding, adhesive, etc.

The implant 6010 is configured to be coupled to the deployment tool 6020. The deployment tool 6020 includes an elongate member 6022 and two or more engaging portions 6024. In the embodiment shown in FIGS. 83 and 84, there are two engaging portions 6024-1 and 6024-2 shown, but it should be understood that more than two engaging portions 6024 can be included. The elongate member 6022 can include a first body portion 6026 coupled to a second body portion 6028. In some embodiments, the first body portion 6026 is threadedly coupled to the second body portion 6028. The first body portion 6026 and the second body portion 6028 are configured to be moved relative to each other. For example, a threaded connection between the first body portion 6026 and the second body portion 6028 can be used to decrease or increase a distance between the first body portion 6026 and the second body portion 6028. The first body portion 6026 and the second body portion 6028 can be a variety of different shapes and sizes, and can be the same shape and/or size, or have a different shape and/or size than each other. For example, in some embodiments, the first body portion includes a straight distal end and a straight proximal end, and the second body portion includes a straight proximal end and a curved or rounded distal end. The curved distal end can assist with the insertion of the deployment tool into a lumen of an implant and also with the insertion of the medical device into a portion of a patient's body.

The first engaging portion 6024-1 can be coupled to the first body portion 6026 and the second engaging portion 6024-2 can be coupled to the second body portion 6028. The engaging portions 6024 can be, for example, substantially rectangular, square, circular, oval, semi-circular, or quarter-moon shaped. The engaging portions 6024, can be spring-loaded devices coupled to the elongate member 6022 of the deployment tool 6020, such that the engaging portions 6024 are biased into a position transverse to a longitudinal axis A defined by the elongate member 6022 and extending from an outer surface of the elongate member 6022. Upon force exerted on the engaging portions 6024, the engaging portions 6024 can be moved or collapsed to a position substantially below the outer surface of the elongate member 6022. The engaging portions 6024 can alternatively be coupled to an actuator (not shown) configured to move the engaging portions 6024 from a position transverse to the longitudinal axis A and extending from an outer surface of the elongate member 6022, to a position substantially below the outer surface of the elongate member 6022.

Figure 94:
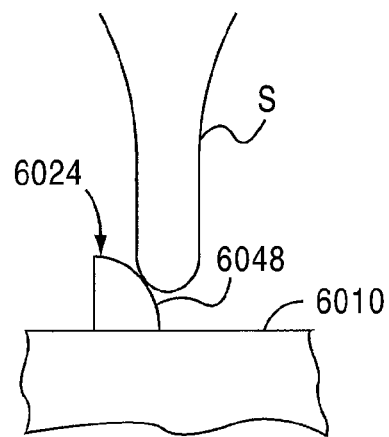
FIG. 94 is a side view of a portion of a medical device according to an embodiment of the invention illustrating an engaging portion in an extended configuration and positioned adjacent a spinous process.
Figure 95:
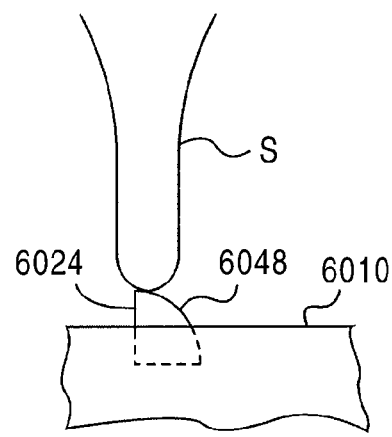
FIG. 95 is a side view of the portion of the medical device of FIG. 94 illustrating the engaging portion in a partially collapsed configuration.
Figure 96:
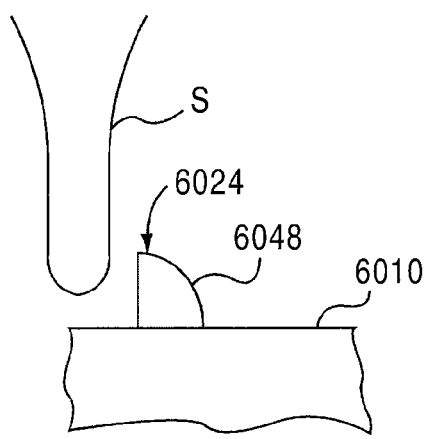
FIG. 96 is a side view of the portion of the medical device of FIG. 94 illustrating the engaging portion in the extended configuration after being inserted past the spinous process.

FIGS. 94-96 illustrate the movement of an engaging portion 6024 as it passes by a spinous process S when an implant and deployment tool (collectively also referred to as medical device) are coupled together and being inserted between adjacent spinous processes. In some cases, as the medical device is being inserted, an engaging portion 6024 extending from a proximal portion of an implant may come into contact with a spinous process (or other tissue). To allow the engaging portion 6024 to pass by the spinous process, the engaging portion 6024 can be moved downward (as described above) so as to clear the spinous process. FIG. 94 illustrates an engaging portion 6024 having a spring-biased construction. The engaging portion 6024 includes a curved portion 6048 that initially contacts the spinous process S as the medical device is being inserted adjacent a spinous process S. As the curved portion 6048 contacts the spinous process S, the engaging portion 6024 is moved downward at least partially into an interior of the implant 6010, as shown in FIG. 95. The engaging portion 6024 moves back to an extended position (e.g., extending transversely from a surface of the implant 6010) after the engaging portion clears the spinous process S, as shown in FIG. 96, due to the bias of the spring (not shown).

Figure 85:
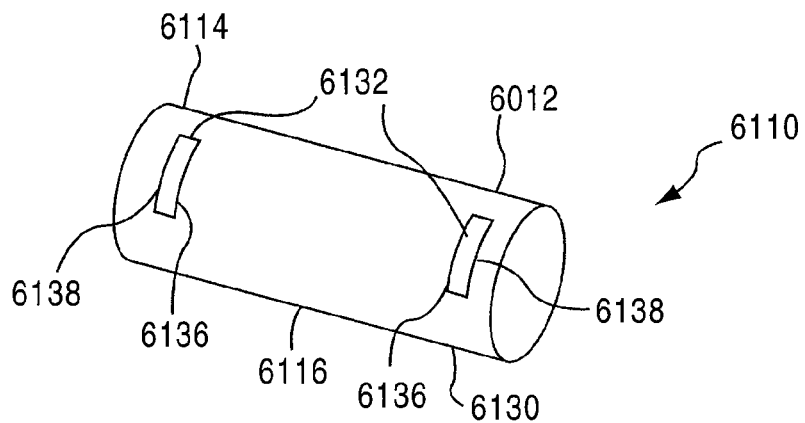
FIG. 85 is a side perspective view of an implant according to an embodiment of the invention in an expanded configuration.
Figure 98:
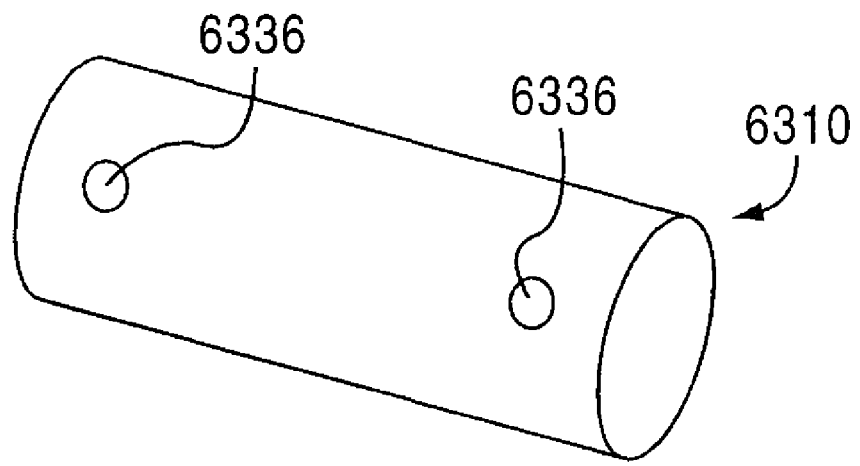
FIG. 98 is a side perspective view of an implant according to another embodiment of the invention.

The deployment tool 6020 can be used to move the implant 6010 from the collapsed configuration to the expanded configuration, and vice versa, as will be discussed in more detail below. The first body portion 6026 and the second body portion 6028 are collectively configured to be inserted at least partially into a lumen (not shown in FIGS. 83 and 84) of the implant 6010, such that at least one engaging portion 6024 extends through an opening (not shown in FIGS. 83 and 84) defined by the implant 6010. The implant 6010 can be configured with one or more such openings, each of which is configured to receive an engaging portion 6024 disposed on the elongate member 6022 (e.g., the first body portion 6026 or the second body portion 6028). The openings defined by the implant 6010 can be, for example, the openings can be circular, oval, square, rectangular, etc. FIG. 85 illustrates an example of an implant 6110 defining curved rectangular openings 6136, and FIG. 98 illustrates an implant 6310 defining curved round or circular openings 6336.

The openings are at least partially defined by an edge (not shown in FIGS. 83 and 84) on the implant 6010. The engaging portions 6024 on the deployment tool 6020 include a surface (not shown in FIGS. 83 and 84) that is configured to engage or contact the edge of the openings of the implant 6010 when the elongate member 6022 is inserted into the lumen of the implant 6010.

In use, the spinous processes S can be distracted prior to inserting the implant 6010. When the spinous processes are distracted, a trocar can be used to define an access passage for the implant 6010. In some embodiments, the trocar can be used to define the passage as well as distract the spinous processes S. Once an access passage is defined, the implant 6010 can be inserted percutaneously and advanced between the spinous processes, distal end 6012 first, until the central portion 6016 is located between the spinous processes S. In some embodiments, the implant 6010 can be coupled to the deployment tool 6020 prior to being inserted between the adjacent spinous processes. In other embodiments, the implant 6010 can be inserted between adjacent spinous processes without being coupled to the deployment tool 6020. In the latter configuration, after the implant 6010 is disposed between the adjacent spinous processes, the deployment tool 6020 can be inserted into the lumen defined by the implant 6010.

Once the implant 6010 is in place between the spinous processes, and the deployment tool 6020 is in position within the lumen of the implant 6010, the implant 6010 can be moved to the second configuration (i.e., the expanded configuration) by actuating the deployment tool 6020. For example, when the deployment tool 6020 is inserted into the lumen of the implant 6010, the first body portion 6026 is positioned at a first distance from the second body portion 6028, and the first engaging portion 6024-1 is positioned at a first distance from the second engaging portion 6024-2, as shown in FIG. 83. The deployment tool 6020 can then be actuated at a proximal end portion (e.g., by turning a handle) (not shown in FIGS. 83 and 84) causing the threaded coupling between the first body portion 6026 and the second body portion 6028 to move the first body portion 6026 and the second body portion 6028 towards each other such that the first body portion 6026 is now at a second distance (closer) from the second body portion 6028, as shown in FIG. 84. This movement likewise moves the first engaging portion 6024-1 and the second engaging portion 6024-2 to a closer position relative to each other. For example, in FIG. 83, the first engaging portion 6024-1 is positioned at a distance from the second engaging portion 6024-2 that is greater than a distance between the first engaging portion 6024-1 and the second engaging portion 6024-2 shown in FIG. 84.

As the engaging portions 6024-1 and 6024-2 are moved relative to each other, the surface (described above and described in more detail below) on the engaging portions 6024 imparts a force on the edge (described above and described in more detail below) of the opening defined by the implant causing the implant to move from the collapsed configuration to the expanded configuration.

The deployment tool 6020 is configured such that the deployment tool 6020 can be removed from the implant 6010 after the implant has been moved to the expanded configuration. The implant can remain disposed between the spinous processes indefinitely or removed as needed. For example, the deployment tool 6020 can be reinserted into the lumen of the implant 6010 and actuated in an opposite direction to cause the implant 6010 to be moved from the expanded configuration back to the collapsed configuration. In the collapsed configuration, the implant can be removed from the patient's body or repositioned to a new location between the spinous processes.

In some embodiments, the implant 6010 is inserted percutaneously (i.e., through an opening in the skin) and in a minimally-invasive manner. For example, as discussed in detail herein, the sizes of portions of the implant are expanded after the implant is inserted between the spinous processes. Once expanded, the sizes of the expanded portions of the implant are greater than the size of the opening. For example, the size of the opening/incision in the skin can be between 3 millimeters in length and 25 millimeters in length across the opening. In some embodiments, the size of the implant in the expanded configuration is between 3 and 25 millimeters across the opening.

Figure 86:
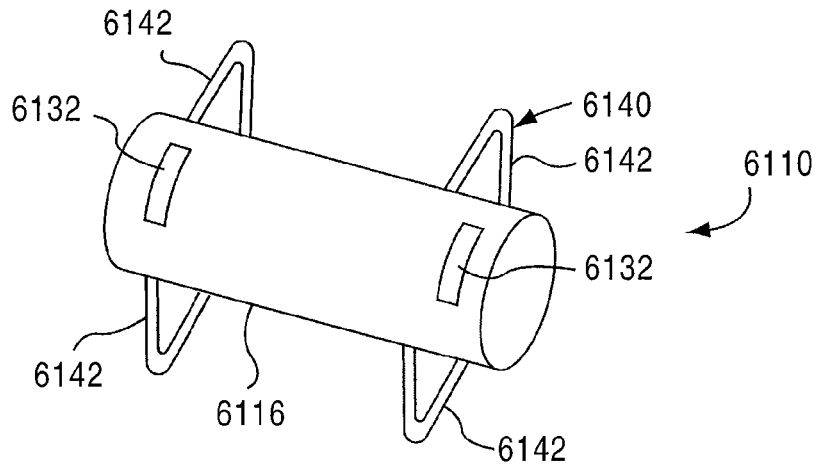
FIG. 86 is a side perspective view of the implant of FIG. 85 shown in a collapsed configuration.
Figure 87:
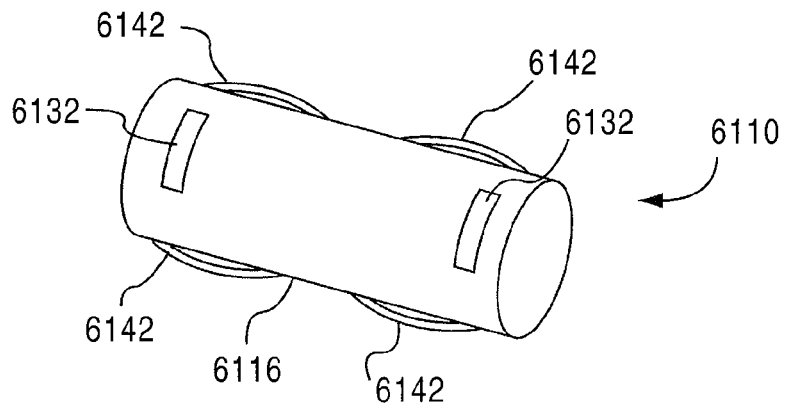
FIG. 87 is a side perspective view of the medical device of FIG. 85 shown in a collapsed configuration.
Figure 97:
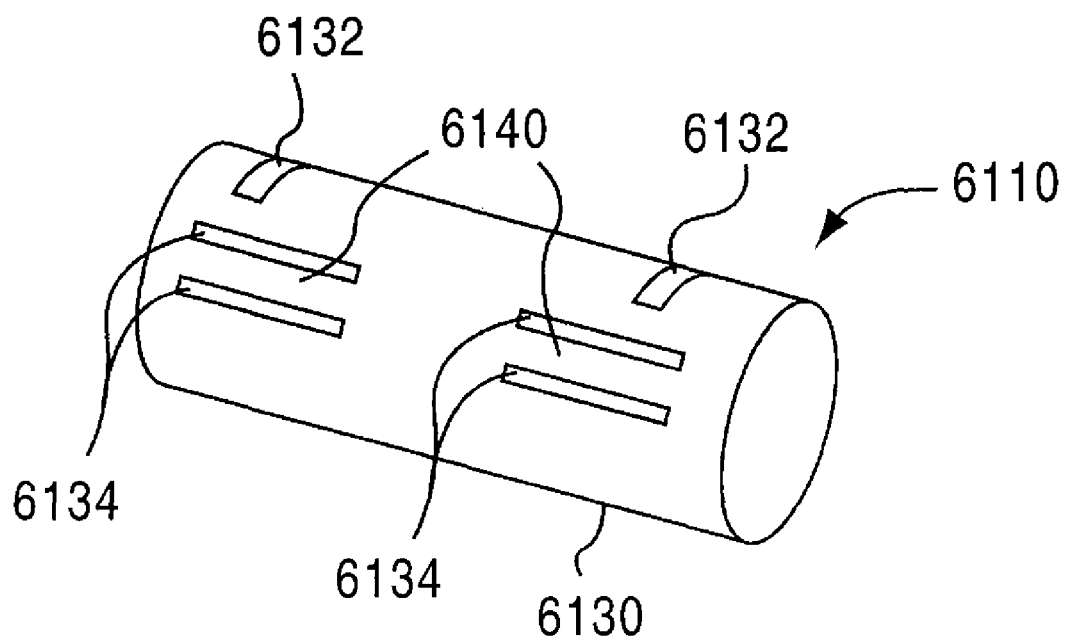
FIG. 97 is a side perspective view of the implant of FIG. 85 shown rotated about a longitudinal axis of the implant.

FIGS. 85-87 illustrate an implant according to an embodiment of the invention. An implant 6110 includes a proximal portion 6114, a distal portion 6112, and a central portion 6116. The implant 6110 also defines multiple openings 6132 on an outer surface of the implant 6110. The openings 6132 are in communication with a lumen 6158 (shown in FIG. 92) defined by the implant 6110. The openings 6132 are partially defined by a first edge 6136 and a second edge 6138. The implant 6110 includes expandable portions disposed at the distal portion 6112 and the proximal portion 6114. The expandable portions 6140 can be coupled to the implant 6110 or formed integral with the implant 6110, as shown in FIG. 97. As shown in FIG. 97, elongated slots 6134 can be defined on an outer surface of the implant 6110. The elongated slots 6134 create weakened areas on the implant 6110 that allow the expandable portions 6140 to fold when exposed to axial force, forming extensions 6142, as shown in FIG. 86.

The implant 6110 can be inserted between adjacent spinous processes (not shown) in a collapsed configuration, as shown in FIG. 85, and then moved to an expanded configuration, as shown in FIG. 86. The implant 6110 can then be moved back to a collapsed configuration as shown in FIG. 87, which illustrates the expandable portions 6140 in a partially collapsed configuration. Although FIG. 87 shows a partially collapsed configuration, in some embodiments, the implant can be moved back to the collapsed configuration as shown in FIG. 85.

Figure 88:
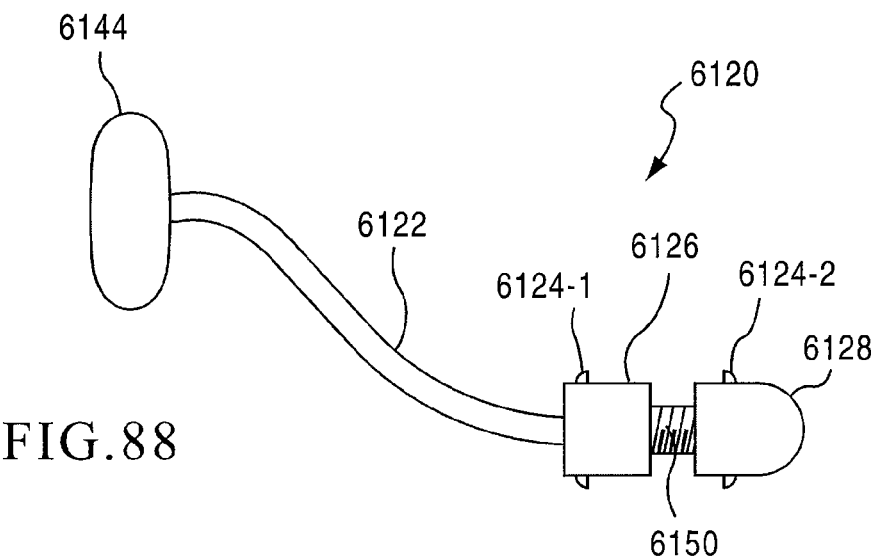
FIG. 88 is a side view of a deployment tool according to an embodiment of the invention.
Figure 89:
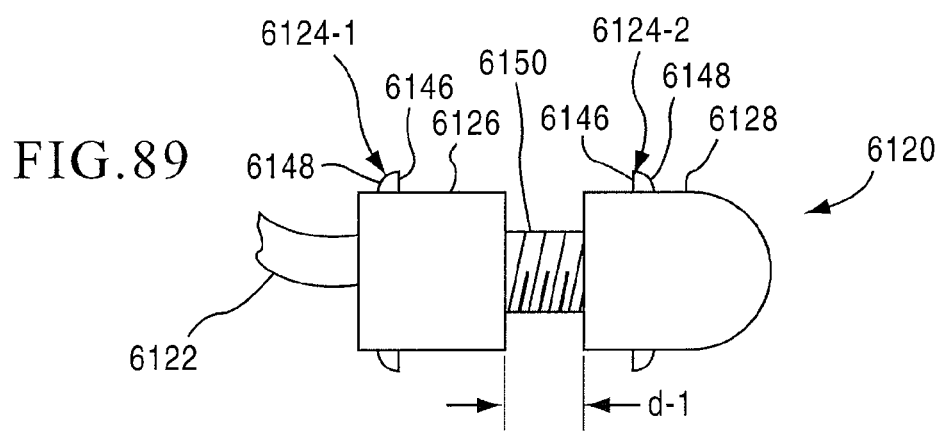
FIG. 89 is a side view of a portion of the deployment tool of FIG. 88 shown in a first configuration.
Figure 90:
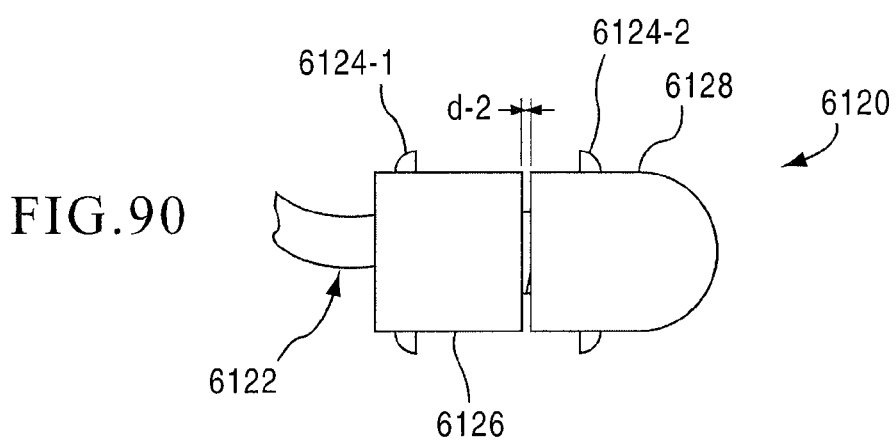
FIG. 90 is a side view of the portion of the deployment tool of FIG. 89 shown in a second configuration.

To move the implant 6110 from the collapsed configuration to the expanded configuration, and vice versa, a deployment tool, as described above and as shown in FIGS. 88-90, can be used. The deployment tool 6120 includes an elongate member 6122 coupled to a handle 6144. The elongate member 6122 includes a first body portion 6126 coupled to a second body portion 6128 through a threaded coupling 6150. A pair of engaging portions 6124-1 are disposed on the first body portion 6126, and a pair of engaging portions 6124-2 are disposed on the second body portion 6128. The engaging portions 6124-1 and 6124-2 (also collectively referred to as engaging portions 6124) include a surface 6146 and a rounded portion 6148. The threaded coupling 6150 between the first body portion 6126 and the second body portion 6128 is used to move the first body portion 6126 and the second body portion 6128 such that a distance between the first body portion 6126 and the second body portion 6128 is changed. For example, FIG. 89 illustrates a first distance d-1 between the first body portion 6126 and the second body portion 6128, and FIG. 90 illustrates a second distance d-2 between the first body portion 6126 and the second body portion 6128. As shown in FIGS. 89 and 90, as the distance between the first body portion 6126 and the second body portion 6128 is changed, a distance between the engaging portions 6124-2 and 6124-2 is also changed.

Figure 91:
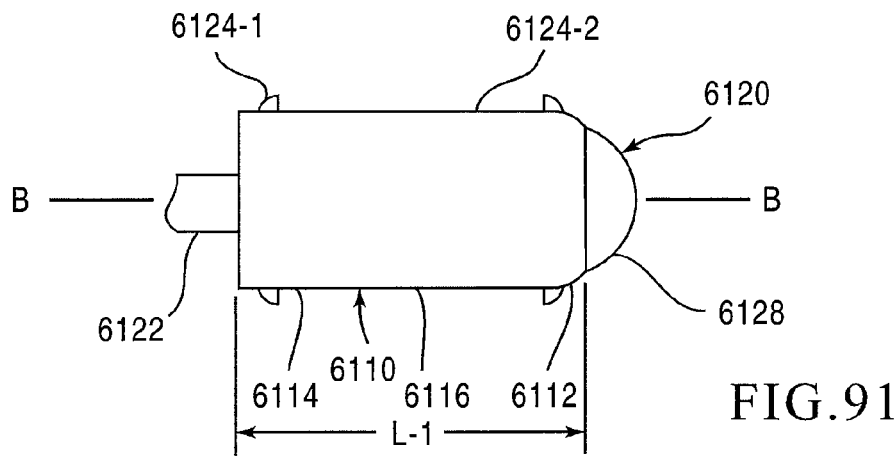
FIG. 91 is a side view of a portion of the deployment tool of FIG. 89 and the implant of FIG. 85 with the implant shown in an expanded configuration.
Figure 92:
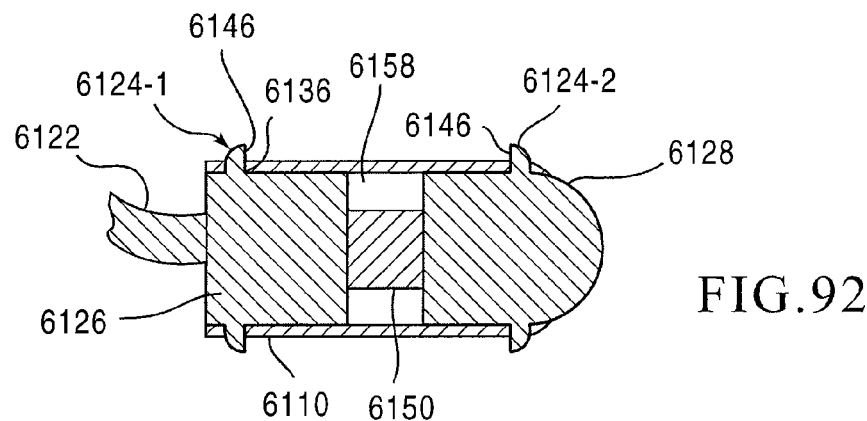
FIG. 92 is a cross-sectional view of the portion of the deployment tool and implant shown in FIG. 91.
Figure 93:
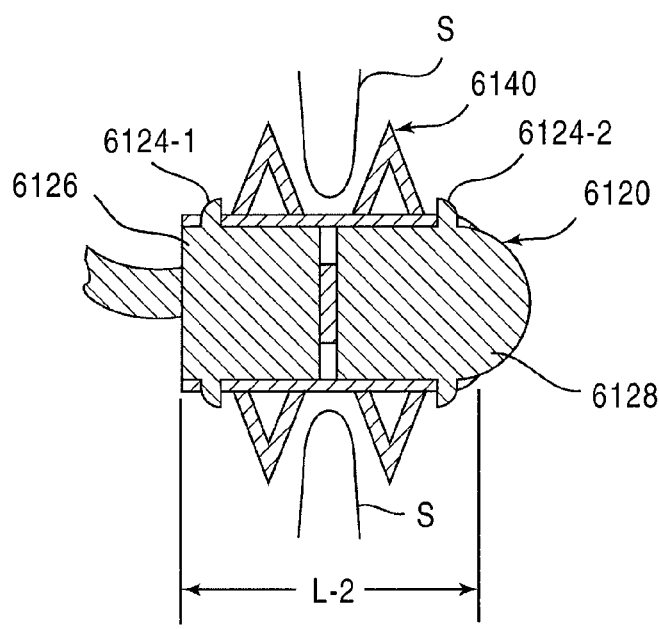
FIG. 93 is a cross-sectional view of the deployment tool and implant of FIG. 91 with the implant shown in a collapsed configuration positioned between adjacent spinous processes.

In use, the first body portion 6126 and the second body portion 6128 are collectively disposed within the lumen 6158 of the implant 6110, such that the engaging portions 6124 extend through the openings 6132 and transverse to an axis B defined by the implant 6110, as shown in FIGS. 91-93. In this position, the surface 6146 of the engaging portions 6124 is configured to contact the edge 6136 of the openings 6132.

FIGS. 91 and 92 illustrate the first body portion 6126 and the second body portion 6128 disposed within the lumen of the implant 6110, when the implant is in a collapsed configuration. In this position, the first body portion 6126 is at a first distance from the second body portion 6128, the engaging portions 6124-1 are at a first distance from the engaging portions 6124-2, and the implant has a first length L-1.

When the implant is positioned between spinous processes S, the deployment tool 6120 can be actuated to move the implant 6110 to the expanded configuration, as shown in FIG. 93. When the deployment tool 6120 is actuated, the first body portion 6126 is moved closer to the second body portion 6128, and the engaging portions 6124-1 are moved closer to the engaging portions 6124-2. When this occurs, the surface 6146 on the engaging portions 6124 impart a force on the edge 6136 of the openings 6132, which axially compresses the implant 6110 until the implant 6110 has a second length L-2, as shown in FIG. 93.

Figure 102:
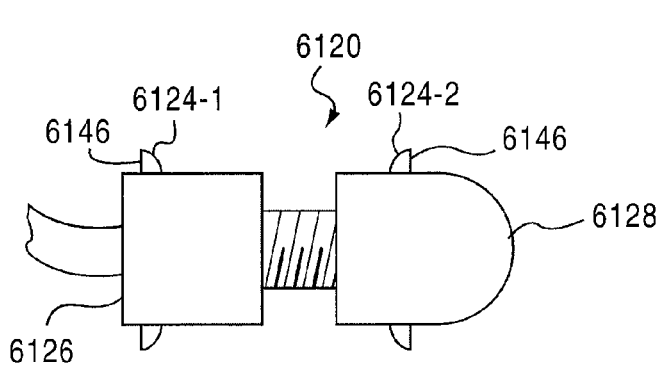
FIG. 102 is a side view of a deployment tool according to another embodiment of the invention.

To move the implant 6110 back to the collapsed configuration, the deployment tool 6120 can be reconfigured such that the surface 6146 of the engaging portions 6124 are positioned facing an opposite direction and configured to contact the edge 6138 of the implant 6110, as shown in FIG. 102. In some embodiments, the engaging portions 6124 can be, for example, removed and re-coupled to the elongate member 6122 (e.g., the first body portion 6126 and the second body portion 6128) such that the same engaging portions 6124 are simply repositioned. In other embodiments, a second deployment tool can be used having engaging portions positioned in the opposite direction. In either case, the deployment tool is inserted into the lumen 6158 of the implant 6110 as done previously, such that the engaging portions 6124 extend through the openings 6132 of the implant 6110 and the surface 6146 contacts the edge 6136 of the implant 6110. The deployment tool 6120 is then actuated in an opposite direction (e.g., turned in an opposite direction) such that the first body portion 6126 and the second body portion 6128 are threadedly moved further away from each other. In doing so, the engaging portions 6124-1 are moved further away from the engaging portions 6124-2, and the surface 6146 of the engaging portions 6124 impart a force on the edge 6138 (instead of edge of 6136) of openings 6132, which moves the implant 6110 back to the collapsed or straightened configuration. Thus, the implant described in all of the embodiments of the invention can be repeatedly moved between the collapsed and expanded configurations as necessary to insert, reposition or remove the implant as desired.

Figure 99:
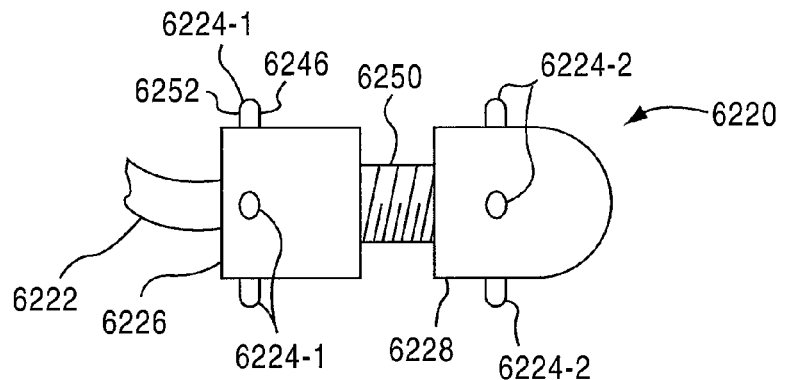
FIG. 99 is a side view of a deployment tool according to another embodiment of the invention.

FIG. 99 illustrates a deployment tool according to another embodiment of the invention. A deployment tool 6220 includes an elongate member 6222 having a first body portion 6226 coupled to a second body portion 6228 through a threaded coupling 6250. In this embodiment, the deployment tool 6220 includes two sets of four (8 total) engaging portions 6224 (only six engaging portions are shown in FIG. 99). A first set of engaging portions 6224-1 are coupled to the first body portion 6226, and a second set of engaging portions 6224-2 are coupled to the second body portion 6228. The engaging portions 6224 include a first surface 6246 and a second surface 6252. When the deployment tool 6220 is coupled to an implant, the first surface 6246 is configured to contact an edge of an opening defined on the implant (such as edge 6136 on implant 6110), and the second surface 6252 is configured to contact an opposite edge on the opening defined by the implant (such as edge 6138 on implant 6110).

Thus, in this embodiment, the deployment tool 6220 can be inserted into an implant and used to move the implant between a collapsed configuration and an expanded configuration without having to reposition the engaging portions 6224, or use a second deployment tool. To move the implant from a collapsed configuration to an expanded configuration, the deployment tool 6220 is actuated in a first direction. To move the implant back to the collapsed configuration, the deployment tool 6220 is actuated in an opposite direction (e.g., turned in an opposite direction). When the deployment tool 6220 is actuated to move the implant from the collapsed configuration to the expanded configuration, the surface 6246 of the engaging portions 6224 impart a force on an edge of an opening (e.g., edge 6136 on implant 6110), causing the implant to be axially compressed, as previously described. When the deployment tool 6220 is actuated to move the implant from the expanded configuration to the collapsed configuration, the surface 6252 of the engaging portions 6224 imparts a force on an opposite edge of the opening (e.g., edge 6138 on implant 6110), causing the implant to be substantially straightened as previously described.

Figure 100:
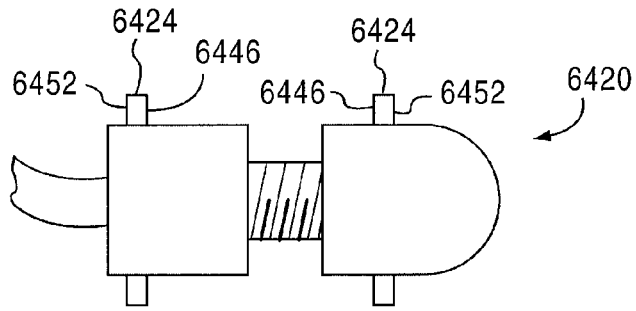
FIG. 100 is a side view of a deployment tool according to another embodiment of the invention.

FIG. 100 illustrates a deployment tool according to another embodiment of the invention. A deployment tool 6420 is similar to the deployment tool 6220 described above, except in this embodiment, there are only two sets of two engaging portions 6424 (4 total). The engaging portions 6424 are similar to the engaging portions 6224 except the engaging portions 6424 are substantially rectangular shaped. The engaging portions 6424 include a surface 6446 configured to contact an edge of an opening defined by an implant, and a surface 6452 configured to contact an opposite edge of the opening defined by the implant.

Figure 101:
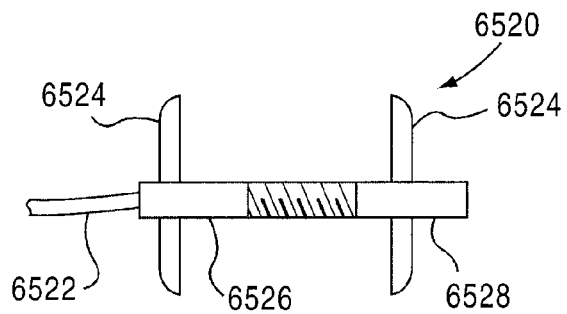
FIG. 101 is a side view of a deployment tool according to another embodiment of the invention.

FIG. 101 illustrates a deployment tool according to yet another embodiment of the invention. A deployment tool 6520 is similarly constructed and functions similarly to the previous embodiments. The deployment tool 6520 includes an elongate member 6522 that includes a first body portion 6526 and a second body portion 6528. In this embodiment, the first body portion 6526 and the second body portion 6528 are smaller than illustrated in the previous embodiments, and engaging portions 6524 are coupled to the first body portion 6526 and the second body portion 6528 that are more elongate than previously shown.

A kit according to an embodiment of the invention can include at least one implant and at least one deployment tool as described above. For example, a kit can include an implant and two deployment tools, one deployment tool configured to be used to move the implant from a collapsed configuration to an expanded configuration, and another deployment tool configured to be used to move the implant from the expanded configuration to the collapsed configuration. Alternatively, a kit can include a single deployment tool have multiple engaging portions as described herein, that can be releasably coupled to an elongate member of a deployment tool. For example, one type or style of engaging portion can be used to move the implant from a collapsed configuration to an expanded configuration, and another type or style of engaging portion can be used to move the implant from the expanded configuration to the collapsed configuration. The kit can include engaging portions having one of a variety of different shapes and sizes, such that a user can select a particular engaging portion(s) for use in a particular application.

Figure 118:
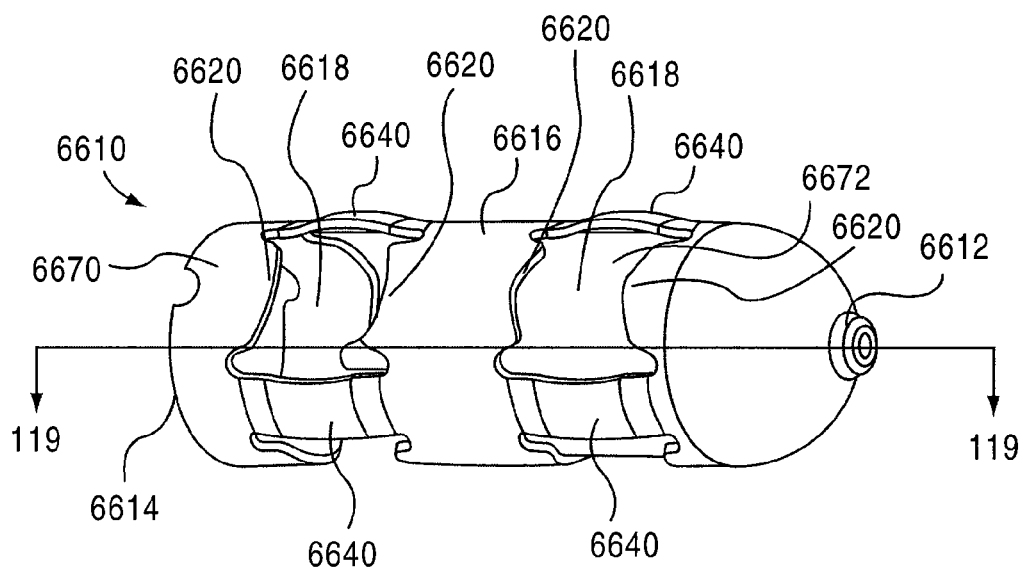
FIG. 118 is a side perspective view of an implant according to an embodiment of the invention shown in a collapsed configuration.
Figure 119:
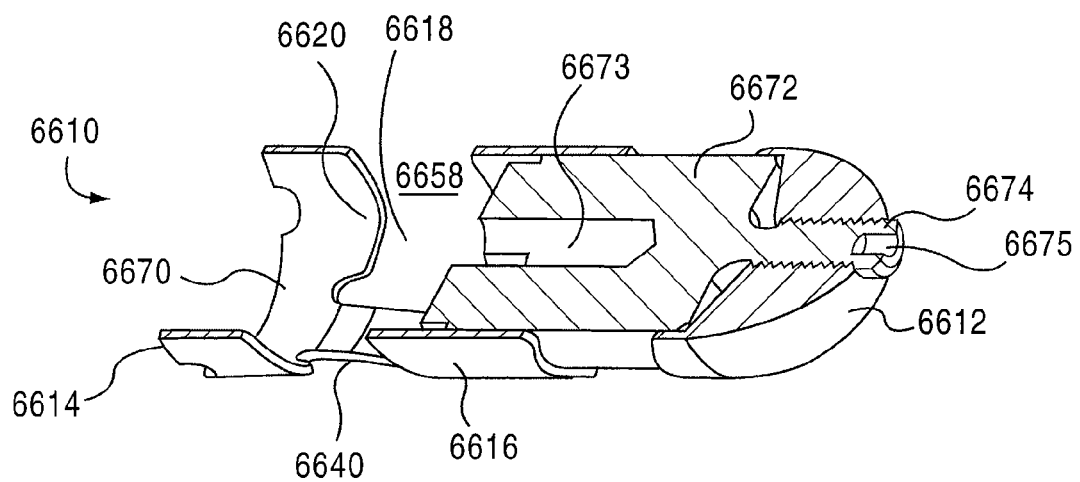
Figure 120:
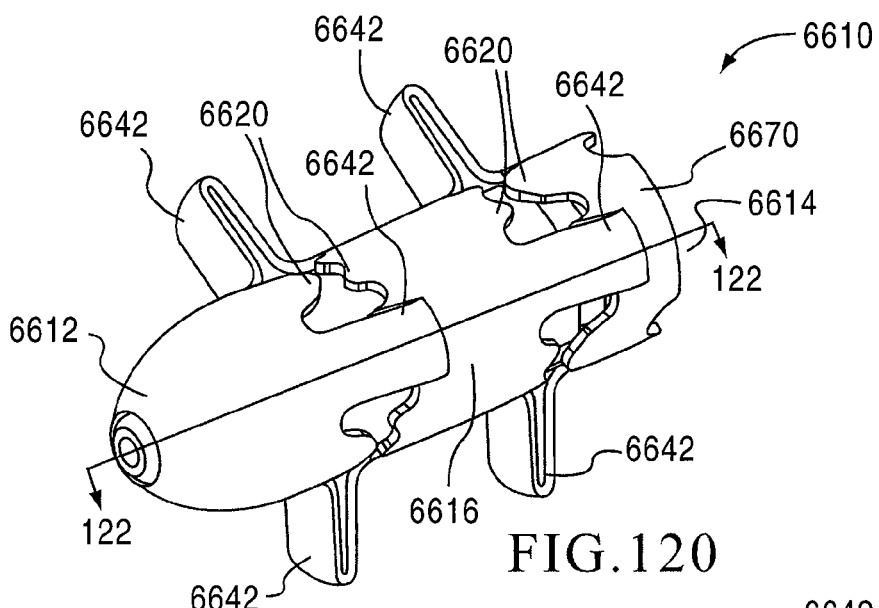
Figure 121:
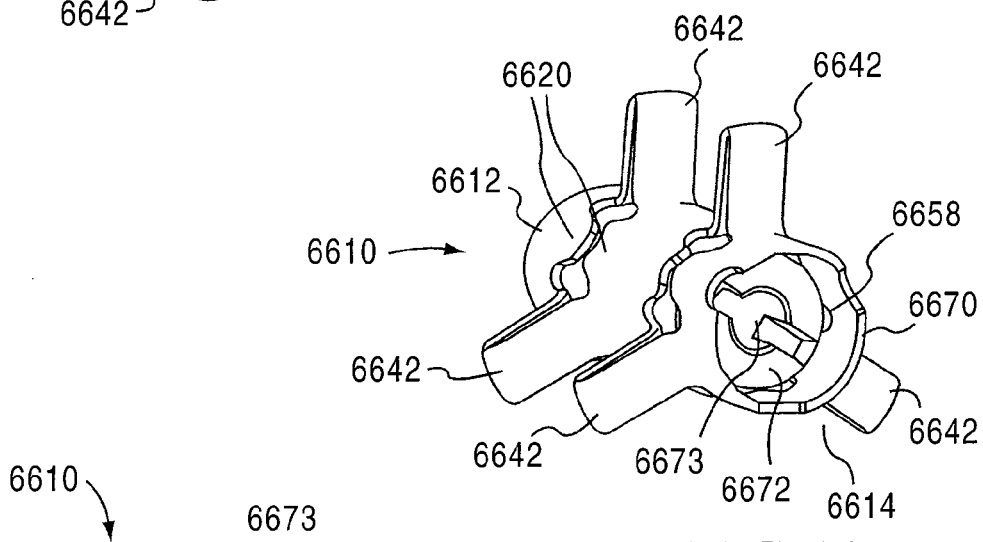
Figure 122:
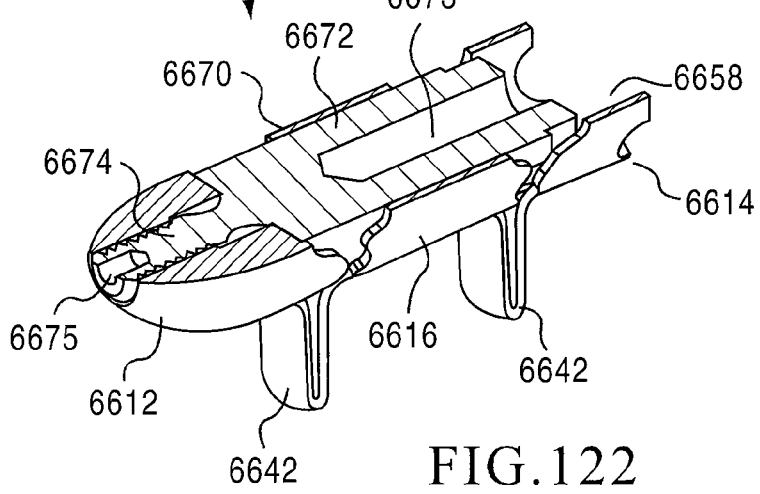
Figure 123:
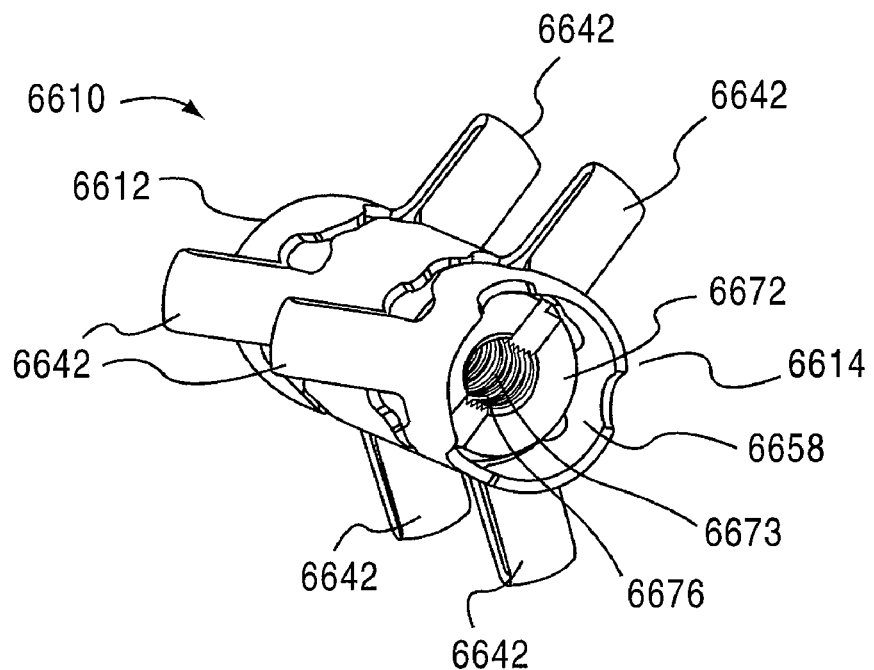
Figure 124:
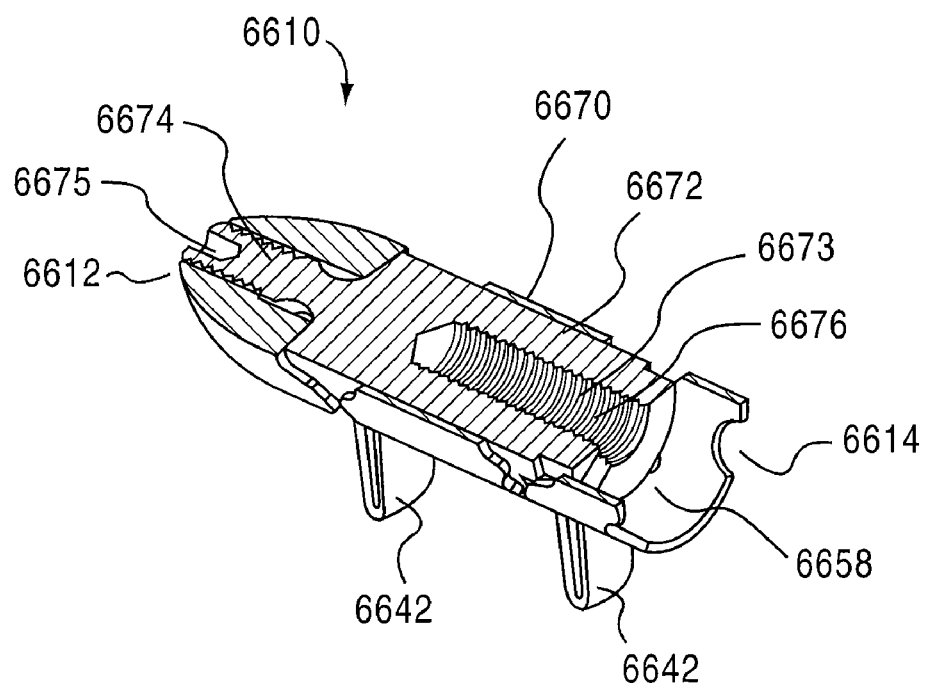
Figure 125:
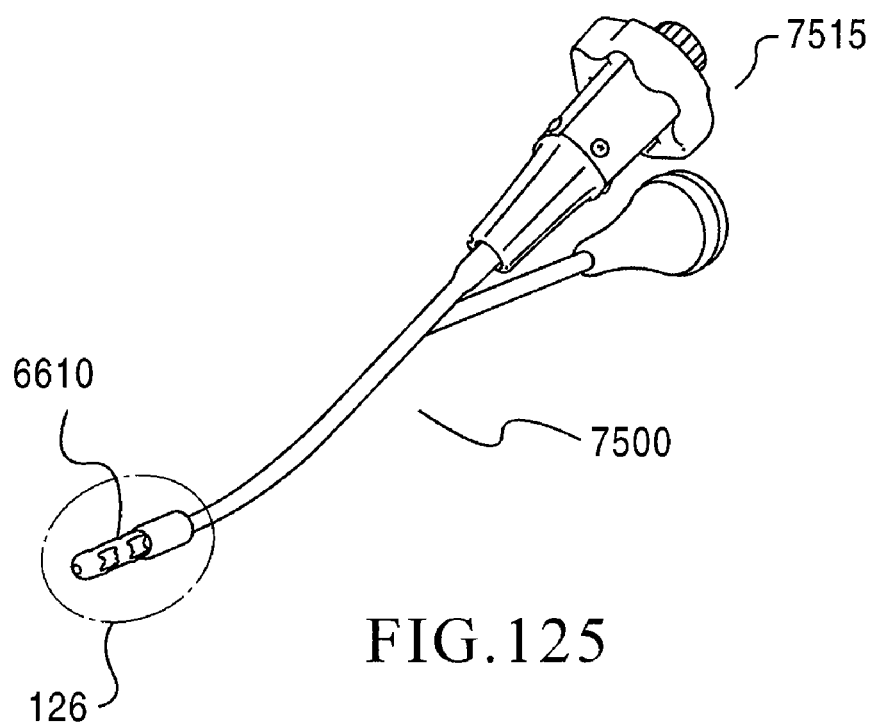
Figure 126:
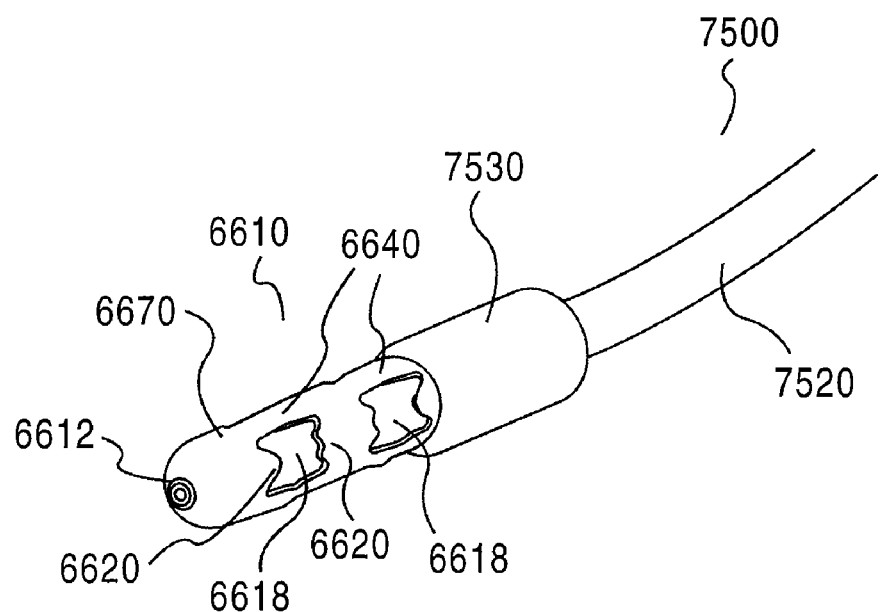
Figure 127:
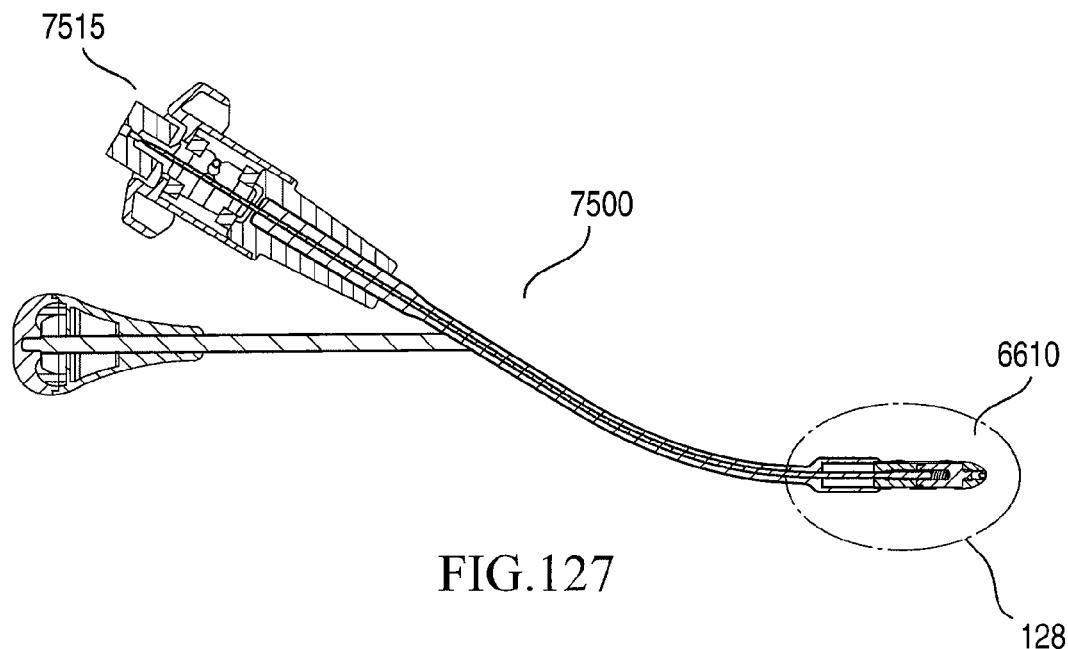
Figure 128:
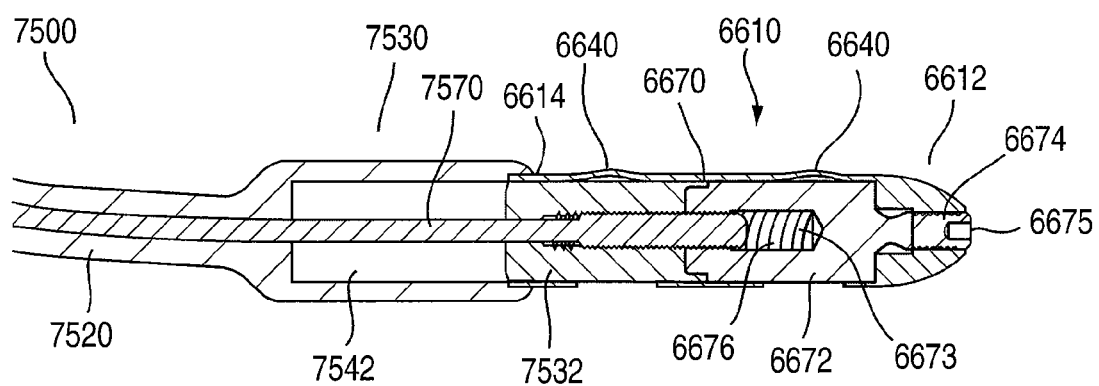

FIGS. 118-120 illustrate an implant 6610 according to another embodiment of the invention. The implant 6610 can be moved between a collapsed configuration, as shown in FIGS. 118 and 119, and an expanded configuration, as shown in FIGS. 120-122. The implant 6610 includes an outer shell 6670 having a distal portion 6612, a proximal portion 6614, and a central portion 6616. The outer shell 6670 defines a series of openings 6618 disposed between the distal portion 6612 and the central portion 6616, and the proximal portion 6614 and the central portion 6616. The outer shell 6670 includes a series of tabs 6620, a pair of which are disposed opposite each other, along the longitudinal axis of the implant 6610, on either side of each opening 6618. The outer shell 6670 also includes expandable portions 6640, which form extensions 6642 that extend radially from the outer shell 6670 when the implant 6610 is in the expanded configuration. As illustrated best in FIGS. 120-122, the arrangement of the openings 6618 and the tabs 6620 effect the shape and/or size of the extensions 6642. In some embodiments, the opposing tabs 6620 can be configured to engage each other when the implant 6610 is in the expanded configuration, thereby serving as a positive stop to limit the amount of expansion. In other embodiments, for example, the opposing tabs 6620 can be configured to engage each other during the expansion process, thereby serving as a positive stop, but remain spaced apart when the implant 6610 is in the expanded configuration (see, for example, FIGS. 120-122). In such embodiments, the elastic properties of the extensions 6642 can cause a slight "spring back," thereby causing the opposing tabs 6620 to be slightly spaced apart when the expansion device (also referred to as an insertion tool or a deployment tool) is disengaged from the implant 6610.

As illustrated best in FIG. 118, when the implant is in the collapsed configuration, the expandable portions 6640 are contoured to extend slightly radially from remaining portions of the outer shell 6670. In this manner, the expandable portions 6640 are biased such that when a compressive force is applied, the expandable portions 6640 will extend outwardly from the outer shell 6670. The expandable portions 6640 can be biased using any suitable mechanism. In some embodiments, for example, the expandable portions can be biased by including a notch in one or more locations along the expandable portion, as previously described. In other embodiments, the expandable portions can be biased by varying the thickness of the expandable portions in an axial direction. In yet other embodiments, the expandable portions can be stressed or bent prior to insertion such that the expandable portions are predisposed to extend outwardly when a compressive force is applied to the implant. In such embodiments, the radius of the expandable portions is greater than that of the remaining portions of the implant (e.g., the remaining cylindrical portions of the implant).

The implant 6610 also includes an inner core 6672 disposed within a lumen 6658 defined by the outer shell 6670. The inner core 6672 is configured to maintain the shape of the implant 6610 during insertion, to prevent the expandable portions from extending inwardly into a region inside of the outer shell 6670 during deployment and/or to maintain the shape of the central portion 6616 once the implant is in its desired position. As such, the inner core 6670 can be constructed to provide increased compressive strength to the outer shell 6670. In other words, the inner core 6672 can provide additional structural support to outer shell 6670 (e.g., in a direction transverse to the axial direction) by filling at least a portion of the region inside outer shell 6670 (e.g., lumen 6658) and contacting the walls of outer shell 6670. This can increase the amount of compressive force that can be applied to the implant 6610 while the implant 6610 still maintains its shape and, for example, the desired spacing between adjacent spinous processes. In some embodiments, the inner core 6672 can define a lumen 6673, while in other embodiments, the inner core 6672 can have a substantially solid construction. As illustrated, the inner core 6672 is fixedly coupled to the outer shell 6670 with a coupling portion 6674, which is configured to be threadedly coupled to the distal portion 6612 of the outer shell 6670. The distal end of the coupling portion 6674 of the inner core 6672 includes an opening 6675 configured to receive a tool configured to deform the distal end of the coupling portion 6674. In this manner once the inner core 6672 is threadedly coupled to the outer shell 6670, the coupling portion 6674 can be deformed or peened to ensure that the inner core 6672 does not become inadvertently decoupled from the outer shell 6670. In some embodiments, an adhesive, such as a thread-locking compound can be applied to the threaded portion of the coupling portion 6674 to ensure the that the inner core 6672 does not inadvertently become decoupled from the outer shell 6670. Although illustrated as being threadedly coupled, the inner core 6672 can be coupled to the outer shell 6670 by any suitable means. In some embodiments, for example, the inner core 6672 can be coupled to the central portion 6616 of the outer shell 6670 by, for example, a friction fit. In other embodiments, the inner core 6672 can be coupled to the outer shell 6670 by an adhesive. The inner core 6672 can have a length such that the inner core 6672 is disposed within the lumen 6658 along substantially the entire length of the outer shell 6670 or only a portion of the length of the outer shell 6670.

The proximal portion of the inner core 6672 includes an opening 6673 configured to receive a portion of an expansion device 7500 (also referred to as an insertion tool or a deployment tool), as shown in FIGS. 125-132. The expansion device 7500 is similar to the expansion device 1500 shown and described above (see e.g. FIGS. 15-17). The expansion device 7500 differs, however, from expansion device 1500 in that the expansion device 7500 includes spacer 7532 configured to cooperate with the inner core 6672 of the implant 6610. In such an arrangement, the threaded portion of rod 7570 of the expansion device 7500 removably engages to the internal threads 6676 of the inner core 6672 of the implant 6610, rather than coupling directly to the distal portion of the implant (as shown in FIGS. 15A and 15B). Although the inner core 6672 is shown as being threadedly coupled to the expansion device 7500, the inner core 6672 can be removably coupled to the expansion device 7500 by any suitable means, such as a protrusion and detent arrangement.

Figure 130:
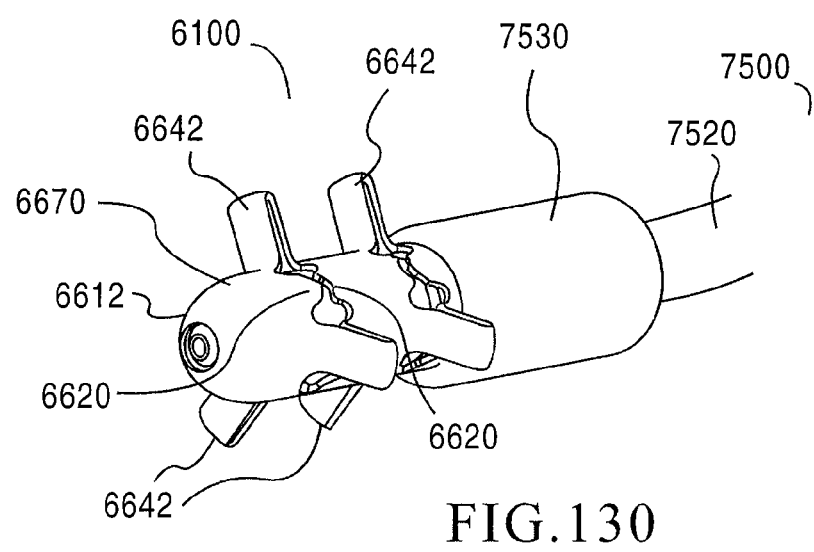

In use, once the implant 6610 is positioned on the implant support portion 7530 of the expansion tool 7500 (see FIGS. 125 and 126), the implant is inserted into the patient's body and disposed between adjacent spinous processes. Once disposed between adjacent spinous processes, the expansion device can be used to move the inner core 6672 axially towards the proximal portion 6614 of the implant 6610 while simultaneously maintaining the position of the proximal portion 6614 of the implant 6610, as shown in FIGS. 130 and 132. In this manner, a compressive force is applied along the longitudinal axis of the outer shell 6670, thereby causing the outer shell 6670 to fold or bend to form extensions 6642 as described above. As illustrated, a portion of the spacer 7532 is received within the receiving area 7542 of the support portion 7530 as the implant 6610 is placed in the expanded configuration. Similarly, to move the implant 6610 from the expanded configuration to the collapsed configuration, the expansion device is actuated in the opposite direction to impart an axial force on the distal portion 6612 of the outer shell 6610 in a distal direction, moving the distal portion 6612 distally, and moving the implant 6610 to the collapsed configuration.

Once the implant 6610 is in its expanded configuration (see FIGS. 129-132), the implant 6610 can be disengaged from the expansion device 7500 by disengaging the distal portion of the rod 7570 from the opening 6673. The rod 7570 can be disengaged by actuating the knob assembly 7515 rotate the rod 7570 relative to the shaft 7520, as discussed above.

Although shown and described above without reference to any specific dimensions, in some embodiments, the outer shell 6670 can have a cylindrical shape having a length of approximately 34.5 mm (1.36 inches) and a diameter between 8.1 and 14.0 mm (0.32 and 0.55 inches). In some embodiments, the wall thickness of the outer shell can be approximately 5.1 mm (0.2 inches).

Similarly, in some embodiments, the inner core 6672 can have a cylindrical shape having an overall length of approximately 27.2 mm (1.11 inches) and a diameter between 8.1 and 14.0 mm (0.32 and 0.55 inches).

In some embodiments, the shape and size of the openings 6618 located adjacent the distal portion 6612 can be the same as that for the openings 6618 located adjacent the proximal portion 6614. In other embodiments, the openings 6618 can have different sizes and/or shapes. In some embodiments, the openings 6618 can have a length of approximately 11.4 mm (0.45 inches) and a width between 4.6 and 10 mm (0.18 and 0.40 inches).

Similarly, the shape and size of the tabs 6620 can be uniform or different as circumstances dictate. In some embodiments, for example, the longitudinal length of the tabs 6620 located adjacent the proximal portion 6614 can be shorter than the longitudinal length of the tabs 6620 located adjacent the distal portion 6612. In this manner, as the implant is moved from the collapsed configuration to the expanded configuration, the tabs adjacent the distal portion will engage each other first, thereby limiting the expansion of the expandable portions 6640 adjacent the distal portion 6612 to a greater degree than the expandable portions 6642 located adjacent the proximal portion 6614. In other embodiments, the longitudinal length of the tabs can be the same. In some embodiments, the longitudinal length of the tabs can be between 1.8 and 2.8 mm (0.07 and 0.11 inches). In some embodiments, the end portions of opposing tabs 6620 can have mating shapes, such as mating radii of curvature, such that the opposing tabs 6620 engage each other in a predefined manner.

Although illustrated as having a generally rectangular shape, the expandable portions 6640 and the resulting extensions 6642 can be of any suitable shape and size. In some embodiments, for example, the expandable portions can have a longitudinal length of approximately 11.4 mm (0.45 inches) and a width between 3.6 and 3.8 mm (0.14 and 0.15 inches). In other embodiments, size and/or shape of the expandable portions located adjacent the proximal portion 6614 can be different than the size and/or shape of the tabs 6620 located adjacent the distal portion 6612. Moreover, as described above, the expandable portions 6640 can be contoured to extend slightly radially from the outer shell 6670. In some embodiments, for example, the expandable portions can have a radius of curvature of approximately 12.7 mm (0.5 inches) along an axis normal to the longitudinal axis of the implant.

In some embodiments, the expandable portions 6640 and the outer shell 6670 are monolithically formed. In other embodiments, the expandable portions 6640 and the outer shell 6670 are formed from separate components having different material properties. For example, the expandable portions 6640 can be formed from a material having a greater amount of flexibility, while the outer shell 6670 can be formed from a more rigid material. In this manner, the expandable portions 6640 can be easily moved from the collapsed configuration to the expanded configuration, while the outer shell 6670 is sufficiently strong to resist undesirable deformation when in use.

Figure 103:
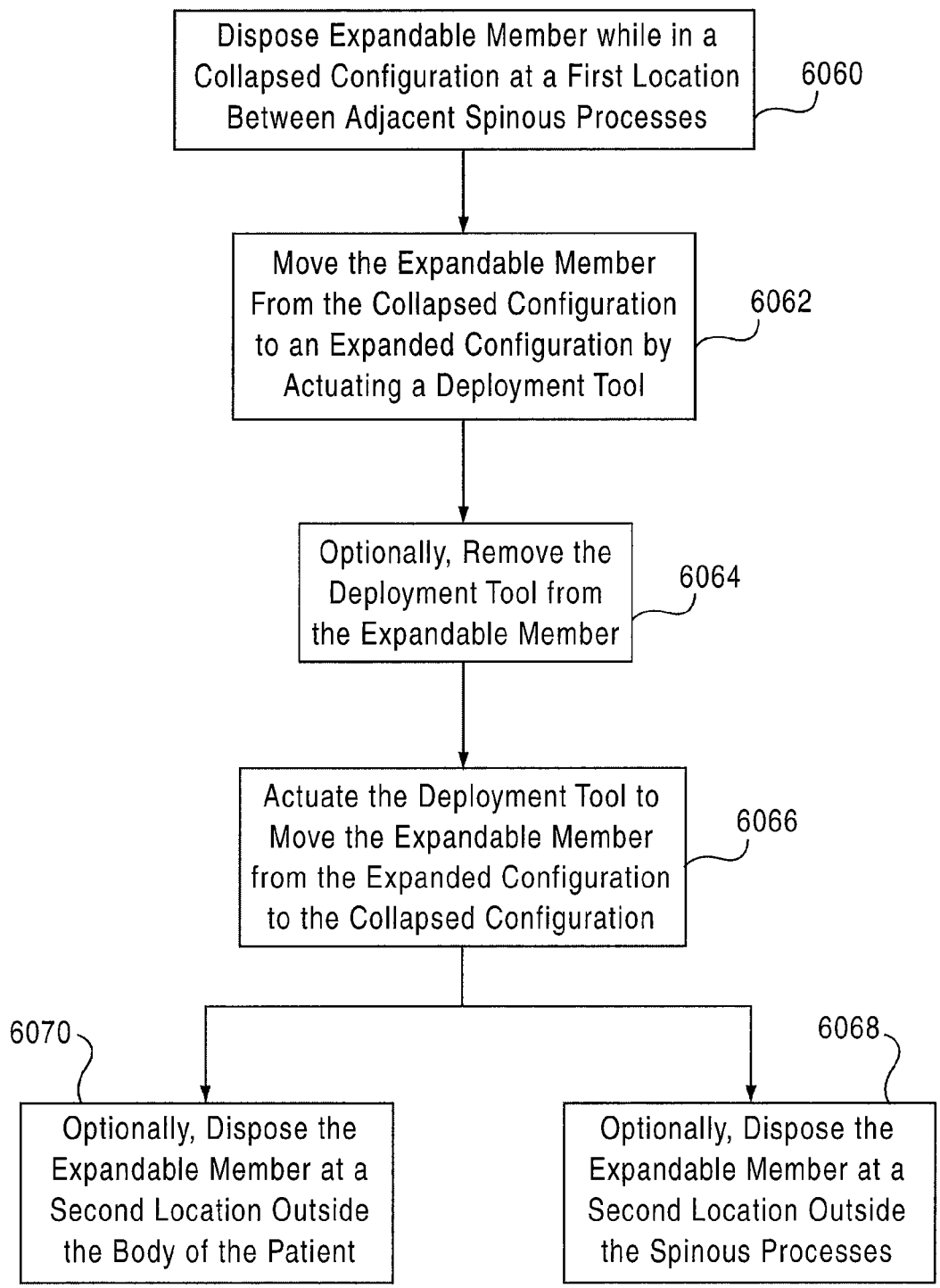
FIG. 103 is a flow chart of a method according to an embodiment of the invention.

FIG. 103 is a flow chart illustrating a method according to an embodiment of the invention. A method includes at 6060, percutaneously disposing an expandable member at a first location between adjacent spinous processes within a body of a patient while the expandable member is in a collapsed configuration. The expandable member is coupled to a deployment tool that includes an engaging portion configured to be received through an opening defined by the expandable member. In other embodiments, the deployment tool can be coupled to the implant after the implant has been disposed between the spinous processes. After the implant has been disposed between the adjacent spinous processes, the expandable member can be moved from the collapsed configuration to an expanded configuration at 6062. To do this, the deployment tool can be actuated while the expandable member is disposed between the adjacent spinous processes such that the engaging portion of the deployment tool imparts a force to a first location on the expandable member and causes the expandable member to move from the collapsed configuration to an expanded configuration. After actuating the deployment tool such that the expandable member is moved from the collapsed configuration to the expanded configuration, the deployment tool can optionally be removed from the expandable member, at 6064. In embodiments where the deployment tool has been removed, the deployment tool can be subsequently reinserted into the expandable member.

At 6066, after the deployment tool has been actuated to move the implant from the collapsed configuration to the expanded configuration, the deployment tool can be actuated again such that the engaging portion imparts a force to a second location on the expandable member different from the first location on the expandable member, and the implant is moved from the expanded configuration to the collapsed configuration.

After actuating the deployment tool such that the expandable member is moved from the expanded configuration to the collapsed configuration, the expandable member can optionally be disposed at a second location between the adjacent spinous processes different from the first location, at 6068. In some embodiments, after the deployment tool is actuated such that the expandable member is moved from the expanded configuration to the collapsed configuration, the expandable member can optionally be disposed at a second location outside of the body of the patient, at 6070.

The various implants and deployment tools described herein can be constructed with various biocompatible materials such as, for example, titanium, titanium alloyed, surgical steel, biocompatible metal alloys, stainless steel, plastic, polyetheretherketone (PEEK), carbon fiber, ultra-high molecular weight (UHMW) polyethylene, biocompatible polymeric materials, etc. The material of a central portion of the implant can have, for example, a compressive strength similar to or higher than that of bone. In one embodiment, the central portion of the implant, which is placed between the two adjacent spinous processes, is configured with a material having an elastic modulus higher than the elastic modulus of the bone, which forms the spinous processes. In another embodiment, the central portion of the implant is configured with a material having a higher elastic modulus than the materials used to configure the distal and proximal portions of the implant. For example, the central portion of the implant may have an elastic modulus higher than bone, while the proximal and distal portions have a lower elastic modulus than bone. In yet another embodiment, where the implant is configured with an outer shell and an inner core. The outer shell can be configured with material having a higher elastic modulus than the inner core (e.g., outer shell is made with titanium alloyed, while the inner core is made with a polymeric material). Alternatively, the outer shell can be configured with a material having a lower elastic modulus than the inner core (e.g., the outer shell is made with a polymeric material while the inner core is made with a titanium alloyed material).

An apparatus includes an elongate member having a proximal portion configured to be repeatedly moved between a first configuration and a second configuration under, for example, an axial load or a radial load. The elongate member has a distal portion configured to be moved from a first configuration to a second configuration under, for example, an axial load or a radial load. A non-expanding central portion is positioned between the proximal portion and the distal portion. The non-expanding central portion is configured to engage adjacent spinous processes upon spinal extension.

In some embodiments, the elongate member can have multiple portions that each move from a first configuration to a second configuration, either simultaneously or serially. Additionally, the device, or portions thereof, can be configured into many intermediate positions during the movement between the first configuration and the second configuration. For ease of reference, the entire device is referred to as being in either a first configuration or a second configuration although it should be understood that the device and/or portions thereof have a range of motion that includes many configuration including the first configuration and the second configuration.

Figure 104:
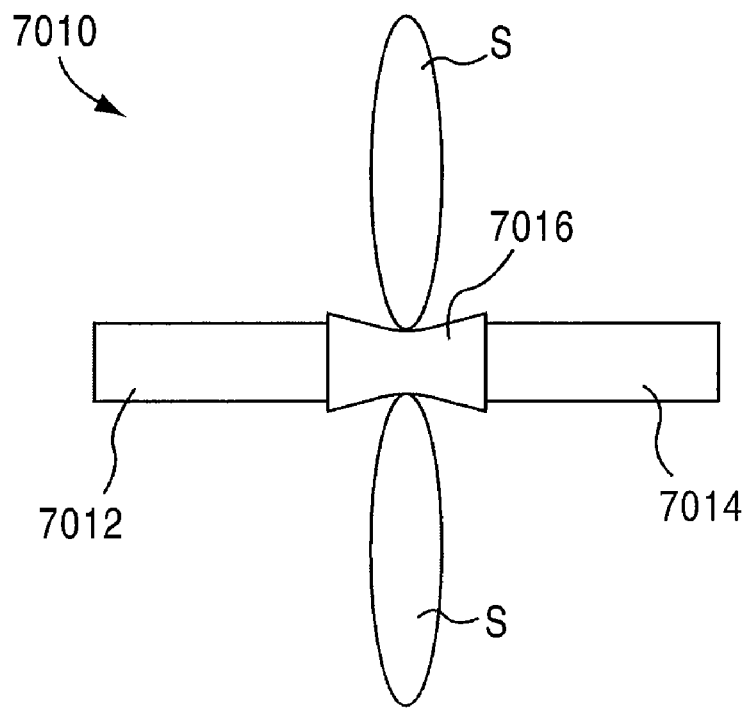
FIG. 104 is a schematic illustration of a posterior view of a medical device according to an embodiment of the invention in a first configuration adjacent two adjacent spinous processes.

FIG. 104 is a schematic illustration of a medical device according to an embodiment of the invention adjacent two adjacent spinous processes. The medical device 7010 includes a proximal portion 7012, a distal portion 7014 and a central portion 7016. The medical device 7010 has a first configuration in which it can be inserted between adjacent spinous processes S or removed from between adjacent spinous processes S. The central portion 7016 is configured to contact the spinous processes S to prevent over-extension/compression of the spinous processes S. In some embodiments, the central portion 7016 does not substantially distract the adjacent spinous processes S. In other embodiments, the central portion 7016 does not distract the adjacent spinous processes S. The medical device 7010 is inserted into a patient's back and moved in between adjacent spinous processes from the side of the spinous processes (i.e., a posterior-lateral approach). The use of a curved insertion shaft assists in the use of a lateral approach to the spinous processes S.

In the first configuration, the proximal portion 7012, the distal portion 7014 and the central portion 7016 share a common longitudinal axis. In other embodiments, these portions do not share a common longitudinal axis. In some embodiments, the proximal portion 7012, the distal portion 7014 and the central portion 7016 define a tube having a constant inner diameter. In other embodiments, the proximal portion 7012, the distal portion 7014 and the central portion 7016 define a tube having a constant outer diameter and/or inner diameter. In yet other embodiments, the proximal portion 7012, the distal portion 7014 and/or the central portion 7016 have different inner diameters and/or outer diameters.

Figure 105:
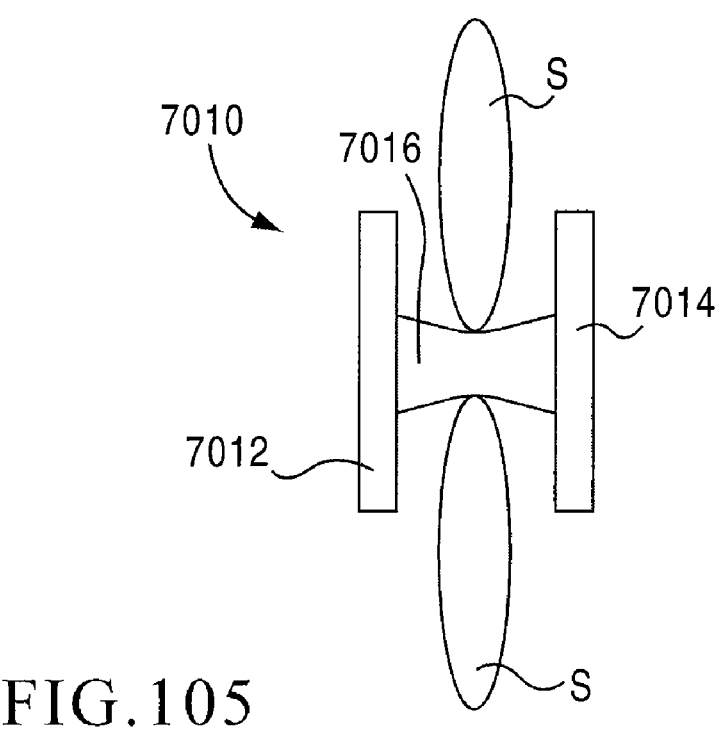
FIG. 105 is a schematic illustration of a posterior view of a medical device according to an embodiment of the invention in a second configuration adjacent two adjacent spinous processes.

The medical device 7010 can be moved from the first configuration to a second configuration as illustrated in FIG. 105. In the second configuration, the proximal portion 7012 and the distal portion 7014 are positioned to limit lateral movement of the device 7010 with respect to the spinous processes S. The proximal portion 7012 and the distal portion 7014 are configured to engage the spinous process (i.e., either directly or through surrounding tissue) in the second configuration. For purposes of clarity, the tissue surrounding the spinous processes S is not illustrated. Note the medical device and/or its portions can engage the spinous processes S during all or just a portion of the range of motion of the spinous processes S associated with the patient's movements.

In some embodiments, the proximal portion 7012, the distal portion 7014 and the central portion 7016 are monolithically formed. In other embodiments, one or more of the proximal portion 7012, the distal portion 7014 and the central portion 7016 are separate components that can be coupled together to form the medical device 7010. For example, the proximal portion 7012 and distal portion 7014 can be monolithically formed and the central portion 7016 can be a separate component that is coupled thereto. The proximal portion 7012, the distal portion 7014 and the central portion 7016 can be the same or different materials. These various portions can be coupled, for example, by a friction fit, welding, adhesive, etc.

In use, the spinous processes S can be distracted prior to inserting the medical device 7010. Distraction of spinous processes is described herein. When the spinous processes are distracted, a trocar can be used to define an access passage for the medical device 7010. In some embodiments, the trocar can be used to define the passage as well as distract the spinous processes S. Once an access passage is defined, the medical device 7010 is inserted percutaneously and advanced between the spinous processes, distal end 7014 first, until the central portion 7016 is located between the spinous processes S. Once the medical device 7010 is in place between the spinous processes, the proximal portion 7012 and the distal portion 7014 are moved to the second configuration, either serially or simultaneously.

In some embodiments, the medical device 7010 is inserted percutaneously (i.e., through an opening in the skin) and in a minimally-invasive manner. For example, as discussed in detail herein, when inserted, the sizes of portions of the implant are smaller than the size of the opening. The sizes of portions of the implant are expanded after the implant is inserted between the spinous processes. Once expanded, the sizes of the expanded portions of the implant are greater than the size of the opening. When collapsed, the sizes of portions of the spinal implant are again smaller than the size of the opening. For example, the size of the opening/incision in the skin can be between 3 millimeters in length and 25 millimeters in length across the opening. In some embodiments, the size of the implant in the expanded configuration is between 3 and 25 millimeters across the opening.

In some embodiments, the proximal portion 7012 and the distal portion 7014 can be moved back to their original configuration or substantially close to their original configuration and either repositioned between the adjacent spinous processes or removed from the body in which they were inserted.

Figure 106:
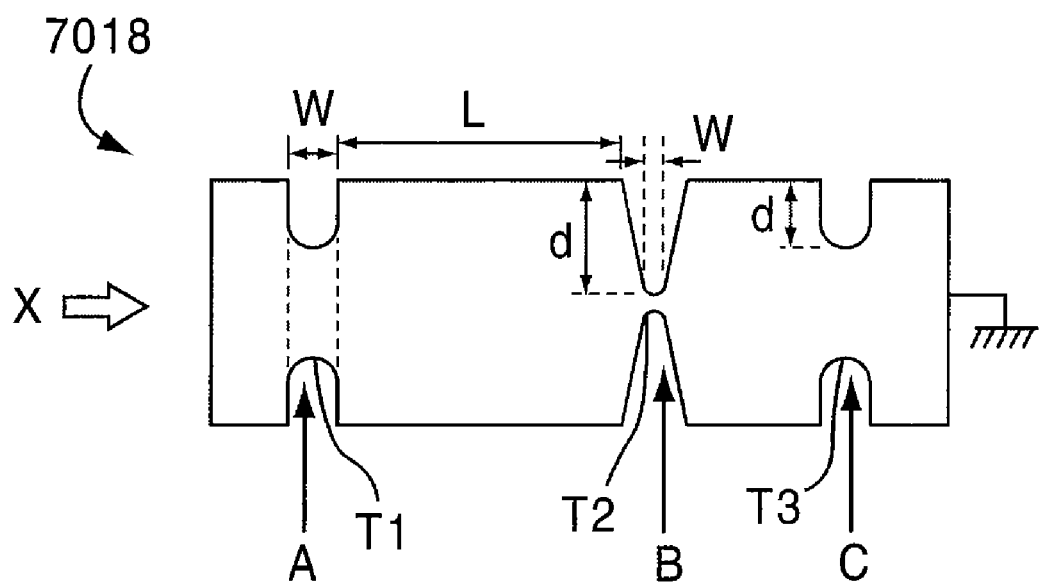
FIG. 106 is a schematic illustration of a deforming element according to an embodiment of the invention in a first configuration.

FIG. 106 is a schematic illustration of a deformable element 7018 that is representative of the characteristics of, for example, the distal portion 7014 of the medical device 7010 in a first configuration. The deformable member 7018 includes cutouts A, B, C along its length to define weak points that allow the deformable member 7018 to deform in a predetermined manner. Depending upon the depth d of the cutouts A, B, C and the width w of the throats T1, T2, T3, the manner in which the deformable member 7018 deforms under an applied load can be controlled and varied. Additionally, depending upon the length L between the cutouts A, B, C (i.e., the length of the material between the cutouts), the manner in which the deformable member 7018 deforms can be controlled and varied.

Figure 107:
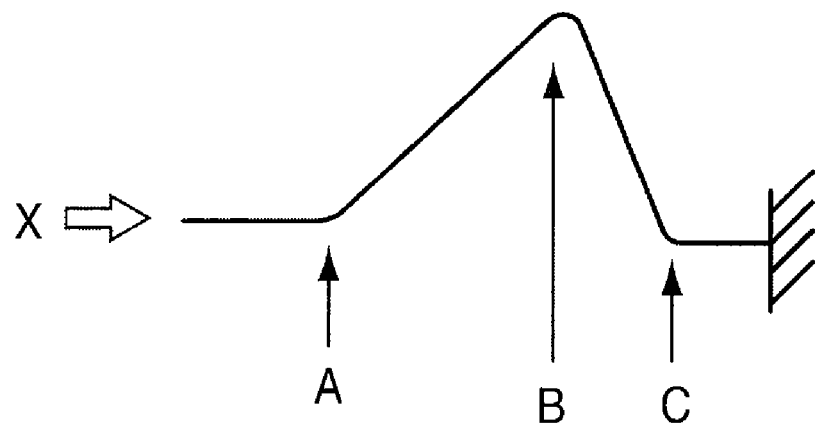
FIG. 107 is a schematic illustration of a side view of the expanding element illustrated in FIG. 106.

FIG. 107 is a schematic illustration of the expansion properties of the deformable member 7018 illustrated in FIG. 106. When a load is applied, for example, in the direction indicated by arrow X, the deformable member 7018 deforms in a predetermined manner based on the characteristics of the deformable member 7018 as described above. As illustrated in FIG. 107, the deformable member 7018 deforms most at cutouts B and C due to the configuration of the cutout C and the short distance between cutouts B and C. In some embodiments, the length of the deformable member 7018 between cutouts B and C is sized to fit one side of adjacent spinous processes.

The deformable member 7018 is stiffer at cutout A due to the shallow depth of cutout A. As indicated in FIG. 107, a smooth transition is defined by the deformable member 7018 between cutouts A and B. Such a smooth transition causes less stress on the tissue surrounding a side of adjacent spinous processes than a more drastic transition (i.e., a steeper angled wall) such as between cutouts B and C. The dimensions and configuration of the deformable member 7018 can also determine the timing of the deformation at the various cutouts. The weaker (i.e., deeper and wider) cutouts deform before the stronger (i.e., shallower and narrower) cutouts.

Figure 108:
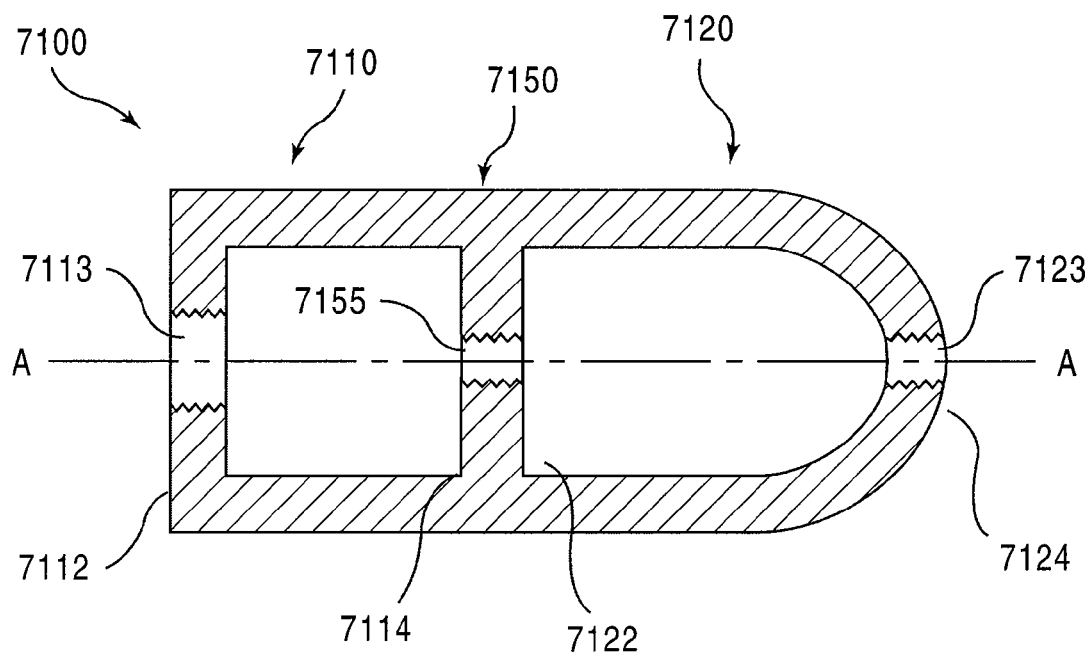
FIG. 108 is a side cross-sectional view of a medical device according to an embodiment of the invention in a first configuration.
Figure 109:
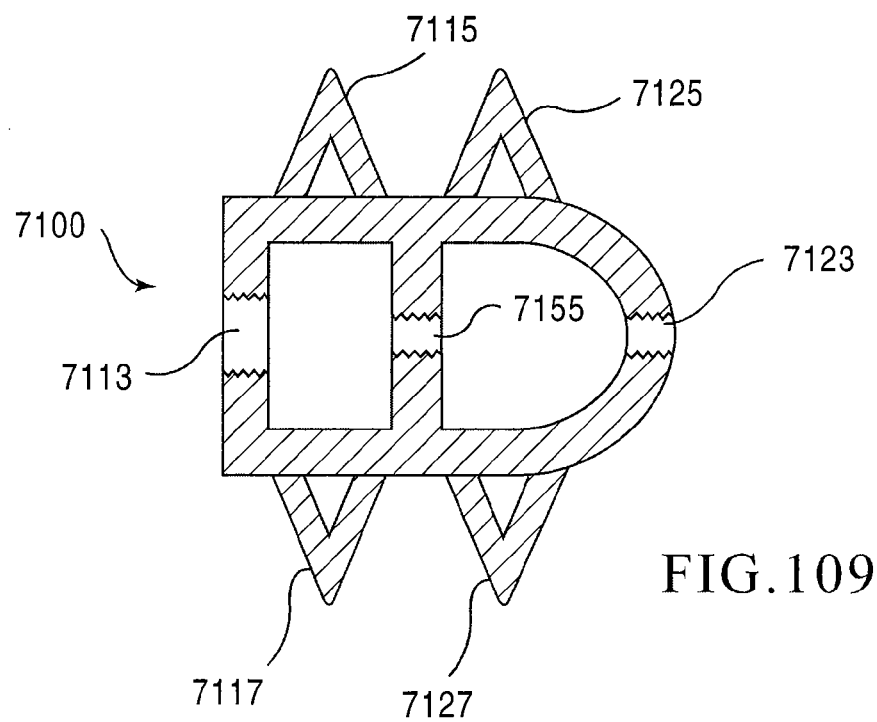
FIG. 109 is a side cross-sectional view of the medical device illustrated in FIG. 108 in a second configuration.

FIGS. 108 and 109 illustrate a spinal implant 7100 in a first configuration and second configuration, respectively. As shown in FIG. 108, the spinal implant 7100 is collapsed in a first configuration and can be inserted between adjacent spinous processes. The spinal implant 7100 has a first deformable portion 7110, a second deform able portion 7120 and a central, non-deformable portion 7150. The first deformable portion 7110 has a first end 7112 and a second end 7114. The second deformable portion 7120 has a first end 7122 and a second end 7124. The central portion 7150 is coupled between second end 7114 and first end 7122. In some embodiments, the spinal implant 7100 is monolithically formed.

The first deformable portion 7110, the second deformable portion 7120 and the central portion 7150 have a common longitudinal axis A along the length of spinal implant 7100. The central portion 7150 can have the same inner diameter as first deformable portion 7110 and the second deformable portion 7120. In some embodiments, the outer diameter of the central portion 7150 is smaller than the outer diameter of the first deformable portion 7110 and the second deformable portion 7120.

In use, spinal implant 7100 is inserted percutaneously between adjacent spinous processes. The first deformable portion 7110 is inserted first and is moved past the spinous processes until the central portion 7150 is positioned between the spinous processes. The outer diameter of the central portion 7150 can be slightly smaller than the space between the spinous processes to account for surrounding ligaments and tissue. In some embodiments, the central portion 7150 directly contacts the spinous processes between which it is positioned. In some embodiments, the central portion of spinal implant 7100 is a fixed size and is not compressible or expandable. Note the spinal implant 7100 and/or the first deformable portion 7110, second deformable portion 7120, and central portion 7150 can engage the spinous processes during all or just a portion of the range of motion of the spinous processes associated with the patient's movement.

The first deform able portion 7110 includes, for example, expanding members 7115, and 7117. Between the expanding members 7115, 7117, openings (not illustrated) are defined. As discussed above, the size and shape of the openings influence the manner in which the expanding members 7115, 7117 deform when an axial load is applied. The second deformable portion 7120 includes expanding members 7125 and 7127. Between the expanding members 7125, 7127, openings (not illustrated) are defined. As discussed above, the sizes and shapes of the openings influence the manner in which the expanding members 7125, 7127 deform when an axial load is applied.

When an axial load is applied to the spinal implant 7100, the spinal implant 7100 expands to a second configuration as illustrated in FIG. 109. In the second configuration, first end 7112 and second end 7114 of the first deformable portion 7110 move towards each other and expanding members 7115, 7117 project substantially laterally away from the longitudinal axis A. Likewise, first end 7122 and second end 7124 of the second deformable portion 7120 move towards one another and expanding members 7125, 7127 project laterally away from the longitudinal axis A. The expanding members 7115, 7117, 7125, 7127 in the second configuration form projections that extend to positions adjacent to the spinous processes between which the spinal implant 7100 is inserted. In the second configuration, the expanding members 7115, 7117, 7125, 7127 inhibit lateral movement of the spinal implant 7100, while the central portion 7150 prevents the adjacent spinous processes from moving together any closer than the distance defined by the diameter of the central portion 7150 during spinal extension.

The first end 7112 of the first deformable portion 7110 defines a threaded opening 7113. The central portion 7150 defines a second threaded opening 7155. The second end 7124 of the second deformable portion 7120 defines a third threaded opening 7123. The threaded openings 7113, 7155, 7123 receive portions of an actuator 7200 (see FIG. 110) to move the first deform able portion 7100 and the second deformable portion 7120 between their respective first configurations and second configurations as described in greater detail herein. In some embodiments, the first threaded opening 7113 has a greater diameter than the second threaded opening 7155 and the third threaded opening 7123 (see FIGS. 108-111). In some embodiments the second threaded opening 7155 and the third threaded opening 7123 have the same diameter (see FIGS. 108-111). In other embodiments, the first threaded opening 7113' and the second threaded opening 7155' have the same diameter (see FIGS. 112-115) and the third threaded opening 7123' has a smaller diameter than the first threaded opening and the second threaded opening. The threaded openings 7113, 7155, 7123, 7113', 7155', 7123' are coaxially aligned. In other embodiments, the threaded openings can be any combination of different or the same sizes.

Figure 110:
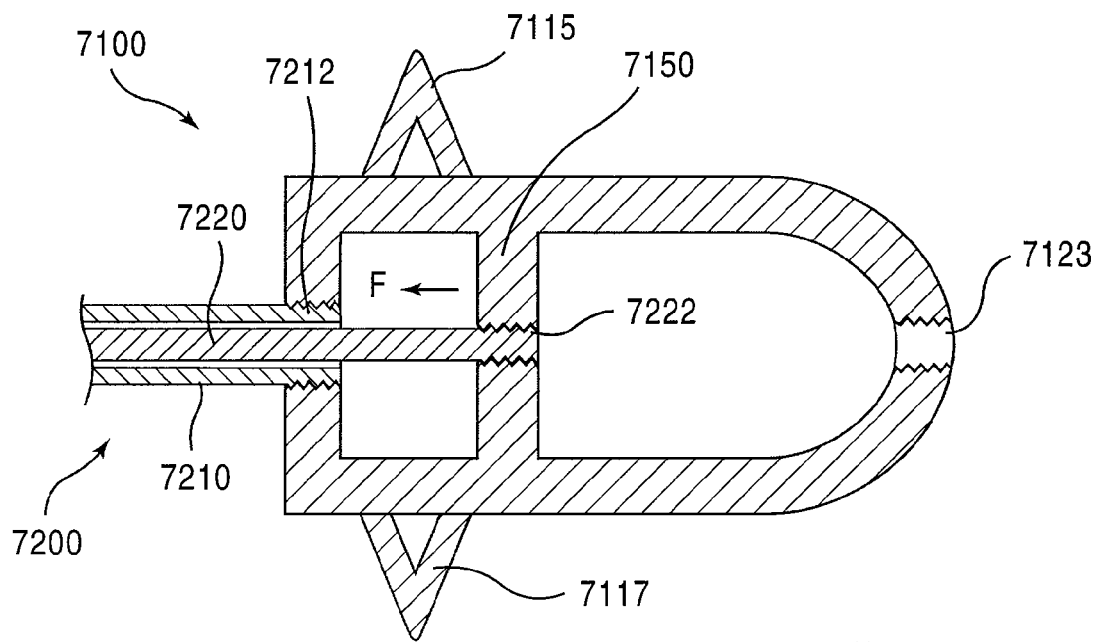
FIG. 110 is a cross-sectional side view of a medical device and an actuator according to an embodiment of the invention with a portion of the medical device deployed in a second configuration.

The spinal implant 7100 is deformed by a compressive force imparted substantially along the longitudinal axis A of the spinal implant 7100. As illustrated in FIG. 110, the compressive force is imparted to the first deformable portion 7110 by actuator 7200. The actuator includes a first portion 7210 and a second portion 7220 movably received within first portion 7210. In some embodiments, the second portion 7220 is slidably received within the first portion 7210. In other embodiments, the first portion 7210 and the second portion 7220 are threadedly coupled. Each of the first portion 7210 and the second portion 7220 is provided with external threads 7212 and 7222, respectively, to engage the threaded openings 7113, 7155, 7123, 7113', 7155', 7123'.

As illustrated in FIG. 110, the compressive force is imparted to the first deformable portion 7110, for example, by attaching the threaded portion 7212 to the first threaded opening 7113, attaching the threaded portion 7222 to the second threaded opening 7155 of the central portion 7150, and drawing the second portion 7220 along the longitudinal axis A while imparting an opposing force against the first end 7112 of the first deformable portion 7110. The opposing force results in a compressive force causing the spinal implant 7100 to expand as discussed above.

Figure 111:
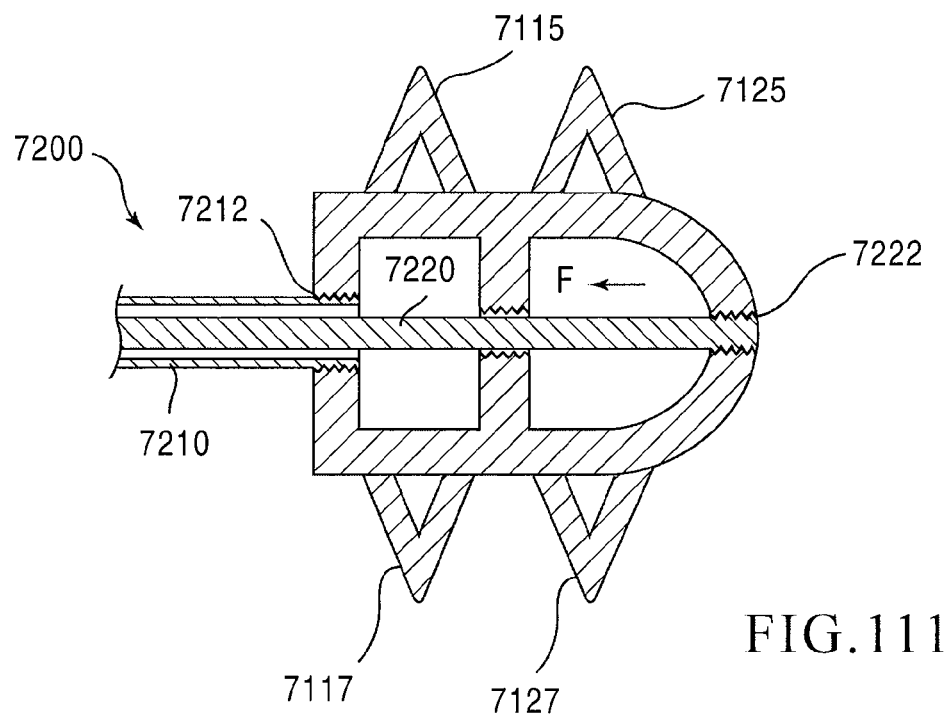
FIG. 111 is a side cross-sectional view of a medical device and an actuator according to an embodiment of the invention with the medical device fully deployed in the second configuration.
Figure 112:
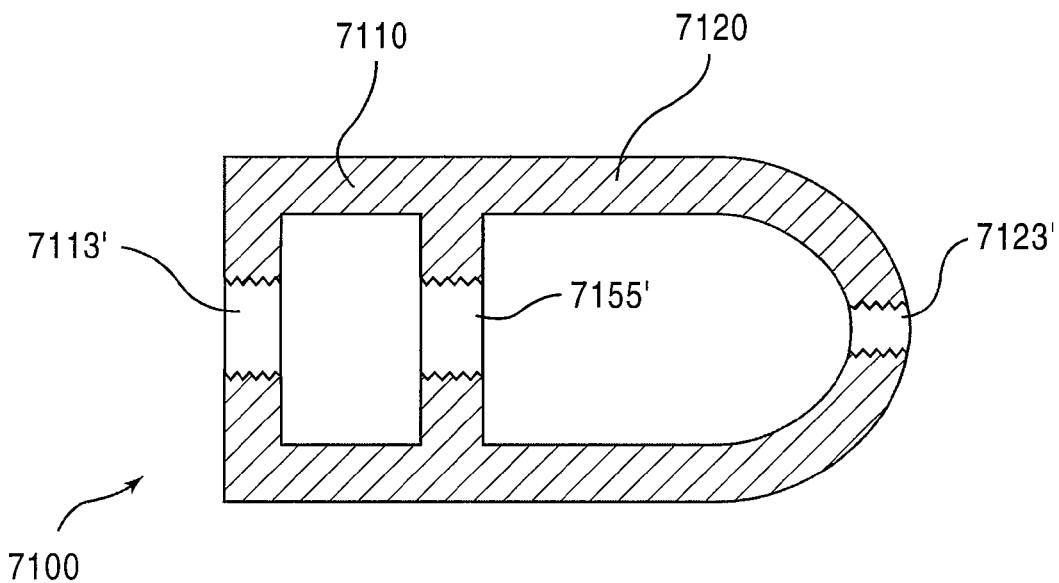
FIG. 112 is a side cross-sectional view of a medical device according to another embodiment of the invention in a first configuration.
Figure 113:
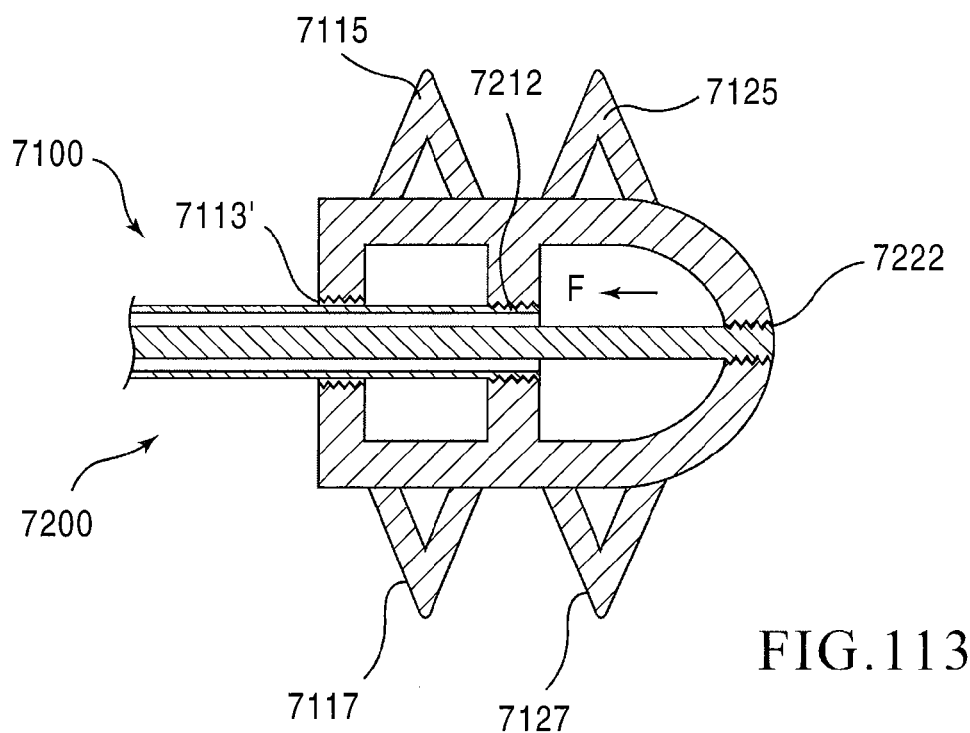
FIG. 113 is a side cross-sectional view of the medical device illustrated in FIG. 112 in a second configuration.

Once the first deformable portion 7110 is moved to its second configuration, the threaded portion 7222 is threaded through the second threaded opening 7155 and threadedly coupled to the third threaded opening 7123. A compressive force is imparted to the second deformable portion 7120 of the spinal implant 7100 by drawing the second portion 7220 of the actuator in the direction indicated by the arrow F while applying an opposing force using the first portion 7210 of the actuator against the spinal implant 7100. The opposing forces result in a compressive force causing the spinal implant to expand as illustrated in FIG. 111.

In some embodiments, the first deformable portion 7110 and the second deformable portion 7120 can be expanded simultaneously when the second portion 7220 of the actuator is coupled to the third threaded opening 7123 and the first portion 7210 is coupled to the first threaded opening 7113 and a compressive force is applied.

In embodiments in which the first threaded opening 7113' has the same diameter as the second threaded opening 7155' (best seen, for example, in FIGS. 112 and 113), the first threaded portion 7212 can be threadedly coupled to the second threaded opening 7155' and the second threaded portion 7222 can be threadedly coupled to the third threaded opening 7123'. A compressive force is then applied between the central portion 7150 and the second end 7124 of the second deformable portion 7120. Once the second deformable portion 7120 is in its second configuration, the first threaded portion 7212 can be threadedly coupled to the first threaded opening 7113' and the first deformable portion 7110 can be deformed into its second configuration.

Figure 114:
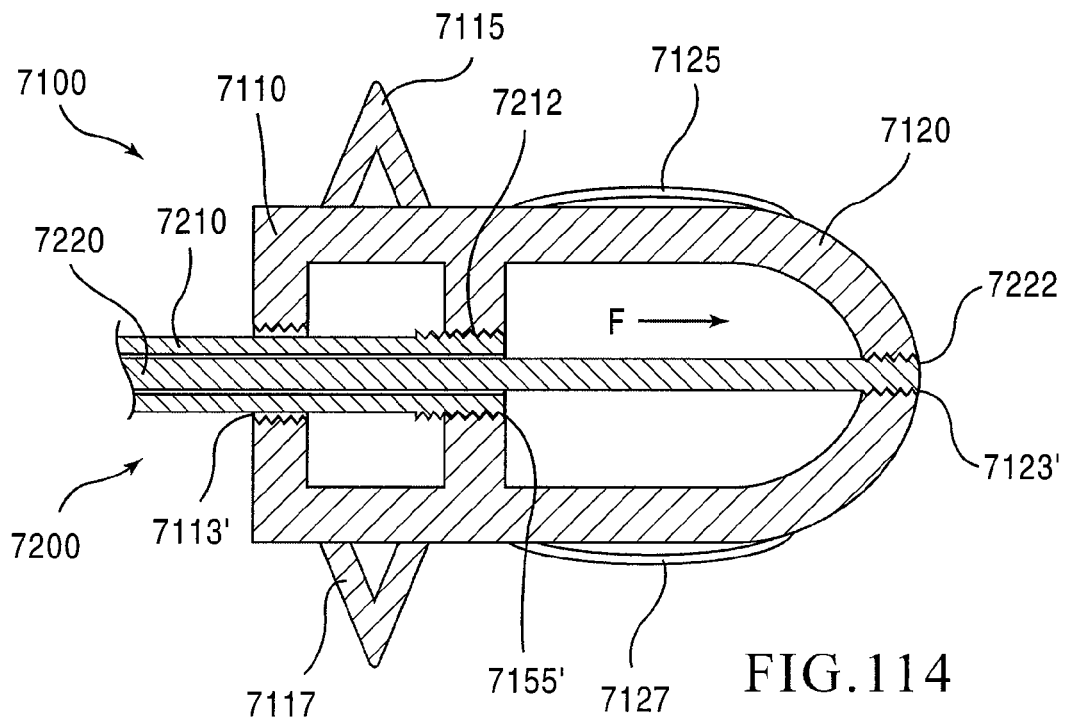
FIG. 114 is a side cross-sectional view of a medical device and an actuator according to an embodiment of the invention with a portion of the medical device moved back to its first configuration.
Figure 115:
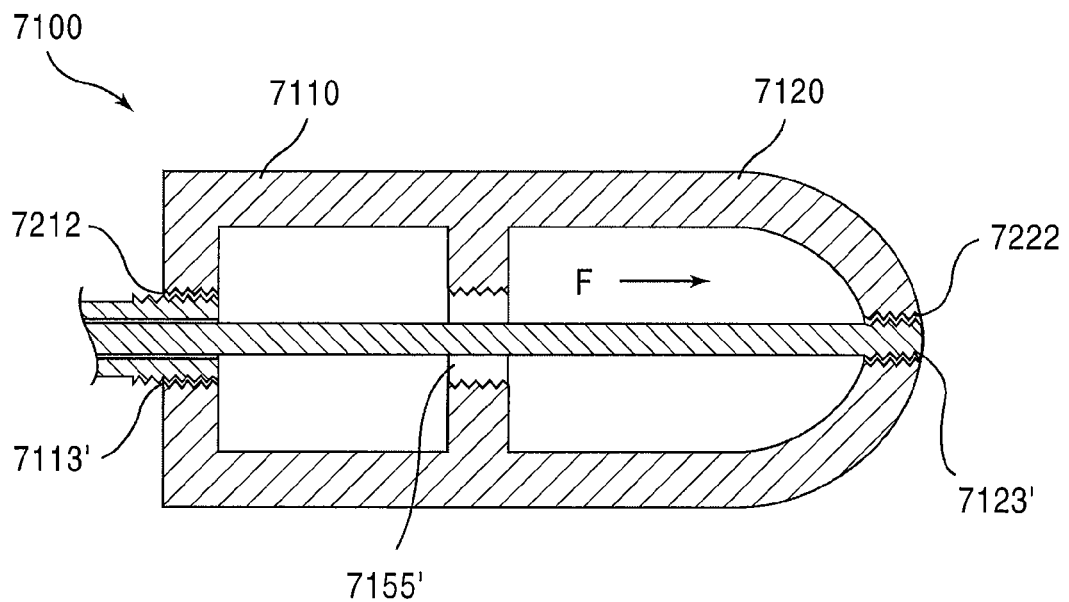
FIG. 115 is a side cross-sectional view of a medical device and an actuator according to an embodiment of the invention with the medical device moved back to its first configuration.

After each of the first deformable portion 7110 and the second deformable portion 7120 are moved to the second expanded configuration, they subsequently can each be moved back to the first collapsed configuration by applying a force in the opposite direction along longitudinal axis A as illustrated, for example, in FIGS. 114-115. In this example, as discussed above, the spinal implant 7100 illustrated in FIGS. 112-115 has a first threaded opening 7113' that has the same diameter as the second threaded opening 7155'.

With the first threaded portion 7212 coupled to the second threaded opening 7155' and the second threaded portion 7222 coupled to the third threaded opening 7123', the second portion 7220 of the actuator 7200 is moved in the direction indicated by arrow F to move the second deformable portion 7120 to its first collapsed configuration.

The first threaded portion 7212 is then coupled to the first threaded opening 7113' and the second portion 7220 of actuator 7200 is again moved in the direction of arrow F to move the first deformable portion 7110 to its first collapsed configuration. When the entire spinal implant 7100 has been completely collapsed, the spinal implant 7100 can be repositioned between the spinous processes, or removed from its position between the spinous processes and removed from the body in which it was previously inserted. In some embodiments, the first deformable portion 7110 and the second deformable portion 7120 are not completely collapsed, but are instead moved to a configuration between fully expanded and fully collapsed. In this manner the spinal implant 7100 may be repositioned or removed without being completely collapsed.

Figure 116:
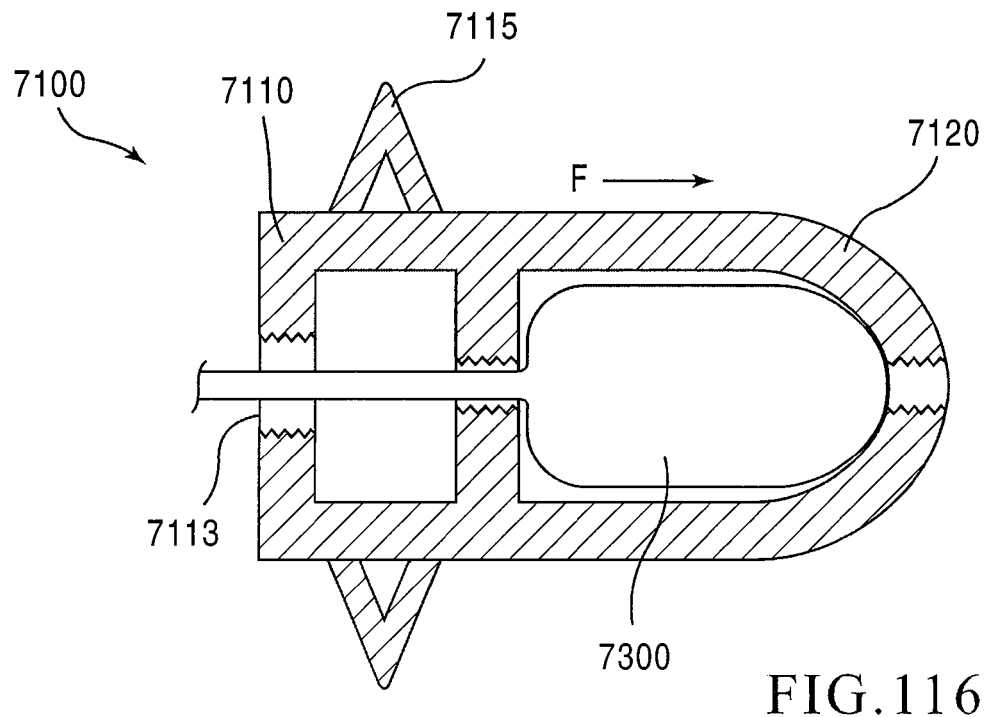
FIG. 116 is a side cross-sectional view of a medical device and an actuator according to an embodiment of the invention with a portion of the medical device moved back to its first configuration.

In some embodiments, the first deformable portion 7110 and the second deformable portion 7120 can be moved between the first and second configuration using a balloon as an actuator. As illustrated in FIG. 116, the second deformable portion 7120 is then moved from the second configuration to the first configuration by imparting a longitudinal force resulting from the inflation of a balloon 7300 with liquid and/or gas. As the balloon 7300 is inflated, it is forced against the central portion 7150 and the second end 7124 of the second deformable portion 7120. The force imparted by the balloon 7300 is generally in the direction indicated by the arrow F. In some embodiments, the balloon 7300 is a low-compliant balloon that is configured to expand to a predefined shape such that a force is imparted primarily in a substantially longitudinal direction indicated by arrow F.

Figure 117:
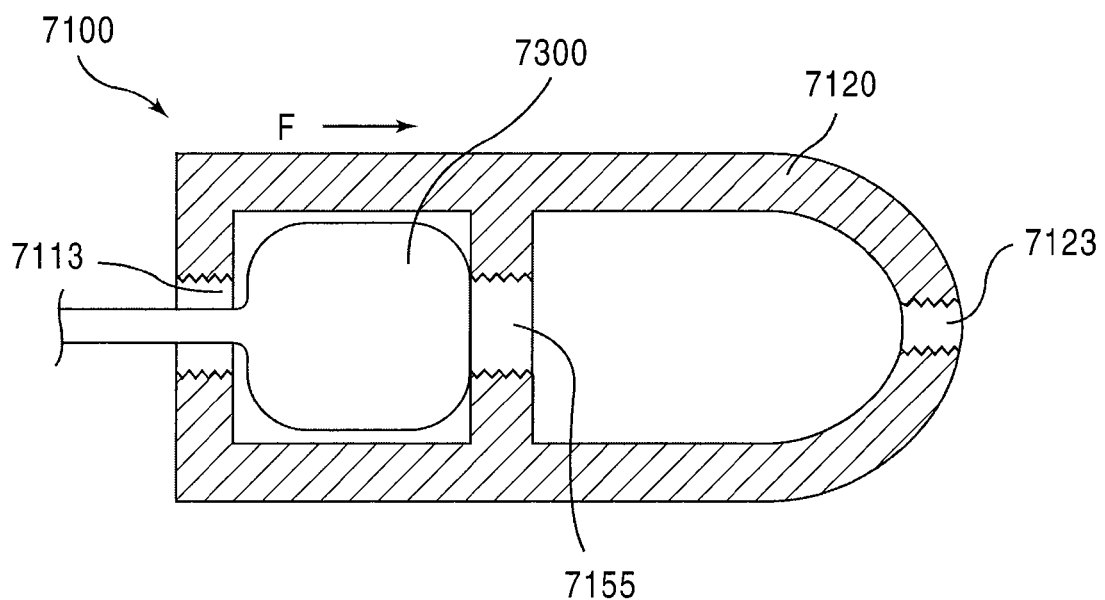
FIG. 117 is a side cross-sectional view of a medical device and an actuator according to an embodiment of the invention with the medical device moved back to its first configuration.

After the second deformable portion 7120 is moved substantially to its collapsed configuration, the balloon 7300 is deflated and moved into the first deformable portion 7110. The balloon 7300 is then inflated as illustrated in FIG. 117 to impart a force in the direction indicated by arrow F. In some embodiments, the same balloon 7300 is used to collapse both the first deformable portion 7110 and the second deformable portion 7120. In other embodiments, a different balloon is used for each portion 7110, 7120. Once the entire implant 7100 is moved to the first configuration, the balloon is deflated and removed. In some embodiments, the balloon 7300 remains in the spinal implant 7100, and the spinal implant 7100 and the balloon 7300 are removed simultaneously.

In some embodiments, the shaft on which the balloon is coupled has external threads (not illustrated) to mate with the first threaded opening 7113, 7113' and/or the second threaded opening 7155, 7155'. In other embodiments, neither the openings nor the shaft on which the balloon is coupled are threaded. In yet other embodiments, the balloon 7300 is inserted through the first portion 7210 of the actuator 7200. Alternatively, the actuator 7200 and the balloon 7300 can be used in conjunction with the spinal implant to expand and/or contract the first deformable portion 7110 and the second deformable portion 7120.

In other embodiments, there are no threaded openings defined in the spinal implant 7100. For example, the spinal implant can have multiple actuator-engaging portions that are not threaded, but are rather contact or bearing surfaces for various types of actuators. For example, an actuator (not illustrated) can be configured to grasp an outer surface of the spinal implant while simultaneously imparting a force against the distal portion of the spinal implant to move the implant to a collapsed configuration.

The spinal implant 7100 can be made from, for example, stainless steel, plastic, polyetheretherketone (PEEK), carbon fiber, ultra-high molecular weight (UHMW) polyethylene, etc. or some combination thereof. For example, the first deformable portion and the second deformable portion can be made from one material and the non-expanding central portion can be made from a different material. The material of such a non-expanding central portion can have a tensile strength similar to or higher than that of bone.

As described above, in some embodiments, the spinal implants shown and described above can be inserted between adjacent spinous processes percutaneously using a posterior-lateral approach. FIGS. 133 and 134 show an implant 8100 and a portion of an insertion tool 8500 being inserted into a body B using a posterior-lateral approach according to an embodiment of the invention. The body B includes spinous processes SP1-SP4, which define a mid-line axis $L_M$. A lateral axis $L_L$ is defined substantially normal to the mid-line axis $L_M$.

To position the implant 8100 between adjacent spinous processes SP2 and SP3, a lateral incision I having a length Y2 is made a distance X from the mid-line axis $L_M$. The length Y2 and the distance X can be selected to allow the implant to be inserted percutaneously in a minimally-invasive manner. In some embodiments, the distance X can be, for example, between 25 mm and 100 mm. In some embodiments, the incision I has a length Y2 that is no greater than the distance Y1 between the adjacent spinous processes, such as, for example, SP2 and SP3. In some embodiments, for example, the length Y2 is no greater than 15 mm and the distance Y1 is between 20 mm and 25 mm. In other embodiments, the length Y2 can exceed the distance Y1 between the adjacent spinous processes SP2 and SP3. In some embodiments, for example, the length Y2 can be as much as 50 mm.

A distraction tool (not shown in FIGS. 133 and 134) is then inserted through the incision I and is used to define the passageway P from the incision I to the adjacent spinous processes SP2 and SP3. The distraction tool can also distract the adjacent spinous processes SP2 and SP3 to define the desired space between, as described above. The distraction tool can be any suitable distraction tool, such as for example, distraction tool 2010 shown and described with reference to FIG. 48.

The insertion tool 8500 including the implant 8100 is then inserted through the incision I and via the passageway P to the space between the adjacent spinous processes SP2 and SP3. The implant 8100 is then disposed between the adjacent spinous processes SP2 and SP3 in any suitable manner, as described above. For example, in some embodiments, the implant 8100 can include one or more expandable portions that are adjacent to and/or engage portions of the spinous processes SP2 and/or SP3 to limit at least a lateral movement of the implant 8100.

As shown in FIGS. 133 and 134, during the insertion operation, the insertion tool 8500 is positioned such that when the implant 8100 is disposed between the adjacent spinous processes SP2 and SP3, the implant 8100 is substantially aligned with the lateral axis $L_L$. Said another way, during insertion, the insertion tool 8500 is positioned such that the longitudinal axis (not shown) of the implant 8100 is substantially coaxial with the lateral axis $L_L$. As described in more detail herein, the insertion tool 8500 is configured to ensure that the implant 8100 is aligned with the lateral axis $L_L$ during insertion.

As shown in FIGS. 135 and 136, the insertion tool 8500, which can be similar to the insertion tools 1500 and 7500 shown and described above, includes a curved portion 8520 and an implant support portion 8530. The insertion tool 8500 defines a center line CL. As shown in FIGS. 135 and 136, which show a side view and a top plan view, respectively, of the insertion tool 8500, the center line CL of the curved portion 8520 defines a radius of curvature R1 about an axis A1 that is substantially normal to the center line CL. The radius of curvature R1 can be any value suitable to define and/or proceed along the passageway P such that the implant 8100 and/or a portion of the center line CL is aligned with the lateral axis $L_L$ during insertion. Moreover, the radius of curvature R1 can be selected to blend with the adjacent portions of the insertion tool 8500 to ensure that the surface of the insertion tool 8500 is continuous.

In some embodiments, for example, an insertion tool 8500 can have a small radius of curvature R1 (e.g., 20 mm to 50 mm), which corresponds to a relatively sharp curve. Such an embodiment can be appropriate, for example, when the distance X between the incision I and the mid-line axis $L_M$ is relatively small (e.g. 20 mm), requiring that passageway P have a relatively sharp curve to ensure that the implant 8100 is properly aligned. In other embodiments, for example, an insertion tool 8500 can have a large radius of curvature R1 (e.g., greater than 300 mm), which corresponds to less curvature. Such an embodiment can be appropriate, for example, when the distance X between the incision I and the mid-line axis $L_M$ is relatively great (e.g. greater than 50 mm). In yet other embodiments, an insertion tool 8500 can have a radius of curvature R1 that is between 50 mm and 300 mm. In some embodiments, for example, an insertion tool 8500 can have a radius of approximately 181 mm.

Although the insertion tool 8500 is shown and described as having a single radius of curvature R1, in some embodiments, an insertion tool can have multiple radii of curvature and/or geometrically complex shapes. For example, FIGS. 137 and 138 show a side view and a top plan view of an insertion tool 9500 according to an embodiment of the invention. The insertion tool 9500 includes a curved portion 9520 and an implant support portion 9530. A center line CL of the curved portion 9520 defines a first radius of curvature R1 about a first axis A1 that is substantially normal to the center line CL. The center line CL of the curved portion 9520 also defines a second radius of curvature R2 about a second axis A2 that is substantially parallel to the first axis A1 and substantially normal to the center line CL. As described above, the radii of curvature R1 and R2 can be any value suitable to define the passageway P such that the implant is aligned with the lateral axis $L_L$ during insertion. Moreover, as shown in FIG. 137, a portion of the elongate member 9500 is disposed between the first axis A1 and the second axis A2. Said another way, the first axis A1 and the second axis A2 are positioned such that the curved portion 9520 forms an "S" shape.

Although the insertion tool 9500 is shown and described as defining axis A1 and axis A2 with insertion tool 9500 therebetween, in other embodiments, an insertion tool can be on the same side of these axes. Similarly, although the insertion tool 9500 is described as defining axes A1 and A2 that are substantially parallel to each other, in other embodiments, as described in more detail below, an insertion tool can define axes A1 and A2 that are not substantially parallel to each other. Said another way, although the insertion tool 9500 is shown as having a two-dimensional curve, in other embodiments, an insertion tool can have a three-dimensional curve.

Although FIGS. 133 and 134 illustrate a single-level insertion (i.e., one spinal implant inserted between a pair of adjacent spinous processes), in some embodiments, the insertion tool 8500 can be used to insert multiple implants between multiple pairs of adjacent spinous processes through a single incision. FIG. 139 shows an example of a multi-level insertion operation according to an embodiment of the invention. FIG. 139 shows a body B having an two implants 8100A and 8100B disposed therein using a posterior-lateral approach through a single incision I'. The body B includes spinous processes SP1-SP5, which define a mid-line axis $L_M$. A first lateral axis $L_{L1}$ is defined substantially normal to the mid-line axis $L_M$ and centered within the space between the first pair of spinous processes SP2 and SP3. Similarly, a second lateral axis $L_{L2}$ is defined substantially normal to the mid-line axis $L_M$ and centered within the space between the second pair of spinous processes SP3 and SP4.

To position the implants 8100A and 8100B between the first pair of spinous processes SP2 and SP3 and the second pair of spinous processes SP3 and SP4, a lateral incision I' having a length Y2' is made a distance X' from the mid-line axis $L_M$. As shown, the lateral incision I' is offset from the space between the first pair of spinous processes SP2 and SP3 and from the space between the second pair of spinous processes SP3 and SP4. Said another way, the lateral incision I' is offset from the first lateral axis $L_{L1}$ and the second lateral axis $L_{L2}$. As described above, the length Y2' and the distance X' can be selected to allow the implant to be inserted percutaneously in a minimally-invasive manner. Additionally, the length Y2' and the distance X' can be selected to reduce or minimize the lateral offset angles α1 and α2.

In some embodiments, the distance X' can be, for example, between 25 mm and 100 mm. In some embodiments, the length Y2' is no greater than the distance between adjacent spinous processes. In some embodiments, for example, the length Y2' is no greater than 15 mm. In other embodiments, the length Y2' can exceed the distance between adjacent spinous processes. In some embodiments, for example, the length Y2' can be as much as 50 mm.

A first distraction tool (not shown in FIG. 139) is then inserted through the incision I' and is used to define a first passageway P1 from the incision I' to the first pair of spinous processes SP2 and SP3. The first distraction tool can also distract the adjacent spinous processes SP2 and SP3 to define the desired space between, as described above. A first insertion tool (not shown in FIG. 139) is then inserted through the incision I' and via the first passageway P1 to the space between the first pair of spinous processes SP2 and SP3. The implant 8100A is then disposed between the first pair of spinous processes SP2 and SP3 in any suitable manner, as described above.

Similarly, a second distraction tool (not shown in FIG. 139) is inserted through the incision I' and is used to define a second passageway P2 from the incision I' to the second pair of spinous processes SP3 and SP4. The second distraction tool can also distract the adjacent spinous processes SP3 and SP4 to define the desired space between, as described above. In some embodiments, the second distraction tool can be identical to the first distraction tool (e.g., the multi-level operation is completed using two identical tools). In other embodiments, the second distraction tool can be different from the first distraction tool. In such embodiments, for example, the second distraction tool may have a different radius of curvature, which can result in the second passageway P2 being different from the first passageway P1. In yet other embodiments, the multi-level operation can be completed using a single distraction tool.

A second insertion tool (not shown in FIG. 139), is then inserted through the incision I' and via second passageway P2 to the space between the second pair of spinous processes SP3 and SP4. The implant 8100B is then disposed between the second pair of spinous processes SP3 and SP4 in any suitable manner, as described above. In this manner, a multi-level insertion can be made through a single incision. As described above for the distraction tools, in some embodiments, the second insertion tool can be identical to the first insertion tool. In other embodiments, the second insertion tool can be different from the insertion distraction tool. In yet other embodiments, the multi-level operation can be completed using a single insertion tool.

As discussed above, during the multi-level insertion operation shown in FIG. 139, the implants 8100A and 8100B can be positioned to reduce or minimize the lateral offset angles α1 and α2. The lateral offset angles α1 and α2 are defined by the angular offset between the longitudinal axes $L_A$ and $L_B$ of the implants 8100A and 8100B and the lateral axes $L_{L1}$ and $L_{L2}$. As the offset angles α1 and α2 decrease, the degree of alignment between the implants 8100A and 8100B and the lateral axes $L_{L1}$ and $L_{L2}$ increases. For example, in embodiments in which the lateral offset angles are substantially zero, the implants 8100A and 8100B are substantially aligned with the lateral axes $L_{L1}$ and $L_{L2}$.

The position of the implants 8100A and 8100B can be a function of many parameters. For example, in some embodiments, the position of the implants 8100A and 8100B can be adjusted by increasing or decreasing the distance X' and/or the length Y2' of the incision I'. In other embodiments, the position implants 8100A and 8100B can be adjusted by placing the implants 8100A and 8100B within the body B using distraction tools and/or insertion tools configured to align substantially the implants 8100A and 8100B with their respective lateral axes $L_{L1}$ and $L_{L2}$. For example, in some embodiments, the first insertion tool and the second insertion tool can have curved portions corresponding to the desired shape of the passageways P1 and P2. In some embodiments, the curved portion of the first insertion tool and the curved portion of the second insertion tool each can be similar to the curved portion 8520 of the insertion tool 8500 shown in FIG. 135.

FIGS. 140 and 141 show a multi-level insertion operation according to an embodiment of the invention in which the distraction tools and/or insertion tools are configured to define a passageways having a three-dimensional curved shape. The embodiment shown in FIG. 140 is similar to the embodiment shown in FIG. 139 and will therefore not be described in great detail. FIG. 140 shows a body B having an two implants 8100A and 8100B disposed therein using a posterior-lateral approach through a single incision I''. The body B includes spinous processes SP1-P5, which define a mid-line axis $L_M$. A first lateral axis $L_{L1}$ is defined substantially normal to the mid-line axis $L_M$ and centered within the space between the first pair of spinous processes SP2 and SP3. Similarly, a second lateral axis $L_{L2}$ is defined substantially normal to the mid-line axis $L_M$ and centered within the space between the second pair of spinous processes SP3 and SP4.

To position the implants 8100A and 8100B within the body B, a lateral incision I' having a length Y2'' is made a distance X'' from the mid-line axis $L_M$. A first distraction tool (not shown in FIG. 139) is then inserted through the incision I' and is used to define a first passageway P1'' having a three-dimensional curved shape. Said another way, the first passageway P1'' has a curved shape when viewed from a posterior perspective (FIG. 140) and when viewed from a side perspective (FIG. 141). In this manner, the implant 8100A can be aligned substantially with the lateral axis. A first insertion tool (not shown in FIGS. 140 and 141) is then inserted through the incision I'' and via the first passageway P1'' to the space between the first pair of spinous processes SP2 and SP3. The implant 8100A is then disposed between the first pair of spinous processes SP2 and SP3 in any suitable manner, as described above.

Similarly, a second distraction tool (not shown in FIGS. 140 and 141) is inserted through the incision I'' and is used to define a second passageway P2'' having a three-dimensional curved shape. A second insertion tool (not shown in FIGS. 140 and 141), is then inserted through the incision I'' and via second passageway P2'' to the space between the second pair of spinous processes SP3 and SP4. The implant 8100B is then disposed between the second pair of spinous processes SP3 and SP4 in any suitable manner, as described above.

Although the insertion tools and/or distraction tools are shown and described above as including two-dimensional curved portions (i.e., the tool is substantially linear when shown in a top plan view, as in FIG. 136, for example), in some embodiments, an insertion tool can have a three-dimensional curvature. As described above with reference to FIGS. 140 and 141, a three-dimension curvature can be used, for example, to promote the alignment of an implant with the lateral axis in a side view (see e.g., FIG. 141 showing the depth alignment of the implant) and in a top plan view (see e.g., FIGS. 139 and 140 showing the offset angle alignment of the implants). FIGS. 142 and 143 show a side view and a top plan view, respectively, of an insertion tool 10500 according to an embodiment of the invention. The insertion tool 10500 includes a curved portion 10520 and an implant support portion 10530. The insertion tool 10500 defines a center line CL. The center line CL of the curved portion 10520 defines a first radius of curvature R1 about a first axis A1 that is substantially normal to the center line CL. The center line CL of the curved portion 10520 also defines a second radius of curvature R2 about a second axis A2 that is substantially normal to the first axis A1 and substantially normal to the center line CL. In this manner, the insertion tool 10500 has a three-dimensional curved portion 10520. As described above, the radii of curvature R1 and R2 can be any value suitable to define the passageway within the body such that the implant is aligned with the lateral axis during insertion.

Although the multi-level insertion operations are shown and described above as including placing two implants between two pairs of adjacent spinous processes, in some embodiments, a multi-level insertion operation can include placing three or more implants between three or more pairs of adjacent spinous processes through a single incision. For example, FIG. 144 shows a posterior view of a multi-level insertion operation in which three implants are disposed within the body B. As shown, the body B includes spinous processes SP1-SP5, which define a mid-line axis $L_M$. As described above, the operation includes using three distraction and/or insertion tools to define three passageways P1''', P2''' and P3''' between an incision I''' and the desired interspinous space. As described above, the passageways can have any suitable shape to promote alignment of the spinal implants during the insertion operation.

FIG. 145 is a flow chart of a method 10000 for inserting a spinal implant according to an embodiment of the invention. The illustrated method includes making an incision having a size no greater than a distance between adjacent spinous processes, 10002. In some embodiments, for example, the incision can be a lateral incision having a length of 15 mm or less. A first support member, such as, for example, a spinal implant of the type shown and described above, is inserted through the incision, 10004. The first support member can be inserted using an insertion tool of the type shown and described above. The first support member is then disposed between a first pair of adjacent spinous processes, 10006. A second support member is inserted through the incision, 10008. As described above, in some embodiments, the second support member can be inserted using an insertion tool having a different shape than the insertion tool used to insert the first support member. In other embodiments, the insertion tool used to insert the first support member can be identical to the insertion tool used to insert the second support member. In yet other embodiments, the first support member and the second support member can be inserted using a single insertion tool. The second support member is then disposed between a second pair of adjacent spinous processes, 10010.

In some embodiments, the first pair of spinous processes is adjacent the second pair of spinous processes. Said another way, as shown in FIG. 139, the first pair of spinous processes can overlap the second pair of spinous processes in that there is a common spinous process (SP3 in FIG. 139) between the pairs. In other embodiments, the first pair of spinous processes can be offset from the second pair of spinous processes in that there is no overlap between the pairs.

FIG. 146 is a flow chart of a method 10020 according to an embodiment of the invention. The illustrated method includes making an incision having a size no greater than approximately half a distance between adjacent spinous processes, 10022. A first tool, such as, for example, an insertion or a distraction tool of the type shown and described above, is inserted through the incision to define a first passageway, 10024. A first support member is then disposed between a first pair of adjacent spinous processes via the first passageway, 10026. In some embodiments, for example, the tool used to define the first passageway can be different than the tool used to dispose the support member between the first pair of spinous processes. In other embodiments, the first tool can define the first passageway and dispose the first support member between the first pair of spinous processes.

A second tool is inserted through the incision to define a second passageway, 10028. A second support member is then disposed between a second pair of adjacent spinous processes via the second passageway, 10030. Similarly, in some embodiments, the second tool used to define the second passageway can be different than the tool used to dispose the second support member between the second pair of spinous processes. In other embodiments, however, the second tool can both define the second passageway and dispose the support member between the second pair of spinous processes.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

For example, although the embodiments above are primarily described as being spinal implants configured to be positioned between adjacent spinous processes, in alternative embodiments, the implants are configured to be positioned adjacent any bone, tissue or other bodily structure where it is desirable to maintain spacing while preventing axial or longitudinal movement of the implant.

While the implants described herein were primarily described as not distracting adjacent spinous processes, in alternative embodiments, the implants can be configured to expand to distract adjacent spinous processes, or can be configured to distract upon insertion.

Although described as being inserted directly between adjacent spinous processes, in alternative embodiments, the implants described above can be delivered through a cannula.

For example, although the swing arm 1700 is described as having an arcuate portion, in alternative embodiments of the invention, the entire swing arm 1700 may have an arcuate configuration. Additionally, the opening defined in the swing arm 1700 may extend the entire length of the swing arm 1700.

Although the swing arm 1700 is described and illustrated as having a circular opening at its end, in alternative embodiments, the opening can be any shape and the shape of the portion of the working tool and/or spacer can be shaped to engage matingly the opening of the swing arm.

Although the connection between the swing arm and the working tool are shown with the swing arm being the female component and the working tool being the male component, in alternative embodiments, the orientation of the male/female relationship may be reversed.

Although the first arm 1170 and second arm 1180 of the first clamp 1100 are described as being resiliently coupled, in alternative embodiments of the invention, the first arm 1170 and the second arm 1180 are pivotably or hingedly coupled.

Although the first clamp and second clamp are disclosed as having jaws that engage opposite sides of a spinous process, in alternative embodiments, the first clamp and second clamp may include other configurations to engage the spinous process such as, for example, suction, adhesive, pins/projections, etc.

While the first clamp and second clamp are disclosed as being movable with respect to one another, in alternative embodiments, the first clamp or the second clamp may be fixed in position, with the other clamp moving relative to the fixed clamp.

While the first arm and the second arm of the clamp are shown as being resiliently biased apart from one another, in alternative embodiments, the first arm and the second arm can be manually moved towards and away from one another using a different configuration (e.g., scissor configuration).

Although embodiments are disclosed that illustrate the wire being coupled to the swing arm using a retainer, in alternative embodiments, a retainer need not be used. The wire can be coupled to the swing arm using other retention methods, such as, for example, a slit in which the wire can be clamped.

Additionally, although the working tool 1840 is disclosed as a trocar tip, the working tool may be any working tool such as, for example, a spacer, a balloon actuator, a bone tamp, etc.

Although the actuator used to move the spinal implant from the expanded configuration to the collapsed configuration is described as a rod assembly or a balloon, in alternative embodiments the actuator can be any device configured to impart a longitudinal force sufficient to move the implant to its collapsed configuration. For example, the actuator can be a piston/cylinder assembly, a ratchet assembly, or the like.

Although the insertion tools 9500 and 10500 are shown and described as having a curved portion defining two radii of curvature, in other embodiments an insertion tool can have any number of curved portions defining any number of radii of curvature. For example, in some embodiments, an insertion tool can include a first curved portion, a second curved portion and a linear portion disposed therebetween.

Although the insertion tools are shown and described as having a curved portion and/or a complex geometrical shape, in some embodiments, a distraction tool can have a geometry and/or a shape similar to that described above with reference to the insertion tools.

What is claimed is:

1. A method, comprising:
   positioning an implant having an end portion and a body portion within a patient's body such that the body portion is disposed between a pair of adjacent spinous processes; the end portion and body portion disposed along a longitudinal axis of the implant; and wherein, during positioning, the end portion and the body portion are both in a collapsed configuration;
   expanding the end portion to a first expanded configuration while the body portion is disposed between the pair of spinous processes, wherein in the first expanded configuration the end portion extends farther outwardly from the longitudinal axis than when the end portion is in the collapsed configuration;
   expanding the body portion to a second expanded configuration while the body portion is disposed between the pair of spinous processes, wherein in the second expanded configuration the body portion extends farther outwardly from the longitudinal axis than when the body portion is in the collapsed configuration;
   wherein the steps of expanding the end portion and expanding the body portion occur independently of each other.

2. The method of claim 1, wherein the positioning includes inserting percutaneously the implant into the patient's body through an opening having a size less than the size of the body portion of the implant in its expanded configuration.

3. The method of claim 1, wherein the positioning includes inserting percutaneously the implant into the patient's body through an opening having a size less than a distance between the pair of adjacent spinous processes.

4. The method of claim 1, wherein the expanding the body portion includes distracting the pair of adjacent spinous processes.

5. The method of claim 1 wherein the expanding the body portion includes inflating at least a part of the body portion.

6. The method of claim 1 wherein expanding the end portion includes plastically deforming at least a part of the end portion.

7. The method of claim 1 wherein expanding the end portion includes applying an axial load to the implant.

8. The method of claim 1, wherein:
   the expanding the end portion of the implant is performed using a first actuator; and
   the expanding the body portion of the implant is performed using a second actuator different from the first actuator.

9. The method of claim 1 wherein expanding the body portion includes inflating at least a part of the body portion and wherein expanding the end portion includes applying an axial load to the implant.

10. A method, comprising:
    inserting through an incision and into a patient's body an implant having a retention portion and a distraction portion disposed sequentially along a longitudinal axis of the implant, the inserting being performed when the retention portion is in a collapsed configuration and the distraction portion is in a collapsed configuration, a size of the retention portion when the retention portion is in its collapsed configuration being less than a size of the incision, a size of the distraction portion when the distraction portion is in its collapsed configuration being less than the size of the incision;
    positioning the implant such that at least a portion of the distraction portion is disposed between a pair of adjacent spinous processes in the patient's body;
    moving the retention portion from its collapsed configuration to a first expanded configuration after the positioning, a size of the retention portion when in its first expanded configuration being greater than the size of the incision;
    moving the distraction portion from its collapsed configuration to a second expanded configuration after the positioning, a size of the distraction portion when in its second expanded configuration being greater than the size of the incision;
    wherein the steps of moving the retention portion and moving the distraction portion occur independently of each other.

11. The method of claim 10, wherein the moving the retention portion is performed at a first time after the positioning; and the moving the distraction portion is performed at a second time after the positioning, the second time different than the first time.

12. The method of claim 10, wherein the moving the distraction portion includes distracting the pair of adjacent spinous processes.

13. The method of claim 10, wherein the moving the distraction portion includes inflating at least a part of the distraction portion.

14. The method of claim 10, wherein the moving the retention portion includes deforming at least a part of the retention portion.

15. The method of claim 10, wherein the moving the retention portion includes applying an axial load to the implant.

16. The method of claim 10, wherein:
the moving the retention portion of the implant is performed using a first actuator; and
the moving the distraction portion of the implant is performed using a second actuator different from the first actuator.

17. A method, comprising:
positioning an implant having an end portion and a body portion within a patient's body when the implant is in a first configuration; the end portion and the body portion disposed along sequentially a longitudinal axis of the implant; wherein, in the first configuration, the end portion and the body portion each have a first height normal to the longitudinal axis;
moving the implant to a second configuration different from the first configuration after the positioning; wherein, in the second configuration, the end portion has a second height normal to the longitudinal axis that is greater than the first height of the end portion and the body portion has a second height normal to the longitudinal axis that is equal to the first height of the body portion;
moving the implant to a third configuration different from the first configuration and the second configuration after the positioning; wherein, in the third configuration, the body portion has a third height normal to the longitudinal axis that is greater than the first height of the body portion and the end portion has a third height normal to the longitudinal axis that is equal to the second height of the end portion.

18. The method of claim 17 wherein the positioning includes inserting percutaneously the implant into the patient's body through an opening in the patient's body having a size less than the second height of the end portion and the second height of the body portion.

19. The method of claim 17, wherein:
the moving the implant to the second configuration is performed at a first time after the positioning; and
the moving the implant to the third configuration is performed at a second time after the positioning, the second time different than the first time.

20. The method of claim 17, wherein the moving the implant to the second configuration is performed independent from the moving the implant to the third configuration.

21. The method of claim 17, wherein the moving the implant to the second configuration includes distracting the pair of adjacent spinous processes.

22. The method of claim 17 wherein the moving the implant to the second configuration includes inflating at least a part of the body portion.

23. The method of claim 17 wherein the moving the implant to the third configuration includes deforming at least a part of the end portion.

24. The method of claim 17, wherein the moving the implant to the third configuration includes applying an axial load to the implant.

* * * * *